United States Patent
Flockerzi et al.

(10) Patent No.: US 9,018,175 B2
(45) Date of Patent: Apr. 28, 2015

(54) 3,4,4A,10B-TETRAHYDRO-1H-THIOPYRANO-[44,3-C] ISOQUINOLINE DERIVATIVES

(75) Inventors: Dieter Flockerzi, Allensbach (DE); Thomas Stengel, Constance (DE); Alexander Mann, Radolfzell (DE); Harald Ohmer, Singen (DE); Ulrich Kautz, Allensbach (DE); Steffen Weinbrenner, Constance (DE); Stefan Fischer, Freinsheim (DE); Christof Zitt, Constance (DE); Armin Hatzelmann, Constance (DE); Torsten Dunkern, Jüchen Gierath (DE); Christian Hesslinger, Zoznegg (DE); Thomas Maier, Stockach (DE); Hermann Tenor, Radolfzell (DE); Clemens Braun, Constance (DE); Raimund Külzer, Constance (DE); Degenhard Marx, Moos (DE)

(73) Assignee: Takeda GmbH, Constance (DE)

( * ) Notice: Subject to any disclaimer, the term of this patent is extended or adjusted under 35 U.S.C. 154(b) by 373 days.

(21) Appl. No.: 13/515,214

(22) PCT Filed: Dec. 15, 2010

(86) PCT No.: PCT/EP2010/069704
§ 371 (c)(1),
(2), (4) Date: Jul. 26, 2012

(87) PCT Pub. No.: WO2011/073231
PCT Pub. Date: Jun. 23, 2011

(65) Prior Publication Data
US 2012/0289474 A1    Nov. 15, 2012

Related U.S. Application Data

(60) Provisional application No. 61/315,552, filed on Mar. 19, 2010.

(30) Foreign Application Priority Data

Dec. 18, 2009   (EP) .................................. 09179982

(51) Int. Cl.
| A61K 31/56 | (2006.01) |
| A61K 31/519 | (2006.01) |
| A61K 31/5585 | (2006.01) |
| C07D 495/04 | (2006.01) |
| C07D 519/00 | (2006.01) |

(52) U.S. Cl.
CPC .................................. C07D 519/00 (2013.01)

(58) Field of Classification Search
CPC . A61K 31/56; A61K 31/519; A61K 31/5585; C07D 495/04; C07D 519/00
USPC ..................... 514/23, 26, 167, 171, 249, 260; 544/278
See application file for complete search history.

(56) References Cited

U.S. PATENT DOCUMENTS

| 6,008,215 | A | 12/1999 | Flockerzi |
| 6,943,253 | B2 | 9/2005 | Vidal Juan et al. |
| 7,589,205 | B2 | 9/2009 | Flockerzi et al. |
| 7,838,521 | B2 | 11/2010 | Flockerzi et al. |
| 2003/0216407 | A1 | 11/2003 | Butt et al. |
| 2004/0038994 | A1 | 2/2004 | Wilson |
| 2014/0113877 | A1* | 4/2014 | Flockerzi et al. ............... 514/23 |

FOREIGN PATENT DOCUMENTS

| JP | 01-213284 A | 8/1989 |
| WO | 98/21208 A1 | 5/1998 |

(Continued)

OTHER PUBLICATIONS

Deng Wan-Ding, et al., "Progress of Drug Therapy for Asthma or Chronic Obstructive Pulmonary Disease", Chinese Journal of Pharmaceuticals, vol. 39, No. 11, 2008, pp. 855-859.
Xie Yicheng, et al., "Progress in Research on Phosphodiesterase-4 Inhibitor for Treatment of Asthma and Chronic Obstructive Pulmonary Disease", World Clinical Drugs, vol. 28, No. 1, 2007, pp. 19-22, English Abstract attached.
Yang Dan-lei, et al., "Effect of Phosphodiesterase Inhibitor on Expression of IL-8mRNA in Peripheral Blood Mononuclear Cells from COPD Patients", Chinese Journal of Cellular and Molecular Immunology, vol. 21, No. 3, 2005, pp. 359-361.
Banner et al. "Dual PDE3/4 inhibitors as therapeutic agents for chronic obstructive pulmonary disease", British Journal of Pharmacology (2009), 157,892-906.

*Primary Examiner* — James O Wilson
*Assistant Examiner* — Ebenezer O Sackey
(74) *Attorney, Agent, or Firm* — Nath, Goldberg & Meyer; Joshua B. Goldberg

(57) ABSTRACT

The compounds of Formula (1),

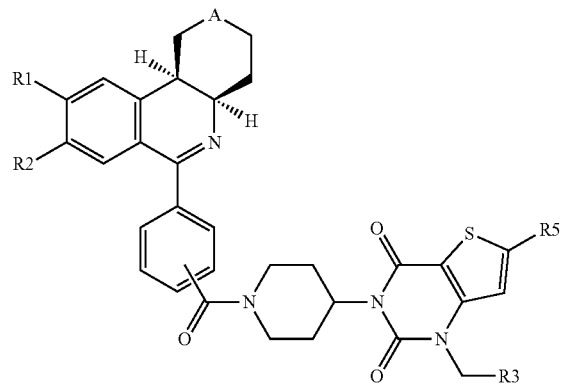

(1)

in which A, R1, R2, R3 and R5 have the meanings as given in the description, are novel effective inhibitors of type 4 and 5 phosphodiesterase.

19 Claims, No Drawings

(56) References Cited

FOREIGN PATENT DOCUMENTS

| WO | 01/94350 A1 | 12/2001 |
| WO | 02/05616 A1 | 1/2002 |
| WO | 03/013571 A1 | 2/2003 |
| WO | 03/063875 A1 | 8/2003 |
| WO | 2004/014916 A1 | 2/2004 |
| WO | 2005/102317 A1 | 11/2005 |
| WO | 2006/027344 A2 | 3/2006 |
| WO | 2006/027345 A2 | 3/2006 |
| WO | 2006/095009 A1 | 9/2006 |
| WO | 2008128647 A1 | 10/2008 |

\* cited by examiner

3,4,4A,10B-TETRAHYDRO-1H-THIOPYRANO-[44,3-C] ISOQUINOLINE DERIVATIVES

This application is filed under 35 U.S.C. 371 as the national stage of PCT/EP2010/069704, filed Dec. 15, 2010, which claims priority to EP 09179982.5, filed Dec. 18, 2009 and U.S. Ser. No. 61/315,552, filed Mar. 19, 2010.

FIELD OF APPLICATION OF THE INVENTION

The invention relates to novel 3,4,4a,10b-tetrahydro-1H-thiopyrano[4,3-c]isoquinoline compounds, which are used in the pharmaceutical industry for the manufacture of pharmaceutical compositions.

KNOWN TECHNICAL BACKGROUND

In the international patent application WO2006027345 3,4,4a,10b-tetrahydro-1H-thiopyrano[4,3-c]isoquinoline compounds are described as type 4 phosphodiesterase inhibitors.

DESCRIPTION OF THE INVENTION

It has now been found that the 3,4,4a,10b-tetrahydro-1H-thiopyrano[4,3-c]isoquinoline compounds, which are described in greater details below, have surprising and particularly advantageous properties.

The invention relates to a compound of formula 1

(1)

wherein
A is S, S(O) or S(O)$_2$,
either
R1 is 1-4C-alkoxy, 3-7C-cycloalkoxy, 3-7C-cycloalkylmethoxy, or 1-4C-alkoxy predominantly or completely substituted by fluorine and
R2 is 1-4C-alkoxy, 3-7C-cycloalkoxy, 3-7C-cycloalkylmethoxy, or 1-4C-alkoxy predominantly or completely substituted by fluorine,
or
R1 and R2 together form a 1-2C-alkylenedioxy group,
R3 is a five membered heterocyclic ring, which is substituted by R4 and is selected from pyrazol-3-yl, pyrazol-4-yl, thiophen-2-yl, thiophen-3-yl, imidazol-2-yl, imidazol-4-yl, isoxazol-3-yl, isoxazol-4-yl, isoxazol-5-yl, 1,3-oxazol-2-yl, 1,3-oxazol-4-yl, 1,3-oxazol-5-yl, 1,3-thiazol-2-yl, 1,3-thiazol-4-yl, 1,3-thiazol-5-yl, 1,2,3-triazol-4-yl, 1,2,4-triazol-3-yl, 1,2,4-oxadiazol-3-yl, 1,2,4-oxadiazol-5-yl, 1,3,4-oxadiazol-2-yl, 1,2,4-thiadiazol-5-yl, 1,2,4-thiadiazol-3-yl, 1,3,4-thiadiazol-2-yl, tetrazol-2-yl or tetrazol-5-yl, wherein
R4 is 1-4C-alkyl, methoxymethyl, methoxyethyl, methoxypropyl, ethoxymethyl, propyloxymethyl, ethoxyethyl, methylsulfanylmethyl, methylsulfanylethyl, methylsulfanylpropyl, ethylsulfanylmethyl, propylsulfanylmethyl or ethylsulfanylethyl,
R5 is unsubstituted phenyl, phenyl substituted by R6 or phenyl substituted by R6 and R7, wherein
R6 is halogen, 1-4C-alkyl or 1-4C-alkoxy, and
R7 is halogen, 1-4C-alkyl or 1-4C-alkoxy,
or
R6 and R7 together form a 1-2C-alkylenedioxy group,
or a stereoisomer of the compound.

1-4C-Alkyl is a straight-chain or branched alkyl group having 1 to 4 carbon atoms. Examples are butyl, isobutyl, sec-butyl, tert-butyl, propyl, isopropyl, ethyl and methyl.

1-2C-Alkyl is a straight-chain alkyl group having 1 to 2 carbon atoms. Examples are ethyl and methyl.

1-4C-Alkoxy is a group which, in addition to the oxygen atom, contains a straight-chain or branched alkyl group having 1 to 4 carbon atoms. Alkoxy groups having 1 to 4 carbon atoms which may be mentioned in this context are, for example, butoxy, isobutoxy, sec-butoxy, tert-butoxy, propoxy, isopropoxy, ethoxy and methoxy.

1-2C-Alkoxy is a group, which in addition to the oxygen atom, contains a straight-chain alkyl group having 1 to 2 carbon atoms. Examples are ethoxy and methoxy.

1-2C-Alkylenedioxy represents, for example, the methylenedioxy [—O—CH$_2$—O-] and the ethylenedioxy [—O—CH$_2$—CH$_2$—O-] group.

1-4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy group are replaced by fluorine atoms.

1-2C-Alkoxy which is completely or predominantly substituted by fluorine is, for example, the perfluoroethoxy, the 1,2,2-trifluoroethoxy, the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-2C-alkoxy group are replaced by fluorine atoms.

3-7C-Cycloalkoxy stands for cyclopropyloxy, cyclobutyloxy, cyclopentyloxy, cyclohexyloxy or cycloheptyloxy.

3-5C-Cycloalkoxy stands for cyclopropyloxy, cyclobutyloxy or cyclopentyloxy.

3-7C-Cycloalkylmethoxy stands for cyclopropylmethoxy, cyclobutylmethoxy, cyclopentylmethoxy, cyclohexylmethoxy or cycloheptylmethoxy.

3-5C-Cycloalkylmethoxy stands for cyclopropylmethoxy, cyclobutylmethoxy or cyclopentylmethoxy.

Halogen stands for fluorine, chlorine, bromine or iodine, with fluorine, chlorine or bromine being preferred.

It is to be understood that in the five membered heterocyclic rings R3 which are substituted by R4, the substituent R4 replaces the hydrogen atom of the —N(H)— group in those five membered heterocyclic rings that contain a —N(H)— group, such as for example, pyrazole, imidazole, 1,2,3-triazole and tetrazol-5-yl. In all other five membered heterocyclic rings, which are substituted by R4, such as for example, isoxazol, 1,3-oxazole, 1,3-thiazole, 1,2,4-oxadiazole, 1,3,4-oxadiazole, 1,2,4-thiadiazole and 1,3,4-thiadiazole, the substituent R4 replaces a hydrogen atom attached to a ring carbon atom. All of the five membered heterocyclic rings R3 are bonded via a ring carbon atom to the rest of the molecule. The only exemption to these rules is the tetrazol-2-yl-ring. In case, R3 stands for tetrazol-2-yl, the tetrazol-2-yl ring is bonded via a ring nitrogen atom to the rest of the molecule and R4 does not replace the hydrogen atom of the —N(H)— group, but the hydrogen atom of the —C(H)— group.

Exemplary five membered heterocyclic rings R3 substituted by R4 which may be mentioned are 1-methyl-1H-imidazol-2-yl, 1-ethyl-1H-imidazol-2-yl, 5-ethyl-thiophen-2-yl, 5-methyl-thiophen-2-yl, 3-methyl-thiophen-2-yl, 3-ethyl-thiophen-2-yl, 1-methyl-pyrazol-3-yl, 1-ethyl-pyrazol-3-yl, 1-methyl-pyrazol-4-yl, 2-ethyl-pyrazol-4-yl, 4-methyl-1,3-oxazol-2-yl, 4-ethyl-1,3-oxazol-2-yl, 5-methyl-1,3-oxazol-2-yl, 5-ethyl-1,3-oxazol-2-yl, 2-methyl-1,3-oxazol-4-yl, 2-methyl-1,3-oxazol-4-yl, 2-ethyl-1,3-oxazol-4-yl, 2-methyl-1,3-oxazol-5-yl, 2-ethyl-1,3-oxazol-5-yl, 4-methyl-1,3-oxazol-5-yl, 4-ethyl-1,3-oxazol-5-yl, 3-methyl-isoxazol-5-yl, 3-ethyl-isoxazol-5-yl, 5-methyl-isoxazol-3-yl, 5-ethyl-isoxazol-3-yl, 4-methyl-1,3-thiazol-2-yl, 4-ethyl-1,3-thiazol-2-yl, 5-methyl-1,3-thiazol-2-yl, 2-methyl-1,3-thiazol-4-yl, 2-ethyl-1,3-thiazol-4-yl, 2-methyl-1,3-thiazol-5-yl, 2-ethyl-1,3-thiazol-5-yl, 3-methoxymethyl-1,2,4-oxadiazol-5-yl, 3-ethoxymethyl-1,2,4-oxadiazol-5-yl, 3-methoxypropyl-1,2,4-oxadiazol-5-yl, 3-propoxymethyl-1,2,4-oxadiazol-5-yl, 3-methylsulfanylmethyl-1,2,4-oxadiazol-5-yl, 3-ethylsulfanylmethyl-1,2,4-oxadiazol-5-yl, 3-methylsulfanylpropyl-1,2,4-oxadiazol-5-yl, 3-propylsulfanylmethyl-1,2,4-oxadiazol-5-yl, 3-methyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 5-tert-butyl-1,3,4-oxadiazol-2-yl, 5-methoxymethyl-1,3,4-oxadiazol-2-yl, 5-ethoxymethyl-1,3,4-oxadiazol-2-yl, 5-methylsulfanylmethyl-1,3,4-oxadiazol-2-yl, 5-ethylsulfanylmethyl-1,3,4-oxadiazol-2-yl, 5-methyl-1,2,4-oxadiazol-3-yl, 5-ethyl-1,2,4-oxadiazol-3-yl, 3-methyl-1,2,4-thiadiazol-5-yl, 3-methyl-1,2,4-thiadiazol-5-yl, 3-ethyl-1,2,4-thiadiazol-5-yl, 2-methyl-1,2,3-triazol-4-yl, 2-ethyl-1,2,3-triazol-4-yl, 1-methyl-1,2,3-triazol-4-yl, 1-ethyl-1,2,3-triazol-4-yl, 1-methyl-1H-1,2,4-triazol-3-yl, 1-ethyl-1H-1,2,4-triazol-3-yl, 1-methyl-1H-tetrazol-5-yl, 1-ethyl-1H-tetrazol-5-yl, 2-methyl-2H-tetrazol-5-yl, 2-ethyl-2H-tetrazol-5-yl, 5-ethyl-2H-tetrazol-2-yl, 5-methyl-2H-tetrazol-2-yl, 1-methoxymethyl-1H-tetrazol-5-yl, 1-ethoxymethyl-1H-tetrazol-5-yl, 2-methoxymethyl-2H-tetrazol-5-yl, 2-ethoxymethyl-2H-tetrazol-5-yl, 1-methylsulfanylmethyl-1H-tetrazol-5-yl, 1-ethylsulfanylmethyl-1H-tetrazol-5-yl, 2-methylsulfanylmethyl-2H-tetrazol-5-yl or 2-ethylsulfanylmethyl-2H-tetrazol-5-yl, of which 1-methyl-1H-imidazol-2-yl, 5-ethyl-thiophen-2-yl, 3-methyl-thiophen-2-yl, 1-ethyl-pyrazol-3-yl, 2-ethyl-pyrazol-4-yl, 4-ethyl-1,3-oxazol-2-yl, 5-ethyl-1,3-oxazol-2-yl, 2-ethyl-1,3-oxazol-4-yl, 2-ethyl-1,3-oxazol-5-yl, 4-methyl-1,3-oxazol-5-yl, 3-ethyl-isoxazol-5-yl, 5-methyl-isoxazol-3-yl, 4-methyl-1,3-thiazol-2-yl, 5-methyl-1,3-thiazol-2-yl, 2-methyl-1,3-thiazol-4-yl, 2-methyl-1,3-thiazol-5-yl, 3-methoxymethyl-1,2,4-oxadiazol-5-yl, 3-methoxypropyl-1,2,4-oxadiazol-5-yl, 3-propoxymethyl-1,2,4-oxadiazol-5-yl, 3-methylsulfanylmethyl-1,2,4-oxadiazol-5-yl, 3-ethyl-1,2,4-oxadiazol-5-yl, 5-ethyl-1,3,4-oxadiazol-2-yl, 5-tert-butyl-1,3,4-oxadiazol-2-yl, 5-methoxymethyl-1,3,4-oxadiazol-2-yl, 5-methyl-1,2,4-oxadiazol-3-yl, 3-ethyl-1,2,4-thiadiazol-5-yl, 1-ethyl-1,2,3-triazol-4-yl, 1-methyl-1H-1,2,4-triazol-3-yl, 1-ethyl-1H-tetrazol-5-yl, 2-ethyl-2H-tetrazol-5-yl, 5-ethyl-2H-tetrazol-2-yl, 1-methoxymethyl-1H-tetrazol-5-yl or 2-methoxymethyl-2H-tetrazol-5-yl are preferred and 5-ethyl-1,3-oxazol-2-yl, 3-ethyl-isoxazol-5-yl, 5-methyl-isoxazol-3-yl, 2-methyl-1,3-thiazol-5-yl, 3-methoxymethyl-1,2,4-oxadiazol-5-yl, 3-methylsulfanylmethyl-1,2,4-oxadiazol-5-yl, 3-ethyl-1,2,4-oxadiazol-5-yl, 5-methyl-1,2,4-oxadiazol-3-yl, 1-ethyl-1H-tetrazol-5-yl, 2-ethyl-2H-tetrazol-5-yl, 2-methoxymethyl-2H-tetrazol-5-yl or 1-methoxymethyl-1H-tetrazol-5-yl are particularly preferred.

Exemplary phenyl rings substituted by R6 or by R6 and R7, which may be mentioned are 1,3-benzodioxol-5-yl, 2-fluorophenyl, 4-fluorophenyl, 2,3-difluorophenyl, 3,4-difluorophenyl, 2-methoxy-4-fluorophenyl, 2-methoxy-5-fluorophenyl or 2,5-dimethoxyphenyl.

The part of the compound of formula 1 that is attached via a carbonyl group to the phenyl group in 6-position of the 3,4,4a,10b-tetrahydro-1H-thiopyrano[4,3-c]isoquinoline ring system can be attached either in ortho, meta or para position in relation to the bond to the 3,4,4a,10b-tetrahydro-1H-thiopyrano[4,3-c]isoquinoline ring system. Preferred is an attachment to the meta or para position, particularly preferred is an attachment in para position.

"Stereoisomer" as part of the phrase "or a stereoisomer of the compound" is meant to mean that in the compounds of formula 1 in case A represents S(O), two stereoisomers exist and both of these two stereoisomers are included within the scope of the invention (respectively within the scope of the particular claim). The absolute configuration of the compounds of formula 1 at the stereogenic centers in positions 4a and 10b is fixed and is R in position 4a and R in position 10b.

In a preferred embodiment, the invention relates to a compound of formula 1, wherein
A is S, S(O) or S(O)$_2$,
either
R1 is 1-2C-alkoxy, or 1-2C-alkoxy predominantly or completely substituted by fluorine and
R2 is 1-2C-alkoxy, or 1-2C-alkoxy predominantly or completely substituted by fluorine,
or
R1 and R2 together form a 1-2C-alkylenedioxy group,
R3 is 1-methyl-1H-imidazol-2-yl, 1-ethyl-1H-imidazol-2-yl, 5-ethyl-thiophen-2-yl, 5-methyl-thiophen-2-yl, 3-methyl-thiophen-2-yl, 3-ethyl-thiophen-2-yl, 1-methyl-pyrazol-3-yl, 1-ethyl-pyrazol-3-yl, 1-methyl-pyrazol-4-yl, 2-ethyl-pyrazol-4-yl, 4-methyl-1,3-oxazol-2-yl, 4-ethyl-1,3-oxazol-2-yl, 5-methyl-1,3-oxazol-2-yl, 5-ethyl-1,3-oxazol-2-yl, 2-methyl-1,3-oxazol-4-yl, 2-methyl-1,3-oxazol-4-yl, 2-ethyl-1,3-oxazol-4-yl, 2-methyl-1,3-oxazol-5-yl, 2-ethyl-1,3-oxazol-5-yl, 4-methyl-1,3-oxazol-5-yl, 4-ethyl-1,3-oxazol-5-yl, 3-methyl-isoxazol-5-yl, 3-ethyl-isoxazol-5-yl, 5-methyl-isoxazol-3-yl, 5-ethyl-isoxazol-3-yl, 4-methyl-1,3-thiazol-2-yl, 4-ethyl-1,3-thiazol-2-yl, 5-methyl-1,3-thiazol-2-yl, 2-methyl-1,3-thiazol-4-yl, 2-ethyl-1,3-thiazol-4-yl, 2-methyl-1,3-thiazol-5-yl, 2-ethyl-1,3-thiazol-5-yl, 3-methoxymethyl-1,2,4-oxadiazol-5-yl, 3-ethoxymethyl-1,2,4-oxadiazol-5-yl, 3-methoxypropyl-1,2,4-oxadiazol-5-yl, 3-propoxymethyl-1,2,4-oxadiazol-5-yl, 3-methylsulfanylmethyl-1,2,4-oxadiazol-5-yl, 3-ethylsulfanylmethyl-1,2,4-oxadiazol-5-yl, 3-methylsulfanylpropyl-1,2,4-oxadiazol-5-yl, 3-propylsulfanylmethyl-1,2,4-oxadiazol-5-yl, 3-methyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 5-tert-butyl-1,3,4-oxadiazol-2-yl, 5-methoxymethyl-1,3,4-oxadiazol-2-yl, 5-ethoxymethyl-1,3,4-oxadiazol-2-yl, 5-methylsulfanylmethyl-1,3,4-oxadiazol-2-yl, 5-ethylsulfanylmethyl-1,3,4-oxadiazol-2-yl, 5-methyl-1,2,4-oxadiazol-3-yl, 5-ethyl-1,2,4-oxadiazol-3-yl, 3-methyl-1,2,4-thiadiazol-5-yl, 3-methyl-1,2,4-thiadiazol-5-yl, 3-ethyl-1,2,4-thiadiazol-5-yl, 2-methyl-1,2,3-triazol-4-yl, 2-ethyl-1,2,3-triazol-4-yl, 1-methyl-1,2,3-triazol-4-yl, 1-ethyl-1,2,3-triazol-4-yl, 1-methyl-1H-1,2,4-triazol-3-yl, 1-ethyl-1H-1,2,4-triazol-3-yl, 1-methyl-1H-tetrazol-5-yl, 1-ethyl-1H-tetrazol-5-yl, 2-methyl-2H-tetrazol-5-yl, 2-ethyl-2H-tetrazol-5-yl, 5-ethyl-2H-tetrazol-2-yl, 5-methyl-2H-tetrazol-2-yl, 1-methoxymethyl-1H-tetrazol-5-yl, 1-ethoxymethyl-1H-tetrazol-5-yl, 2-methoxymethyl-2H-tetrazol-5-yl, 2-ethoxymethyl-2H-tetrazol-5-yl, 1-methylsulfanylmethyl-1H-tetrazol-5-yl, 1-ethylsulfanylmethyl-1H-tetrazol-5-yl, 2-methylsulfanylmethyl-2H-tetrazol-5-yl or 2-ethylsulfanylmethyl-2H-tetrazol-5-yl, R5 is unsubstituted phenyl, phenyl substituted by R6 or phenyl substituted by R6 and R7 wherein R6 is fluorine, methyl or methoxy, and R7 is fluorine, methyl or methoxy, or a stereoisomer of the compound.

In another preferred embodiment, the invention relates to a compound of formula 1, wherein A is S, S(O) or S(O)$_2$, either R1 is 1-2C-alkoxy, or 1-2C-alkoxy predominantly or completely substituted by fluorine and R2 is 1-2C-alkoxy, or 1-2C-alkoxy predominantly or completely substituted by fluorine, or R1 and R2 together form a 1-2C-alkylenedioxy group, R3 is 1-methyl-pyrazol-3-yl, 1-ethyl-pyrazol-3-yl, 1-methyl-pyrazol-4-yl, 2-ethyl-pyrazol-4-yl, 4-methyl-1,3-oxazol-2-yl, 4-ethyl-1,3-oxazol-2-yl, 5-methyl-1,3-oxazol-2-yl, 5-ethyl-1,3-oxazol-2-yl, 2-methyl-1,3-oxazol-4-yl, 2-methyl-1,3-oxazol-4-yl, 2-ethyl-1,3-oxazol-4-yl, 2-methyl-1,3-oxazol-5-yl, 2-ethyl-1,3-oxazol-5-yl, 3-methyl-isoxazol-5-yl, 3-ethyl-isoxazol-5-yl, 5-methyl-isoxazol-3-yl, 5-ethyl-isoxazol-3-yl, 4-methyl-1,3-thiazol-2-yl, 4-ethyl-1,3-thiazol-2-yl, 5-methyl-1,3-thiazol-2-yl, 2-methyl-1,3-thiazol-4-yl, 2-ethyl-1,3-thiazol-4-yl, 2-methyl-1,3-thiazol-5-yl, 2-ethyl-1,3-thiazol-5-yl, 3-methoxymethyl-1,2,4-oxadiazol-5-yl, 3-ethoxymethyl-1,2,4-oxadiazol-5-yl, 3-methylsulfanylmethyl-1,2,4-oxadiazol-5-yl, 3-ethylsulfanylmethyl-1,2,4-oxadiazol-5-yl, 3-methyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 5-methoxymethyl-1,3,4-oxadiazol-2-yl, 5-ethoxymethyl-1,3,4-oxadiazol-2-yl, 5-methylsulfanylmethyl-1,3,4-oxadiazol-2-yl, 5-ethylsulfanylmethyl-1,3,4-oxadiazol-2-yl, 5-methyl-1,2,4-oxadiazol-3-yl, 5-ethyl-1,2,4-oxadiazol-3-yl, 3-methyl-1,2,4-thiadiazol-5-yl, 3-methyl-1,2,4-thiadiazol-5-yl, 3-ethyl-1,2,4-thiadiazol-5-yl, 2-methyl-1,2,3-triazol-4-yl, 2-ethyl-1,2,3-triazol-4-yl, 1-methyl-1,2,3-triazol-4-yl, 1-ethyl-1,2,3-triazol-4-yl, 1-methyl-1H-tetrazol-5-yl, 1-ethyl-1H-tetrazol-5-yl, 2-methyl-2H-tetrazol-5-yl, 2-ethyl-2H-tetrazol-5-yl, 1-methoxymethyl-1H-tetrazol-5-yl, 1-ethoxymethyl-1H-tetrazol-5-yl, 2-methoxymethyl-2H-tetrazol-5-yl, 2-ethoxymethyl-2H-tetrazol-5-yl, 1-methylsulfanylmethyl-1H-tetrazol-5-yl, 1-ethylsulfanylmethyl-1H-tetrazol-5-yl, 2-methylsulfanylmethyl-2H-tetrazol-5-yl or 2-ethylsulfanylmethyl-2H-tetrazol-5-yl, and R5 is unsubstituted phenyl, or a stereoisomer of the compound.

In another preferred embodiment, the invention relates to a compound of formula 1, wherein A is S, S(O) or S(O)$_2$, R1 is methoxy or ethoxy, R2 is methoxy, R3 is 1-methyl-1H-imidazol-2-yl, 5-ethyl-thiophen-2-yl, 3-methyl-thiophen-2-yl, 1-ethyl-pyrazol-3-yl, 2-ethyl-pyrazol-4-yl, 4-ethyl-1,3-oxazol-2-yl, 5-ethyl-1,3-oxazol-2-yl, 2-ethyl-1,3-oxazol-4-yl, 2-ethyl-1,3-oxazol-5-yl, 4-methyl-1,3-oxazol-5-yl, 3-ethyl-isoxazol-5-yl, 5-methyl-isoxazol-3-yl, 4-methyl-1,3-thiazol-2-yl, 5-methyl-1,3-thiazol-2-yl, 2-methyl-1,3-thiazol-4-yl, 2-methyl-1,3-thiazol-5-yl, 3-methoxymethyl-1,2,4-oxadiazol-5-yl, 3-methoxypropyl-1,2,4-oxadiazol-5-yl, 3-propoxymethyl-1,2,4-oxadiazol-5-yl, 3-methylsulfanylmethyl-1,2,4-oxadiazol-5-yl, 3-ethyl-1,2,4-oxadiazol-5-yl, 5-ethyl-1,3,4-oxadiazol-2-yl, 5-tert-butyl-1,3,4-oxadiazol-2-yl, 5-methoxymethyl-1,3,4-oxadiazol-2-yl, 5-methyl-1,2,4-oxadiazol-3-yl, 3-ethyl-1,2,4-thiadiazol-5-yl, 2-ethyl-1,2,3-triazol-4-yl, 1-ethyl-1,2,3-triazol-4-yl, 1-methyl-1H-1,2,4-triazol-3-yl, 1-ethyl-1H-tetrazol-5-yl, 2-ethyl-2H-tetrazol-5-yl, 5-ethyl-2H-tetrazol-2-yl, 1-methoxymethyl-1H-tetrazol-5-yl or 2-methoxymethyl-2H-tetrazol-5-yl, and R5 is phenyl, 1,3-benzodioxol-5-yl, 2-fluorophenyl, 4-fluorophenyl, 2,3-difluorophenyl, 3,4-difluorophenyl, 2-methoxy-4-fluorophenyl, 2-methoxy-5-fluorophenyl or 2,5-dimethoxyphenyl.

or a stereoisomer of the compound.

In another preferred embodiment, the invention relates to a compound of formula 1, wherein A is S, S(O) or S(O)$_2$, R1 is methoxy or ethoxy, R2 is methoxy, R3 is 1-ethyl-pyrazol-3-yl, 2-ethyl-pyrazol-4-yl, 4-ethyl-1,3-oxazol-2-yl, 5-ethyl-1,3-oxazol-2-yl, 2-ethyl-1,3-oxazol-4-yl, 2-ethyl-1,3-oxazol-5-yl, 3-ethyl-isoxazol-5-yl, 5-methyl-isoxazol-3-yl, 4-methyl-1,3-thiazol-2-yl, 5-methyl-1,3-thiazol-2-yl, 2-methyl-1,3-thiazol-4-yl, 2-methyl-1,3-thiazol-5-yl, 3-methoxymethyl-1,2,4-oxadiazol-5-yl, 3-methylsulfanylmethyl-1,2,4-oxadiazol-5-yl, 3-ethyl-1,2,4-oxadiazol-5-yl, 5-ethyl-1,3,4-oxadiazol-2-yl, 5-methoxymethyl-1,3,4-oxadiazol-2-yl, 5-methyl-1,2,4-oxadiazol-3-yl, 3-ethyl-1,2,4-thiadiazol-5-yl, 2-ethyl-1,2,3-triazol-4-yl, 1-ethyl-1,2,3-triazol-4-yl, 1-ethyl-1H-tetrazol-5-yl, 2-ethyl-2H-tetrazol-5-yl, 1-methoxymethyl-1H-tetrazol-5-yl or 2-methoxymethyl-2H-tetrazol-5-yl, and R5 is unsubstituted phenyl, or a stereoisomer of the compound.

In another preferred embodiment, the invention relates to a compound of formula 1, wherein A is S, S(O) or S(O)$_2$, R1 is methoxy or ethoxy, R2 is methoxy, R3 is 3-methoxypropyl-1,2,4-oxadiazol-5-yl, 3-ethyl-1,2,4-oxadiazol-5-yl or 2-ethyl-2H-tetrazol-5-yl, R5 is 1,3-benzodioxol-5-yl, 2-fluorophenyl, 4-fluorophenyl, 2,3-difluorophenyl, 3,4-difluorophenyl, 2-methoxy-4-fluorophenyl, 2-methoxy-5-fluorophenyl or 2,5-dimethoxyphenyl, or a stereoisomer of the compound.

In another preferred embodiment, the invention relates to a compound of formula 1, wherein A is S, S(O) or S(O)$_2$,
R1 is methoxy or ethoxy,
R2 is methoxy,
R3 is 3-methoxypropyl-1,2,4-oxadiazol-5-yl, 1-methyl-1H-1,2,4-triazol-3-yl, 1-methyl-1H-imidazol-2-yl, 5-ethyl-thiophen-2-yl, 3-methyl-thiophen-2-yl, 4-methyl-1,3-oxazol-5-yl, 5-tert-butyl-1,3,4-oxadiazol-2-yl, 3-propoxymethyl-1,2,4-oxadiazol-5-yl or 5-ethyl-2H-tetrazol-2-yl, and
R5 is unsubstituted phenyl,
or a stereoisomer of the compound.

In another preferred embodiment, the invention relates to a compound of formula 1, wherein A is S, S(O) or S(O)$_2$,
R1 is ethoxy,
R2 is methoxy,
R3 is 2-ethyl-2H-tetrazol-5-yl or 3-methoxymethyl-1,2,4-oxadiazol-5-yl,
R5 is 1,3-benzodioxol-5-yl, 2-fluorophenyl, 2-methoxy-4-fluorophenyl or 2-methoxy-5-fluorophenyl,
or a stereoisomer of the compound.

In another preferred embodiment, the invention relates to a compound of formula 1, wherein A is S, S(O) or S(O)$_2$,
R1 is ethoxy,
R2 is methoxy,
R3 is 5-ethyl-1,3-oxazol-2-yl, 3-ethyl-isoxazol-5-yl, 5-methyl-isoxazol-3-yl, 2-methyl-1,3-thiazol-5-yl, 3-methoxymethyl-1,2,4-oxadiazol-5-yl, 3-methylsulfanylmethyl-1,2,4-oxadiazol-5-yl, 3-ethyl-1,2,4-oxadiazol-5-yl, 5-methyl-1,2,4-oxadiazol-3-yl, 1-ethyl-1H-tetrazol-5-yl, 2-ethyl-2H-tetrazol-5-yl, 1-methoxymethyl-1H-tetrazol-5-yl or 2-methoxymethyl-2H-tetrazol-5-yl,
R5 is unsubstituted phenyl,
or a stereoisomer of the compound.

In another preferred embodiment, the invention relates to a compound of formula 1, wherein A is S, S(O) or S(O)$_2$,
R1 is ethoxy,
R2 is methoxy,
R3 is 5-ethyl-1,3-oxazol-2-yl, 3-ethyl-isoxazol-5-yl, 5-methyl-isoxazol-3-yl, 2-methyl-1,3-thiazol-5-yl, 3-methoxymethyl-1,2,4-oxadiazol-5-yl, 3-ethyl-1,2,4-oxadiazol-5-yl, 5-methyl-1,2,4-oxadiazol-3-yl, 1-ethyl-1H-tetrazol-5-yl, 2-ethyl-2H-tetrazol-5-yl, 1-methoxymethyl-1H-tetrazol-5-yl or 2-methoxymethyl-2H-tetrazol-5-yl,
R5 is unsubstituted phenyl,
or a stereoisomer of the compound.

In a further preferred embodiment, the invention relates to a compound of formulae 1p or 1m

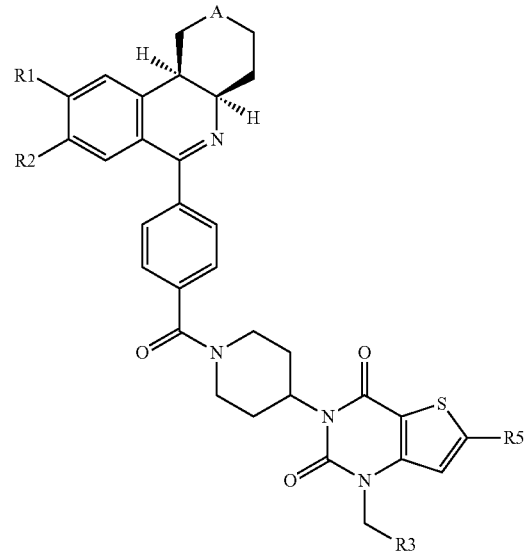

(1p)

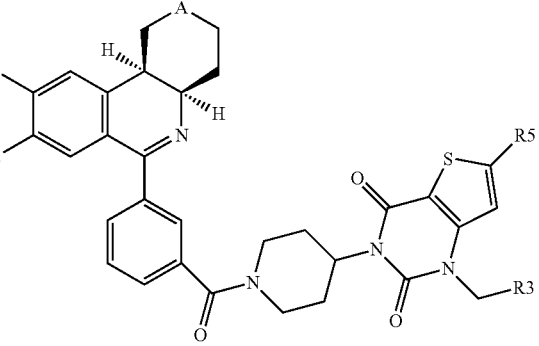

(1m)

wherein A, R1, R2, R3 and R5 are as defined above,
or a stereoisomer of the compound.

In a further preferred embodiment, the invention relates to a compound of formulae 1p or 1m wherein R5 is unsubstituted phenyl and A, R1, R2 and R3 are as defined above,
or a stereoisomer of the compound.

In a further preferred embodiment, the invention relates to a compound of formula 1p or a stereoisomer thereof, wherein A, R1, R2, R3 and R5 are as defined above.

In a further preferred embodiment, the invention relates to a compound of formula 1p or a stereoisomer thereof, wherein R5 is unsubstituted phenyl and A, R1, R2 and R3 are as defined above.

In a further preferred embodiment, the invention relates to a compound of formula 1m or a stereoisomer thereof, wherein A, R1, R2, R3 and R5 are as defined above.

In a further preferred embodiment, the invention relates to a compound of formula 1m or a stereoisomer thereof, wherein R5 is unsubstituted phenyl and A, R1, R2 and R3 are as defined above.

In a further preferred embodiment, the invention relates to a compound of formula 1, wherein A is S, and R1, R2, R3 and R5 are as defined above.

In a further preferred embodiment, the invention relates to a compound of formula 1, wherein A is S, R5 is unsubstituted phenyl and R1, R2 and R3 are as defined above.

In a further preferred embodiment, the invention relates to a compound of formulae 1p or 1m, wherein A is S, and R1, R2, R3 and R5 are as defined above.

In a further preferred embodiment, the invention relates to a compound of formulae 1p or 1m, wherein A is S, R5 is unsubstituted phenyl and R1, R2 and R3 are as defined above.

In a further preferred embodiment, the invention relates to a compound of formula 1p, wherein A is S, and R1, R2, R3 and R5 are as defined above.

In a further preferred embodiment, the invention relates to a compound of formula 1p, wherein A is S, R5 is unsubstituted phenyl and R1, R2 and R3 are as defined above.

In a further preferred embodiment, the invention relates to a compound of formula 1m, wherein A is S, and R1, R2, R3 and R5 are as defined above.

In a further preferred embodiment, the invention relates to a compound of formula 1m, wherein A is S, R5 is unsubstituted phenyl and R1, R2 and R3 are as defined above.

In a further preferred embodiment, the invention relates to a compound of formula 1, wherein A is S, R1 is ethoxy, R2 is methoxy and R3 and R5 are as defined above.

In a further preferred embodiment, the invention relates to a compound of formula 1, wherein A is S, R1 is ethoxy, R2 is methoxy, R5 is unsubstituted phenyl and R3 is as defined above.

In a further preferred embodiment, the invention relates to a compound of formulae 1p or 1m, wherein A is S, R1 is ethoxy, R2 is methoxy and R3 and R5 are as defined above.

In a further preferred embodiment, the invention relates to a compound of formulae 1p or 1m, wherein A is S, R1 is ethoxy, R2 is methoxy, R5 is unsubstituted phenyl and R3 is as defined above.

In a further preferred embodiment, the invention relates to a compound of formula 1p, wherein A is S, R1 is ethoxy, R2 is methoxy and R3 and R5 are as defined above.

In a further preferred embodiment, the invention relates to a compound of formula 1p, wherein A is S, R1 is ethoxy, R2 is methoxy, R5 is unsubstituted phenyl and R3 is as defined above.

In a further preferred embodiment, the invention relates to a compound of formula 1m, wherein A is S, R1 is ethoxy, R2 is methoxy and R3 and R5 are as defined above.

In a further preferred embodiment, the invention relates to a compound of formula 1m, wherein A is S, R1 is ethoxy, R2 is methoxy, R5 is unsubstituted phenyl and R3 is as defined above.

In a further preferred embodiment, the invention relates to a compound of formula 1 or a stereoisomer thereof, wherein A is S(O), and R1, R2, R3 and R5 are as defined above.

In a further preferred embodiment, the invention relates to a compound of formula 1 or a stereoisomer thereof, wherein A is S(O), R5 is unsubstituted phenyl and R1, R2 and R3 are as defined above.

In a further preferred embodiment, the invention relates to a compound of formulae 1p or 1m or a stereoisomer thereof, wherein A is S(O), and R1, R2, R3 and R5 are as defined above.

In a further preferred embodiment, the invention relates to a compound of formulae 1p or 1m or a stereoisomer thereof, wherein A is S(O), R5 is unsubstituted phenyl and R1, R2 and R3 are as defined above.

In a further preferred embodiment, the invention relates to a compound of formula 1p or a stereoisomer thereof, wherein A is S(O), and R1, R2, R3 and R5 are as defined above.

In a further preferred embodiment, the invention relates to a compound of formula 1p or a stereoisomer thereof, wherein A is S(O), R5 is unsubstituted phenyl and R1, R2 and R3 are as defined above.

In a further preferred embodiment, the invention relates to a compound of formula 1m or a stereoisomer thereof, wherein A is S(O), and R1, R2, R3 and R5 are as defined above.

In a further preferred embodiment, the invention relates to a compound of formula 1m or a stereoisomer thereof, wherein A is S(O), R5 is unsubstituted phenyl and R1, R2 and R3 are as defined above.

In a further preferred embodiment, the invention relates to a compound of formula 1 or a stereoisomer thereof, wherein A is S(O), R1 is ethoxy, R2 is methoxy and R3 and R5 are as defined above.

In a further preferred embodiment, the invention relates to a compound of formula 1 or a stereoisomer thereof, wherein A is S(O), R1 is ethoxy, R2 is methoxy, R5 is unsubstituted phenyl and R3 is as defined above.

In a further preferred embodiment, the invention relates to a compound of formulae 1p or 1m or a stereoisomer thereof, wherein A is S(O), R1 is ethoxy, R2 is methoxy and R3 and R5 are as defined above.

In a further preferred embodiment, the invention relates to a compound of formulae 1p or 1m or a stereoisomer thereof, wherein A is S(O), R1 is ethoxy, R2 is methoxy, R5 is unsubstituted phenyl and R3 is as defined above.

In a further preferred embodiment, the invention relates to a compound of formula 1p or a stereoisomer thereof, wherein A is S(O), R1 is ethoxy, R2 is methoxy and R3 and R5 are as defined above.

In a further preferred embodiment, the invention relates to a compound of formula 1p or a stereoisomer thereof, wherein A is S(O), R1 is ethoxy, R2 is methoxy, R5 is unsubstituted phenyl and R3 is as defined above.

In a further preferred embodiment, the invention relates to a compound of formula 1m or a stereoisomer thereof, wherein A is S(O), R1 is ethoxy, R2 is methoxy and R3 and R5 are as defined above.

In a further preferred embodiment, the invention relates to a compound of formula 1m or a stereoisomer thereof, wherein A is S(O), R1 is ethoxy, R2 is methoxy, R5 is unsubstituted phenyl and R3 is as defined above.

In a further preferred embodiment, the invention relates to a compound of formula 1, wherein A is $S(O)_2$, and R1, R2, R3 and R5 are as defined above.

In a further preferred embodiment, the invention relates to a compound of formula 1, wherein A is $S(O)_2$, R5 is unsubstituted phenyl and R1, R2 and R3 are as defined above.

In a further preferred embodiment, the invention relates to a compound of formulae 1p or 1m, wherein A is $S(O)_2$, and R1, R2, R3 and R5 are as defined above.

In a further preferred embodiment, the invention relates to a compound of formulae 1p or 1m, wherein A is $S(O)_2$, R5 is unsubstituted phenyl and R1, R2 and R3 are as defined above.

In a further preferred embodiment, the invention relates to a compound of formula 1p, wherein A is $S(O)_2$, and R1, R2 and R3 are as defined above.

In a further preferred embodiment, the invention relates to a compound of formula 1p, wherein A is $S(O)_2$, R5 is unsubstituted phenyl and R1, R2 and R3 are as defined above.

In a further preferred embodiment, the invention relates to a compound of formula 1m, wherein A is $S(O)_2$, and R1, R2, R3 and R5 are as defined above.

In a further preferred embodiment, the invention relates to a compound of formula 1m, wherein A is $S(O)_2$, R5 is unsubstituted phenyl and R1, R2 and R3 are as defined above.

In a further preferred embodiment, the invention relates to a compound of formula 1, wherein A is $S(O)_2$, R1 is ethoxy, R2 is methoxy and R3 and R5 are as defined above.

In a further preferred embodiment, the invention relates to a compound of formula 1, wherein A is $S(O)_2$, R1 is ethoxy, R2 is methoxy, R5 is unsubstituted phenyl and R3 is as defined above.

In a further preferred embodiment, the invention relates to a compound of formula 1p or 1m, wherein A is $S(O)_2$, R1 is ethoxy, R2 is methoxy and R3 and R5 are as defined above.

In a further preferred embodiment, the invention relates to a compound of formula 1p or 1m, wherein A is $S(O)_2$, R1 is ethoxy, R2 is methoxy, R5 is unsubstituted phenyl and R3 is as defined above.

In a further preferred embodiment, the invention relates to a compound of formula 1p, wherein A is $S(O)_2$, R1 is ethoxy, R2 is methoxy and R3 and R5 are as defined above.

In a further preferred embodiment, the invention relates to a compound of formula 1p, wherein A is $S(O)_2$, R1 is ethoxy, R2 is methoxy, R5 is unsubstituted phenyl and R3 is as defined above.

In a further preferred embodiment, the invention relates to a compound of formula 1m, wherein A is $S(O)_2$, R1 is ethoxy, R2 is methoxy and R3 and R5 are as defined above.

In a further preferred embodiment, the invention relates to a compound of formula 1m, wherein A is $S(O)_2$, R1 is ethoxy, R2 is methoxy, R5 is unsubstituted phenyl and R3 is as defined above.

In a further preferred embodiment, the invention relates to a compound of formula 1 or a stereoisomer thereof, wherein A is S, S(O) or $S(O)_2$, R3 is 3-ethyl-1,2,4-oxadiazol-5-yl and R1, R2 and R5 are as defined above.

In a further preferred embodiment, the invention relates to a compound of formula 1 or a stereoisomer thereof, wherein A is S, S(O) or $S(O)_2$, R3 is 3-ethyl-1,2,4-oxadiazol-5-yl, R5 is unsubstituted phenyl and R1 and R2 are as defined above.

In a further preferred embodiment, the invention relates to a compound of formulae 1p or 1m or a stereoisomer thereof, wherein A is S, S(O) or $S(O)_2$, R3 is 3-ethyl-1,2,4-oxadiazol-5-yl and R1, R2 and R5 are as defined above.

In a further preferred embodiment, the invention relates to a compound of formulae 1p or 1m or a stereoisomer thereof, wherein A is S, S(O) or $S(O)_2$, R3 is 3-ethyl-1,2,4-oxadiazol-5-yl, R5 is unsubstituted phenyl and R1 and R2 are as defined above.

In a further preferred embodiment, the invention relates to a compound of formula 1p or a stereoisomer thereof, wherein A is S, S(O) or $S(O)_2$, R3 is 3-ethyl-1,2,4-oxadiazol-5-yl and R1, R2 and R5 are as defined above.

In a further preferred embodiment, the invention relates to a compound of formula 1p or a stereoisomer thereof, wherein A is S, S(O) or $S(O)_2$, R3 is 3-ethyl-1,2,4-oxadiazol-5-yl, R5 is unsubstituted phenyl and R1 and R2 are as defined above.

In a further preferred embodiment, the invention relates to a compound of formula 1m or a stereoisomer thereof, wherein A is S, S(O) or $S(O)_2$, R3 is 3-ethyl-1,2,4-oxadiazol-5-yl and R1, R2 and R5 are as defined above.

In a further preferred embodiment, the invention relates to a compound of formula 1m or a stereoisomer thereof, wherein A is S, S(O) or $S(O)_2$, R3 is 3-ethyl-1,2,4-oxadiazol-5-yl, R5 is unsubstituted phenyl and R1 and R2 are as defined above.

In a further preferred embodiment, the invention relates to a compound of formula 1 or a stereoisomer thereof, wherein A is S, S(O) or $S(O)_2$, R3 is 2-methyl-1,3-thiazol-5-yl and R1, R2 and R5 are as defined above.

In a further preferred embodiment, the invention relates to a compound of formula 1 or a stereoisomer thereof, wherein A is S, S(O) or $S(O)_2$, R3 is 2-methyl-1,3-thiazol-5-yl, R5 is unsubstituted phenyl and R1 and R2 are as defined above.

In a further preferred embodiment, the invention relates to a compound of formulae 1p or 1m or a stereoisomer thereof, wherein A is S, S(O) or $S(O)_2$, R3 is 2-methyl-1,3-thiazol-5-yl and R1, R2 and R5 are as defined above.

In a further preferred embodiment, the invention relates to a compound of formulae 1p or 1m or a stereoisomer thereof, wherein A is S, S(O) or $S(O)_2$, R3 is 2-methyl-1,3-thiazol-5-yl, R5 is unsubstituted phenyl and R1 and R2 are as defined above.

In a further preferred embodiment, the invention relates to a compound of formula 1p or a stereoisomer thereof, wherein A is S, S(O) or $S(O)_2$, R3 is 2-methyl-1,3-thiazol-5-yl and R1, R2 and R5 are as defined above.

In a further preferred embodiment, the invention relates to a compound of formula 1p or a stereoisomer thereof, wherein A is S, S(O) or $S(O)_2$, R3 is 2-methyl-1,3-thiazol-5-yl, R5 is unsubstituted phenyl and R1 and R2 are as defined above.

In a further preferred embodiment, the invention relates to a compound of formula 1m or a stereoisomer thereof, wherein A is S, S(O) or $S(O)_2$, R3 is 2-methyl-1,3-thiazol-5-yl and R1, R2 and R5 are as defined above.

In a further preferred embodiment, the invention relates to a compound of formula 1m or a stereoisomer thereof, wherein A is S, S(O) or $S(O)_2$, R3 is 2-methyl-1,3-thiazol-5-yl, R5 is unsubstituted phenyl and R1 and R2 are as defined above.

In a further preferred embodiment, the invention relates to a compound of formula 1 or a stereoisomer thereof, wherein A is S, S(O) or $S(O)_2$, R3 is 2-ethyl-2H-tetrazol-5-yl and R1, R2 and R5 are as defined above.

In a further preferred embodiment, the invention relates to a compound of formula 1 or a stereoisomer thereof, wherein A is S, S(O) or $S(O)_2$, R3 is 2-ethyl-2H-tetrazol-5-yl, R5 is unsubstituted phenyl and R1 and R2 are as defined above.

In a further preferred embodiment, the invention relates to a compound of formulae 1p or 1m or a stereoisomer thereof, wherein A is S, S(O) or $S(O)_2$, R3 is 2-ethyl-2H-tetrazol-5-yl and R1, R2 and R5 are as defined above.

In a further preferred embodiment, the invention relates to a compound of formulae 1p or 1m or a stereoisomer thereof, wherein A is S, S(O) or $S(O)_2$, R3 is 2-ethyl-2H-tetrazol-5-yl, R5 is unsubstituted phenyl and R1 and R2 are as defined above.

In a further preferred embodiment, the invention relates to a compound of formula 1p or a stereoisomer thereof, wherein A is S, S(O) or $S(O)_2$, R3 is 2-ethyl-2H-tetrazol-5-yl and R1, R2 and R5 are as defined above.

In a further preferred embodiment, the invention relates to a compound of formula 1p or a stereoisomer thereof, wherein A is S, S(O) or $S(O)_2$, R3 is 2-ethyl-2H-tetrazol-5-yl, R5 is unsubstituted phenyl and R1 and R2 are as defined above.

In a further preferred embodiment, the invention relates to a compound of formula 1m or a stereoisomer thereof, wherein A is S, S(O) or $S(O)_2$, R3 is 2-ethyl-2H-tetrazol-5-yl and R1, R2 and R5 are as defined above.

In a further preferred embodiment, the invention relates to a compound of formula 1m or a stereoisomer thereof, wherein A is S, S(O) or $S(O)_2$, R3 is 2-ethyl-2H-tetrazol-5-yl, R5 is unsubstituted phenyl and R1 and R2 are as defined above.

In a further preferred embodiment, the invention relates to a compound of formula 1 or a stereoisomer thereof, wherein A is S, S(O) or $S(O)_2$, R3 is 2-methoxymethyl-2H-tetrazol-5-yl and R1, R2 and R5 are as defined above.

In a further preferred embodiment, the invention relates to a compound of formula 1 or a stereoisomer thereof, wherein A is S, S(O) or S(O)₂, R3 is 2-methoxymethyl-2H-tetrazol-5-yl, R5 is unsubstituted phenyl and R1 and R2 are as defined above.

In a further preferred embodiment, the invention relates to a compound of formulae 1p or 1m or a stereoisomer thereof, wherein A is S, S(O) or S(O)₂, R3 is 2-methoxymethyl-2H-tetrazol-5-yl and R1, R2 and R5 are as defined above.

In a further preferred embodiment, the invention relates to a compound of formulae 1p or 1m or a stereoisomer thereof, wherein A is S, S(O) or S(O)₂, R3 is 2-methoxymethyl-2H-tetrazol-5-yl, R5 is unsubstituted phenyl and R1 and R2 are as defined above.

In a further preferred embodiment, the invention relates to a compound of formula 1p or a stereoisomer thereof, wherein A is S, S(O) or S(O)₂, R3 is 2-methoxymethyl-2H-tetrazol-5-yl and R1, R2 and R5 are as defined above.

In a further preferred embodiment, the invention relates to a compound of formula 1p or a stereoisomer thereof, wherein A is S, S(O) or S(O)₂, R3 is 2-methoxymethyl-2H-tetrazol-5-yl, R5 is unsubstituted phenyl and R1 and R2 are as defined above.

In a further preferred embodiment, the invention relates to a compound of formula 1m or a stereoisomer thereof, wherein A is S, S(O) or S(O)₂, R3 is 2-methoxymethyl-2H-tetrazol-5-yl and R1, R2 and R5 are as defined above.

In a further preferred embodiment, the invention relates to a compound of formula 1m or a stereoisomer thereof, wherein A is S, S(O) or S(O)₂, R3 is 2-methoxymethyl-2H-tetrazol-5-yl, R5 is unsubstituted phenyl and R1 and R2 are as defined above.

In a further preferred embodiment, the invention relates to a compound of formula 1 or a stereoisomer thereof, wherein A is S, S(O) or S(O)₂, R3 is 3-methoxymethyl-1,2,4-oxadiazol-5-yl and R1, R2 and R5 are as defined above.

In a further preferred embodiment, the invention relates to a compound of formula 1 or a stereoisomer thereof, wherein A is S, S(O) or S(O)₂, R3 is 3-methoxymethyl-1,2,4-oxadiazol-5-yl, R5 is unsubstituted phenyl and R1 and R2 are as defined above.

In a further preferred embodiment, the invention relates to a compound of formulae 1p or 1m or a stereoisomer thereof, wherein A is S, S(O) or S(O)₂, R3 is 3-methoxymethyl-1,2,4-oxadiazol-5-yl and R1, R2 and R5 are as defined above.

In a further preferred embodiment, the invention relates to a compound of formulae 1p or 1m or a stereoisomer thereof, wherein A is S, S(O) or S(O)₂, R3 is 3-methoxymethyl-1,2,4-oxadiazol-5-yl, R5 is unsubstituted phenyl and R1 and R2 are as defined above.

In a further preferred embodiment, the invention relates to a compound of formula 1p or a stereoisomer thereof, wherein A is S, S(O) or S(O)₂, R3 is 3-methoxymethyl-1,2,4-oxadiazol-5-yl and R1, R2 and R5 are as defined above.

In a further preferred embodiment, the invention relates to a compound of formula 1p or a stereoisomer thereof, wherein A is S, S(O) or S(O)₂, R3 is 3-methoxymethyl-1,2,4-oxadiazol-5-yl, R5 is unsubstituted phenyl and R1 and R2 are as defined above.

In a further preferred embodiment, the invention relates to a compound of formula 1m or a stereoisomer thereof, wherein A is S, S(O) or S(O)₂, R3 is 3-methoxymethyl-1,2,4-oxadiazol-5-yl and R1, R2 and R5 are as defined above.

In a further preferred embodiment, the invention relates to a compound of formula 1m or a stereoisomer thereof, wherein A is S, S(O) or S(O)₂, R3 is 3-methoxymethyl-1,2,4-oxadiazol-5-yl, R5 is unsubstituted phenyl and R1 and R2 are as defined above.

The compounds of formula 1 include stereogenic centers in the positions 4a and 10b of the thiophenanthridine ring system. An additional stereogenic center can arise in position 2 of the thiophenanthridine ring system, in case A represents S(O). The absolute configuration at the stereogenic centers in positions 4a and 10b is fixed and is R in position 4a and R in position 10b ("R" and "S" nomenclature according to the rules of Cahn, Ingold and Prelog).

Accordingly, only one stereoisomer exists in case A represents S or S(O)₂. The absolute configuration at the sterogenic centers 4a and 10b of this stereoisomer is R in position 4a and R in position 10b.

Two stereoisomers exist, in case A represents S(O). The absolute configuration at the stereogenic centers 2, 4a and 10b can be (2R,4aR,10bR) or (2S,4aR,10bR). For the numbering in the thiophenanthridine ring system see below formula 1*.

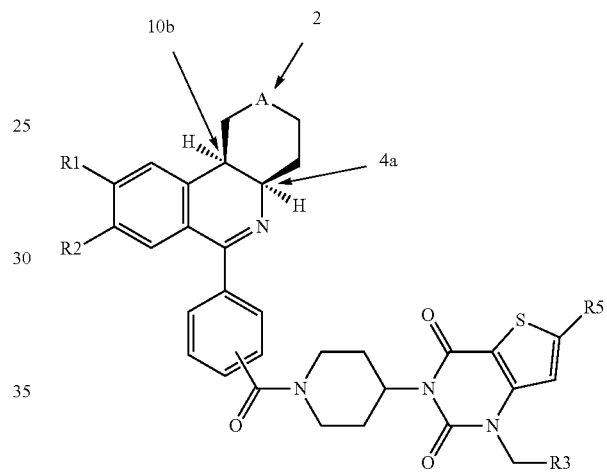

(1*)

The invention further includes the pure stereoisomers mentioned above, as well as all mixtures of the stereoisomers mentioned above, independent of the ratio.

The compounds according to the invention can be prepared according to reaction schemes 1 to 9.

As shown in reaction scheme 1 the compounds of formula 1, wherein A, R1, R2 and R3 have the above-mentioned meanings and R5 is unsubstituted phenyl can be prepared by coupling a benzoic acid compound of formula 2, wherein A, R1 and R2 have the above-mentioned meanings, with a secondary amine of formula 3, wherein R3 has the above-mentioned meanings and R5 is unsubstituted phenyl using any standard amide bond coupling method, such as for example the use of coupling agents or the use of activated acid compounds, like acid anhydrides or esters. A review of suitable amide bond coupling methods can be found, for example, in C. A. G. N. Montalbetti, V. Falque, Tetrahedron, 61 (2005), 10827-10852.

The preparation of the benzoic acid compounds of formula 2 is described below in reaction scheme 6.

The secondary amine of formula 3, wherein R3 has the above mentioned meanings and R5 is unsubstituted phenyl can be prepared from the corresponding N-tert-butyloxycarbonyl protected compounds of formula 4 by using standard conditions for the removal of the tert-butyloxycarbonyl group, such as for example hydrogen chloride or trifluoroacetic acid in an appropriate solvent, such as dioxane or dichloromethane, and if necessary in the presence of a cation scavenger, such as for example anisole or thiophenol. Additional alternative reaction conditions for the removal of the tert-butyloxycarbonyl group can be found, for example, in Greene and Wuts, Protective Groups in Organic Synthesis, 3$^{rd}$ edition, John Wiley & Sons, New York 1999.

The N-tert-butyloxycarbonyl protected compounds of formula 4, wherein R3 has the above-mentioned meanings and R5 is unsubstituted phenyl can be prepared by reacting tert-butyl 4-(2,4-dioxo-6-phenyl-1,4-dihydrothieno[3,2-d]pyrimidin-3(2H)-yl)piperidine-1-carboxylate (Experimental Part—Example B50) with a compound of formula 5, wherein R3 has the above-mentioned meanings and LG stands for a suitable leaving group, such as for example a halide, preferably chlorine or bromine, or a mesyl or tosyl group. The reaction is carried out in an appropriate solvent such as dimethyl sulfoxide or N,N-dimethylformamide in the presence of a base, such as for example potassium carbonate, sodium carbonate, diisopropylethylamine or triethylamine and preferably at elevated temperature, preferably at 100° C.

The preparation of tert-butyl 4-(2,4-dioxo-6-phenyl-1,4-dihydrothieno[3,2-d]pyrimidin-3(2H)-yl)piperidine-1-carboxylate is described in reaction scheme 3 as well as in the experimental part of this application.

The compounds of formula 5 are commercially available or can be prepared according to procedures known in the art or in analogy thereto. Additional information with regard to the preparation of the compounds of formula 5 is provided in the experimental part of this application.

An alternative method for the preparation of the N-tert-butyloxycarbonyl protected compounds of formula 4, wherein R3 is a tetrazol-5-yl ring substituted by R4, R4 has the above-mentioned meanings and R5 is unsubstituted phenyl is shown in reaction scheme 2. According to reaction scheme 2 the heterocyclic group R3 is not introduced via reaction with a compound of formula 5 as shown in reaction scheme 1, but is build up in a multi-step procedure. In a first step tert-butyl 4-(2,4-dioxo-6-phenyl-1,4-dihydrothieno[3,2-d]pyrimidin-3(2H)-yl)piperidine-1-carboxylate (Experimental part—Example B50) is reacted with chloroacetonitrile in an appropriate solvent such as chloroform, tetrahydrofuran, acetonitrile, N,N-dimethylformamide or dimethyl sulfoxide in the presence of a base such as potassium carbonate, sodium carbonate, diisopropylethylamine or triethylamine preferably at elevated temperature preferably at 100° C. to yield tert-butyl 4-[1-(cyanomethyl)-2,4-dioxo-6-phenyl-1,4-dihydrothieno[3,2-d]pyrimidin-3(2H)-yl]piperidine-1-carboxylate (Experimental part—Example B14a). Transformation of the cyano group of tert-butyl 4-[1-(cyanomethyl)-2,4-dioxo-6-phenyl-1,4-dihydrothieno[3,2-d]pyrimidin-3(2H)-yl]piperidine-1-carboxylate to the corresponding tetrazole moiety (tert-butyl 4-[2,4-dioxo-6-phenyl-1-(1H-tetrazol-5-ylmethyl)-1,4-dihydrothieno[3,2-d]pyrimidin-3(2H)-yl]piperidine-1-carboxylate and tert-butyl 4-[2,4-dioxo-6-phenyl-1-(2H-tetrazol-5-ylmethyl)-1,4-dihydrothieno[3,2-d]pyrimidin-3(2H)-yl]piperidine-1-carboxylate; Experimental Part—Example 14b) can be accomplished by conversion with sodium azide in the presence of triethyl ammonium chloride in a suitable solvent such as for example N,N-dimethylformamide at elevated temperature preferably at 100° C. In a subsequent reaction step the tautomeric compounds tert-butyl 4-[2,4-dioxo-6-phenyl-1-(1H-tetrazol-5-ylmethyl)-1,4-dihydrothieno[3,2-d]pyrimidin-3(2H)-yl]piperidine-1-carboxylate and tert-butyl 4-[2,4-dioxo-6-phenyl-1-(2H-tetrazol-5-ylmethyl)-1,4-dihydrothieno[3,2-d]pyrimidin-3(2H)-yl]piperidine-1-carboxylate are alkylated with a compound of formula 6, wherein R4 has the above-mentioned meanings and LG stands for a suitable leaving group, such as for example a halide, preferably chlorine or bromine, or a mesyl or tosyl group in the presence of a base such as for example lithium hydride, sodium hydride or potassium carbonate, sodium carbonate, diisopropylethylamine, triethylamine in an appropriate solvent such as for example N,N-dimethylformamide or dimethyl sulfoxide at elevated temperature, preferably at 40° C. to yield tert-butyl 4-{1-[(2-(R4)-2H-tetrazol-5-yl)methyl]-2,4-dioxo-6-phenyl-1,4-dihydrothieno[3,2-d]pyrimidin-3(2H)-yl}piperidine-1-carboxylate and 4-{1-[(1-(R4)-1H-tetrazol-5-yl)methyl]-2,4-dioxo-6-phenyl-1,4-dihydrothieno[3,2-d]pyrimidin-3(2H)-yl}piperidine-1-carboxylate.

A method of preparation for compound B50 is shown in reaction scheme 3. In a first step methyl 3-amino-5-phenylthiophene-2-carboxylate is reacted with triphosgene followed by tert-butyl 4-aminopiperidine-1-carboxylate in an appropriate solvent such as dichloromethane, chloroform, tetrahydrofuran, acetonitrile, N,N-dimethylformamide or dimethyl sulfoxide at low temperature, preferably at 0° C. Treatment of the resulting tert-butyl 4-({[2-(methoxycarbonyl)-5-phenyl-3-thienyl]carbamoyl}amino)piperidine-1-carboxylate (Experimental part—example B51) with sodium methoxide in an appropriate solvent such as methanol in the presence of a base such as potassium carbonate, sodium carbonate, diisopropylethylamine or triethylamine at elevated temperature, preferably at 65° C. yields tert-butyl 4-(2,4-dioxo-6-phenyl-1,4-dihydrothieno[3,2-d]pyrimidin-3(2H)-yl)piperidine-1-carboxylate (Experimental part—example B50).

In reaction scheme 4 an alternative route of preparation for compounds of formula 1, wherein A, R1, R2 and R3 have the above-mentioned meanings and R5 is unsubstituted phenyl is described. In addition, the route of preparation described in scheme 4 is in particular suitable for the preparation of compounds of formula 1, wherein A, R1, R2 and R3 have the above-mentioned meanings and R5 is phenyl substituted by R6 or phenyl substituted by R6 and R7.

According to reaction scheme 4 compounds of formula 1, wherein A, R1, R2 R3 and R5 have the above-mentioned meanings can be prepared by coupling a benzoic acid compound of formula 2, wherein A, R1 and R2 have the above-mentioned meanings, with a secondary amine of formula 3, wherein R3 has the above-mentioned meanings and R5 is either unsubstituted phenyl or phenyl substituted by R6 or phenyl substituted by R6 and R7, using any standard amide bond coupling method, such as for example the use of coupling agents or the use of activated acid compounds, like acid anhydrides or esters.

The preparation of the benzoic acid compounds of formula 2 is described below in reaction scheme 6.

The secondary amine of formula 3 can be prepared from the corresponding N-tert-butyloxycarbonyl protected compounds of formula 4 by using standard conditions for the removal of the tert-butyloxycarbonyl group, such as for example hydrogen chloride or trifluoroacetic acid in an appropriate solvent, such as dioxane or dichloromethane, and if necessary in the presence of a cation scavenger, such as for example anisole or thiophenol.

The N-tert-butyloxycarbonyl protected compounds of formula 4, wherein R3 and R5 have the above-mentioned meanings can be prepared, for example, by using a palladium catalyzed coupling reaction:

Compounds of formula 8, wherein R3 has the above-mentioned meanings are reacted with a phenyl boronic acid or a phenyl boronic acid ester of formula 7, wherein R5 has the above-mentioned meanings and R may be hydrogen, 1-4C-alkyl or the two R groups may form together an alkylene bridge optionally further substituted by methyl groups (for example forming a pinacol ester), in an inert solvent, such as for example 1,2-dimethoxyethane or 1,4-dioxane in presence of an aqueous solution of a base, such as for example potassium carbonate, cesium carbonate or potassium phosphate, and a palladium catalyst, such as for example dichlorobis (tricyclohexylphosphine)palladium, at a temperature in the range from 60° C. to 160° C., preferably at about 150° C. and additionally under microwave irradiation.

The N-tert-butyloxycarbonyl protected compounds of formula 8 can be prepared as described in reaction scheme 1 by reacting tert-butyl 4-(6-bromo-2,4-dioxo-1,4-dihydrothieno[3,2-d]pyrimidin-3(2H)-yl)piperidine-1-carboxylate (Experimental Part—Example B53) with a compound of formula 5, wherein R3 has the above-mentioned meanings and LG stands for a suitable leaving group, such as for example a halide, preferably chlorine or bromine, or a mesyl or tosyl group. The reaction is carried out in an appropriate solvent such as N,N-dimethylformamide in the presence of a base, such as for example potassium carbonate, sodium carbonate, diisopropylethylamine or triethylamine and preferably at elevated temperature, preferably at 100° C.

Not explicitly shown in reaction scheme 4 is a further alternative method for the preparation of compounds of formula 4. This alternative method also starts with compound B53, but the sequence of introduction of the R3-CH$_2$— group and the R5 group is inverted in comparison to reaction scheme 4. Suitable reaction conditions for this alternative method are described in the experimental part in the description of the preparation of compounds B63 and B62.

In reaction scheme 5 the synthesis of compound B53 is described. The intermediate 3-amino-5-bromo-thiophene-2-carboxylic acid methyl ester (compound B54b) is obtained according to a procedure described in literature (Bioorganic & Medicinal Chemistry Letters 17 (2007) 2535-2539) by conversion of methyl 3-aminothiophene-2-carboxylate to methyl 3-[(trifluoroacetyl)amino]thiophene-2-carboxylate with trifluoroacetic acid anhydride followed by a lithiation/bromination sequence using n-butyllithium and 1,2-dibromoethane to give methyl 5-bromo-3-[(trifluoroacetyl)amino]thiophene-2-carboxylate which is hydrolysed under basic conditions using potassium carbonate to obtain 3-amino-5-bromo-thiophene-2-carboxylic acid methyl ester (compound B54b).

The synthesis of compound B53 is accomplished analogously as already described in reaction scheme 3:

Compound B54b is reacted with triphosgene followed by tert-butyl 4-aminopiperidine-1-carboxylate in an appropriate solvent such as dichloromethane, chloroform, tetrahydrofuran, acetonitrile, N,N-dimethylformamide or dimethyl sulfoxide at low temperature, preferably at 0° C. Treatment of the resulting tert-butyl 4-({[5-bromo-2-(methoxycarbonyl)thiophen-3-yl]carbamoyl}amino)piperidine-1-carboxylate (Experimental part—example B54a) with sodium methoxide in an appropriate solvent such as methanol in the presence of a base such as potassium carbonate, sodium carbonate, diisopropylethylamine or triethylamine at elevated temperature, preferably at 65° C. yields tert-butyl 4-(6-bromo-2,4-dioxo-1,4-dihydrothieno[3,2-d]pyrimidin-3(2H)-yl)piperidine-1-carboxylate (Experimental part—example B53).

Reaction Scheme 1:

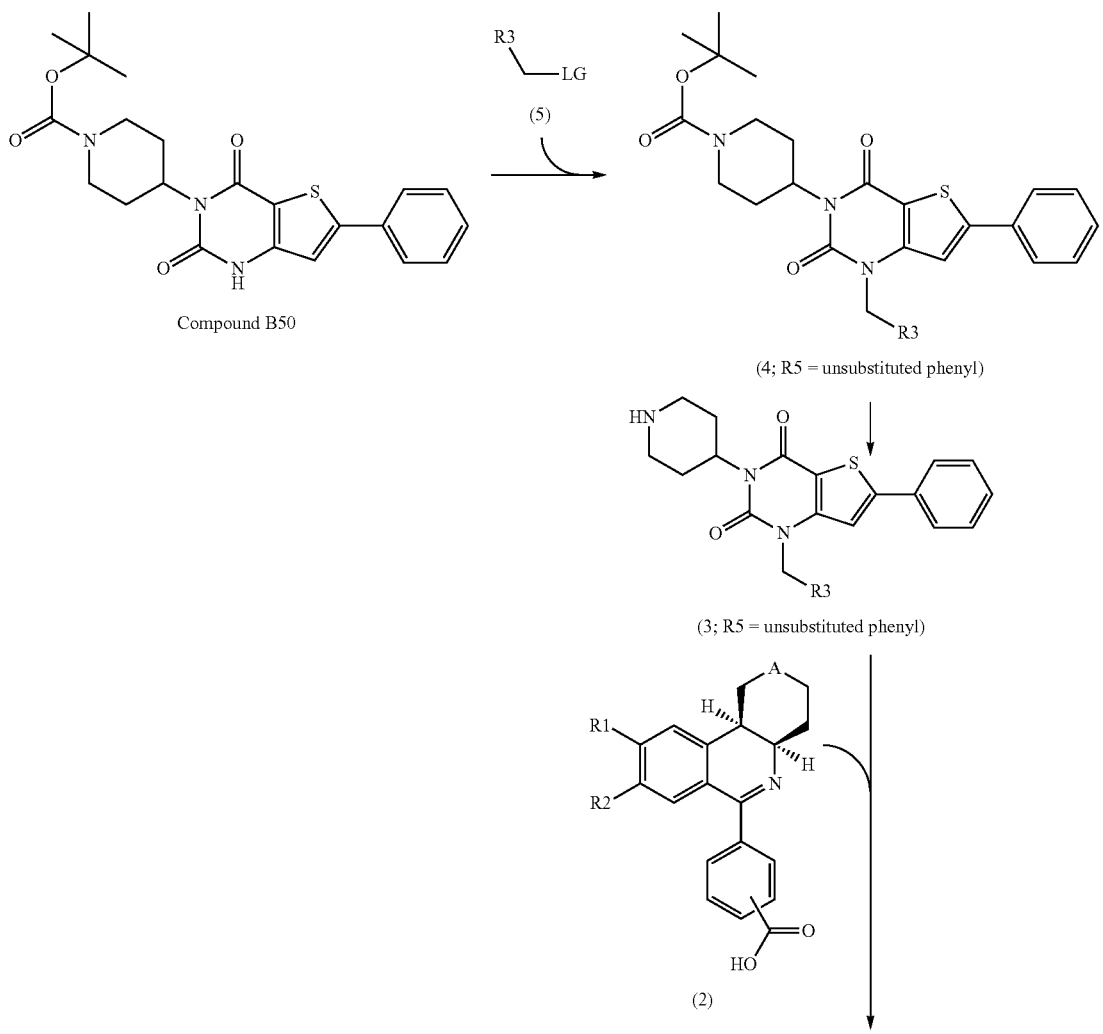

-continued
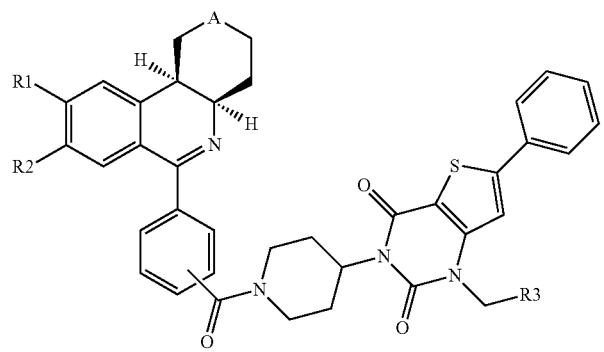
(1; R5 = unsubstituted phenyl)
Reaction Scheme 2:
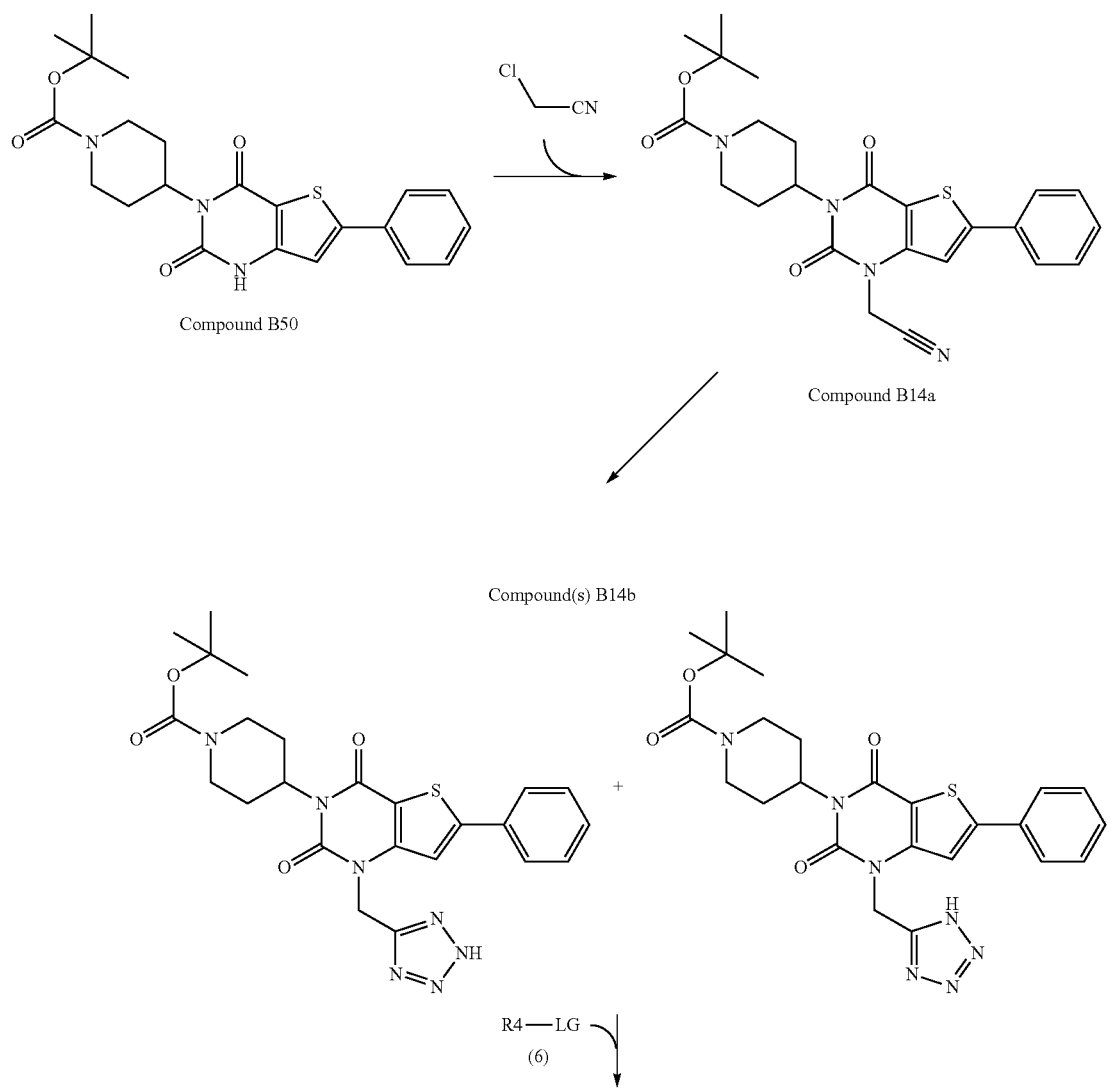

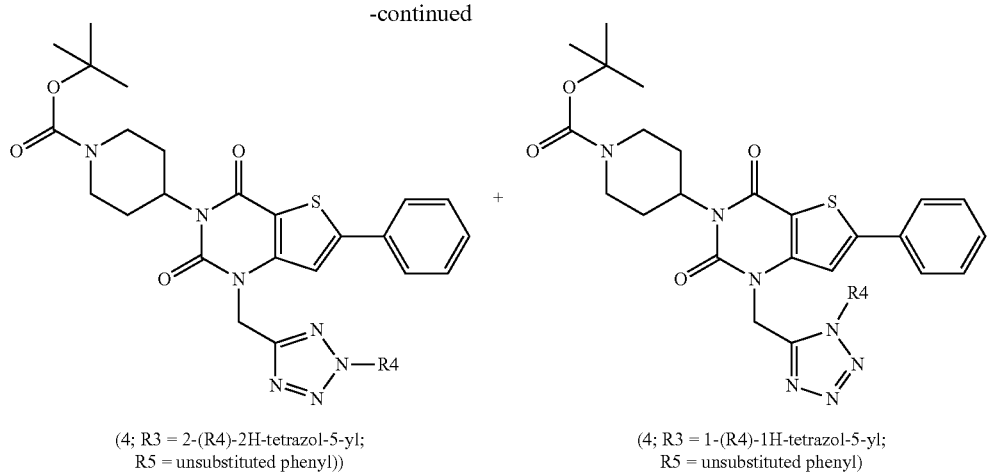
(4; R3 = 2-(R4)-2H-tetrazol-5-yl;
R5 = unsubstituted phenyl))
(4; R3 = 1-(R4)-1H-tetrazol-5-yl;
R5 = unsubstituted phenyl)
Reaction Scheme 3:
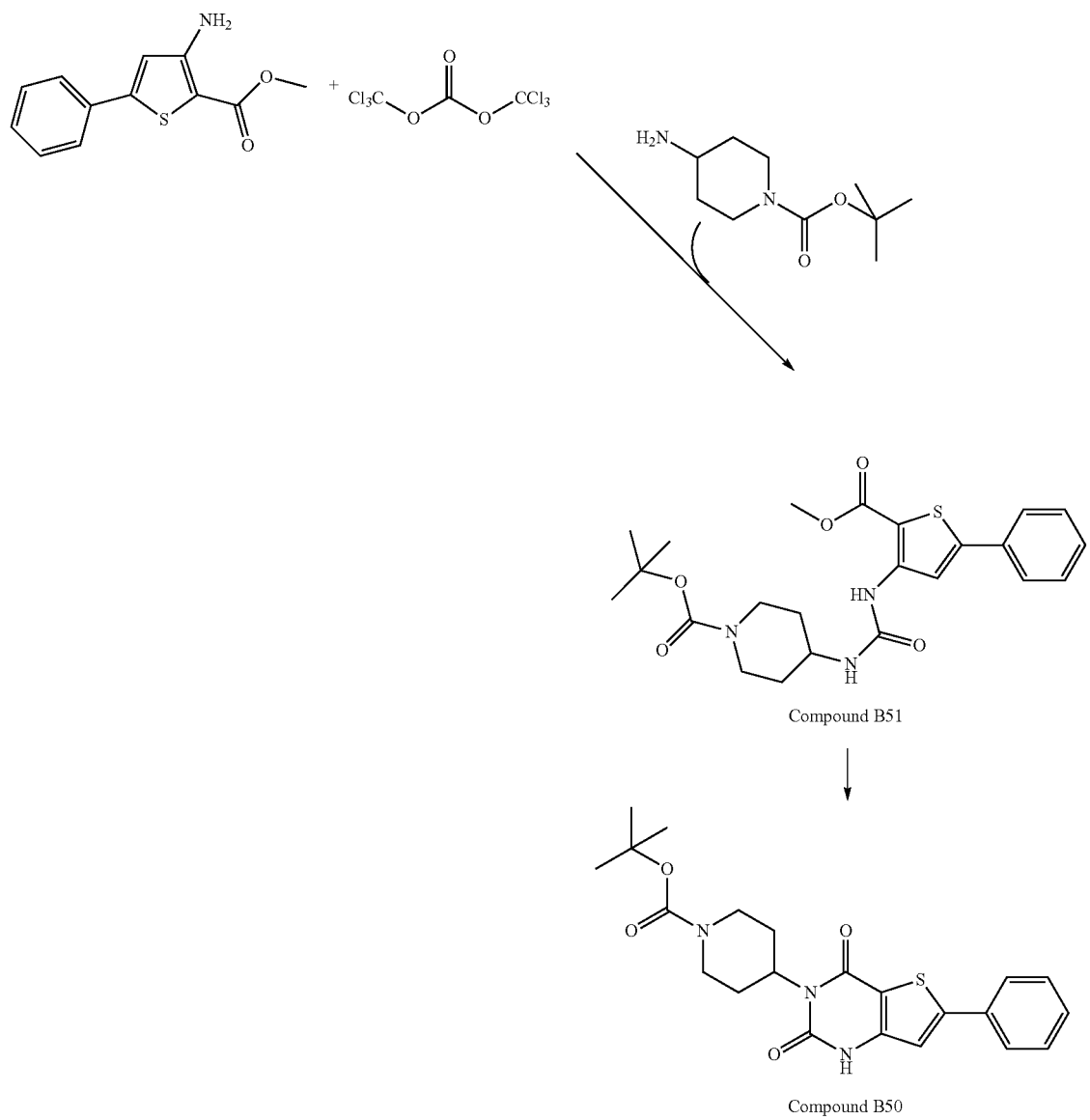
Compound B51
Compound B50

Reaction Scheme 4:
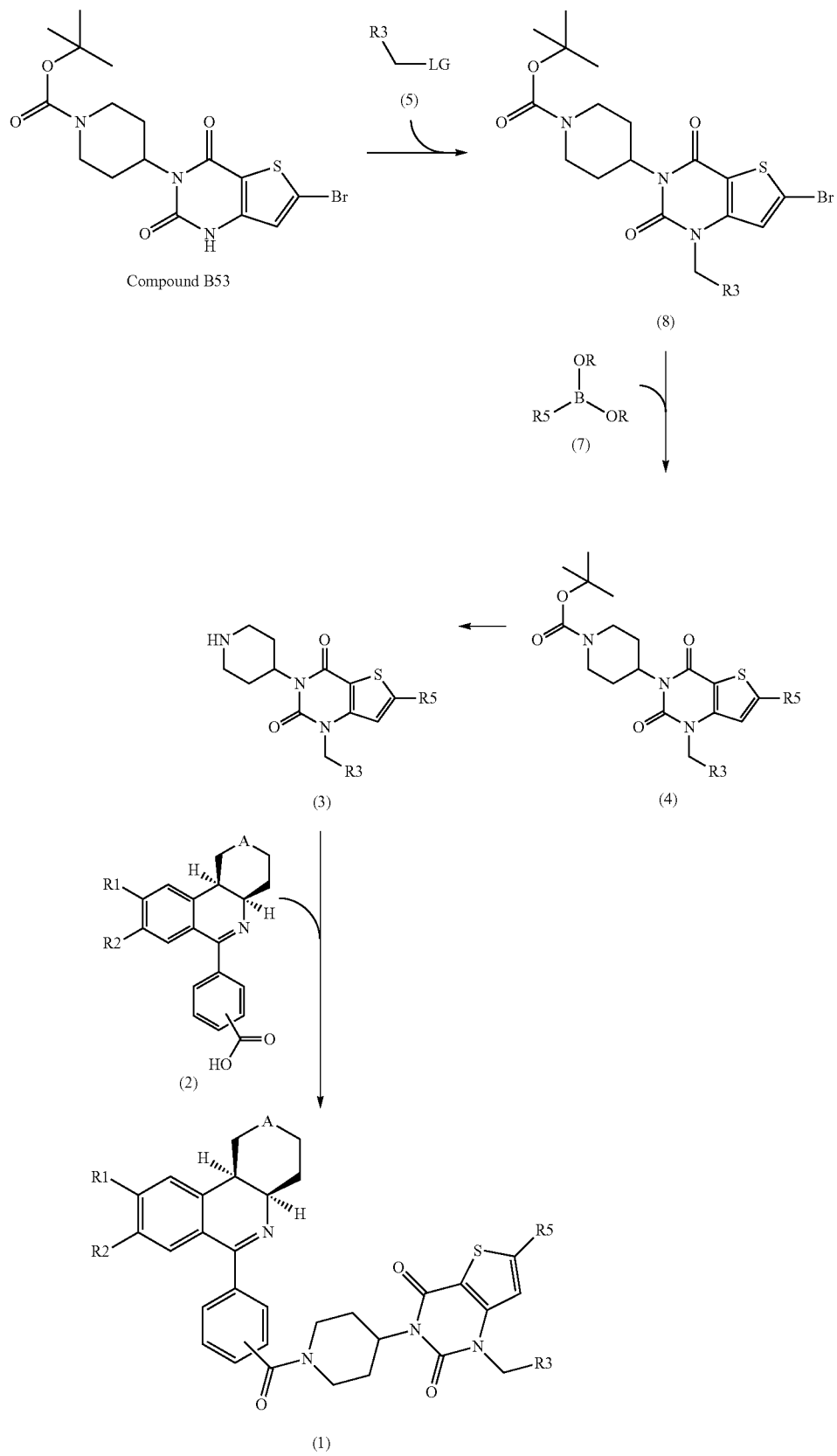

Reaction Scheme 5:
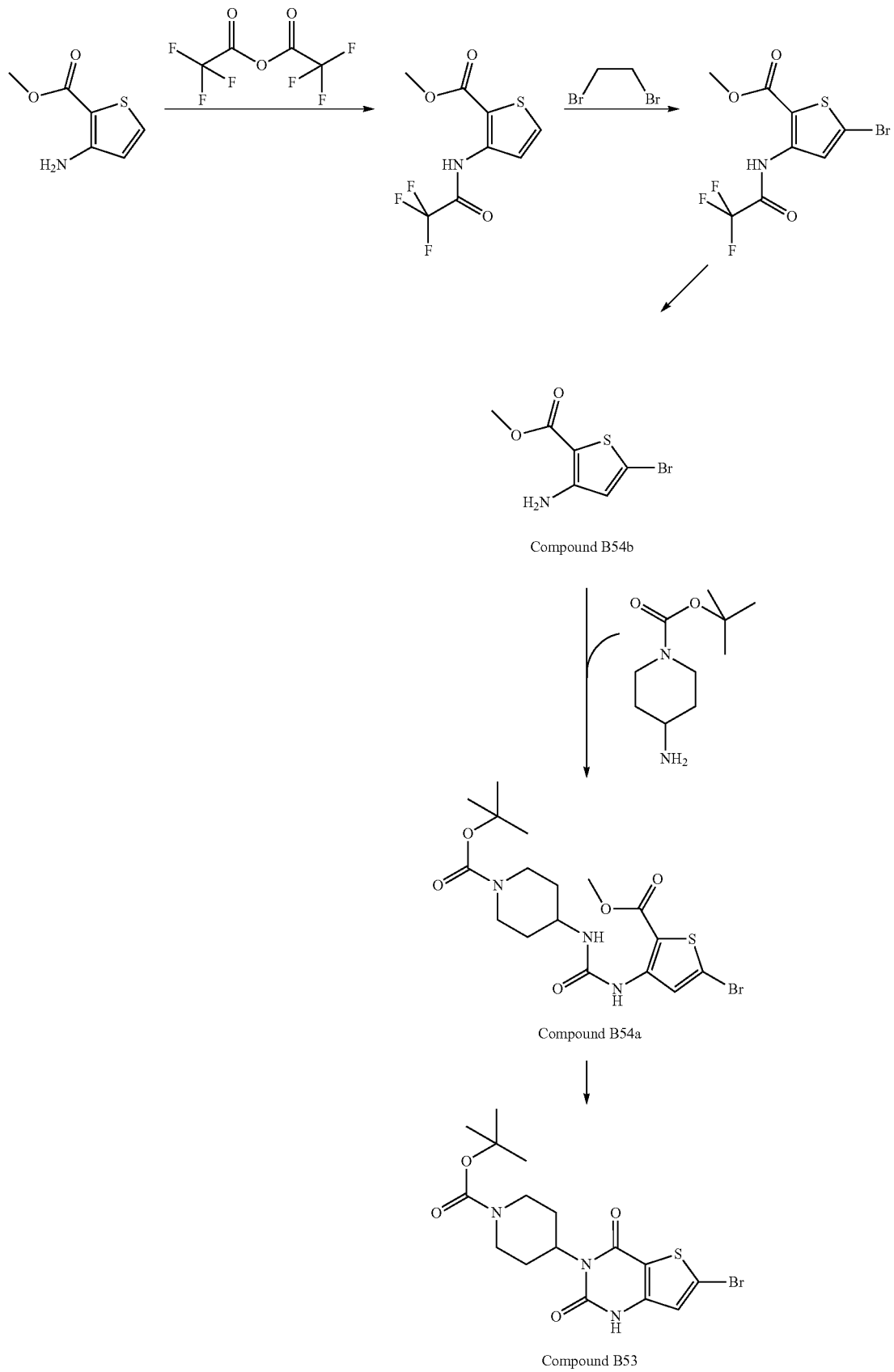

In reaction scheme 6 the preparation of acid compounds of formula 2, wherein A is S and R1 and R2 have the above-mentioned meanings is shown.

The conversion of the tetrahydrothiopyranone derivative of formula 15, wherein R1 and R2 have the above-mentioned meanings with (1R)-1-(1-4C-alkoxy substituted or unsubstituted)arylethanamine, such as preferably (1R)-1-(4-methoxyphenyl)ethanamine or (1R)-1-phenylethanamine is carried out according to standard procedures for condensation reactions known to the person skilled in the art, preferably in the presence of a suitable catalyst, for example p-toluenesulfonic acid, under water separation conditions in a suitable solvent, such as for example, n-hexane, benzene or toluene, at elevated temperatures, preferably at the boiling point of the solvent used.

The hydrogenation of the obtained imine/enamine of formulae 14a/14b, in which R1 and R2 have the above mentioned meanings is carried out according to standard methods known to the person skilled in the art, for example, in the presence of a platin on carbon catalyst using a suitable solvent, such as for example, methanol, ethanol, THF or 1,4-dioxane under a hydrogen pressure of about 100 mbar and at elevated temperatures, preferably between 40 and 80° C.

Alternatively, the hydrogenation of the obtained imine/enamine of formulae 14a/14b, in which R1 and R2 have the above mentioned meanings is carried out in the presence of hydrogen transfer agents like alkali borohydride, alkali cyanoborohydride, alkali triacetoxyborohydride or alkali acyloxyborohydrides using dichloromethane, toluene or THF as a solvent preferably at RT. The alkali acyloxyborohydrides are prepared, for example from $NaBH_4$ and various carboxylic acids (for example 2-methyl-hexanoic acid) according to methods known to the person skilled in the art, for example, as described in Tetrahedron Letters, 37 (1996), 3977-3980.

The separation of the (1R)-1-(1-4C-alkoxy substituted or unsubstituted)arylethyl group by hydrogenation from the compounds of formula 13 is also carried out according to standard methods known to the person skilled in the art, preferably in the presence of 1 to 1.2 equivalents of concentrated hydrochloric acid and a palladium on carbon catalyst using an alcohol, such as methanol or ethanol as a solvent under a hydrogen pressure of about 0.1 to 10 bar, preferably 0.1 to 1 bar, and at elevated temperatures, preferably between 40 and 60° C.

Alternatively, the separation of the (1R)-1-(1-4C-alkoxy or unsubstituted)arylethyl group is carried out under acidic conditions using neat trifluoroacetic acid or neat formic acid at elevated temperatures, preferably between 50 and 100° C.

The resulting compounds of formula 12, in which R1 and R2 have the above-mentioned meanings are reacted with a compound of formula 11, wherein X is a suitable leaving group, for example a halide, preferably chlorine or bromine. This benzoylation is carried out, for example, according to the Einhorn process, the Schotten-Baumann variant or as described in J. Chem. Soc C, 1971, 1805-1808.

The cyclocondensation of the compounds of formula 10 is carried out in a manner known to the person skilled in the art, for example according to Bischler-Napieralski (e.g. as described in J. Chem. Soc., 1956, 4280-4282) or a Bischler-Napieralski variation (e.g. as described in Heterocycles 60 (2003), No. 12, 2707-2715) in the presence of a suitable condensing agent, such as, for example, polyphosphoric acid, phosphorus pentachloride, phosphorus trichloride, phosphorus pentoxide, thionyl chloride or trifluoromethanesulfonic anhydride and 4-dimethylaminopyridine, in a suitable inert solvent, e.g. in a chlorinated hydrocarbon such as dichloromethane, or in a cyclic hydrocarbon such as toluene or xylene, or another inert solvent such as acetonitrile, preferably at elevated temperature, in particular at the boiling point of the solvent used.

Finally the compounds of formula 9, wherein R1 and R2 have the above-mentioned meanings are saponified to yield the corresponding acid compounds of formula 2 in the presence of a suitable base, such as, for example, lithium hydroxide, sodium hydroxide, potassium hydroxide, sodium carbonate, potassium carbonate or cesium carbonate, in a suitable solvent, e.g. water, water-methanol, water-dioxane or water-2-propanol.

In reactions schemes 7 and 8 the preparation of compounds of formula 2, wherein A represents S(O) or $S(O)_2$ and R1 and R2 have the above-mentioned meanings is shown.

Reaction scheme 7 shows that compounds of formula 9, wherein A represents S(O) or $S(O)_2$ and R1 and R2 have the above-mentioned meanings can be obtained by reaction of corresponding compounds of formula 2, wherein A represents S with m-chloroperoxybenzoic acid in an appropriate solvent such as dichloromethane at low temperatures, preferably between −50° C. and 0° C. Separation of the diastereomeric sulfoxides and of the sulfon is achieved by flash chromatography using a suitable eluent system, such as in case of methyl 4-[(2R,4aR,10bR)-9-ethoxy-8-methoxy-2-oxido-3,4,4a,10b-tetrahydro-1H-thiopyrano[4,3-c]isoquinolin-6-yl] benzoate, methyl 4-[(2S,4aR,10bR)-9-ethoxy-8-methoxy-2-oxido-3,4,4a,10b-tetrahydro-1H-thiopyrano[4,3-c]isoquinolin-6-yl]benzoate and methyl 4-[(4aR,10bR)-9-ethoxy-8-methoxy-2,2-dioxido-3,4,4a,10b-tetrahydro-1H-thiopyrano[4,3-c]isoquinolin-6-yl]benzoate—EtOAc/MeOH/n-hexane, 19/1/6 to 19/1/0 (v/v/v).

Finally the compounds of formula 9, wherein A represents S(O) or $S(O)_2$ and R1 and R2 have the above-mentioned meanings are converted to the corresponding compounds of formula 2 by saponification of the ester group, which is achieved in the presence of a suitable base, such as LiOH, NaOH or KOH in a solvent such as 1,4-dioxane, 2-propanol or tetrahydrofuran, preferably at room temperature.

For compounds of formula 2, wherein A represents $S(O)_2$ and R1 and R2 have the above-mentioned meanings the more preferred preparation method is shown in reaction scheme 8. In this case compounds of formula 10, wherein A represents S and R1 and R2 have the above-mentioned meanings are reacted with m-chloroperoxybenzoic acid in an appropriate solvent such as dichloromethane at low temperatures preferably at 0° C. (ice bath) to give the corresponding compounds of formula 16, wherein A represents $S(O)_2$. The subsequent reaction steps (cyclocondensation->corresponding compound of formula 9 and saponification->corresponding compound of formula 2) are carried out as described for the analogous reaction steps in reaction scheme 6.

Reaction scheme 9 shows the preparation of the tetrahydrothiopyranone derivative of formula 15, wherein R1 and R2 have the above-mentioned meanings.

The conversion of the racemic mixture of 3-(3-alkoxy-4-alkoxy-phenyl)-1-(1-4C-alkyl)piperidin-4-one of formula 17 to the tetrahydrothiopyranone of formula 15 is started by an quarternization of the nitrogen atom of the piperidin-4-one ring by reaction with a suitable alkylation reagent, such as for example methyliodide, ethyliodide, trifluoromethansulfonic acid methylester or trifluoromethansulfonic acid ethylester in a suitable solvent, such as for example toluene, dichloromethane, diethylether and preferably 4-methyl-pentan-2-one at low temperatures, preferably between 0° C. and 20° C. In the second reaction step the quarternary nitrogen atom is replaced by a sulfur atom through reaction with $Na_2S$ or one of its hydrates, such as for example the nonahydrate in the presence of sodium hydrogensulfide or one of its hydrates, preferable the monohydrate in a water/toluene, water/diethylether, water/dichloromethan, or preferably in a water/4-methyl-pentan-2-one solvent system at reflux temperature.

A further aspect of the invention is a process for the preparation of compounds of formula 15, wherein
R1 is 1-4C-alkoxy, 3-7C-cycloalkoxy, 3-7C-cycloalkylmethoxy, or 1-4C-alkoxy predominantly or completely substituted by fluorine and
R2 is 1-4C-alkoxy, 3-7C-cycloalkoxy, 3-7C-cycloalkylmethoxy, or 1-4C-alkoxy predominantly or completely substituted by fluorine,
or
R1 and R2 together form a 1-2C-alkylenedioxy group,
or preferably
R1 is 1-2C-alkoxy, or 1-2C-alkoxy predominantly or completely substituted by fluorine and
R2 is 1-2C-alkoxy, or 1-2C-alkoxy predominantly or completely substituted by fluorine,
or
R1 and R2 together form a 1-2C-alkylenedioxy group,
or more preferably
R1 is ethoxy and
R2 is methoxy.

The process for the preparation of compounds of formula 15, wherein R1 and R2 have the above-mentioned meanings is characterized in that
(a) the nitrogen ring-atom of the compound of formula 17,

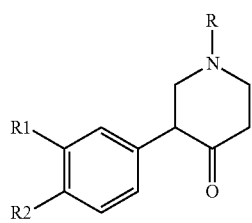

(17)

wherein R1 and R2 have the above-mentioned meanings and R is 1-4C-alkyl, preferably methyl, is quarternized by reaction with an alkylation reagent, preferably trifluoromethansulfonic acid methylester, and
(b) the quarternary ring nitrogen atom is replaced by a sulfur atom through reaction with Na$_2$S or one of the hydrates of Na$_2$S in the presence of sodium hydrogensulfide or one of the hydrates of sodium hydrogensulfide.

An alternative method of preparation for compounds of formula 15 is described in the international patent application WO2006027345.

Compounds of formula 17 can be prepared as described in U.S. Pat. No. 3,899,494 or in analogy thereto.

As can be seen from reaction scheme 1 the compounds of formula 2, wherein R1, R2 and A have the above-mentioned meanings, are key intermediates. They make it possible to introduce into the compounds of formula 1 the 3,4,4a,10b-tetrahydro-1H-thiopyrano[4,3-c]isochinolin structure. While the compounds of formula 2, wherein R1, R2 and A have the above-mentioned meanings are disclosed in generic form in WO2006027345, no specific examples of such compounds of formula 2 are disclosed in WO2006027345. Therefore, specific examples of compounds of formula 2, wherein R1, R2 and A have the above-mentioned meanings and their use for the preparation of compounds of formula 1, wherein A, R1, R2, R3 and R5 have the above-mentioned meanings are another aspect of the present invention.

Examples of compounds of formula 2, which may be mentioned in this connection are:
4-[(2R,4aR,10bR)-9-ethoxy-8-methoxy-2-oxido-3,4,4a, 10b-tetrahydro-1H-thiopyrano[4,3-c]isoquinolin-6-yl] benzoic acid;
4-[(2S,4aR,10bR)-9-ethoxy-8-methoxy-2-oxido-3,4,4a, 10b-tetrahydro-1H-thiopyrano[4,3-c]isoquinolin-6-yl] benzoic acid;
4-[(4aR,10bR)-9-ethoxy-8-methoxy-2,2-dioxido-3,4,4a, 10b-tetrahydro-1H-thiopyrano[4,3-c]isoquinolin-6-yl] benzoic acid;
3-[(4aR,10bR)-9-ethoxy-8-methoxy-3,4,4a,10b-tetrahydro-1H-thiopyrano[4,3-c]isoquinolin-6-yl]benzoic acid; or
4-[(4aR,10bR)-9-ethoxy-8-methoxy-3,4,4a,10b-tetrahydro-1H-thiopyrano[4,3-c]isoquinolin-6-yl]benzoic acid.

Reaction Scheme 6:

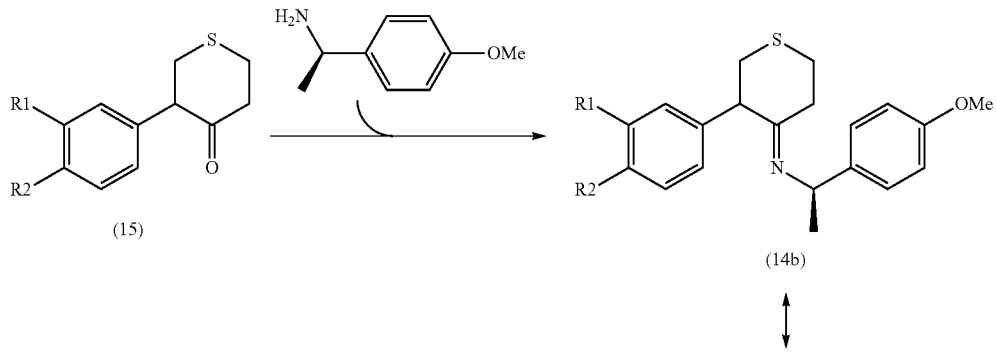

31
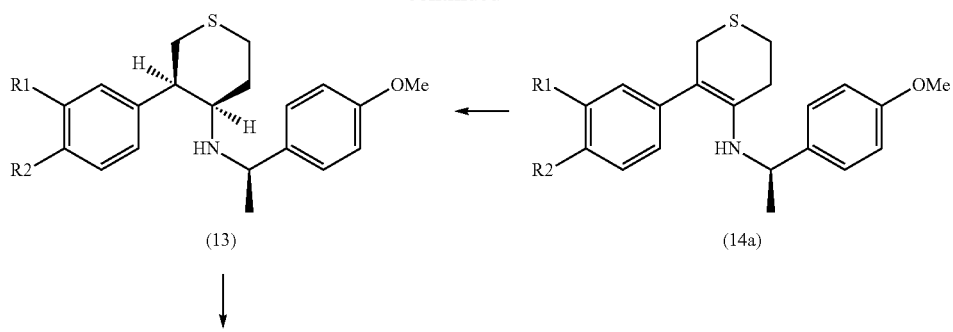
32
-continued
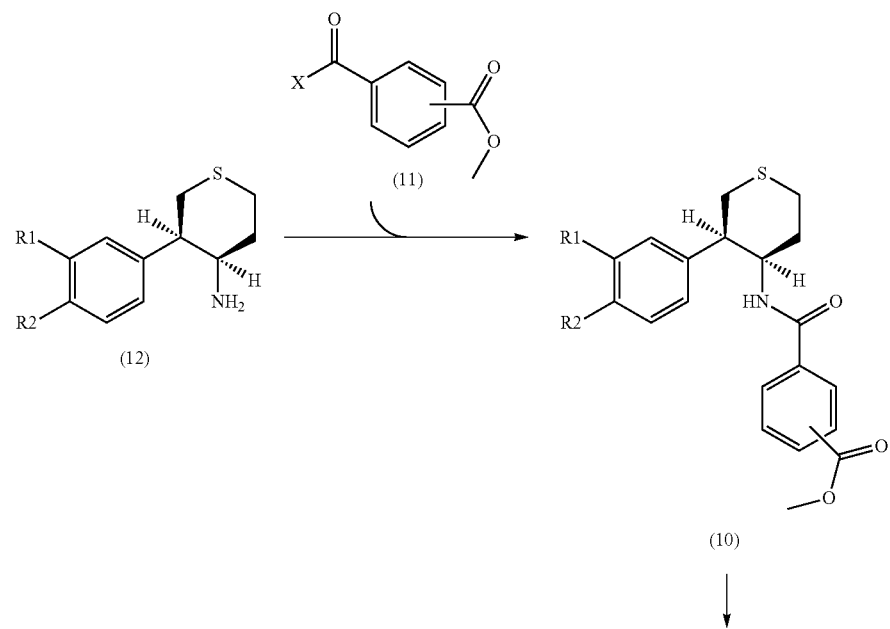
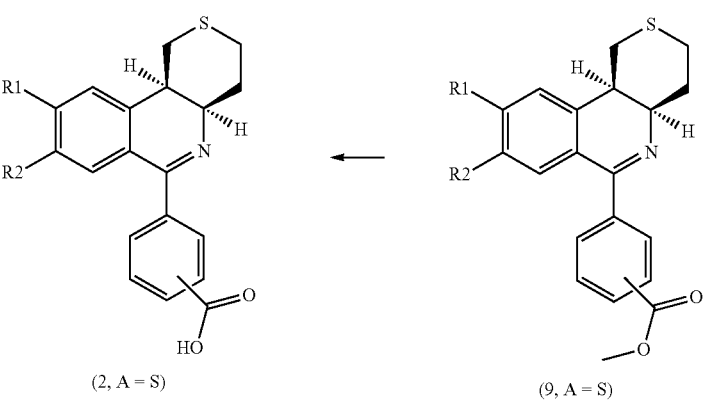

Reaction Scheme 7:
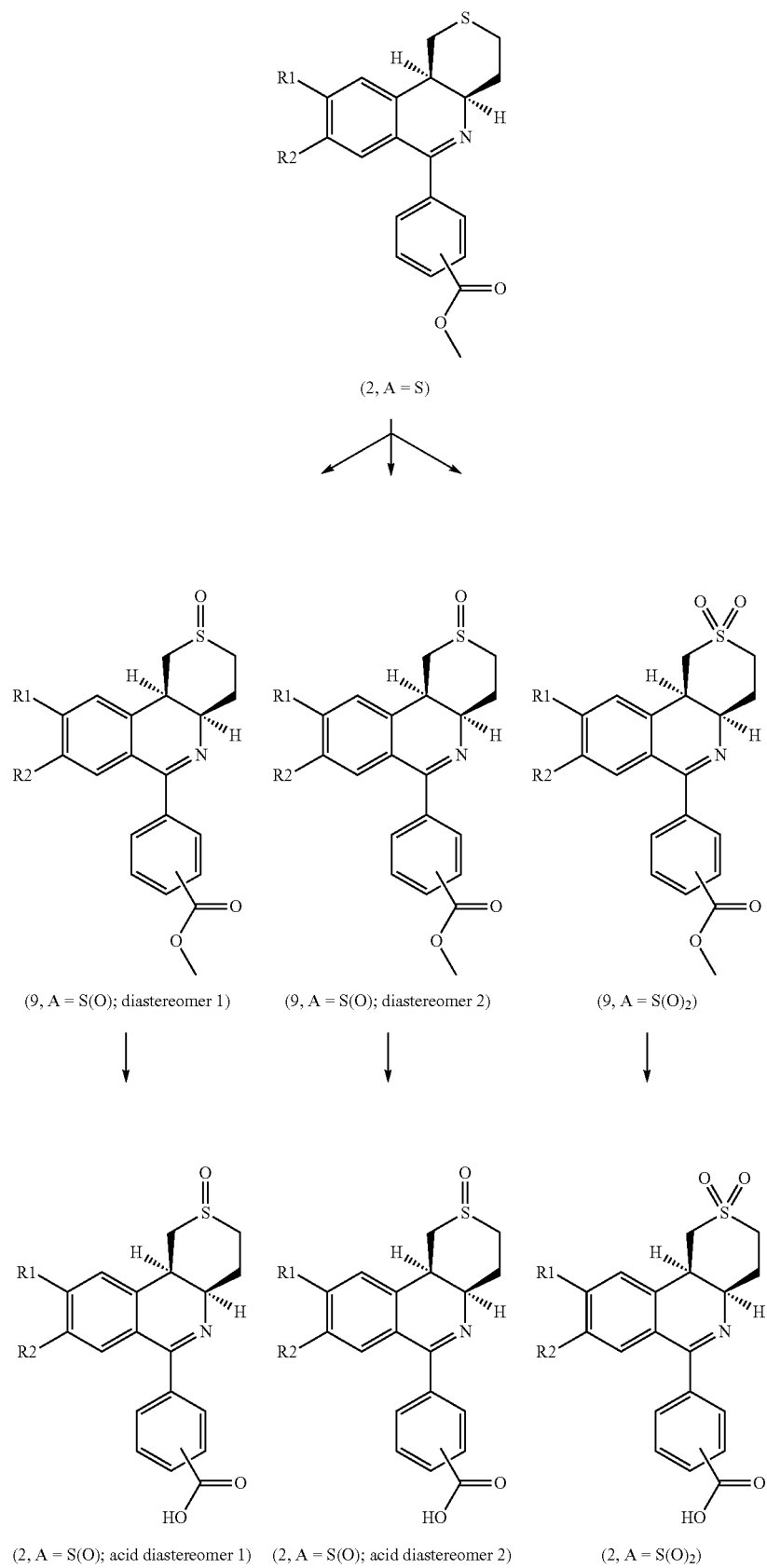

Reaction scheme 8:

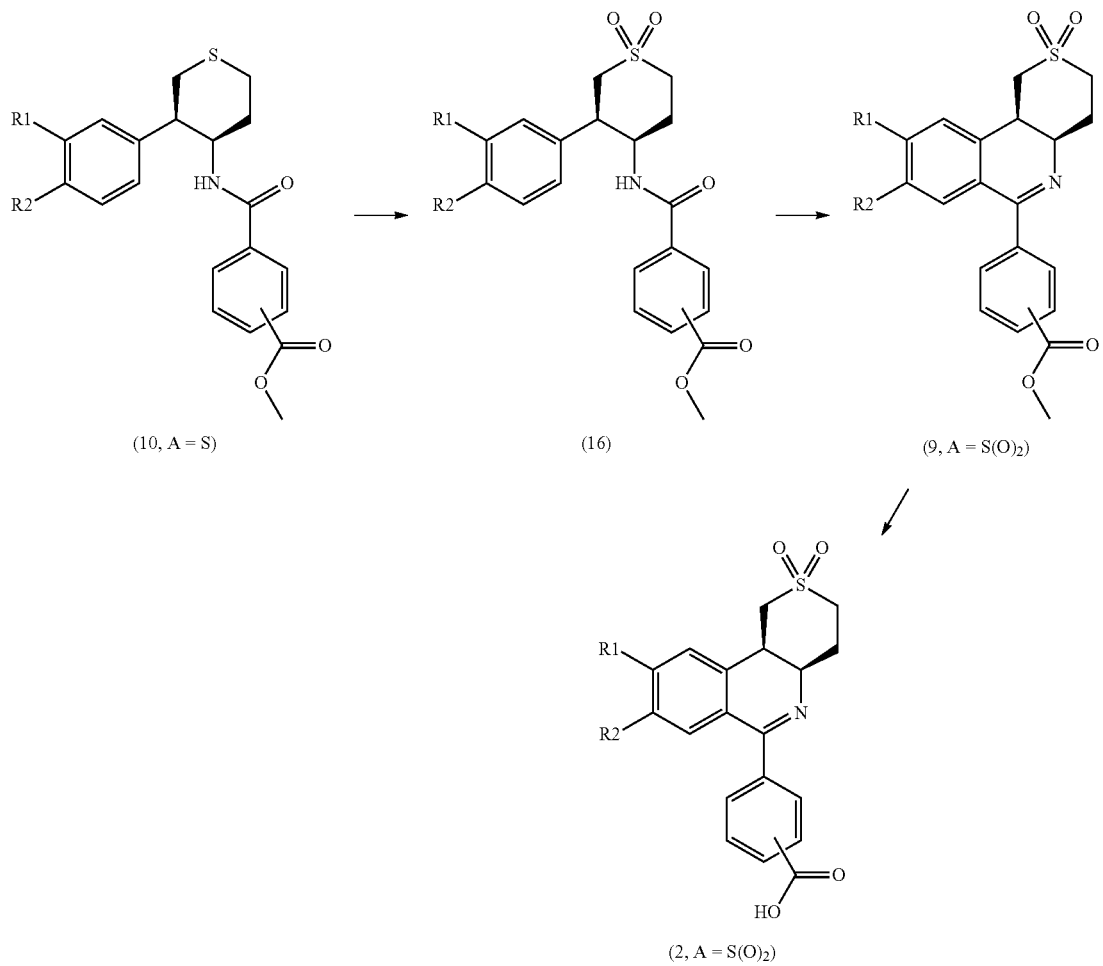

Reaction Scheme 9:

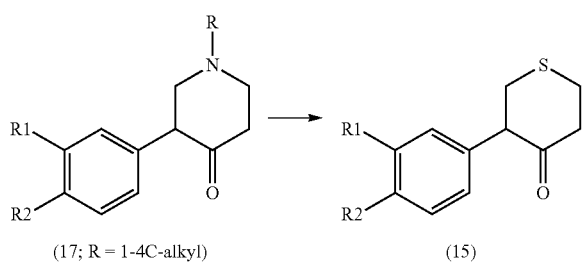

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

As will be appreciated by persons skilled in the art, the invention is not limited to the particular embodiments described herein, but covers all modifications that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples represent preferred embodiments of the invention.

EXAMPLES

The following abbreviations are used:
TOTU: O-[(Ethoxycarbonyl)cyanomethylenamino]-N,N,N',N'-tetramethyluronium tetrafluoroborate COMU: (1-Cyano-2-ethoxy-2-oxoethylidenaminooxy)dimethylamino-morpholino-carbenium hexafluorophosphate; HBTU: O-(Benzotriazol-1-yl)-N,N,N',N'-tetramethyluronium hexafluorophosphate; HATU: O-(7-Azabenzotriazol-1-O—

N,N,N',N'-tetramethyluronium hexafluorophosphate; HOAT: 1-hydroxy-7-azabenzotriazole; EDCI: 1-ethyl-3-(3-dimethyl-aminopropyl)carbodiimide hydrochloride; Boc: t-butoxycarbonyl; ACN: Acetonitril; DIP: diisopropyl ether; DMF: N,N-dimethylformamide; DIPEA: diisopropylethylamine; m-CPBA: meta chloroperbenzoic acid; DCM: dichloromethane; DME: 1,2-dimethoxyethan; EtOAc: ethyl acetate; MeOH: methanol; THF: tetrahydrofuran; RT: room temperature; h: hour(s); min: minute(s); calc.: calculated; (v/v): (volume/volume); (v/v/v): (volume/volume/volume); w/w: weight/weight; Rf: ratio of fronts; ESI electrospray ionization; MS: mass spectrometry; HRMS: high resolution mass spectrometry; TLC: thin layer chromatography; HPLC: high-performance liquid chromatography; M.p.: Melting point.

Unless otherwise stated compound purification is achieved by flash column chromatography, preparative TLC and preparative HPLC. HPLC purifications are carried out using a Phenomenex Gemini 5 μm C18 (75×30 mm) or a Phenomenex Gemini 5 μm C6-Phenyl (75×30 mm) or a Phenomenex Gemini 5 μm C18 Axia (75×30 mm) column, a binary gradient (solvent A: water, solvent B: acetonitrile), a flow rate of 40 ml/min, formic acid as a buffer or a buffer system consisting of formic acid and ammonium formiate and UV detection at 240 nm.

All mass spectra are obtained using ESI technique. HRMS data of examples 1 to 59 are reported as MH$^+$.

Final Products

The chemical names have been generated using the software ACD/NAME Library DLL: NAMIPLIB.dll; Version: 11.1.0.22379.

1. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-ethyl-1,3-oxazol-2-yl)methyl]-6-phenylthieno[3,2-d]pyrimidine-2,4(1H,3H)-dione To a suspension of 4-[(4aR,10bR)-9-ethoxy-8-methoxy-3,4,4a,10b-tetrahydro-1H-thiopyrano[4,3-c]isoquinolin-6-yl]benzoic acid (159 mg; compound C10), 1-[(5-ethyl-1,3-oxazol-2-yl)methyl]-6-phenyl-3-(piperidin-4-yl)thieno[3,2-d]pyrimidine-2,4(1H,3H)-dione hydrochloride (191.5 mg; compound B26) and HBTU (167 mg) in DCM (10 ml) is added DIPEA (0.28 ml) and the mixture is stirred for 1 h at RT. After 1 h an additional amount of 4-[(4aR,10bR)-9-ethoxy-8-methoxy-3,4,4a,10b-tetrahydro-1H-thiopyrano[4,3-c]isoquinolin-6-yl]benzoic acid (40 mg) is added and the mixture is stirred for 15 min in order to complete the reaction. Subsequently the solvent is removed and the residue is purified by flash column chromatography [amino phase silica gel, eluent: EtOAc/MeOH, 97.5/2.5 (v/v)] and afterwards by preparative HPLC to yield the title compound as a solid.

HRMS [$C_{45}H_{46}N_5O_6S_2$]: calc.: 816.2884 found: 816.2887

2. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-methyl-1,2,4-oxadiazol-3-yl)methyl]-6-phenylthieno[3,2-d]pyrimidine-2,4(1H,3H)-dione To a suspension of 1-[(5-methyl-1,2,4-oxadiazol-3-yl)methyl]-6-phenyl-3-piperidin-4-ylthieno[3,2-d]pyrimidine-2,4(1H,3H)-dione hydrochloride (200 mg; compound B27), 4-[(4aR,10bR)-9-ethoxy-8-methoxy-3,4,4a,10b-tetrahydro-1H-thiopyrano[4,3-c]isoquinolin-6-yl]benzoic acid (188 mg; compound C10) and HBTU (196 mg) in DCM (7.5 ml) is added DIPEA (0.33 ml). The reaction mixture is stirred at RT for 14 h. Additional DCM (10 ml) and saturated aqueous sodium bicarbonate solution (10 ml) are added and the mixture is filtered using a phase separator. The organic layer is concentrated under reduced pressure and the residue is purified by flash column chromatography [silica gel, eluation gradient: DCM/MeOH, 1/0 to 1/1 (v/v)] followed by preparative HPLC to yield the title compound as a solid.

HRMS [$C_{43}H_{43}N_6O_6S_2$]: calc.: 803.2680 found: 803.2659

3. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(3-ethylisoxazol-5-yl)methyl]-6-phenylthieno[3,2-d]pyrimidine-2,4(1H,3H)-dione 1-[(3-Ethylisoxazol-5-yl)methyl]-6-phenyl-3-(piperidin-4-yl)thieno[3,2-d]pyrimidine-2,4(1H,3H)-dione hydrochloride (200 mg; compound B28) is reacted with 4-[(4aR,10bR)-9-ethoxy-8-methoxy-3,4,4a,10b-tetrahydro-1H-thiopyrano[4,3-c]isoquinolin-6-yl]benzoic acid (168 mg; compound C10) and HBTU (191 mg) in DCM (10 ml) in the presence of DIPEA (0.29 ml) according to the procedure described in example 2 to afford the title compound after purification by flash column chromatography [amino phase silica gel, eluation gradient: cyclohexane/EtOAc, 3/1 to 0/1 (v/v)] and preparative HPLC as a solid.

HRMS [$C_{45}H_{46}N_5O_6S_2$]: calc.: 816.2884 found: 816.2887

4. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-ethyl-1,3,4-oxadiazol-2-yl)methyl]-6-phenylthieno[3,2-d]pyrimidine-2,4(1H,3H)-dione 1-[(5-ethyl-1,3,4-oxadiazol-2-yl)methyl]-6-phenyl-3-(piperidin-4-yl)thieno[3,2-d]pyrimidine-2,4(1H,3H)-dione hydrochloride (200 mg; compound B29) is reacted with 4-[(4aR,10bR)-9-ethoxy-8-methoxy-3,4,4a,10b-tetrahydro-1H-thiopyrano[4,3-c]isoquinolin-6-yl]benzoic acid (168 mg; compound C10) and HBTU (191 mg) in DCM (10 ml) in the presence of DIPEA (0.29 ml) according to the procedure described in example 2 to afford the title compound after purification by twofold flash column chromatography [silica gel, eluation gradient: cyclohexane/EtOAc, 3/2 to 0/1 and DCM/MeOH, 1/0 to 1/1 (v/v)] as a solid.

HRMS [$C_{44}H_{45}N_6O_6S_2$]: calc.: 817.2837 found: 817.2827

5. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(4-ethyl-1,3-oxazol-2-yl)methyl]-6-phenylthieno[3,2-d]pyrimidine-2,4(1H,3H)-dione 1-[(4-ethyl-1,3-oxazol-2-yl)methyl]-6-phenyl-3-(piperidin-4-yl)thieno[3,2-d]pyrimidine-2,4(1H,3H)-dione hydrochloride (200 mg; compound B30) is reacted with 4-[(4aR,10bR)-9-ethoxy-8-methoxy-3,4,4a,10b-tetrahydro-1H-thiopyrano[4,3-c]isoquinolin-6-yl]benzoic acid (168 mg; compound C10) and HBTU (191 mg) in DCM (10 ml) in the presence of DIPEA (0.29 ml) according to the procedure described in example 2 to afford the title compound after purification by twofold flash column chromatography [silica

6. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-methylisoxazol-3-yl)methyl]-6-phenylthieno[3,2-d]pyrimidine-2,4(1H,3H)-dione 1-[(5-methylisoxazol-3-yl)methyl]-6-phenyl-3-(piperidin-4-yl)thieno[3,2-d]pyrimidine-2,4(1H,3H)-dione hydrochloride (250 mg; compound B31) is reacted with 4-[(4aR,10bR)-9-ethoxy-8-methoxy-3,4,4a,10b-tetrahydro-1H-thiopyrano[4,3-c]isoquinolin-6-yl]benzoic acid (238 mg; compound C10) and HBTU (246 mg) in DCM (15 ml) in the presence of DIPEA (0.38 ml) according to the procedure described in example 2 to afford the title compound after purification by flash column chromatography [silica gel, eluation gradient: DCM/MeOH, 1/0 to 3/2 (v/v)] and preparative HPLC as a solid.

HRMS [$C_{44}H_{44}N_5O_6S_2$]: calc.: 802.2728 found: 802.2728

7. 3-(1-{4-[(4aR,10bR)-9-ethoxy-8-methoxy-3,4,4a,10b-tetrahydro-1H-thiopyrano[4,3-c]isoquinolin-6-yl]benzoyl}piperidin-4-yl)-1-[(3-ethyl-1,2,4-oxadiazol-5-yl)methyl]-6-phenylthieno[3,2-d]pyrimidine-2,4(1H,3H)-dione To a mixture of 4-[(4aR,10bR)-9-ethoxy-8-methoxy-3,4,4a,10b-tetrahydro-1H-thiopyrano[4,3-c]isoquinolin-6-yl]benzoic acid (99.4 mg; compound C10), 1-(3-Ethyl-[1,2,4]oxadiazol-5-ylmethyl)-6-phenyl-3-piperidin-4-yl-1H-thieno[3,2-d]pyrimidine-2,4-dione (109 mg; compound B52) and HOBT (38 mg) in DCM (2.5 ml) is added EDCI (48.9 mg). The mixture is stirred for 2.5 h at RT. EtOAc (25 ml) is added and the mixture is extracted with 1 M aqueous hydrochloride solution (5 ml) (three times). The combined aqueous phases are washed with EtOAc (15 ml) and subsequently the combined organic phases are washed with water (5 ml) (three times) and afterwards with saturated solution of sodium bicarbonate (10 ml) (three times). The organic phase is dried over magnesium sulfate, concentrated in vacuo and the resulting residue is purified by flash column chromatography [amino phase silica gel, eluation gradient: EtOAc/cyclohexane=0/100 to 20/80 (v/v)] to give the title compound as a solid.

HRMS [$C_{44}H_{45}N_6O_6S_2$]: calc.: 817.2837 found: 817.2826

8. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-{[5-(methoxymethyl)-1,3,4-oxadiazol-2-yl]methyl}-6-phenylthieno[3,2-d]pyrimidine-2,4(1H,3H)-dione 1-{[5-(methoxymethyl)-1,3,4-oxadiazol-2-yl]methyl}-6-phenyl-3-(piperidin-4-yl)thieno[3,2-d]pyrimidine-2,4(1H,3H)-dione hydrochloride (250 mg; compound B33) is reacted with 4-[(4aR,10bR)-9-ethoxy-8-methoxy-3,4,4a,10b-tetrahydro-1H-thiopyrano[4,3-c]isoquinolin-6-yl]benzoic acid (223 mg; compound C10) and HBTU (232 mg) in DCM (15 ml) in the presence of DIPEA (0.36 ml) according to the procedure described in example 2 to afford the title compound after purification by flash column chromatography [silica gel, eluation gradient: DCM/MeOH, 1/0 to 3/2 (v/v)] and preparative HPLC as a solid.

HRMS [$C_{44}H_{45}N_6O_7S_2$]: calc.: 833.2786 found: 833.2784

9. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-1,3-oxazol-5-yl)methyl]-6-phenylthieno[3,2-d]pyrimidine-2,4(1H,3H)-dione The title compound is prepared analogously as described for example 1 using 4-[(4aR,10bR)-9-ethoxy-8-methoxy-3,4,4a,10b-tetrahydro-1H-thiopyrano[4,3-c]isoquinolin-6-yl]benzoic acid (167 mg; compound C10), 1-[(2-ethyl-1,3-oxazol-5-yl)methyl]-6-phenyl-3-(piperidin-4-yl)thieno[3,2-d]pyrimidine-2,4(1H,3H)-dione hydrochloride (200 mg; compound B34), HBTU (175 mg), DIPEA (0.29 ml) and DCM (3 ml). Purification by flash column chromatography [amino phase silica gel, eluent: EtOAc/methanol, 97.5/2.5 (v/v)] and afterwards by preparative HPLC gives the title compound as a solid.

HRMS [$C_{45}H_{46}N_5O_6S_2$]: calc.: 816.2884 found: 816.2873

10. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-methyl-1,3-thiazol-4-yl)methyl]-6-phenylthieno[3,2-d]pyrimidine-2,4(1H,3H)-dione The title compound is prepared analogously as described for example 1 using 4-[(4aR,10bR)-9-ethoxy-8-methoxy-3,4,4a,10b-tetrahydro-1H-thiopyrano[4,3-c]isoquinolin-6-yl]benzoic acid (159 mg; compound C10), 1-[(2-methyl-1,3-thiazol-4-yl)methyl]-6-phenyl-3-(piperidin-4-yl)thieno[3,2-d]pyrimidine-2,4(1H,3H)-dione hydrochloride (190 mg; compound B35), HBTU (167 mg), DIPEA (0.28 ml) and DCM (3 ml). The crude product is purified by flash column chromatography for three consecutive times (amino phase silica gel, eluent: EtOAc) to yield the title compound as a solid.

HRMS [$C_{44}H_{44}N_5O_5S_3$]: calc.: 818.2499 found: 818.2499

11. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-({3-[(methylsulfanyl)methyl]-1,2,4-oxadiazol-5-yl}methyl)-6-phenylthieno[3,2-d]pyrimidine-2,4(1H,3H)-dione To a suspension of 1-({3-[(methylsulfanyl)methyl]-1,2,4-oxadiazol-5-yl}methyl)-6-phenyl-3-(piperidin-4-yl)thieno[3,2-d]pyrimidine-2,4(1H,3H)-dione hydrochloride (202.4 mg; compound B36), 4-[(4aR,10bR)-9-ethoxy-8-methoxy-3,4,4a,10b-tetrahydro-1H-thiopyrano[4,3-c]isoquinolin-6-yl]benzoic acid (159 mg; compound C10) and HBTU (167 mg) in DCM (8 ml) is added DIPEA (207 mg). The reaction mixture is stirred for 3 h at RT. Additional 4-[(4aR,10bR)-9-ethoxy-8-methoxy-3,4,4a,10b-tetrahydro-1H-thiopyrano[4,3-c]isoquinolin-6-yl]benzoic acid (80 mg; compound C10) and HBTU (84 mg) are added in order to complete the reaction. A saturated aqueous sodium bicarbonate solution (5 ml) is added and the mixture is extracted with DCM (25 ml). The phases are separated and the aqueous phase is extracted with further DCM (10 ml). The organic phases are combined and filtered using a phase separator. The organic layer is concentrated under reduced pressure and the residue is purified two times by flash column chromatography [amino phase silica gel, eluation gradient: cyclohexane/EtOAc, 100/0 to 0/100 (v/v)] to yield the title compound as a solid.

HRMS [$C_{44}H_{45}N_6O_6S_3$]: calc.: 849.2557 found: 849.2555

12. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-methyl-1,3-thiazol-2-yl)methyl]-6-phenylthieno[3,2-d]pyrimidine-2,4(1H,3H)-dione The title compound is prepared analogously as described for example 1 (however, stirring is performed for 12 h at RT) using 4-[(4aR,10bR)-9-ethoxy-8-methoxy-3,4,4a,10b-tetrahydro-1H-thiopyrano[4,3-c]isoquinolin-6-yl]benzoic acid (159 mg; compound C10), 1-[(5-methyl-1,3-thiazol-2-yl)methyl]-6-phenyl-3-(piperidin-4-yl)thieno[3,2-d]pyrimidine-2,4(1H,3H)-dione hydrochloride (190 mg; compound B37), HBTU (167 mg), DIPEA (207 mg) and DCM (10 ml). The crude product is purified by flash column chromatography for three times [amino phase silica gel, eluation gradient: cyclohexane/EtOAc, 100/0 to 0/100 (v/v)] to yield the title compound as a solid.

HRMS [$C_{44}H_{44}N_5O_5S_3$]: calc.: 818.2499 found: 818.2503

13. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(4-methyl-1,3-thiazol-2-yl)methyl]-6-phenylthieno[3,2-d]pyrimidine-2,4(1H,3H)-dione The title compound is prepared analogously as described for example 1 using 4-[(4aR,10bR)-9-ethoxy-8-methoxy-3,4,4a,10b-tetrahydro-1H-thiopyrano[4,3-c]isoquinolin-6-yl]benzoic acid (159 mg; compound C10), 1-[(4-methyl-1,3-thiazol-2-yl)methyl]-6-phenyl-3-(piperidin-4-yl)thieno[3,2-d]pyrimidine-2,4(1H,3H)-dione hydrochloride (190 mg; compound B38), HBTU (167 mg) (additional 76 mg of HBTU are added after 90 min), DIPEA (0.28 ml) and DCM (3 ml). The crude product is purified by flash column chromatography (amino phase silica gel, eluent: EtOAc) and subsequent preparative thin layer chromatography [eluent: DCM/MeOH/triethylamine, 95/5/0.5 (v/v/v)] to yield the title compound as a solid.

HRMS [$C_{44}H_{44}N_5O_5S_3$]: calc.: 818.2499 found: 818.2494

14. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione To 4-[(4aR,10bR)-9-ethoxy-8-methoxy-3,4,4a,10b-tetrahydro-1H-thiopyrano[4,3-c]isoquinolin-6-yl]benzoic acid (160 mg; compound C10) dissolved in DCM (20 ml) HBTU (167 mg) and DIPEA (0.21 ml) are added and the reaction mixture is stirred for 30 min at RT. Subsequently, 1-[(2-ethyl-2H-tetrazol-5-yl)methyl]-6-phenyl-3-(piperidin-4-yl)thieno[3,2-d]pyrimidine-2,4(1H,3H)-dione (175 mg; compound B39) is added and the reaction mixture is stirred for 24 h at RT. After extraction with a saturated solution of sodium hydrogen carbonate and a saturated solution of sodium chloride the organic phase is separated and dried over $Na_2SO_4$. After filtration the solvent is removed under reduced pressure to give the crude title product. After purification by flash column chromatography (silica gel, eluent: EtOAc) the title compound is obtained as a solid.

HRMS [$C_{43}H_{45}N_8O_5S_2$]: calc.: 817.2949 found: 817.2981

15. 3-(1-{4-[(4aR,10bR)-9-ethoxy-8-methoxy-3,4,4a,10b-tetrahydro-1H-thiopyrano[4,3-c]isoquinolin-6-yl]benzoyl}piperidin-4-yl)-1-{[3-(methoxymethyl)-1,2,4-oxadiazol-5-yl]methyl}-6-phenylthieno[3,2-d]pyrimidine-2,4(1H,3H)-dione 1-{[3-(methoxymethyl)-1,2,4-oxadiazol-5-yl]methyl}-6-phenyl-3-piperidin-4-ylthieno[3,2-d]pyrimidine-2,4(1H,3H)-dione hydrochloride (148 mg; compound B40) is reacted with 4-[(4aR,10bR)-9-ethoxy-8-methoxy-3,4,4a,10b-tetrahydro-1H-thiopyrano[4,3-c]isoquinolin-6-yl]benzoic acid (120 mg; compound C10) and HBTU (126 mg) in DCM (8 ml) in the presence of DIPEA (155 mg) according to the procedure described in example 2 to afford the title compound after purification by flash column chromatography [silica gel, eluation gradient: cyclohexane/EtOAc, 1/1.5 to 0/1 (v/v)] as a solid.

HRMS [$C_{44}H_{45}N_6O_7S_2$]: calc.: 833.2786 found: 833.2799

16. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-1,3-oxazol-4-yl)methyl]-6-phenylthieno[3,2-d]pyrimidine-2,4(1H,3H)-dione The title compound is prepared analogously as described for example 11 using 4-[(4aR,10bR)-9-ethoxy-8-methoxy-3,4,4a,10b-tetrahydro-1H-thiopyrano[4,3-c]isoquinolin-6-yl]benzoic acid (159 mg; compound C10), 1-[(2-ethyl-1,3-oxazol-4-yl)methyl]-6-phenyl-3-(piperidin-4-yl)thieno[3,2-d]pyrimidine-2,4(1H,3H)-dione hydrochloride (190 mg; compound B41), HBTU (167 mg), DIPEA (207 mg) and DCM (8 ml). After 3 h additional HBTU (91 mg) and 4-[(4aR,10bR)-9-ethoxy-8-methoxy-3,4,4a,10b-tetrahydro-1H-thiopyrano[4,3-c]isoquinolin-6-yl]benzoic acid (20 mg; compound C10) are added and the mixture is stirred for 22 h at RT. Saturated aqueous sodium bicarbonate solution (2.5 ml) is added and the mixture is extracted twice with DCM (2×5 ml). The combined organic layers are applied to a phase separator and the solvent is removed under vacuo. The resulting residue is purified by flash column chromatography for three times [amino phase silica gel, eluation gradient: cyclohexane/EtOAc, 100/0 to 0/100 (v/v)] to yield the title compound as a solid.

HRMS [$C_{45}H_{46}N_5O_6S_2$]: calc.: 816.2884 found: 816.2879

17. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(1-ethyl-1H-pyrazol-4-yl)methyl]-6-phenylthieno[3,2-d]pyrimidine-2,4(1H,3H)-dione To a suspension of 1-[(1-ethyl-1H-pyrazol-4-yl)methyl]-6-phenyl-3-(piperidin-4-yl)thieno[3,2-d]pyrimidine-2,4(1H,3H)-dione hydrochloride (300 mg; compound B42), 4-[(4aR,10bR)-9-ethoxy-8-methoxy-3,4,4a,10b-tetrahydro-1H-thiopyrano[4,3-c]isoquinolin-6-yl]benzoic acid (253 mg; compound C10), EDCI (122 mg) and HOBT hydrate (86 mg) in DCM (10 ml) DIPEA (0.28 ml) is added. After 45 min additional 4-[(4aR,10bR)-9-ethoxy-8-methoxy-3,4,4a,10b-tetrahydro-1H-thiopyrano[4,3-c]isoquinolin-6-yl]benzoic acid (126 mg; compound C10) is added and the reaction mixture is stirred for 14 h at RT. Water and aqueous potassium hydrogen sulfate solution (10% w/w) are added and the mixture is extracted with DCM. The combined organic layers are dried (sodium sulfate) and concentrated under reduced pressure. The residue is purified by flash column chromatography [silica gel, eluation gradient: DCM/MeOH, 1/0 to 1/1 (v/v)] and preparative HPLC to afford the title compound as a solid.

HRMS [$C_{45}H_{47}N_6O_5S_2$]: calc.: 815.3044 found: 815.3044

18. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(1-ethyl-1H-pyrazol-3-yl)methyl]-6-phenylthieno[3,2-d]pyrimidine-2,4(1H,3H)-dione To a suspension of 1-[(1-ethyl-1H-pyrazol-3-yl)methyl]-6-phenyl-3-(piperidin-4-yl)thieno[3,2-d]pyrimidine-2,4(1H,3H)-dione trifluoroacetate (250 mg; compound B43), 4-[(4aR,10bR)-9-ethoxy-8-methoxy-3,4,4a,10b-tetrahydro-1H-thiopyrano[4,3-c]isoquinolin-6-yl]benzoic acid (181 mg; compound C10), EDCI (87 mg) and HOBT hydrate (61 mg) in DCM (15 ml) DIPEA (0.24 ml) is added. After 14 h at RT additional EDCI (87 mg) and HOBT hydrate (61 mg) are added and the reaction mixture is stirred for additional 3 d at RT. Aqueous potassium hydrogen sulfate solution (10% w/w) is added and the mixture is filtered using a phase separator. The organic layer is concentrated under reduced pressure and the residue is purified by flash column chromatography [silica gel, eluation gradient: DCM/MeOH, 1/0 to 1/1 (v/v)] to afford the title compound as a solid.

HRMS [$C_{45}H_{47}N_6O_5S_2$]: calc.: 815.3044 found: 815.3036

19. 3-[1-({4-[(4aR,10bR)-9-ethoxy-8-methoxy-2,2-dioxido-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione The title compound is prepared analogously as described for example 1 (however, stirring is performed for 12 h at RT) using 4-[(4aR,10bR)-9-ethoxy-8-methoxy-2,2-dioxido-3,4,4a,10b-tetrahydro-1H-thiopyrano[4,3-c]isoquinolin-6-yl]benzoic acid (330 mg; compound C4), 1-[(2-ethyl-2H-tetrazol-5-yl)methyl]-6-phenyl-3-(piperidin-4-yl)thieno[3,2-d]pyrimidine-2,4(1H,3H)-dione hydrochloride (365 mg; hydrochloride salt of compound B39), HBTU (322 mg), DIPEA (0.65 ml) and DCM (20 ml). The crude product is purified by flash column chromatography [silica gel, eluant: DCM/MeOH, 19/1 (v/v)] to yield the title compound as a solid.

HRMS [$C_{43}H_{45}N_8O_7S_2$]: calc.: 849.2847 found: 849.2838

20. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-methyl-1,3-thiazol-5-yl)methyl]-6-phenylthieno[3,2-d]pyrimidine-2,4(1H,3H)-dione A solution of 4-[(4aR,10bR)-9-ethoxy-8-methoxy-3,4,4a,10b-tetrahydro-1H-thiopyrano[4,3-c]isoquinolin-6-yl]benzoic acid (199 mg; compound C10), TOTU (213 mg) and HOAT (102 mg) in DIPEA (259 mg) is stirred for 50 min at RT. Subsequently, 1-[(2-methyl-1,3-thiazol-5-yl)methyl]-6-phenyl-3-(piperidin-4-yl)thieno[3,2-d]pyrimidine-2,4(1H,3H)-dione trifluoroacetate (276 mg; compound B44) is added and the reaction mixture is stirred for additional 60 min at RT. The solvent is removed under reduced pressure and to the resulting residue DCM (15 ml) and saturated aqueous sodium bicarbonate solution (3 ml) are added. The organic phase is separated and the aqueous phase is extracted with DCM (10 ml). The combined organic phases are applied to a phase separator, dried over magnesium sulfate and the solvent is removed under reduced pressure to give the crude title compound. The residue is first purified by flash chromatography [amino phase silica gel, eluation gradient: cyclohexane/EtOAc, 100/0 to 0/100 (v/v)]. After a second purification step applying preparative TLC [20×20 cm TLC plates with 0.5 mm thickness, eluent: EtOAc/triethylamine, 97/3 (v/v)] the title compound is obtained as a solid.

HRMS [$C_{44}H_{44}N_5O_5S_3$]: calc.: 818.2499 found: 818.2495

21. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-1,2,3-triazol-4-yl)methyl]-6-phenylthieno[3,2-d]pyrimidine-2,4(1H,3H)-dione To a suspension of 1-[(2-ethyl-2H-1,2,3-triazol-4-yl)methyl]-6-phenyl-3-(piperidin-4-yl)thieno[3,2-d]pyrimidine-2,4(1H,3H)-dione trifluoroacetate (300 mg; compound B45), 4-[(4aR,10bR)-9-ethoxy-8-methoxy-3,4,4a,10b-tetrahydro-1H-thiopyrano[4,3-c]isoquinolin-6-yl]benzoic acid (217 mg; compound C10), EDCI (104 mg) and HOBT hydrate (74 mg) in DCM (10 ml) DIPEA (0.24 ml) is added. After 14 h at RT water and aqueous potassium hydrogen sulfate solution (10% w/w) are added and the mixture is extracted with DCM. The combined organic layers are dried (sodium sulfate) and concentrated under reduced pressure. The residue is purified by twofold flash column chromatography [silica gel, eluation gradient: DCM/MeOH, 1/0 to 1/1 (v/v)] and preparative HPLC to afford the title compound as a solid.

HRMS [$C_{44}H_{46}N_7O_5S_2$]: calc.: 816.2996 found: 816.2997

22. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(3-ethyl-1,2,4-thiadiazol-5-yl)methyl]-6-phenylthieno[3,2-d]pyrimidine-2,4(1H,3H)-dione To a suspension of 1-[(3-ethyl-1,2,4-thiadiazol-5-yl)methyl]-6-phenyl-3-(piperidin-4-yl)thieno[3,2-d]pyrimidine-2,4(1H,3H)-dione trifluoroacetate (250 mg; compound B46), 4-[(4aR,10bR)-9-ethoxy-8-methoxy-3,4,4a,10b-tetrahydro-1H-thiopyrano[4,3-c]isoquinolin-6-yl]benzoic acid (175 mg; compound C10), EDCI (84 mg) and HOBT hydrate (60 mg) in DCM (15 ml) DIPEA (0.23 ml) is added. After 14 h at RT additional EDCI (84 mg) and HOBT hydrate (60 mg) are added and the reaction mixture is stirred for additional 3 d at RT. Aqueous potassium hydrogen sulfate solution (10% w/w) is added and the mixture is filtered using a phase separator. The organic layer is concentrated under reduced pressure and the residue is purified by flash column chromatography [silica gel, eluation gradient: DCM/MeOH, 17/3 to 1/1 (v/v)] to afford the title compound as a solid.

HRMS [$C_{44}H_{45}N_6O_5S_3$]: calc.: 833.2608 found: 833.2607

23. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(1-ethyl-1H-1,2,3-triazol-4-yl)methyl]-6-phenylthieno[3,2-d]pyrimidine-2,4(1H,3H)-dione To a suspension of 1-[(1-ethyl-1H-1,2,3-triazol-4-yl)methyl]-6-phenyl-3-(piperidin-4-yl)thieno[3,2-d]pyrimidine-2,4(1H,3H)-dione trifluoroacetate (250 mg; compound B47), 4-[(4aR,10bR)-9-ethoxy-8-methoxy-3,4,4a,10b-tetrahydro-1H-thiopyrano[4,3-c]isoquinolin-6-yl]benzoic acid (180 mg; compound C10), EDCI (174 mg) and HOBT hydrate (123 mg) in DCM (12 ml) DIPEA (0.24 ml) is added. After 1.5 h at RT additional 4-[(4aR,10bR)-9-ethoxy-8-methoxy-3,4,4a,10b-tetrahydro-1H-thiopyrano[4,3-c]isoquinolin-6-yl]benzoic acid (100 mg; compound C10) is added and the reaction mixture is stirred for additional 5 d at RT. Aqueous potassium hydrogen sulfate solution (10% w/w) is added and the mixture is filtered using a phase separator. The organic layer is concentrated under reduced pressure and the residue is purified by flash column chromatography [silica gel, eluent: DCM/MeOH, 95/5 (v/v)] to afford the title compound as a solid.

HRMS [$C_{44}H_{46}N_7O_5S_2$]: calc.: 816.2996 found: 816.2993

24. One of 3-[1-({4-[(2R,4aR,10bR)-9-ethoxy-8-methoxy-2-oxido-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione or 3-[1-({4-[(2S,4aR,10bR)-9-ethoxy-8-methoxy-2-oxido-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione To a solution of Acid Diastereomer 1 (which is either 4-[(2R,4aR,10bR)-9-ethoxy-8-methoxy-2-oxido-3,4,4a,10b-tetrahydro-1H-thiopyrano[4,3-c]isoquinolin-6-yl]benzoic acid or 4-[(2S,4aR,10bR)-9-ethoxy-8-methoxy-2-oxido-3,4,4a,10b-tetrahydro-1H-thiopyrano[4,3-c]isoquinolin-6-yl]benzoic acid; 249 mg; compound C2) and HBTU (240 mg) in DCM (30 ml), DIPEA (0.31 ml) is added and the solution is stirred for 24 h at RT. To this solution 1-[(2-ethyl-2H-tetrazol-5-yl)methyl]-6-phenyl-3-(piperidin-4-yl)thieno[3,2-d]pyrimidine-2,4(1H,3H)-dione (260 mg; compound B39) is added and the reaction mixture is stirred for additional 12 h at RT. The solvent is removed under reduced pressure and the resulting residue is dissolved in DCM (5 ml) and applied to flash column chromatography [silica gel, eluent: DCM/triethylamine, 19/1 (v/v)] to give the title compound as a solid.

HRMS [$C_{43}H_{45}N_8O_6S_2$]: calc.: 833.2898 found: 833.2923 or 833.2930

25. One of 3-[1-({4-[(2R,4aR,10bR)-9-ethoxy-8-methoxy-2-oxido-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione or 3-[1-({4-[(2S,4aR,10bR)-9-ethoxy-8-methoxy-2-oxido-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione In analogy to the procedure described for example 14, Acid Diastereomer 2 (which is either 4-[(2R,4aR,10bR)-9-ethoxy-8-methoxy-2-oxido-3,4,4a,10b-tetrahydro-1H-thiopyrano[4,3-c]isoquinolin-6-yl]benzoic acid or 4-[(2S,4aR,10bR)-9-ethoxy-8-methoxy-2-oxido-3,4,4a,10b-tetrahydro-1H-thiopyrano[4,3-c]isoquinolin-6-yl]benzoic acid; 249 mg; compound C3) is reacted with HBTU (240 mg), 1-[(2-ethyl-2H-tetrazol-5-yl)methyl]-6-phenyl-3-(piperidin-4-yl)thieno[3,2-d]pyrimidine-2,4(1H,3H)-dione (260 mg; compound B39) and DIPEA (0.31 ml) in DCM (30 ml). After purification by flash column chromatography [silica gel, eluent: DCM/triethylamine, 19/1 (v/v)] the title compound is obtained as a solid.

HRMS [$C_{43}H_{45}N_8O_6S_2$]: calc.: 833.2898 found: 833.2923 or 833.2930

26. 3-[1-({3-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione In analogy to the procedure described for example 14 3-[(4aR,10bR)-9-ethoxy-8-methoxy-3,4,4a,10b-tetrahydro-1H-thiopyrano[4,3-c]isoquinolin-6-yl]benzoic acid (120 mg; compound C8) is reacted with HBTU (120 mg), 1-[(2-ethyl-2H-tetrazol-5-yl)methyl]-6-phenyl-3-(piperidin-4-yl)thieno[3,2-d]pyrimidine-2,4(1H,3H)-dione (132 mg; compound B39) and DIPEA (0.16 ml) in DCM (10 ml). After purification by flash column chromatography (silica gel, eluent: EtOAc) the title compound is obtained as a solid.

HRMS [$C_{43}H_{45}N_8O_5S_2$]: calc.: 817.2949 found: 817.2968

27. 3-[1-({3-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(3-ethyl-1,2,4-oxadiazol-5-yl)methyl]-6-phenylthieno[3,2-d]pyrimidine-2,4(1H,3H)-dione The title compound is prepared analogously as described for example 1 using 3-[(4aR,10bR)-9-ethoxy-8-methoxy-3,4,4a,10b-tetrahydro-1H-thiopyrano[4,3-c]isoquinolin-6-yl]benzoic acid (159 mg; compound C8), 1-[(3-ethyl-1,2,4-oxadiazol-5-yl)methyl]-6-phenyl-3-piperidin-4-ylthieno[3,2-d]pyrimidine-2,4(1H,3H)-dione hydrochloride (190 mg; compound B32), HBTU (167 mg), DIPEA (0.28 ml) and DCM (3 ml). The crude product is purified by flash column chromatography (amino phase silica gel, eluent gradient: EtOAc/methanol, 98/2 to 95/5 (v/v)) and afterwards by preparative TLC [silica gel, eluent: EtOAc/MeOH/triethylamine, 92.5/5/2.5 (v/v/v)] to yield the title compound as a solid.

HRMS [$C_{44}H_{45}N_6O_6S_2$]: calc.: 817.2837 found: 817.2831

28. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-{[2-(methoxymethyl)-2H-tetrazol-5-yl]methyl}-6-phenylthieno[3,2-d]pyrimidine-2,4(1H,3H)-dione A mixture of 4-[(4aR,10bR)-9-ethoxy-8-methoxy-3,4,4a,10b-tetrahydro-1H-thiopyrano[4,3-c]isoquinolin-6-yl]benzoic acid (251 mg; compound C10), TOTU (270 mg), HOAT (129 mg), DIPEA (327 mg) in DCM (8 ml) is stirred for 1 h at RT. To this mixture 1-{[2-(methoxymethyl)-2H-tetrazol-5-yl]methyl}-6-phenyl-3-(piperidin-4-yl)thieno[3,2-d]pyrimidine-2,4(1H,3H)-dione trifluoroacetate (359 mg; compound B25) is added and the reaction mixture is stirred for additional 3 h at RT. Additional 4-[(4aR,10bR)-9-ethoxy-8-methoxy-3,4,4a,10b-tetrahydro-1H-thiopyrano[4,3-c]isoquinolin-6-yl]benzoic acid (125 mg; compound C10), TOTU (207 mg) and HOAT (86 mg) are added to drive the reaction to completion. After stirring for 1 h at RT the reaction is quenched by addition of DCM (10 ml) and a saturated aqueous solution of sodium bicarbonate (10 ml). The organic phase is separated and the aqueous phase is extracted with DCM (5 ml). The combined organic phases are applied to a phase separator and the solvent is removed under vacuum. The resulting residue is purified by flash column chromatography [amino phase silica gel, eluation gradient: cyclohexane/EtOAc, 100/0 to 0/100 (v/v)] to yield the title compound as a solid.

HRMS [$C_{43}H_{45}N_8O_6S_2$]: calc.: 833.2898 found: 833.2897

29. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-{[1-(methoxymethyl)-1H-tetrazol-5-yl]methyl}-6-phenylthieno[3,2-d]pyrimidine-2,4(1H,3H)-dione The title compound is prepared analogously as described for example 28 using 1-{[1-(methoxymethyl)-1H-tetrazol-5-yl]methyl}-6-phenyl-3-(piperidin-4-yl)thieno[3,2-d]pyrimidine-2,4(1H,3H)-dione trifluoroacetate (compound B48) (235 mg), 4-[(4aR,10bR)-9-ethoxy-8-methoxy-3,4,4a,10b-tetrahydro-1H-thiopyrano[4,3-c]isoquinolin-6-yl]benzoic acid (165 mg; compound C10), TOTU (177 mg), HOAT (85 mg) and DIPEA (214 mg) in DCM (8 ml). After stirring for 4.5 h at RT additional 4-[(4aR,10bR)-9-ethoxy-8-methoxy-3,4,4a,10b-tetrahydro-1H-thiopyrano[4,3-c]isoquinolin-6-yl]benzoic acid (82.5 mg; compound C10), TOTU (177 mg) and HOAT (85 mg) are added. Purification by flash column chromatography [amino phase silica gel, eluation gradient: cyclohexane/EtOAc, 100/0 to 0/100 (v/v)] gives the title compound as a solid.

HRMS [$C_{43}H_{45}N_8O_6S_2$]: calc.: 833.2898 found: 833.2897

30. 6-(1,3-benzodioxol-5-yl)-3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]thieno[3,2-d]pyrimidine-2,4(1H,3H)-dione 6-(1,3-benzodioxol-5-yl)-1-[(2-ethyl-2H-tetrazol-5-yl)methyl]-3-(piperidin-4-yl)thieno[3,2-d]pyrimidine-2,4(1H,3H)-dione hydrochloride (94 mg; compound B77) is reacted with 4-[(4aR,10bR)-9-ethoxy-8-methoxy-3,4,4a,10b-tetrahydro-1H-thiopyrano[4,3-c]isoquinolin-6-yl]benzoic acid (72 mg; compound C10) and HBTU (151 mg) in DCM/DMF (15 ml/1 ml) in the presence of DIPEA (188 mg) according to the procedure described in example 2 to afford the title compound after purification by two-time flash column chromatography [amino phase silica gel, eluation gradient: Cyclohexane/EtOAc/DCM, 100/0/0 to 65/30/5 to 30/60/10 to 0/90/10 (v/v/v)].

HRMS [$C_{44}H_{45}N_8O_7S_2$]: calc.: 861.2847 found: 861.2844

31. 6-(1,3-benzodioxol-5-yl)-3-[1-({3-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]thieno[3,2-d]pyrimidine-2,4(1H,3H)-dione 6-(1,3-benzodioxol-5-yl)-1-[(2-ethyl-2H-tetrazol-5-yl)methyl]-3-(piperidin-4-yl)thieno[3,2-d]pyrimidine-2,4(1H,3H)-dione hydrochloride (94 mg; compound B77) is reacted with 3-[(4aR,10bR)-9-ethoxy-8-methoxy-3,4,4a,10b-tetrahydro-1H-thiopyrano[4,3-c]isoquinolin-6-yl]benzoic acid (72 mg; compound C8) and HBTU (151 mg) in DCM/DMF (14 ml/1 ml) in the presence of DIPEA (188 mg) according to the procedure described in example 2 to afford the title compound after purification by flash column chromatography [amino phase silica gel, eluation gradient: Cyclohexane/EtOAc/DCM, 100/0/0 to 50/40/10 to 30/60/10 to 0/90/10 (v/v/v)] and preparative HPLC as a solid.

HRMS [$C_{44}H_{45}N_8O_7S_2$]: calc.: 861.2847 found: 861.2848

32. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-(4-fluoro-2-methoxyphenyl)thieno[3,2-d]pyrimidine-2,4(1H, 3H)-dione 1-[(2-ethyl-2H-tetrazol-5-yl)methyl]-6-(4-fluoro-2-methoxyphenyl)-3-(piperidin-4-yl)thieno[3,2-d]pyrimidine-2,4(1H,3H)-dione hydrochloride (191 mg; compound B78) is reacted with 4-[(4aR,10bR)-9-ethoxy-8-methoxy-3,4,4a,10b-tetrahydro-1H-thiopyrano[4,3-c]isoquinolin-6-yl]benzoic acid (145 mg; compound C10) and HBTU (304 mg) in DCM/DMF (14 ml/1 ml) in the presence of DIPEA (377 mg) according to the procedure described in example 2 to afford the title compound after purification by flash column chromatography [amino phase silica gel, eluation gradient: Cyclohexane/EtOAc/DCM, 100/0/0 to 65/30/5 to 30/60/10 to 0/90/10 (v/v/v)] and preparative HPLC as a solid.

HRMS [$C_{44}H_{46}FN_8O_6S_2$]: calc.: 865.2960 found: 865.2956

33. 3-[1-({3-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-(4-fluoro-2-methoxyphenyl)thieno[3,2-d]pyrimidine-2,4(1H, 3H)-dione 1-[(2-ethyl-2H-tetrazol-5-yl)methyl]-6-(4-fluoro-2-methoxyphenyl)-3-(piperidin-4-yl)thieno[3,2-d]pyrimidine-2,4(1H,3H)-dione hydrochloride (191 mg; compound B78) is reacted with 3-[(4aR,10bR)-9-ethoxy-8-methoxy-3,4,4a,10b-tetrahydro-1H-thiopyrano[4,3-c]isoquinolin-6-yl]benzoic acid (145 mg; compound C8) and HBTU (304 mg) in DCM/DMF (14 ml/1 ml) in the presence of DIPEA (377 mg) according to the procedure described in example 2 to afford the title compound after purification by flash column chromatography [amino phase silica gel, eluation gradient: Cyclohexane/EtOAc/DCM, 100/0/0 to 50/40/10 to 30/60/10 to 0/90/10 (v/v/v)] and preparative HPLC as a solid.

HRMS [$C_{44}H_{46}FN_8O_6S_2$]: calc.: 865.2960 found: 865.2961

34. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-(5-fluoro-2-methoxyphenyl)thieno[3,2-d]pyrimidine-2,4(1H, 3H)-dione 1-[(2-ethyl-2H-tetrazol-5-yl)methyl]-6-(5-fluoro-2-methoxyphenyl)-3-(piperidin-4-yl)thieno[3,2-d]pyrimidine-2,4(1H,3H)-dione hydrochloride (190 mg; compound B79) is reacted with 4-[(4aR,10bR)-9-ethoxy-8-methoxy-3,4,4a,10b-tetrahydro-1H-thiopyrano[4,3-c]isoquinolin-6-yl]benzoic acid (145 mg; compound C10) and HBTU (304 mg) in DCM/DMF (15 ml/2 ml) in the presence of DIPEA (377 mg) according to the procedure described in example 2 to afford the title compound after purification by flash column chromatography [amino phase silica gel, eluation gradient: Cyclohexane/EtOAc/DCM, 100/0/0 to 50/40/10 to 30/60/10 to 0/90/10 (v/v/v)] and twice by preparative TLC [20×20 cm TLC plates with 0.5 mm thickness, eluation gradient: EtOAc/methanol/triethylamine, 91/5/4 (v/v/v)] as a solid.

HRMS [$C_{44}H_{46}FN_8O_6S_2$]: calc.: 865.2960 found: 865.2954

35. 3-[1-({3-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-(5-fluoro-2-methoxyphenyl)thieno[3,2-d]pyrimidine-2,4(1H,3H)-dione 1-[(2-ethyl-2H-tetrazol-5-yl)methyl]-6-(5-fluoro-2-methoxyphenyl)-3-(piperidin-4-yl)thieno[3,2-d]pyrimidine-2,4(1H,3H)-dione hydrochloride (190 mg; compound B79) is reacted with 3-[(4aR,10bR)-9-ethoxy-8-methoxy-3,4,4a,10b-tetrahydro-1H-thiopyrano[4,3-c]isoquinolin-6-yl]benzoic acid (145 mg; compound C8) and HBTU (304 mg) in DCM/DMF (15 ml/2 ml) in the presence of DIPEA (377 mg) according to the procedure described in example 2 to afford the title compound after purification by flash column chromatography [amino phase silica gel, eluation gradient: Cyclohexane/EtOAc/DCM, 100/0/0 to 50/40/10 to 30/60/10 to 0/90/10 (v/v/v)] and preparative HPLC as a solid.

HRMS [$C_{44}H_{46}FN_8O_6S_2$]: calc.: 865.2960 found: 865.2963

36. 6-(2,5-dimethoxyphenyl)-3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]thieno[3,2-d]pyrimidine-2,4(1H,3H)-dione 6-(2,5-dimethoxyphenyl)-1-[(2-ethyl-2H-tetrazol-5-yl)methyl]-3-(piperidin-4-yl)thieno[3,2-d]pyrimidine-2,4(1H,3H)-dione hydrochloride (137 mg; compound B80) is reacted with 4-[(4aR,10bR)-9-ethoxy-8-methoxy-3,4,4a,10b-tetrahydro-1H-thiopyrano[4,3-c]isoquinolin-6-yl]benzoic acid (145 mg; compound C10) and HBTU (102 mg) in DCM (10 ml) in the presence of DIPEA (264 mg) according to the procedure described in example 2 to afford the title compound after purification by flash column chromatography [amino phase silica gel, eluation gradient: Cyclohexane/EtOAc/DCM, 100/0/0 to 50/40/10 to 30/60/10 to 0/90/10 (v/v/v)] and preparative HPLC as a solid.

HRMS [$C_{45}H_{49}N_8O_7S_2$]: calc.: 877.3160 found: 877.3158

37. 6-(2,5-dimethoxyphenyl)-3-[1-({3-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]thieno[3,2-d]pyrimidine-2,4(1H,3H)-dione 6-(2,5-dimethoxyphenyl)-1-[(2-ethyl-2H-tetrazol-5-yl)methyl]-3-(piperidin-4-yl)thieno[3,2-d]pyrimidine-2,4(1H,3H)-dione hydrochloride (137 mg; compound B80) is reacted with 3-[(4aR,10bR)-9-ethoxy-8-methoxy-3,4,4a,10b-tetrahydro-1H-thiopyrano[4,3-c]isoquinolin-6-yl]benzoic acid (102 mg; compound C8) and HBTU (213 mg) in DCM (10 ml) in the presence of DIPEA (264 mg) according to the procedure described in example 2 to afford the title compound after purification by flash column chromatography [amino phase silica gel, eluation gradient: Cyclohexane/EtOAc/DCM, 100/0/0 to 50/40/10 to 30/60/10 to 0/90/10 (v/v/v)] and preparative HPLC as a solid.

HRMS [$C_{45}H_{49}N_8O_7S_2$]: calc.: 877.3160 found: 877.3158

38. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-(2-fluorophenyl)thieno[3,2-d]pyrimidine-2,4(1H,3H)-dione 1-[(2-ethyl-2H-tetrazol-5-yl)methyl]-6-(2-fluorophenyl)-3-(piperidin-4-yl)thieno[3,2-d]pyrimidine-2,4(1H,3H)-dione hydrochloride (154 mg; compound B81) is reacted with 4-[(4aR,10bR)-9-ethoxy-8-methoxy-3,4,4a,10b-tetrahydro-1H-thiopyrano[4,3-c]isoquinolin-6-yl]benzoic acid (124 mg; compound C10) and HBTU (261 mg) in DCM/DMF (15 ml/1 ml) in the presence of DIPEA (324 mg) according to the procedure described in example 2 to afford the title compound after purification by flash column chromatography [amino phase silica gel, eluation gradient: Cyclohexane/EtOAc/DCM, 100/0/0 to 50/40/10 to 30/60/10 to 0/90/10 (v/v/v)] and by preparative HPLC as a solid.

HRMS [$C_{43}H_{44}FN_8O_5S_2$]: calc.: 835.2855 found: 835.2869

39. 1-(3,5-difluoro-4-methoxybenzyl)-3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-6-(4-fluoro-2-methoxyphenyl)thieno[3,2-d]pyrimidine-2,4(1H,3H)-dione 1-[(2-ethyl-2H-tetrazol-5-yl)methyl]-6-(2-fluorophenyl)-3-(piperidin-4-yl)thieno[3,2-d]pyrimidine-2,4(1H,3H)-dione hydrochloride (154 mg; compound B81) is reacted with 3-[(4aR,10bR)-9-ethoxy-8-methoxy-3,4,4a,10b-tetrahydro-1H-thiopyrano[4,3-c]isoquinolin-6-yl]benzoic acid (124 mg; compound C8) and HBTU (261 mg) in DCM/DMF (15 ml/1 ml) in the presence of DIPEA (324 mg) according to the procedure described in example 2 to afford the title compound after purification by flash column chromatography [amino phase silica gel, eluation gradient: Cyclohexane/EtOAc/DCM, 100/0/0 to 50/40/10 to 30/60/10 to 0/90/10 (v/v/v)] and preparative HPLC as a solid.

HRMS [$C_{43}H_{44}FN_8O_5S_2$]: calc.: 835.2855 found: 835.2854

40. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-(4-fluorophenyl)thieno[3,2-d]pyrimidine-2,4(1H,3H)-dione 1-[(2-ethyl-2H-tetrazol-5-yl)methyl]-6-(4-fluorophenyl)-3-(piperidin-4-yl)thieno[3,2-d]pyrimidine-2,4(1H,3H)-dione hydrochloride (108 mg; compound B82) is reacted with 4-[(4aR,10bR)-9-ethoxy-8-methoxy-3,4,4a,10b-tetrahydro-1H-thiopyrano[4,3-c]isoquinolin-6-yl]benzoic acid (88 mg; compound C10) and HBTU (183 mg) in DCM/DMF (18 ml/1 ml) in the presence of DIPEA (227 mg) according to the procedure described in example 2 to afford the title compound after purification by flash column chromatography

[amino phase silica gel, eluation gradient: Cyclohexane/ EtOAc, 60/40 to 40/60 (v/v)] and by preparative TLC [20×20 cm TLC plates with 0.5 mm thickness, eluation gradient: EtOAc/methanol/triethylamine, 91/5/4 (v/v/v)] as a solid.

HRMS $[C_{43}H_{44}FN_8O_5S_2]$: calc.: 835.2855. found: 835.2851

41. 3-[1-({3-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-(4-fluorophenyl)thieno[3, 2-d]pyrimidine-2,4(1H,3H)-dione 1-[(2-ethyl-2H-tetrazol-5-yl)methyl]-6-(4-fluorophenyl)-3-(piperidin-4-yl)thieno[3,2-d]pyrimidine-2,4(1H,3H)-dione hydrochloride (108 mg; compound B82) is reacted with 3-[(4aR,10bR)-9-ethoxy-8-methoxy-3,4,4a,10b-tetrahydro-1H-thiopyrano[4,3-c]isoquinolin-6-yl]benzoic acid (88 mg; compound C8) and HBTU (183 mg) in DCM/DMF (10 ml/1 ml) in the presence of DIPEA (227 mg) according to the procedure described in example 2 to afford the title compound after purification by flash column chromatography [amino phase silica gel, eluation gradient: Cyclohexane/ EtOAc/DCM, 100/0/0 to 50/40/10 to 30/60/10 to 0/90/10 (v/v/v)] as a solid.

HRMS $[C_{43}H_{44}FN_8O_5S_2]$: calc.: 835.2855 found: 835.285

42. 6-(2,3-difluorophenyl)-3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]thieno[3,2-d]pyrimidine-2,4(1H,3H)-dione 6-(2,3-difluorophenyl)-1-[(2-ethyl-2H-tetrazol-5-yl)methyl]-3-(piperidin-4-yl)thieno[3,2-d]pyrimidine-2,4(1H, 3H)-dione hydrochloride (40 mg; compound B83) is reacted with 4-[(4aR,10bR)-9-ethoxy-8-methoxy-3,4,4a,10b-tetrahydro-1H-thiopyrano[4,3-c]isoquinolin-6-yl]benzoic acid (31 mg; compound C10) and HBTU (33 mg) in DCM/DMF (15 ml/1 ml) in the presence of DIPEA (41 mg) according to the procedure described in example 2 to afford the title compound after purification by flash column chromatography [amino phase silica gel, eluation gradient: Cyclohexane/ EtOAc/DCM, 100/0/0 to 65/30/5 to 30/60/10 to 0/90/10 (v/v/ v)] and by preparative TLC [20×20 cm TLC plates with 0.5 mm thickness, eluation gradient: EtOAc/methanol/triethylamine, 91/5/4 (v/v/v)] as a solid.

HRMS $[C_{43}H_{43}F_2N_8O_5S_2]$: calc.: 853.2760 found: 853.2770

43. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-[(3-ethyl-1,2,4-oxadiazol-5-yl)methyl]-6-(4-fluoro-2-methoxyphenyl)thieno[3,2-d]pyrimidine-2,4(1H, 3H)-dione 1-[(3-Ethyl-1,2,4-oxadiazol-5-yl)methyl]-6-(4-fluoro-2-methoxyphenyl)-3-(piperidin-4-yl)thieno[3,2-d]pyrimidine-2,4(1H,3H)-dione hydrochloride (250 mg; compound B85) is reacted with 4-[(4aR,10bR)-9-ethoxy-8-methoxy-3,4,4a, 10b-tetrahydro-1H-thiopyrano[4,3-c]isoquinolin-6-yl]benzoic acid (205 mg; compound C10) and HBTU (215 mg) in DCM (7 ml) in the presence of DIPEA (0.36 ml) according to the procedure described in example 2 to afford the title compound after purification by flash column chromatography [amino phase silica gel, eluation gradient: DCM/MeOH, 1/0 to 1/1 (v/v)] and preparative HPLC as a solid.

HRMS $[C_{45}H_{46}FN_6O_7S_2]$: calc.: 865.2848 found: 865.2849

44. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-6-(4-fluoro-2-methoxyphenyl)-1-{[3-(methoxymethyl)-1,2,4-oxadiazol-5-yl]methyl}thieno[3,2-d]pyrimidine-2,4 (1H,3H)-dione 6-(4-fluoro-2-methoxyphenyl)-1-{[3-(methoxymethyl)-1, 2,4-oxadiazol-5-yl]methyl}-3-(piperidin-4-yl)thieno[3,2-d] pyrimidine-2,4(1H,3H)-dione hydrochloride (415 mg; compound B84) is reacted with 4-[(4aR,10bR)-9-ethoxy-8-methoxy-3,4,4a,10b-tetrahydro-1H-thiopyrano[4,3-c] isoquinolin-6-yl]benzoic acid (383 mg; compound C10) and HBTU (322 mg) in DCM (10 ml) in the presence of DIPEA (498 mg) according to the procedure described in example 2 to afford the title compound after purification by flash column chromatography [amino phase silica gel, eluation gradient: Cyclohexane/EtOAc, 100/0/to 0/100 (v/v)] and by preparative HPLC as a solid.

HRMS $[C_{45}H_{46}FN_6O_8S_2]$: calc.: 881.2797 found: 881.2804

45. 3-[1-({3-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-6-(4-fluoro-2-methoxyphenyl)-1-{[3-(methoxymethyl)-1,2,4-oxadiazol-5-yl]methyl}thieno[3,2-d]pyrimidine-2,4 (1H,3H)-dione 6-(4-fluoro-2-methoxyphenyl)-1-{[3-(methoxymethyl)-1, 2,4-oxadiazol-5-yl]methyl}-3-(piperidin-4-yl)thieno[3,2-d] pyrimidine-2,4(1H,3H)-dione hydrochloride (415 mg; compound B84) is reacted with 3-[(4aR,10bR)-9-ethoxy-8-methoxy-3,4,4a,10b-tetrahydro-1H-thiopyrano[4,3-c] isoquinolin-6-yl]benzoic acid (408 mg; compound C8) and HBTU (322 mg) in DCM (10 ml) in the presence of DIPEA (498 mg) according to the procedure described in example 2 to afford the title compound after purification by flash column chromatography [amino phase silica gel, eluation gradient: Cyclohexane/EtOAc, 100/0 to 0/100 (v/v)] and by preparative HPLC as a solid.

HRMS $[C_{45}H_{46}FN_6O_8S_2]$: calc.: 881.2797 found: 881.2799

46. 6-(1,3-benzodioxol-5-yl)-3-[1-({4-[(4aR,10bR)-9-ethoxy-8-methoxy-3,4,4a,10b-tetrahydro-1H-thiopyrano[4,3-c]isoquinolin-6-yl]phenyl}carbonyl) piperidin-4-yl]-1-[(3-ethyl-1,2,4-oxadiazol-5-yl) methyl]thieno[3,2-d]pyrimidine-2,4(1H,3H)-dione To a solution of 6-(1,3-benzodioxol-5-yl)-1-[(3-ethyl-1,2, 4-oxadiazol-5-yl)methyl]-3-(piperidin-4-yl)thieno[3,2-d] pyrimidine-2,4(1H,3H)-dione hydrochloride (232 mg; compound B86) and 4-[(4aR,10bR)-9-ethoxy-8-methoxy-3,4,4a, 10b-tetrahydro-1H-thiopyrano[4,3-c]isoquinolin-6-yl] benzoic acid (191 mg; compound C10) in DMF (10 ml) is added HOBt (74 mg) and EDCI (92 mg) and the reaction mixture is stirred at RT for 48 h. One additional equivalent of EDCI (92 mg) is added in order to complete the reaction. The reaction mixture is extracted for three times with DCM/H$_2$O/ saturated sodium chloride solution (150 ml/100 ml/35 ml).

The organic phase is separated and dried with $Na_2SO_4$. After filtration and evaporation of all volatiles the resulting residue is purified by flash column chromatography [amino phase silica gel, eluation gradient: DCM/ethanol, 100/0/to 95/5 (v/v)] and by preparative HPLC to give the title compound as a solid.

HRMS [$C_{45}H_{45}N_6O_8S_2$]: calc.: 861.2735 found: 861.2754

47. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-[(3-ethyl-1,2, 4-oxadiazol-5-yl)methyl]-6-(4-fluorophenyl)thieno [3,2-d]pyrimidine-2,4(1H,3H)-dione 1-[(3-ethyl-1,2,4-oxadiazol-5-yl)methyl]-6-(4-fluorophenyl)-3-(piperidin-4-yl)thieno[3,2-d]pyrimidine-2,4(1H,3H)-dione hydrochloride (310 mg; compound B87) is reacted with 4-[(4aR,10bR)-9-ethoxy-8-methoxy-3,4,4a,10b-tetrahydro-1H-thiopyrano[4,3-c]isoquinolin-6-yl]benzoic acid (216 mg; compound C10) and HOBt (83 mg) and EDCI (104 mg) in DMF (10 ml) according to the procedure described in example 46 to afford the title compound after purification by flash column chromatography [amino phase silica gel, eluation gradient: DCM/ethanol, 100/0/to 90/10 (v/v)] and by preparative HPLC as a solid.

HRMS [$C_{44}H_{44}FN_6O_6S_2$]: calc.: 835.2742 found: 835.2754

48. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-[(3-ethyl-1,2, 4-oxadiazol-5-yl)methyl]-6-(2-fluorophenyl)thieno [3,2-d]pyrimidine-2,4(1H,3H)-dione 1-[(3-ethyl-1,2,4-oxadiazol-5-yl)methyl]-6-(2-fluorophenyl)-3-(piperidin-4-yl)thieno[3,2-d]pyrimidine-2,4(1H,3H)-dione hydrochloride (272 mg; compound B88) is reacted with 4-[(4aR,10bR)-9-ethoxy-8-methoxy-3,4,4a,10b-tetrahydro-1H-thiopyrano[4,3-c]isoquinolin-6-yl]benzoic acid (237 mg; compound C10) and HBTU (249 mg) in DCM (7 ml) in the presence of DIPEA (0.42 ml) according to the procedure described in example 2 to afford the title compound after purification by flash column chromatography [amino phase silica gel, eluation gradient: DCM/MeOH, 1/0 to 1/1 (v/v)] and preparative HPLC as a solid.

HRMS [$C_{44}H_{44}FN_6O_6S_2$]: calc.: 835.2742 found: 835.2747

49. 6-(3,4-difluorophenyl)-3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(3-ethyl-1,2,4-oxadiazol-5-yl)methyl] thieno[3,2-d]pyrimidine-2,4(1H,3H)-dione 6-(3,4-difluorophenyl)-1-[(3-ethyl-1,2,4-oxadiazol-5-yl) methyl]-3-(piperidin-4-yl)thieno[3,2-d]pyrimidine-2,4(1H, 3H)-dione hydrochloride (228 mg; compound B89) is reacted with 4-[(4aR,10bR)-9-ethoxy-8-methoxy-3,4,4a,10b-tetrahydro-1H-thiopyrano[4,3-c]isoquinolin-6-yl]benzoic acid (191 mg; compound C10) and HOBt (74 mg) and EDCI (92 mg) in DMF (10 ml) according to the procedure described in example 46 to afford the title compound after purification by flash column chromatography [amino phase silica gel, eluation gradient: DCM/ethanol, 100/0/to 95/5 (v/v)] and by preparative HPLC as a solid.

HRMS [$C_{44}H_{43}F_2N_6O_6S_2$]: calc. 853.2648 found: 853.2651

50. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-{[3-(3-methoxypropyl)-1,2,4-oxadiazol-5-yl]methyl}-6-phenylthieno[3,2-d]pyrimidine-2,4(1H,3H)-dione 1-{[3-(3-methoxypropyl)-1,2,4-oxadiazol-5-yl]methyl}-6-phenyl-3-(piperidin-4-yl)thieno[3,2-d]pyrimidine-2,4(1H, 3H)-dione hydrochloride (210 mg; compound B90) is reacted with 4-[(4aR,10bR)-9-ethoxy-8-methoxy-3,4,4a,10b-tetrahydro-1H-thiopyrano[4,3-c]isoquinolin-6-yl]benzoic acid (159 mg; compound C10) and HBTU (167 mg) in DCM (3.5 ml) in the presence of DIPEA (207 mg) according to the procedure described in example 2 to afford the title compound after purification by flash column chromatography [amino phase silica gel, eluent: EtOAc] as a solid.

HRMS [$C_{46}H_{49}N_6O_7S_2$]: calc.: 861.3099 found: 861.3089

51. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-6-phenyl-1-{[3-(propoxymethyl)-1,2,4-oxadiazol-5-yl] methyl}thieno[3,2-d]pyrimidine-2,4(1H,3H)-dione A solution of 4-[(4aR,10bR)-9-ethoxy-8-methoxy-3,4,4a, 10b-tetrahydro-1H-thiopyrano[4,3-c]isoquinolin-6-yl]benzoic acid (159 mg; compound C10), TOTU (131 mg), HOAt (54 mg) and DIPEA (0.21 ml) in DMF (4 ml) is stirred for 0.5 h at RT. Subsequently, 6-phenyl-3-(piperidin-4-yl)-1-{[3-(propoxymethyl)-1,2,4-oxadiazol-5-yl]methyl}thieno[3,2-d]pyrimidine-2,4(1H,3H)-dione trifluoroacetate (238 mg; compound B91) is added and the reaction mixture is stirred for 1 h at RT. Saturated aqueous sodium bicarbonate solution (2 ml) are added and the mixture is filtered using a phase separator. The organic layer is concentrated under reduced pressure and the residue is purified by flash column chromatography [amino phase silica gel, eluation gradient: EtOAc/MeOH, 100/0 to 97/3 (v/v)] followed by preparative HPLC to yield the title compound as a solid.

HRMS [$C_{46}H_{49}N_6O_7S_2$]: calc.: 861.3099 found: 861.3098

52. 3-[1-({4-[(4aR,10bR)-9-ethoxy-8-methoxy-3,4, 4a,10b-tetrahydro-1H-thiopyrano[4,3-c]isoquinolin-6-yl]phenyl}carbonyl)piperidin-4-yl]-1-[(1-methyl-1H-1,2,4-triazol-3-yl)methyl]-6-phenylthieno[3,2-d] pyrimidine-2,4(1H,3H)-dione To a suspension of 1-[(1-methyl-1H-1,2,4-triazol-3-yl) methyl]-6-phenyl-3-(piperidin-4-yl)thieno[3,2-d]pyrimidine-2,4(1H,3H)-dione hydrochloride (249 mg, compound B92), 4-[(4aR,10bR)-9-ethoxy-8-methoxy-3,4,4a,10b-tetrahydro-1H-thiopyrano[4,3-c]isoquinolin-6-yl]benzoic acid (210 mg; compound C10) and HATU (267 mg) in DCM (7.0 ml) is added DIPEA (0.28 ml). The reaction mixture is stirred at RT for 14 h. Aqueous potassium bisulfate solution (10% w/w, 10 ml) is added and the mixture is extracted with DCM.

After filtration using a phase separator the organic layer is concentrated under reduced pressure and the residue is purified by preparative HPLC to yield the title compound as a solid.

HRMS [$C_{43}H_{44}N_7O_5S_2$]: calc.: 802.284 found: 802.2847

53. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(1-methyl-1H-imidazol-2-yl)methyl]-6-phenylthieno[3,2-d]pyrimidine-2,4(1H,3H)-dione 1-[(1-Methyl-1H-imidazol-2-yl)methyl]-6-phenyl-3-(piperidin-4-yl)thieno[3,2-d]pyrimidine-2,4(1H,3H)-dione hydrochloride (251 mg; compound B93) is reacted with 4-[(4aR,10bR)-9-ethoxy-8-methoxy-3,4,4a,10b-tetrahydro-1H-thiopyrano[4,3-c]isoquinolin-6-yl]benzoic acid (218 mg; compound C10) and HATU (271 mg) in DCM (7 ml) in the presence of DIPEA (0.29 ml) according to the procedure described in example 52 to afford the title compound after purification by preparative HPLC as a solid.

HRMS [$C_{44}H_{45}N_6O_5S_2$]: calc.: 801.2890 found: 801.2876

54. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(4-methyl-1,3-oxazol-5-yl)methyl]-6-phenylthieno[3,2-d]pyrimidine-2,4(1H,3H)-dione 1-[(4-Methyl-1,3-oxazol-5-yl)methyl]-6-phenyl-3-(piperidin-4-yl)thieno[3,2-d]pyrimidine-2,4(1H,3H)-dione hydrochloride (253 mg; compound B94) is reacted with 4-[(4aR,10bR)-9-ethoxy-8-methoxy-3,4,4a,10b-tetrahydro-1H-thiopyrano[4,3-c]isoquinolin-6-yl]benzoic acid (207 mg; compound C10) and HATU (257 mg) in DCM (7 ml) in the presence of DIPEA (0.27 ml) according to the procedure described in example 52 to afford the title compound after purification by preparative HPLC as a solid.

HRMS [$C_{46}H_{47}N_4O_5S_3$]: calc.: 831.2703 found: 831.269

55. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-ethylthiophen-2-yl)methyl]-6-phenylthieno[3,2-d]pyrimidine-2,4(1H,3H)-dione To a suspension of 1-[(5-ethylthiophen-2-yl)methyl]-6-phenyl-3-(piperidin-4-yl)thieno[3,2-d]pyrimidine-2,4(1H,3H)-dione hydrochloride (198 mg, compound B95) 4-[(4aR,10bR)-9-ethoxy-8-methoxy-3,4,4a,10b-tetrahydro-1H-thiopyrano[4,3-c]isoquinolin-6-yl]benzoic acid (159 mg; compound C10) and HBTU (167 mg) in DCM (4.0 ml) is added DIPEA (0.28 ml). The reaction mixture is stirred at RT for 1 h. Saturated aqueous sodium bicarbonate solution (2 ml) is added and the mixture is filtered using a phase separator. The organic layer is concentrated under reduced pressure and the residue is purified twice by flash column chromatography [amino phase silica gel, eluent: EtOAC] to yield the title compound as a solid.

HRMS [$C_{46}H_{47}N_4O_5S_3$]: calc.: 831.2703 found: 831.269

56. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(3-methylthiophen-2-yl)methyl]-6-phenylthieno[3,2-d]pyrimidine-2,4(1H,3H)-dione 1-[(3-methylthiophen-2-yl)methyl]-6-phenyl-3-(piperidin-4-yl)thieno[3,2-d]pyrimidine-2,4(1H,3H)-dione hydrochloride (191 mg; compound B96) is reacted with 4-[(4aR,10bR)-9-ethoxy-8-methoxy-3,4,4a,10b-tetrahydro-1H-thiopyrano[4,3-c]isoquinolin-6-yl]benzoic acid (159 mg; compound C10) and HBTU (167 mg) in DCM (4 ml) in the presence of DIPEA (0.28 ml) according to the procedure described in example 55 to afford the title compound after purification by flash column chromatography as a solid.

HRMS [$C_{45}H_{45}N_4O_5S_3$]: calc.: 817.2547 found: 817.2545

57. 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-ethyl-2H-tetrazol-2-yl)methyl]-6-phenylthieno[3,2-d]pyrimidine-2,4(1H,3H)-dione To a suspension of 1-[(5-ethyl-2H-tetrazol-2-yl)methyl]-6-phenyl-3-(piperidin-4-yl)thieno[3,2-d]pyrimidine-2,4(1H,3H)-dione hydrochloride (170 mg, compound B97), 4-[(4aR,10bR)-9-ethoxy-8-methoxy-3,4,4a,10b-tetrahydro-1H-thiopyrano[4,3-c]isoquinolin-6-yl]benzoic acid (143 mg; compound C10) and COMU (167 mg) in DCM (3.0 ml) is added DIPEA (0.25 ml). The reaction mixture is stirred at RT for 1 h. Saturated aqueous sodium bicarbonate solution (2 ml) is added and the mixture is filtered using a phase separator. The organic layer is concentrated under reduced pressure and the residue is purified by flash column chromatography [amino phase silica gel, eluent: EtOAc] and by preparative HPLC to yield the title compound as a solid.

HRMS [$C_{43}H_{45}N_8O_5S_2$]: calc.: 817.2949 found: 817.2941

58. 1-[(5-tert-butyl-1,3,4-oxadiazol-2-yl)methyl]-3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-6-phenylthieno[3,2-d]pyrimidine-2,4(1H,3H)-dione 1-[(5-tert-butyl-1,3,4-oxadiazol-2-yl)methyl]-6-phenyl-3-(piperidin-4-yl)thieno[3,2-d]pyrimidine-2,4(1H,3H)-dione hydrochloride (1.63 g; compound B98) is reacted with 4-[(4aR,10bR)-9-ethoxy-8-methoxy-3,4,4a,10b-tetrahydro-1H-thiopyrano[4,3-c]isoquinolin-6-yl]benzoic acid (1.39 g; compound C10) and HBTU (1.48 g) in DCM (40 ml) in the presence of DIPEA (2.38 ml) according to the procedure described in example 55 to afford the title compound after purification by flash column chromatography [amino phase silica gel, eluent: EtOAc/cyclohexane, 90/10 (v/v)] as a solid HRMS [$C_{46}H_{49}N_6O_6S_2$]: calc.: 845.3150 found: 845.3138

59. 3-[1-({4-[(4aR,10bR)-8,9-dimethoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione To a suspension of 1-[(2-ethyl-2H-tetrazol-5-yl)methyl]-6-phenyl-3-(piperidin-4-yl)thieno[3,2-d]pyrimidine-2,4(1H,3H)-dione hydrochloride (190 mg, compound B39), 4-[(4aR,10bR)-8,9-dimethoxy-3,4,4a,10b-tetrahydro-1H-thiopyrano[4,3-c]isoquinolin-6-yl]benzoic acid (220 mg; compound C16) and HBTU (167 mg) in DCM (4.0 ml) is added DIPEA (0.28 ml). The reaction mixture is stirred at RT for 1 h. Saturated aqueous sodium bicarbonate solution (2 ml) is added and the mixture is filtered using a phase separator. The organic layer is concentrated under reduced pressure and the residue is purified by flash column chromatography [amino phase silica gel, eluent: EtOAc] and subsequently by preparative HPLC and preparative TLC [20×20 cm TLC plates with 0.5 mm thickness, eluent: EtOAc/MeOH/triethylamine, 91/5/4 (v/v/v)] to yield the title compound as a solid.

HRMS [$C_{42}H_{43}N_8O_5S_2$]: calc.: 803.2792 found: 803.2785

Intermediates and Starting Compounds

General Procedure 1 (GP1): Alkylation of Compound B50

To a solution of tert-butyl 4-(2,4-dioxo-6-phenyl-1,4-dihydrothieno[3,2-d]pyrimidin-3(2H)-yl)piperidine-1-carboxylate (compound B50) in DMF are added potassium carbonate and one of the compounds D1-D21, D25, D27-D29, D31 and D32. The mixture is stirred at 100° C. (complete conversion of the starting materials is usually achieved within 2-4 h). Unless otherwise stated the work-up of the reaction and isolation of the title compounds can be achieved using either work-up procedure 1 (WU1) or work-up procedure 2 (WU2).

Work-up procedure 1 (WU1): The reaction mixture is poured into ice-cold water. The resulting precipitate is filtered off, washed with water and dried under reduced pressure to give a compound of formula 4, which can be used without further purification in the next synthesis step unless otherwise stated.

WU2: All volatile materials are removed in vacuo and the residue is purified by flash column chromatography on silica gel to give a compound of formula 4.

B1. tert-butyl 4-{1-[(5-ethyl-1,3-oxazol-2-yl)methyl]-2,4-dioxo-6-phenyl-1,4-dihydrothieno[3,2-d]pyrimidin-3(2H)-yl}piperidine-1-carboxylate To a solution of tert-butyl 4-(2,4-dioxo-6-phenyl-1,4-dihydrothieno[3,2-d]pyrimidin-3(2H)-yl)piperidine-1-carboxylate (800 mg; compound B50) in DMF (15 ml) are added potassium carbonate (520 mg) and 2-(chloromethyl)-5-ethyl-1,3-oxazole (270 mg; compound D1). After stirring for 1 h at 100° C. further 2-(chloromethyl)-5-ethyl-1,3-oxazole (200 mg; compound D1) and potassium carbonate (400 mg) are added to the reaction mixture. The mixture is stirred for additional 30 min at 100° C. Afterwards all volatile materials are removed in vacuo and the residue is purified by flash chromatography [silica gel, eluent: cyclohexane/EtOAc, 3/2 (v/v)] to give the title compound as a solid.

MS: calc.: $C_{28}H_{32}N_4O_5S$ (536.65) found: [MH$^+$]=536.73; [MH$^+$-Boc]=437.20

B2. tert-butyl 4-{1-[(5-methyl-1,2,4-oxadiazol-3-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (200 mg; compound B50) is reacted with 3-(chloromethyl)-5-methyl-1,2,4-oxadiazole (62 mg; compound D2) in the presence of potassium carbonate (65 mg) in DMF (5 ml). Using WU1 the title compound is obtained as a solid.

MS: calc.: $C_{26}H_{29}N_5O_5S$ (523.61) found: [MH$^+$]=523.62; [MH$^+$-Boc]=424.07

B3. tert-butyl 4-{1-[(3-ethylisoxazol-5-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (750 mg; compound B50) is reacted with 5-(chloromethyl)-3-ethylisoxazole (255 mg; compound D3) in the presence of potassium carbonate (242 mg) in DMF (10 ml). Using WU1 the title compound is obtained as a solid.

MS: calc.: $C_{28}H_{32}N_4O_5S$ (536.65) found: [MH$^+$]=536.78

B4. tert-butyl 4-{1-[(5-ethyl-1,3,4-oxadiazol-2-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (750 mg; compound B50) is reacted with 2-(chloromethyl)-5-ethyl-1,3,4-oxadiazole (257 mg; compound D4) in the presence of potassium carbonate (242 mg) in DMF (10 ml). Using WU1 the title compound is obtained as a solid.

MS: calc.: $C_{27}H_{31}N_5O_5S$ (537.64) found: [MH$^+$]=537.76

B5. tert-butyl 4-{1-[(4-ethyl-1,3-oxazol-2-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (750 mg; compound B50) is reacted with 2-(chloromethyl)-4-ethyl-1,3-oxazole (255 mg; compound D5) in the presence of potassium carbonate (242 mg) in DMF (10 ml). Using WU1 the title compound is obtained as a solid.

MS: calc.: $C_{28}H_{32}N_4O_5S$ (536.65) found: [MH$^+$]=536.83

B6. tert-butyl 4-{1-[(5-methylisoxazol-3-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (750 mg; compound B50) is reacted with 3-(chloromethyl)-5-methylisoxazole (231 mg; compound D6) in the presence of potassium carbonate (242 mg) in DMF (7 ml). Using WU1 the title compound is obtained as a solid.

MS: calc.: $C_{27}H_{30}N_4O_5S$ (522.62) found: [MH$^+$]=522.76

B7. tert-butyl 4-{1-[(3-ethyl-1,2,4-oxadiazol-5-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (7.70 g; compound B50) is reacted with 5-(chloromethyl)-3-ethyl-1,2,4-oxadiazole (2.64 g; compound D7) in the presence of potassium carbonate (2.49 g) in DMF (50 ml). Using WU1 a solid is obtained which is recrystallized from EtOAc (400 ml) at 65° C. to give the title compound.

MS: calc.: $C_{27}H_{31}N_5O_5S$ (537.64) found: [MH$^+$]=537.46

B8. tert-butyl 4-[4-{[5-(methoxymethyl)-1,3,4-oxadiazol-2-yl]methyl}-2,4-dioxo-6-phenyl-1,4-dihydrothieno[3,2-d]pyrimidin-3(2H)-yl]piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (750 mg; compound B50) is reacted with 2-(chloromethyl)-5-(methoxymethyl)-1,3,4-oxadiazole (285 mg; compound D8) in the presence of potassium carbonate (242 mg) in DMF (7 ml). Using WU1 the title compound is obtained as a solid.

MS: calc.: $C_{27}H_{31}N_5O_6S$ (553.64) found: [MH$^+$]=553.82

B9. tert-butyl 4-{1-[(2-ethyl-1,3-oxazol-5-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (170 mg; compound B50) is reacted with 5-(chloromethyl)-2-ethyl-1,3-oxazole (60 mg; compound D9) in the presence of potassium carbonate (111 mg) in DMF (5 ml). Using WU2 the title compound is obtained after flash column chromatography [silica gel, eluent: cyclohexane/EtOAc=1/2 (v/v)] as a solid.

MS: calc.: $C_{28}H_{32}N_4O_5S$ (536.65) found: $[MH^+]$=536.69

B10. tert-butyl 4-{1-[(2-methyl-1,3-thiazol-4-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (855 mg; compound B50) is reacted with 4-(chloromethyl)-2-methyl-1,3-thiazole (295 mg; compound D10) in the presence of potassium carbonate (276 mg) in DMF (15 ml). Using WU1 the title compound is obtained as a solid.

MS: calc.: $C_{27}H_{30}N_4O_4S_2$ (538.69) found: $[MH^+]$=538.76

B11. tert-butyl 4-[1-({3-[(methylsulfanyl)methyl]-1,2,4-oxadiazol-5-yl}methyl)-2,4-dioxo-6-phenyl-1,4-dihydrothieno[3,2-d]pyrimidin-3(2H)-yl]piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (1 g; compound B50) is reacted with 5-(chloromethyl)-3-[(methylsulfanyl)methyl]-1,2,4-oxadiazole (410 mg; compound D11) in the presence of potassium carbonate (320 mg) in DMF (20 ml). The reaction mixture is stirred at 100° C. for 1 h. Ice cold water is added and the mixture is extracted with DCM 4 times. The combined organic layers are dried (sodium sulfate) and concentrated in vacuo. The residue is purified by flash column chromatography [silica gel, eluation gradient: cyclohexane/EtOAc, 1/0 to 1/1 (v/v)] to afford the title compound as a solid.

MS: calc.: $C_{27}H_{31}N_5O_5S_2$ (569.70) found: $[MH^+]$=592.08

B12. tert-butyl 4-{1-[(5-methyl-1,3-thiazol-2-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (855 mg; compound B50) is reacted with 2-(chloromethyl)-5-methyl-1,3-thiazole (366 mg; compound D12) in the presence of potassium carbonate (554 mg) in DMF (10 ml). Using WU1 the title compound is obtained as a solid.

MS: calc.: $C_{27}H_{30}N_4O_4S_2$ (538.69) found: $[MH^+]$=538.83

B13. tert-butyl 4-{1-[(4-methyl-1,3-thiazol-2-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (855 mg; compound B50) is reacted with 2-(chloromethyl)-4-methyl-1,3-thiazole (368 mg; compound D13) in the presence of potassium carbonate (276 mg) in DMF (15 ml). Using WU1 a solid is obtained which is purified by flash chromatography [silica gel, eluation gradient: DCM/MeOH, 100/0 to 95/5 (v/v)] to give the title compound as a solid.

MS: calc.: $C_{27}H_{30}N_4O_4S_2$ (538.69) found: $[MH^+]$=538.84

B14. tert-butyl 4-{1-[(2-ethyl-2H-tetrazol-5-yl)methyl]-2,4-dioxo-6-phenyl-1,4-dihydrothieno[3,2-d]pyrimidin-3(2H)-yl}piperidine-1-carboxylate

B15. tert-butyl 4-{1-[(1-ethyl-1H-tetrazol-5-yl)methyl]-2,4-dioxo-6-phenyl-1,4-dihydrothieno[3,2-d]pyrimidin-3(2H)-yl}piperidine-1-carboxylate Step 1:

To a solution of tert-butyl 4-(2,4-dioxo-6-phenyl-1,4-dihydrothieno[3,2-d]pyrimidin-3(2H)-yl)piperidine-1-carboxylate (5 g; compound B50) and chloroacetonitrile (883 mg) in DMF (45 ml) is added potassium carbonate (1.62 g). The mixture is stirred for 1 h at 100° C. and then poured into ice-cold water. The resulting precipitate is filtered off, washed with water and dried under reduced pressure to give tert-butyl 4-[1-(cyanomethyl)-2,4-dioxo-6-phenyl-1,4-dihydrothieno[3,2-d]pyrimidin-3(2H)-yl]piperidine-1-carboxylate (compound B14a) as a solid, which is used without further purification for the next step.

Step 2:

To a solution of tert-butyl 4-[1-(cyanomethyl)-2,4-dioxo-6-phenyl-1,4-dihydrothieno[3,2-d]pyrimidin-3(2H)-yl]piperidine-1-carboxylate (10.8 g; compound B14a) in DMF (120 ml) are added ammonium chloride (1.86 g) and sodium azide (2.41 g). The mixture is stirred for 1 h at 125° C. The solvent is removed under reduced pressure and the residue is taken up in dioxane and heated under reflux. All remaining solids are filtered off and the filtrate is concentrated in vacuo to give a mixture of the two tautomers tert-butyl 4-[2,4-dioxo-6-phenyl-1-(2H-tetrazol-5-ylmethyl)-1,4-dihydrothieno[3,2-d]pyrimidin-3(2H)-yl]piperidine-1-carboxylate and tert-butyl 4-[2,4-dioxo-6-phenyl-1-(1H-tetrazol-5-ylmethyl)-1,4-dihydrothieno[3,2-d]pyrimidin-3(2H)-yl]piperidine-1-carboxylate (compound B14b) as a solid, which is used without further purification for the next step.

Step 3:

To a solution of the tautomeric mixture of tert-butyl 4-[2,4-dioxo-6-phenyl-1-(2H-tetrazol-5-ylmethyl)-1,4-dihydrothieno[3,2-d]pyrimidin-3(2H)-yl]piperidine-1-carboxylate and tert-butyl 4-[2,4-dioxo-6-phenyl-1-(1H-tetrazol-5-ylmethyl)-1,4-dihydrothieno[3,2-d]pyrimidin-3(2H)-yl]piperidine-1-carboxylate (255 mg; compound B14b) in DMF (5 ml) under nitrogen atmosphere is added lithium hydride (5.0 mg). After 10 min at RT bromoethane (163 mg) is added. The mixture is stirred for 1.5 h at 40° C. then all volatile materials are removed in vacuo. The residue is purified by flash column chromatography [silica gel, eluation gradient: hexanes/EtOAc/triethylamine, 16/3/1 to 5/4/1 (v/v/v)] to give the two separated isomers tert-butyl 4-{1-[(1-ethyl-1H-tetrazol-5-yl)methyl]-2,4-dioxo-6-phenyl-1,4-dihydrothieno[3,2-d]pyrimidin-3(2H)-yl}piperidine-1-carboxylate (compound B15) and tert-butyl 4-{1-[(2-ethyl-2H-tetrazol-5-yl)methyl]-2,4-dioxo-6-phenyl-1,4-dihydrothieno[3,2-d]pyrimidin-3(2H)-yl}piperidine-1-carboxylate (compound B14) as solids.

tert-butyl 4-{1-[(2-ethyl-2H-tetrazol-5-yl)methyl]-2,4-dioxo-6-phenyl-1,4-dihydrothieno[3,2-d]pyrimidin-3(2H)-yl}piperidine-1-carboxylate (compound B14)

MS: calc.: $C_{26}H_{31}N_7O_4S$ (537.64) found: [MH$^+$]=537.7 tert-butyl 4-{1-[(1-ethyl-1H-tetrazol-5-yl)methyl]-2,4-dioxo-6-phenyl-1,4-dihydrothieno[3,2-d]pyrimidin-3(2H)-yl}piperidine-1-carboxylate (compound B15)

MS: calc.: $C_{26}H_{31}N_7O_4S$ (537.64) found: [MH$^+$]=538.0

B16. tert-butyl 4-[1-{[3-(methoxymethyl)-1,2,4-oxadiazol-5-yl]methyl}-2,4-dioxo-6-phenyl-1,4-dihydrothieno[3,2-d]pyrimidin-3(2H)-yl]piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (6.41 g; compound B50) is reacted with 5-(chloromethyl)-3-(methoxymethyl)-1,2,4-oxadiazole (2.44 g; compound D14) in the presence of potassium carbonate (2.07 g) in DMF (45 ml). Using WU1 a solid is obtained which is dissolved in EtOAc (400 ml) at 65° C. The solvent is removed in vacuo to a volume of 40 ml at 40° C. To this solution 20 ml of diethyl ether is added at RT and the resulting suspension is filtered off and the filter cake is washed with little amounts of EtOAc and diethyl ether. The solid is dried in vacuo at 60° C. for 1 h to give the title compound.

MS: calc.: $C_{27}H_{31}N_5O_6S$ (553.64) found: [MH$^+$]=553.32

B17. tert-butyl 4-{1-[(2-ethyl-1,3-oxazol-4-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (590 mg; compound B50) is reacted with 4-(chloromethyl)-2-ethyl-1,3-oxazole (200 mg; compound D15) in the presence of potassium carbonate (190 mg) in DMF (15 ml). Using WU2 the title compound is obtained after flash column chromatography [silica gel, eluent: cyclohexane/EtOAc, 3/2 (v/v)] as a solid.

MS: calc.: $C_{28}H_{32}N_4O_5S$ (536.65) found: [MH$^+$]=536.75

B18. tert-butyl 4-{1-[(1-ethyl-1H-pyrazol-4-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (1.29 g; compound B50) is reacted with 4-(chloromethyl)-1-ethyl-1H-pyrazole (434 mg; compound D16) in the presence of potassium carbonate (832 mg) in DMF (20 ml). Using WU2 the title compound is obtained after flash column chromatography [silica gel, eluent: cyclohexane/EtOAc, 3/2 (v/v)] as a solid.

MS: calc.: $C_{28}H_{33}N_5O_4S$ (535.67) found: [MH$^+$]=535.79

B19. tert-butyl 4-{1-[(1-ethyl-1H-pyrazol-3-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (969 mg; compound B50) is reacted with 3-(chloromethyl)-1-ethyl-1H-pyrazole (454 mg) in the presence of potassium carbonate (630 mg; compound D17) in DMF (15 ml). Using WU2 the title compound is obtained after flash column chromatography [silica gel, eluent: cyclohexane/EtOAc, 15/1 (v/v)] as a solid.

MS: calc.: $C_{28}H_{33}N_5O_4S$ (535.67) found: [MH$^+$]=535.84

B20. tert-butyl 4-{1-[(2-methyl-1,3-thiazol-5-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (627 mg; compound B50) is reacted with 5-(chloromethyl)-2-methyl-1,3-thiazole (273 mg; compound D18) in the presence of potassium carbonate (405 mg) in DMF (10 ml). Using WU2 the title compound is obtained after flash column chromatography [silica gel, eluent: cyclohexane/EtOAc, 1/1 (v/v)] as a solid.

MS: calc.: $C_{27}H_{30}N_4O_4S_2$ (538.69) found: [MH$^+$-Boc]=439.23

B21. tert-butyl 4-{1-[(2-ethyl-2H-1,2,3-triazol-4-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (2.20 g; compound B50) is reacted with 4-(chloromethyl)-2-ethyl-2H-1,2,3-triazole (748 mg; compound D19) in the presence of potassium carbonate (1.42 g) in DMF (39 ml). Using WU2 the title compound is obtained after flash column chromatography [silica gel, eluation gradient: cyclohexane/EtOAc, 3/1 to 1/1 (v/v)] as a solid.

MS: calc.: $C_{27}H_{32}N_6O_4S$ (536.65) found: [MH$^+$]=537.20

B22. tert-butyl 4-{1-[(3-ethyl-1,2,4-thiadiazol-5-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (563 mg; compound B50) is reacted with 5-(chloromethyl)-3-ethyl-1,2,4-thiadiazole (226 mg; compound D20) in the presence of potassium carbonate (364 mg) in DMF (10 ml). After 3 h and additionally after 6 h at 100° C. additional 5-(chloromethyl)-3-ethyl-1,2,4-thiadiazole (214 mg and 107 mg; compound D20) in DMF (5 ml each) is added, and the mixture is stirred at 100° C. for another 5 h. Using WU2 the title compound is obtained after flash column chromatography [silica gel, eluent: cyclohexane/EtOAc, 3/1 (v/v)] as a solid.

MS: calc.: $C_{27}H_{31}N_5O_4S_2$ (553.70) found: [MH$^+$]=554.98

B23. tert-butyl 4-{1-[(1-ethyl-1H-1,2,3-triazol-4-yl)methyl]-2,4-dioxo-6-phenyl-1,4-dihydrothieno[3,2-d]pyrimidin-3(2H)-yl}piperidine-1-carboxylate According to GP1 tert-butyl 4-(2,4-dioxo-6-phenyl-1,4-dihydrothieno[3,2-d]pyrimidin-3(2H)-yl)piperidine-1-carboxylate (1.88 g; compound B50) is reacted with 4-(chloromethyl)-1-ethyl-1H-1,2,3-triazole (827 mg; compound D21) in the presence of potassium carbonate (1.22 mg) in DMF (30 ml). Using WU2 the title compound is obtained after flash column chromatography [silica gel, eluent: cyclohexane/EtOAc, 1/1 (v/v)] as a solid.

MS: calc.: $C_{27}H_{32}N_6O_4S$ (536.65) found: $[MH^+]=537.05$

B24. tert-butyl 4-[1-{[1-(methoxymethyl)-1H-tetrazol-5-yl]methyl}-2,4-dioxo-6-phenyl-1,4-dihydrothieno[3,2-d]pyrimidin-3(2H)-yl]piperidine-1-carboxylate

B25. tert-butyl 4-[1-{[2-(methoxymethyl)-2H-tetrazol-5-yl]methyl}-2,4-dioxo-6-phenyl-1,4-dihydrothieno[3,2-d]pyrimidin-3(2H)-yl]piperidine-1-carboxylate To a stirred suspension of sodium hydride (206 mg, 60% dispersion in mineral oil) in 7 ml absolute THF in a sealed tube is added a solution of a tautomeric mixture of tert-butyl 4-[2,4-dioxo-6-phenyl-1-(1H-tetrazol-5-ylmethyl)-1,4-dihydrothieno[3,2-d]pyrimidin-3(2H)-yl]piperidine-1-carboxylate and 4-[2,4-dioxo-6-phenyl-1-(2H-tetrazol-5-ylmethyl)-1,4-dihydro-2H-thieno[3,2-d]pyrimidin-3-yl-]-piperidine-1-carboxylic acid tert-butyl ester (1.74 g; compound 14b) in absolute THF (7 ml) and absolute DMF (7 ml) at 0° C. After stirring for 40 min at 40° C. chloromethyl methyl ether (452 mg) dissolved in absolute DMF (3.5 ml) is added. The reaction mixture is stirred for 3 h at 50° C. and for 16 h at RT. The reaction is quenched by addition of a saturated aqueous solution of sodium bicarbonate and extracted with diethyl ether (two times). The combined organic phases are dried over magnesium sulfate, filtered and the solvent is removed under reduced pressure. The resulting residue is purified by flash chromatography [silica gel, eluent: cyclohexane/diethyl ether, 1/1 (v/v)] to give the separated title compounds as solids.

tert-butyl 4-[1-{[1-(methoxymethyl)-1H-tetrazol-5-yl]methyl}-2,4-dioxo-6-phenyl-1,4-dihydrothieno[3,2-d]pyrimidin-3(2H)-yl]piperidine-1-carboxylate MS: calc.: $C_{26}H_{31}N_7O_5S$ (553.64) found: $[MH^+\text{-}Boc]=454.23$ tert-butyl 4-[1-{[2-(methoxymethyl)-2H-tetrazol-5-yl]methyl}-2,4-dioxo-6-phenyl-1,4-dihydrothieno[3,2-d]pyrimidin-3(2H)-yl]piperidine-1-carboxylate MS: calc.: $C_{26}H_{31}N_7O_5S$ (553.64) found: $[MH^+\text{-}Boc]=454.24$

B26. 1-[(5-ethyl-1,3-oxazol-2-yl)methyl]-6-phenyl-3-(piperidin-4-yl)thieno[3,2-d]pyrimidine-2,4(1H,3H)-dione hydrochloride Tert-butyl 4-{1-[(5-ethyl-1,3-oxazol-2-yl)methyl]-2,4-dioxo-6-phenyl-1,4-dihydrothieno[3,2-d]pyrimidin-3(2H)-yl}piperidine-1-carboxylate (530 mg; compound B1) is dissolved in a solution of hydrogen chloride in 1,4-dioxane (10 ml, 6.8 M). The solution is stirred for 0.5 h at RT. The resulting precipitate is filtered off, washed with diethyl ether and dried in vacuo to give the title compound as a solid.

MS: calc.: $C_{23}H_{24}N_4O_3S$ (436.53) found: $[MH^+]=437.20$

B27. 1-[(5-methyl-1,2,4-oxadiazol-3-yl)methyl]-6-phenyl-3-piperidin-4-ylthieno[3,2-d]pyrimidine-2,4(1H,3H)-dione hydrochloride To a solution of tert-butyl 4-{1-[(5-methyl-1,2,4-oxadiazol-3-yl)methyl]-2,4-dioxo-6-phenyl-1,4-dihydrothieno[3,2-d]pyrimidin-3(2H)-yl}piperidine-1-carboxylate (2.86 g; compound B2) in DCM (100 ml) is added a solution of hydrogen chloride in 1,4-dioxane (10 ml, 4.0 M). The reaction mixture is stirred for 1 d at RT. The precipitate is filtered off, washed with diethyl ether and dried in vacuo to afford the title compound as a solid.

MS: calc.: $C_{21}H_{21}N_5O_3S$ (423.49) found: $[MH^+]=424.07$

B28. 1-[(3-ethylisoxazol-5-yl)methyl]-6-phenyl-3-(piperidin-4-yl)thieno[3,2-d]pyrimidine-2,4(1H,3H)-dione hydrochloride To a solution of tert-butyl 4-{1-[(3-ethylisoxazol-5-yl)methyl]-2,4-dioxo-6-phenyl-1,4-dihydrothieno[3,2-d]pyrimidin-3(2H)-yl}piperidine-1-carboxylate (820 mg; compound B3) in DCM (20 ml) is added a solution of hydrogen chloride in 1,4-dioxane (3 ml, 4.0 M). The reaction mixture is stirred for 1 d at RT. Diethyl ether is added and the resulting precipitate is filtered off, washed with diethyl ether and dried in vacuo to afford the title compound as a solid.

MS: calc.: $C_{23}H_{24}N_4O_3S$ (436.53) found: $[MH^+]=437.30$

B29. 1-[(5-ethyl-1,3,4-oxadiazol-2-yl)methyl]-6-phenyl-3-(piperidin-4-yl)thieno[3,2-d]pyrimidine-2,4(1H,3H)-dione hydrochloride A solution of tert-butyl 4-{1-[(5-ethyl-1,3,4-oxadiazol-2-yl)methyl]-2,4-dioxo-6-phenyl-1,4-dihydrothieno[3,2-d]pyrimidin-3(2H)-yl}piperidine-1-carboxylate (750 mg; compound B4) in DCM (20 ml) is reacted with a solution of hydrogen chloride in 1,4-dioxane (3 ml, 4.0 M) according to the procedure described in example B28 to afford the title compound as a solid.

MS: calc.: $C_{22}H_{23}N_5O_3S$ (437.52) found: $[MH^+]=438.23$

B30. 1-[(4-ethyl-1,3-oxazol-2-yl)methyl]-6-phenyl-3-(piperidin-4-yl)thieno[3,2-d]pyrimidine-2,4(1H,3H)-dione hydrochloride A solution of tert-butyl 4-{1-[(4-ethyl-1,3-oxazol-2-yl)methyl]-2,4-dioxo-6-phenyl-1,4-dihydrothieno[3,2-d]pyrimidin-3(2H)-yl}piperidine-1-carboxylate (780 mg; compound B5) in DCM (20 ml) is reacted with a solution of hydrogen chloride in 1,4-dioxane (3 ml, 4.0 M) according to the procedure described in example B28 to afford the title compound as a solid.

MS: calc.: $C_{23}H_{24}N_4O_3S$ (436.53) found: $[MH^+]=437.25$

B31. 1-[(5-methylisoxazol-3-yl)methyl]-6-phenyl-3-(piperidin-4-yl)thieno[3,2-d]pyrimidine-2,4(1H,3H)-dione hydrochloride A solution of tert-butyl 4-{1-[(5-methylisoxazol-3-yl)methyl]-2,4-dioxo-6-phenyl-1,4-dihydrothieno[3,2-d]pyrimidin-3(2H)-yl}piperidine-1-carboxylate (841 mg; compound B6) in DCM (15 ml) is reacted with a solution of hydrogen chloride in 1,4-dioxane (1.5 ml, 4.0 M) according to the procedure described in example B28 to afford the title compound as a solid.

MS: calc.: $C_{22}H_{22}N_4O_3S$ (422.51) found: $[MH^+]=423.19$

B32. 1-[(3-ethyl-1,2,4-oxadiazol-5-yl)methyl]-6-phenyl-3-piperidin-4-ylthieno[3,2-d]pyrimidine-2,4(1H,3H)-dione hydrochloride A solution of tert-butyl 4-{1-[(3-ethyl-1,2,4-oxadiazol-5-yl)methyl]-2,4-dioxo-6-phenyl-1,4-dihydrothieno[3,2-d]pyrimidin-3(2H)-yl}piperidine-1-carboxylate (12.46 g; compound B7) in DCM (100 ml) is reacted with a solution of hydrogen chloride in 1,4-dioxane (15 ml, 4.0 M) according to the procedure described in example B28 to afford the title compound as a solid.

MS: calc.: $C_{22}H_{23}N_5O_3S$ (437.52) found: [MH$^+$]=438.26

B33. 1-{[5-(methoxymethyl)-1,3,4-oxadiazol-2-yl]methyl}-6-phenyl-3-(piperidin-4-yl)thieno[3,2-d]pyrimidine-2,4(1H,3H)-dione hydrochloride A solution of tert-butyl 4-[1-{[5-(methoxymethyl)-1,3,4-oxadiazol-2-yl]methyl}-2,4-dioxo-6-phenyl-1,4-dihydrothieno[3,2-d]pyrimidin-3(2H)-yl]piperidine-1-carboxylate (872 mg; compound B8) in DCM (15 ml) is reacted with a solution of hydrogen chloride in 1,4-dioxane (1.5 ml, 4.0 M) according to the procedure described in example B28 to afford the title compound as a solid.

MS: calc.: $C_{22}H_{23}N_5O_4S$ (453.52) found: [MH$^+$]=454.21

B34. 1-[(2-ethyl-1,3-oxazol-5-yl)methyl]-6-phenyl-3-(piperidin-4-yl)thieno[3,2-d]pyrimidine-2,4(1H,3H)-dione hydrochloride tert-butyl 4-{1-[(2-ethyl-1,3-oxazol-5-yl)methyl]-2,4-dioxo-6-phenyl-1,4-dihydrothieno[3,2-d]pyrimidin-3(2H)-yl}piperidine-1-carboxylate (120 mg; compound B9) is dissolved in a solution of hydrogen chloride in 1,4-dioxane (5 ml, 6.8 M). The solution is stirred for 0.5 h at RT. The resulting precipitate is filtered off, washed with diethyl ether and dried in vacuo to give the title compound as a solid.

MS: calc.: $C_{23}H_{24}N_4O_3S$ (436.53) found: [MH$^+$]=437.22

B35. 1-[(2-methyl-1,3-thiazol-4-yl)methyl]-6-phenyl-3-(piperidin-4-yl)thieno[3,2-d]pyrimidine-2,4(1H,3H)-dione hydrochloride A suspension of tert-butyl 4-{1-[(2-methyl-1,3-thiazol-4-yl)methyl]-2,4-dioxo-6-phenyl-1,4-dihydrothieno[3,2-d]pyrimidin-3(2H)-yl}piperidine-1-carboxylate (1.0 g; compound B10) in a solution of hydrogen chloride in 1,4-dioxane (12 ml, 4.0 M) is stirred for 2.5 h at RT. The suspension is filtered and the filter cake is washed with 1,4-dioxane to give the title compound as a solid.

MS: calc.: $C_{22}H_{22}N_4O_2S$ (438.57) found: [MH$^+$]=439.19

B36. 1-({3-[(methylsulfanyl)methyl]-1,2,4-oxadiazol-5-yl}methyl)-6-phenyl-3-(piperidin-4-yl)thieno[3,2-d]pyrimidine-2,4(1H,3H)-dione hydrochloride A solution of tert-butyl 4-[1-({3-[(methylsulfanyl)methyl]-1,2,4-oxadiazol-5-yl}methyl)-2,4-dioxo-6-phenyl-1,4-dihydrothieno[3,2-d]pyrimidin-3(2H)-yl]piperidine-1-carboxylate (715 mg; compound B11) in DCM (15 ml) is reacted with a solution of hydrogen chloride in 1,4-dioxane (3 ml, 4.0 M) according to the procedure described in example B28 to afford the title compound as a solid.

MS: calc.: $C_{22}H_{23}N_5O_3S_2$ (469.59) found: [MH$^+$]=470.14

B37. 1-[(5-methyl-1,3-thiazol-2-yl)methyl]-6-phenyl-3-(piperidin-4-yl)thieno[3,2-d]pyrimidine-2,4(1H,3H)-dione hydrochloride A solution of tert-butyl 4-{1-[(5-methyl-1,3-thiazol-2-yl)methyl]-2,4-dioxo-6-phenyl-1,4-dihydrothieno[3,2-d]pyrimidin-3(2H)-yl}piperidine-1-carboxylate (980 mg; compound B12) in DCM (5 ml) and 1,4-dioxane (20 ml) is reacted with a solution of hydrogen chloride in 1,4-dioxane (2.3 ml, 4.0 M) under stirring at RT. After 1 h and after 2.5 h additional amounts of a solution of hydrogen chloride in 1,4-dioxane (4.6 ml and 2.3 ml) are added and the reaction mixture is stirred for another 10 min. All volatiles are removed under reduced pressure and the resulting residue is treated with diethyl ether. Removal of the solvent under reduced pressure gives the title compound as a solid.

MS: calc.: $C_{22}H_{22}N_4O_2S_2$ (438.57) found: [MH$^+$]=439.21

B38. 1-[(4-Methyl-1,3-thiazol-2-yl)methyl]-6-phenyl-3-(piperidin-4-yl)thieno[3,2-d]pyrimidine-2,4(1H,3H)-dione hydrochloride A suspension of tert-butyl 4-{1-[(4-methyl-1,3-thiazol-2-yl)methyl]-2,4-dioxo-6-phenyl-1,4-dihydrothieno[3,2-d]pyrimidin-3(2H)-yl}piperidine-1-carboxylate (500 mg; compound B13) in a solution of hydrogen chloride in 1,4-dioxane (7 ml, 4.0 M) is stirred for 2.5 h at RT. The suspension is filtered and the filter cake is washed with 1,4-dioxane to give the title compound as a solid.

MS: calc.: $C_{22}H_{22}N_4O_2S_2$ (438.57) found: [MH$^+$]=439.21

B39. 1-[(2-ethyl-2H-tetrazol-5-yl)methyl]-6-phenyl-3-(piperidin-4-yl)thieno[3,2-d]pyrimidine-2,4(1H,3H)-dione Tert-butyl 4-{1-[(2-ethyl-2H-tetrazol-5-yl)methyl]-2,4-dioxo-6-phenyl-1,4-dihydrothieno[3,2-d]pyrimidin-3(2H)-yl}piperidine-1-carboxylate (12.9 g; compound B14) is dissolved in a solution of hydrogen chloride in 1,4-dioxane (39.3 ml, 4.0 M). The solution is stirred for 1 h at RT. The hydrochloride of the title compound can be obtained by removal of all volatile materials in vacuo. The title compound is obtained by addition of water (50 ml) and pH adjustment to pH 13 by addition of 5.0 M aqueous sodium hydroxide solution. The volume is reduced to about 50 ml under reduced pressure and extracted with DCM (four times). The combined organic phases are dried over sodium sulfate. After filtration the solvent is removed under reduced pressure to give the title compound as a solid.

MS: calc.: $C_{21}H_{23}N_7O_2S$ (437.53) found: [MH$^+$]=438.18

B40. 1-{[3-(Methoxymethyl)-1,2,4-oxadiazol-5-yl]methyl}-6-phenyl-3-piperidin-4-ylthieno[3,2-d]pyrimidine-2,4(1H,3H)-dione hydrochloride A solution of tert-butyl 4-[1-{[3-(methoxymethyl)-1,2,4-oxadiazol-5-yl]methyl}-2,4-dioxo-6-phenyl-1,4-dihydrothieno[3,2-d]pyrimidin-3(2H)-yl]piperidine-1-carboxylate (6.61 g; compound B16) in DCM (50 ml) is reacted with a solution of hydrogen chloride in 1,4-dioxane (7.5 ml, 4.0 M) according to the procedure described in example B28 to afford the title compound as a solid.

MS: calc.: $C_{22}H_{23}N_5O_4S$ (453.52) found: [MH$^+$]=454.25

B41. 1-[(2-ethyl-1,3-oxazol-4-yl)methyl]-6-phenyl-3-(piperidin-4-yl)thieno[3,2-d]pyrimidine-2,4(1H,3H)-dione hydrochloride Tert-butyl 4-{1-[(2-ethyl-1,3-oxazol-4-yl)methyl]-2,4-dioxo-6-phenyl-1,4-dihydrothieno[3,2-d]pyrimidin-3(2H)-yl}piperidine-1-carboxylate (650 mg; compound B17) is dissolved in a solution of hydrogen chloride in 1,4-dioxane (10 ml, 6.8 M). The solution is stirred for 0.5 h at RT. The resulting precipitate is filtered off, washed with diethyl ether and dried in vacuo to give the title compound as a solid.

MS: calc.: $C_{23}H_{24}N_4O_3S$ (436.53) found: [MH$^+$]=437.20

B42. 1-[(1-Ethyl-1H-pyrazol-4-yl)methyl]-6-phenyl-3-(piperidin-4-yl)thieno[3,2-d]pyrimidine-2,4(1H,3H)-dione hydrochloride Tert-butyl 4-{1-[(1-ethyl-1H-pyrazol-4-yl)methyl]-2,4-dioxo-6-phenyl-1,4-dihydrothieno[3,2-d]pyrimidin-3(2H)-yl}piperidine-1-carboxylate (763 mg; compound B18) is dissolved in a solution of hydrogen chloride in 1,4-dioxane (10 ml, 4.0 M). The solution is stirred for 1 h at RT. The resulting precipitate is filtered off, washed with diethyl ether and dried to give the crude title compound. To remove impurities the free base is submitted to flash column chromatography (silica gel, eluent: MeOH). The purified free base of the title compound is taken up in diethyl ether and the solution is treated with chlorotrimethylsilane. The resulting precipitate is filtered off and dried to afford the title compound as a solid.

MS: calc.: $C_{23}H_{25}N_5O_2S$ (435.55) found: [MH$^+$]=436.19

B43. 1-[(1-Ethyl-1H-pyrazol-3-yl)methyl]-6-phenyl-3-(piperidin-4-yl)thieno[3,2-d]pyrimidine-2,4(1H,3H)-dione trifluoroacetate To a solution of tert-butyl 4-{1-[(1-ethyl-1H-pyrazol-3-yl)methyl]-2,4-dioxo-6-phenyl-1,4-dihydrothieno[3,2-d]pyrimidin-3(2H)-yl}piperidine-1-carboxylate (665 mg; compound B19) in DCM (5 ml) is added trifluoroacetic acid (5 ml). The reaction mixture is stirred for 3 h at RT. All volatile materials are removed in vacuo and the residue is taken up in diethyl ether. The resulting suspension is stirred at RT, then all solids are filtered off and dried in vacuo. The procedure is repeated a second time to afford the title compound as a solid.

MS: calc.: $C_{23}H_{25}N_5O_2S$ (435.55) found: [MH$^+$]=436.27

B44. 1-[(2-Methyl-1,3-thiazol-5-yl)methyl]-6-phenyl-3-(piperidin-4-yl)thieno[3,2-d]pyrimidine-2,4(1H,3H)-dione trifluoroacetate A solution of tert-butyl 4-{1-[(2-methyl-1,3-thiazol-5-yl)methyl]-2,4-dioxo-6-phenyl-1,4-dihydrothieno[3,2-d]pyrimidin-3(2H)-yl}piperidine-1-carboxylate (715 mg; compound B20) in DCM (15 ml) is reacted with trifluoroacetic acid (3 ml) according to the procedure described in example B43 to afford the title compound as a solid.

MS: calc.: $C_{22}H_{22}N_4O_2S_2$ (438.57) found: [MH$^+$]=439.23

B45. 1-[(2-Ethyl-2H-1,2,3-triazol-4-yl)methyl]-6-phenyl-3-(piperidin-4-yl)thieno[3,2-d]pyrimidine-2,4(1H,3H)-dione trifluoroacetate A solution of tert-butyl 4-{1-[(2-ethyl-2H-1,2,3-triazol-4-yl)methyl]-2,4-dioxo-6-phenyl-1,4-dihydrothieno[3,2-d]pyrimidin-3(2H)-yl}piperidine-1-carboxylate (2.10 g; compound B21) in DCM (50 ml) is reacted with trifluoroacetic acid (10 ml) according to the procedure described in example B43 to afford the title compound as a solid.

MS: calc.: $C_{22}H_{24}N_6O_2S$ (436.54) found: [MH$^+$]=437.28

B46. 1-[(3-Ethyl-1,2,4-thiadiazol-5-yl)methyl]-6-phenyl-3-(piperidin-4-yl)thieno[3,2-d]pyrimidine-2,4(1H,3H)-dione trifluoroacetate A solution of tert-butyl 4-{1-[(3-ethyl-1,2,4-thiadiazol-5-yl)methyl]-2,4-dioxo-6-phenyl-1,4-dihydrothieno[3,2-d]pyrimidin-3(2H)-yl}piperidine-1-carboxylate (321 mg; compound B22) in DCM (10 ml) is reacted with trifluoroacetic acid (2 ml) according to the procedure described in example B43 to afford the title compound as a solid.

MS: calc.: $C_{22}H_{23}N_5O_2S_2$ (453.59) found: [MH$^+$]=454.24

B47. 1-[(1-Ethyl-1H-1,2,3-triazol-4-yl)methyl]-6-phenyl-3-(piperidin-4-yl)thieno[3,2-d]pyrimidine-2,4(1H,3H)-dione trifluoroacetate A solution of tert-butyl 4-{1-[(1-ethyl-1H-1,2,3-triazol-4-yl)methyl]-2,4-dioxo-6-phenyl-1,4-dihydrothieno[3,2-d]pyrimidin-3(2H)-yl}piperidine-1-carboxylate (1.27 g; compound B23) in DCM (20 ml) is reacted with trifluoroacetic acid (5 ml) according to the procedure described in example B43 to afford the title compound as a solid.

MS: calc.: $C_{22}H_{24}N_6O_2S$ (436.54) found: [MH$^+$]=437.21

B48. 4-{[1-(Methoxymethyl)-1H-tetrazol-5-yl]methyl}-6-phenyl-3-(piperidin-4-yl)thieno[3,2-d]pyrimidine-2,4(1H,3H)-dione trifluoroacetate The title compound is prepared analogously as described for example B49 using tert-butyl 4-[1-{[1-(methoxymethyl)-1H-tetrazol-5-yl]methyl}-2,4-dioxo-6-phenyl-1,4-dihydrothieno[3,2-d]pyrimidin-3(2H)-yl]piperidine-1-carboxylate (196 mg; compound B24) and trifluoroacetic acid (409 pl) in DCM (1.2 ml). The title compound is obtained as a solid.

MS: calc.: $C_{21}H_{23}N_7O_3S$ (453.53) found: [MH+]=454.15

B49. 1-{[2-(Methoxymethyl)-2H-tetrazol-5-yl]methyl}-6-phenyl-3-(piperidin-4-yl)thieno[3,2-d]pyrimidine-2,4(1H,3H)-dione trifluoroacetate To a solution of tert-butyl 4-[1-{[2-(methoxymethyl)-2H-tetrazol-5-yl]methyl}-2,4-dioxo-6-phenyl-1,4-dihydrothieno[3,2-d]pyrimidin-3(2H)-yl]piperidine-1-carboxylate (270 mg; compound B24) in DCM (1.69 ml) is slowly added trifluoroacetic acid (0.56 ml) at 0° C. The reaction mixture is stirred for 10 min at 0° C. and for 50 min at RT. All volatiles are removed in vacuo to give the title compound as a solid, which is used for the next step without further purification.

MS: calc.: $C_{21}H_{23}N_7O_3S$ (453.53) found: [MH$^+$]=454.15

B50. Tert-butyl 4-(2,4-dioxo-6-phenyl-1,4-dihydrothieno[3,2-d]pyrimidin-3(2H)-yl)piperidine-1-carboxylate To a solution of tert-butyl 4-({[2-(methoxycarbonyl)-5-phenyl-3-thienyl]carbamoyl}amino)piperidine-1-carboxylate (2.00 g; compound B51) in MeOH (20 ml) is added sodium methoxide (300 mg) in three portions at RT. The reaction mixture is refluxed for 3 d and then allowed to come to RT. Ice cold water (30 ml) is added and the pH is adjusted to 4 by addition of citric acid. The resulting suspension is stirred for 2 h at RT; then the precipitate is filtered off, washed with water and dried in vacuo at 50° C. The crude title compound is taken up in MeOH (25 ml) and refluxed for 3 h. The hot suspension is filtered, and the filter cake is washed with hot MeOH three times and dried in vacuo at 45° C. to afford the title compound as a solid.

MS: calc.: $C_{22}H_{25}N_3O_4S$ (427.52) found: [MNa$^+$]=450.07; [MH$^+$-Boc]=328.24

B51. Tert-butyl 4-({[2-(methoxycarbonyl)-5-phenyl-3-thienyl]carbamoyl}amino)piperidine-1-carboxylate To a solution of triphosgene (421 mg) in THF (15 ml) under nitrogen atmosphere is added at 0° C. a solution of 3-amino- 5-phenylthiophene-2-carboxylate (1.00 g) in THF (10 ml) within 2 h. The mixture is stirred at 0° C. for 1 h and at RT for additional 14 h. The resulting suspension is cooled to 0° C. and a solution tert-butyl 4-aminopiperidine-1-carboxylate (867 mg) in THF (10 ml) is added dropwise. After 15 min at 0° C. DIPEA (1.75 ml) is slowly added. The reaction mixture is stirred for 15 min at 0° C. and for 2.5 h at RT and then washed with an aqueous sodium chloride solution (5% w/w, three times with 20 ml each) and with brine (20 ml). The organic layer is dried over magnesium sulfate. All volatile materials are removed in vacuo to give the title compound as a solid.

MS (ESI): calc.: $C_{23}H_{29}N_3O_5S$ (459.56) found: $[MH^+]$= 459.98; $[MH^+]$=482.22

B52. 1-(3-Ethyl-[1,2,4]oxadiazol-5-ylmethyl)-6-phenyl-3-piperidin-4-yl-1H-thieno[3,2-d]pyrimidine-2,4-dione A solution of tert-butyl 4-{1-[(3-ethyl-1,2,4-oxadiazol-5-yl)methyl]-2,4-dioxo-6-phenyl-1,4-dihydrothieno[3,2-d]pyrimidin-3(2H)-yl}piperidine-1-carboxylate (2.79 g; compound B7) in DCM (20 ml) is reacted with a solution of hydrogen chloride in 1,4-dioxane (15 ml, 4.0 M) for 12 h at RT. Subsequently water is added (50 ml) and the pH is adjusted to about pH14 by addition of aqueous sodium hydroxide solution (5 M). The mixture is extracted with DCM (3×100 ml) and the combined organic layers are dried over sodium sulfate. After filtration and evaporation of the solvent a residue is obtained which is recrystallized from DCM to yield the title compound as a solid.

B53. tert-butyl 4-(6-bromo-2,4-dioxo-1,4-dihydrothieno[3,2-d]pyrimidin-3(2H)-yl)piperidine-1-carboxylate To a solution of tert-butyl 4-({[5-bromo-2-(methoxycarbonyl)thiophen-3-yl]carbamoyl}amino)piperidine-1-carboxylate (37.6 g; compound B54a) in dry MeOH (205 ml) under argon atmosphere is added sodium methoxide (6.16 g) at RT. The reaction mixture is refluxed for 3 h, allowed to cool to RT and then poured into a solution of citric acid (21.9 g) in ice cold water (961 ml). The precipitated solid is filtered off, washed with ice cold water and dried in vacuo. The residue is taken up in MeOH (205 ml) and the resulting suspension is refluxed for 1 h. After cooling to RT all solids are filtered off, washed with MeOH and dried in vacuo to afford the title compound as a solid.

MS: calc.: $C_{16}H_{20}BrN_3O_4S$ (430.32) found: $[MH^+]$= 431.44; $[MH^+-Boc]$=331.98

B54a. tert-butyl 4-({[5-bromo-2-(methoxycarbonyl)thiophen-3-yl]carbamoyl}amino)piperidine-1-carboxylate Triphosgene (8.22 g) is dissolved in dry THF (345 ml) under argon atmosphere. The solution is cooled to 0° C. and a solution of methyl 3-amino-5-bromothiophene-2-carboxylate (19.8 g) in dry THF (173 ml) is added dropwise keeping the temperature below 10° C. The mixture is stirred for 14 h at RT. The reaction mixture is cooled to 0° C. again and a solution of tert-butyl 4-aminopiperidine-1-carboxylate (17.0 g) in dry THF (173 ml) is added within 15 min keeping the temperature below 10° C. After 15 min at 0° C. and additional 3 h at RT water (495 ml) and saturated aqueous sodium chloride solution (124 ml) are added. The organic layer is separated and the aqueous layer is extracted with THF three times (124 ml each). The combined organic layers are washed with half concentrated aqueous sodium chloride solution three times (250 ml each) and with saturated aqueous sodium chloride solution (250 ml) once. After drying over sodium sulfate all volatile materials are removed in vacuo to yield the title compound as a solid which is used without further purification.

B54b. Methyl 3-amino-5-bromothiophene-2-carboxylate

The title compound can be prepared starting from commercially available methyl 3-aminothiophene-2-carboxylate as described in Bioorganic & Medicinal Chemistry Letters, 17, (2007) 2535-2539.

B55. tert-butyl 4-[6-(1,3-benzodioxol-5-yl)-1-[(2-ethyl-2H-tetrazol-5-yl)methyl]-2,4-dioxo-1,4-dihydrothieno[3,2-d]pyrimidin-3(2H)-yl]piperidine-1-carboxylate Tert-butyl 4-{6-bromo-1-[(2-ethyl-2H-tetrazol-5-yl)methyl]-2,4-dioxo-1,4-dihydrothieno[3,2-d]pyrimidin-3(2H)-yl}piperidine-1-carboxylate (203 mg, B101), 1,3-benzodioxol-5-ylboronic acid (69 mg), dichlorobis(tricyclohexylphosphine)palladium (37 mg) and aqueous cesium carbonate solution (0.375 ml, 2.0 M) are placed in a microwave tube and DME (10 ml) is added. The reaction vessel is sealed and the mixture is subjected to microwave irradiation at 150° C. with stirring for 45 min. After addition of water and extraction with DCM the combined organic layers are washed with saturated aqueous sodium chloride solution and after filtration using a phase separator the organic layer is concentrated. The residue is purified by flash column chromatography [silica gel, elution gradient: cyclohexane/EtOAc, 100/0 to 50/50 to 30/70 (v/v)] to afford the title compound as a solid.

MS: calc.: $C_{27}H_{31}N_7O_6S$ (581.65) found: $[MH^+-Boc]$= 482.16

B56. tert-butyl 4-{1-[(2-ethyl-2H-tetrazol-5-yl)methyl]-6-(4-fluoro-2-methoxyphenyl)-2,4-dioxo-1,4-dihydrothieno[3,2-d]pyrimidin-3(2H)-yl}piperidine-1-carboxylate Tert-butyl 4-{6-bromo-1-[(2-ethyl-2H-tetrazol-5-yl)methyl]-2,4-dioxo-1,4-dihydrothieno[3,2-d]pyrimidin-3(2H)-yl}piperidine-1-carboxylate (405 mg, compound B101), (4-fluoro-2-methoxyphenyl)boronic acid (140 mg), dichlorobis(tricyclohexylphosphine)palladium (55 mg) and aqueous cesium bicarbonate solution (0.563 ml, 2.0 M) in DME (10 ml) are reacted according to the procedure described in example B55 to afford the title compound after purification by flash column chromatography [silica gel, elution gradient: cyclohexane/EtOAc, 100/0 to 50/50 to 30/70 (v/v)] as a solid.

MS: calc.: $C_{27}H_{32}FN_7O_5S$ (585.66) found: $[MH^+-Boc]$= 486.17

B57. tert-butyl 4-{1-[(2-ethyl-2H-tetrazol-5-yl)methyl]-6-(5-fluoro-2-methoxyphenyl)-2,4-dioxo-1,4-dihydrothieno[3,2-d]pyrimidin-3(2H)-yl}piperidine-1-carboxylate Tert-butyl 4-{6-bromo-1-[(2-ethyl-2H-tetrazol-5-yl)methyl]-2,4-dioxo-1,4-dihydrothieno[3,2-d]pyrimidin-3(2H)-yl}piperidine-1-carboxylate (811 mg, compound B101), (5-fluoro-2-methoxyphenyl)boronic acid (280 mg), dichlorobis(tricyclohexylphosphine)palladium (110 mg) and aqueous cesium carbonate solution (1.125 ml, 2.0 M) in DME (10 ml) are reacted according to the procedure described in example B55 to afford the title compound after purification by flash column chromatography [silica gel, elution gradient: cyclohexane/EtOAc, 100/0 to 50/50 to 30/70 (v/v)] as a solid.

MS: calc.: $C_{27}H_{32}FN_7O_5S$ (585.66) found: [MH$^+$-Boc]= 486.14

B58. tert-butyl 4-[6-(2,5-dimethoxyphenyl)-1-[(2-ethyl-2H-tetrazol-5-yl)methyl]-2,4-dioxo-1,4-dihydrothieno[3,2-d]pyrimidin-3(2H)-yl]piperidine-1-carboxylate Tert-butyl 4-[6-bromo-1-[(2-ethyl-2H-tetrazol-5-yl)methyl]-2,4-dioxo-1,4-dihydrothieno[3,2-d]pyrimidin-3(2H)-yl]piperidine-1-carboxylate (203 mg, compound B101), (2,5-dimethoxyphenyl)boronic acid (100 mg), dichlorobis(tricyclohexylphosphine)palladium (37 mg) and aqueous cesium carbonate solution (0.375 ml, 2.0 M) in DME (10 ml) are reacted according to the procedure described in example B55 to afford the title compound after purification by flash column chromatography [silica gel, elution gradient: cyclohexane/EtOAc, 100/0 to 50/50 to 30/70 (v/v)] as a solid.

MS: calc.: $C_{28}H_{35}N_7O_6S$ (597.69) found: [MH$^+$-Boc]= 498.18

B59. tert-butyl 4-{1-[(2-ethyl-2H-tetrazol-5-yl)methyl]-6-(2-fluorophenyl)-2,4-dioxo-1,4-dihydrothieno[3,2-d]pyrimidin-3(2H)-yl}piperidine-1-carboxylate Tert-butyl 4-{6-bromo-1-[(2-ethyl-2H-tetrazol-5-yl)methyl]-2,4-dioxo-1,4-dihydrothieno[3,2-d]pyrimidin-3(2H)-yl}piperidine-1-carboxylate (405 mg, compound B101), (2-fluorophenyl)boronic acid (116 mg), dichlorobis(tricyclohexylphosphine)palladium (55 mg) and aqueous cesium carbonate solution (0.563 ml, 2.0 M) in DME (10 ml) are reacted according to the procedure described in example B55 to afford the title compound after two times purification by flash column chromatography [silica gel, elution gradient: cyclohexane/EtOAc, 100/0 to 50/50 to 30/70 (v/v)] as a solid.

MS: calc.: $C_{26}H_{30}FN_7O_4S$ (555.63) found: [MH$^+$-Boc]= 456.16

B60. tert-butyl 4-{1-[(2-ethyl-2H-tetrazol-5-yl)methyl]-6-(4-fluorophenyl)-2,4-dioxo-1,4-dihydrothieno[3,2-d]pyrimidin-3(2H)-yl}piperidine-1-carboxylate Tert-butyl 4-{6-bromo-1-[(2-ethyl-2H-tetrazol-5-yl)methyl]-2,4-dioxo-1,4-dihydrothieno[3,2-d]pyrimidin-3(2H)-yl}piperidine-1-carboxylate (405 mg, compound B101), (4-fluorophenyl)boronic acid (105 mg), dichlorobis(tricyclohexylphosphine)palladium (28 mg) and aqueous cesium carbonate solution (0.563 ml, 2.0 M) in DME (10 ml) are reacted according to the procedure described in example B55 to afford the title compound after two times purification by flash column chromatography [silica gel, elution gradient: cyclohexane/EtOAc, 100/0 to 50/50 to 30/70 (v/v) and amino phase silica gel elution gradient: cyclohexane/EtOAc, 100/0 to 50/50 to 30/70 (v/v)] as a solid.

MS: calc.: $C_{26}H_{30}FN_7O_4S$ (555.63) found: [MH$^+$-Boc]= 456.15

B61. tert-butyl 4-[6-(2,3-difluorophenyl)-1-[(2-ethyl-2H-tetrazol-5-yl)methyl]-2,4-dioxo-1,4-dihydrothieno[3,2-d]pyrimidin-3(2H)-yl]piperidine-1-carboxylate Tert-butyl 4-{6-bromo-1-[(2-ethyl-2H-tetrazol-5-yl)methyl]-2,4-dioxo-1,4-dihydrothieno[3,2-d]pyrimidin-3(2H)-yl}piperidine-1-carboxylate (405 mg, compound B101), (2,3-difluorophenyl)boronic acid (118 mg), dichlorobis(tricyclohexylphosphine)palladium (28 mg) and aqueous cesium carbonate solution (0.563 ml, 2.0 M) in DME (10 ml) are reacted according to the procedure described in example B55 to afford the title compound after two times purification by flash column chromatography [silica gel, elution gradient: cyclohexane/EtOAc, 100/0 to 50/50 to 30/70 (v/v) and amino phase silica gel elution gradient: cyclohexane/EtOAc, 100/0 to 50/50 to 30/70 (v/v)] as a solid.

MS): calc.: $C_{26}H_{29}F_2N_7O_4S$ (573.62) found: [MH$^+$-Boc]= 474.16

B62. tert-butyl 4-[6-(4-fluoro-2-methoxyphenyl)-1-{[3-(methoxymethyl)-1,2,4-oxadiazol-5-yl]methyl}-2,4-dioxo-1,4-dihydrothieno[3,2-d]pyrimidin-3(2H)-yl]piperidine-1-carboxylate To a solution of tert-butyl 4-[6-(4-fluoro-2-methoxyphenyl)-2,4-dioxo-1,4-dihydrothieno[3,2-d]pyrimidin-3(2H)-yl]piperidine-1-carboxylate (1.0 g, compound B63) and 5-(chloromethyl)-3-(methoxymethyl)-1,2,4-oxadiazole (342 mg) in dry DMF (20 ml) is added potassium carbonate (291 mg). The mixture is stirred for 2 h at 100° C. and subsequently poured into ice-cold water. After stirring for 5 min the resulting precipitate is filtered off and dried in vacuo. The residue is purified by flash column chromatography [amino phase silica gel, elution gradient: cyclohexane/EtOAc, 100/0 to 50/50 (v/v)] to afford the title compound as a solid.

MS: calc.: $C_{28}H_{32}FN_5O_7S$ (601.65) found: [MH$^+$-Boc]= 502.17

B63. tert-butyl 4-[6-(4-fluoro-2-methoxyphenyl)-2,4-dioxo-1,4-dihydrothieno[3,2-d]pyrimidin-3(2H)-yl]piperidine-1-carboxylate Tert-butyl 4-(6-bromo-2,4-dioxo-1,4-dihydrothieno[3,2-d]pyrimidin-3(2H)-yl)piperidine-1-carboxylate (3.00 g, compound B53), (4-fluoro-2-methoxyphenyl)boronic acid (1.30 g) and dichlorobis(tricyclohexylphosphine)palladium (257 mg) are reacted in the presence of aqueous cesium carbonate solution (5.23 ml, 2.0 M) in DME (12 ml) according to the procedure described in example B55. The reaction mixture is poured into ice-cold water and the mixture is extracted with DCM. The organic layer is washed with saturated aqueous sodium chloride solution and filtered using a phase separator. All volatile materials are removed in vacuo to yield the title compound as a solid.

MS: calc.: $C_{23}H_{26}FN_3O_5S$ (475.53) found: [MH$^+$-Boc]= 376.18

B64. tert-butyl 4-[6-(1,3-benzodioxol-5-yl)-1-[(3-ethyl-1,2,4-oxadiazol-5-yl)methyl]-2,4-dioxo-1,4-dihydrothieno[3,2-d]pyrimidin-3(2H)-yl]piperidine-1-carboxylate Tert-butyl 4-{6-bromo-1-[(3-ethyl-1,2,4-oxadiazol-5-yl)methyl]-2,4-dioxo-1,4-dihydrothieno[3,2-d]pyrimidin-3(2H)-yl}piperidine-1-carboxylate 405 mg, compound B99), 1,3-benzodioxol-5-ylboronic acid (368 mg), dichlorobis(tricyclohexylphosphine)palladium (137 mg) and aqueous cesium carbonate solution (1.39 ml, 2.0 M) in dioxane (18 ml) are reacted according to the procedure described in example B55 to afford the title compound after purification by flash column chromatography [silica gel, elution gradient: cyclohexane/EtOAc, 80/20 to 50/50 (v/v)] as a solid.

MS: calc.: $C_{28}H_{31}N_5O_7S$ (581.65) found: [MH$^+$]=582.34; [MH$^+$-Boc]=482.01

B65. tert-butyl 4-{1-[(3-ethyl-1,2,4-oxadiazol-5-yl)methyl]-6-(4-fluorophenyl)-2,4-dioxo-1,4-dihydrothieno[3,2-d]pyrimidin-3(2H)-yl}piperidine-1-carboxylate Tert-butyl 4-{6-bromo-1-[(3-ethyl-1,2,4-oxadiazol-5-yl)methyl]-2,4-dioxo-1,4-dihydrothieno[3,2-d]pyrimidin-3(2H)-yl}piperidine-1-carboxylate (500 mg, compound B99), 2-(4-fluorophenyl)-4,4,5,5-tetramethyl-1,3,2-dioxaborolane (246 mg), dichlorobis(tricyclohexylphosphine)palladium (68 mg) and aqueous cesium carbonate solution (0.694 ml, 2.0 M) in dioxane (18 ml) are reacted according to the procedure described in example B55 to afford the title compound after purification by flash column chromatography [silica gel, elution gradient: DCM/EtOH, 100/0 to 70/30 (v/v)] as a solid.

MS: calc.: $C_{27}H_{30}FN_5O_5S$ (555.63) found: [MH$^+$]=556.40; [MH$^+$-Boc]=456.21

B66. tert-butyl 4-{1-[(3-ethyl-1,2,4-oxadiazol-5-yl)methyl]-6-(2-fluorophenyl)-2,4-dioxo-1,4-dihydrothieno[3,2-d]pyrimidin-3(2H)-yl}piperidine-1-carboxylate Tert-butyl 4-{6-bromo-1-[(3-ethyl-1,2,4-oxadiazol-5-yl)methyl]-2,4-dioxo-1,4-dihydrothieno[3,2-d]pyrimidin-3(2H)-yl}piperidine-1-carboxylate (250 mg, compound B99), (2-fluorophenyl)boronic acid (65 mg), dichlorobis(tricyclohexylphosphine)palladium (17 mg) and aqueous cesium carbonate solution (0.35 ml, 2.0 M) are placed in a microwave tube and DME (8 ml) is added. The reaction vessel is sealed and the mixture is subjected to microwave irradiation at 150° C. with stirring for 20 min. The mixture is allowed to cool to RT and additional (2-fluorophenyl)boronic acid (19 mg) and dichlorobis(tricyclohexylphosphine)palladium (9 mg) are added. The mixture is again subjected to microwave irradiation at 150° C. with stirring for 20 min and then allowed to cool to RT. After addition of water and extraction with EtOAc the combined organic layers are washed with saturated aqueous sodium chloride solution and dried over sodium sulfate. All volatile materials are removed in vacuo and the residue is purified by flash column chromatography [silica gel, eluent: cyclohexane/EtOAc, 3/1 (v/v)] to afford tert-butyl 4-{1-[(3-ethyl-1,2,4-oxadiazol-5-yl)methyl]-6-(2-fluorophenyl)-2,4-dioxo-1,4-dihydrothieno[3,2-d]pyrimidin-3(2H)-yl}piperidine-1-carboxylate as a solid.

MS: calc.: $C_{27}H_{30}FN_5O_5S$ (555.63) found: [MNa$^+$]=578.02

B67. tert-butyl 4-[6-(3,4-difluorophenyl)-1-[(3-ethyl-1,2,4-oxadiazol-5-yl)methyl]-2,4-dioxo-1,4-dihydrothieno[3,2-d]pyrimidin-3(2H)-yl]piperidine-1-carboxylate Tert-butyl 4-{6-bromo-1-[(3-ethyl-1,2,4-oxadiazol-5-yl)methyl]-2,4-dioxo-1,4-dihydrothieno[3,2-d]pyrimidin-3(2H)-yl}piperidine-1-carboxylate (540 mg, compound B99), (3,4-difluorophenyl)boronic acid (158 mg), dichlorobis(tricyclohexylphosphine)palladium (37 mg) and aqueous cesium carbonate solution (489 mg, 2.0 M) in DME (10 ml) are reacted according to the procedure described in example B55 to afford the title compound after purification by flash column chromatography [silica gel, elution gradient: cyclohexane/EtOAc, 70/30 to 50/50 to 30/70 (v/v)] as a solid.

MS: calc.: $C_{27}H_{29}F_2N_5O_5S$ (573.62) found: [MH$^+$]=596.00; [MH$^+$-Boc]=474.10

B68. tert-butyl 4-[1-{[3-(3-methoxypropyl)-1,2,4-oxadiazol-5-yl]methyl}-2,4-dioxo-6-phenyl-1,4-dihydrothieno[3,2-d]pyrimidin-3(2H)-yl]piperidine-1-carboxylate To a solution of [3-(3-methoxypropyl)-1,2,4-oxadiazol-5-yl]methanol (450 mg, compound D23) in dry DCM (5 ml) is added tetrabromomethane (1.00 g) and triphenylphosphane (790 mg) and the reaction mixture is stirred for 15 min at RT. This solution is added to a stirred suspension of tert-butyl dioxo-6-phenyl-1,4-dihydrothieno[3,2-d]pyrimidin-3(2H)-yl)piperidine-1-carboxylate (800 mg, compound B50) and potassium carbonate (640 mg) in DMF. The mixture is stirred for 3 h at 65° C. and subsequently all volatile materials are removed in vacuo. The residue is taken up in EtOAc/cyclohexane (1/1, (v/v)) and all insoluble components are filtered off. The filtrate is concentrated in vacuo and the residue is purified by flash column chromatography [silica gel, eluent: cyclohexane/EtOAc, 1/1 (v/v)] to afford the title compound as a solid.

MS: calc.: $C_{29}H_{35}N_5O_6S$ (581.69) found: [MH$^+$]=582.66; [MH$^+$-Boc]=482.11

B69. tert-butyl 4-[2,4-dioxo-6-phenyl-1-{[3-(propoxymethyl)-1,2,4-oxadiazol-5-yl]methyl}-1,4-dihydrothieno[3,2-d]pyrimidin-3(2H)-yl]piperidine-1-carboxylate To a solution of [3-(propoxymethyl)-1,2,4-oxadiazol-5-yl]methanol (250 mg, compound D22) and CBr$_4$ (620 mg) in DCM (5 ml) are added triphenylphosphine (490 mg) and the reaction mixture is stirred for 15 min at RT. This solution is added to a stirred suspension of tert-butyl 4-(2,4-dioxo-6-phenyl-1,4-dihydrothieno[3,2-d]pyrimidin-3(2H)-yl)piperidine-1-carboxylate (0.5 g; compound B50) and potassium carbonate (323 mg) in DMF and the reaction mixture is stirred for 3 h at 65° C. Afterwards the solvent is removed under vacuo, the resulting residue is treated with EtOAc/cyclohexane (1:1) and the suspension is filtered. The filtrate is purified by flash chromatography (silica gel, eluent EtOAc/cyclohexane 1:1) and the product fraction are washed with diethylether to give the title compound as a solid.

MS: calc.: $C_{29}H_{35}N_5O_6S$ (581.69) found: [MH$^+$]=582.77; [MH$^+$-Boc]=482.09

B70. tert-butyl 4-{1-[(1-methyl-1H-1,2,4-triazol-3-yl)methyl]-2,4-dioxo-6-phenyl-1,4-dihydrothieno[3,2-d]pyrimidin-3(2H)-yl}piperidine-1-carboxylate Step 1

To a solution of (1-methyl-1H-1,2,4-triazol-3-yl)methanol (489 mg, compound D24) in dry DCM (0.6 ml) are added tetrabromomethane (1.87 g) and triphenylphosphane (1.48 g). The mixture is stirred for 1 h at RT to give 3-(bromomethyl)-1-methyl-1H-1,2,4-triazole. The reaction mixture is directly used in step 2.

Step 2

To the solution from step 1 are added tert-butyl 4-(2,4-dioxo-6-phenyl-1,4-dihydrothieno[3,2-d]pyrimidin-3(2H)- yl)piperidine-1-carboxylate (1.00 g, compound B50), dry DMF (150 ml) and potassium carbonate (1.23 g). The mixture is stirred for 4 h at 50° C. and subsequently poured into ice-cold water. After stirring for 5 min the resulting precipitate is filtered off and dried in vacuo. The residue is taken up in EtOAc, filtered off and dried in vacuo to afford the title compound as a solid.

MS: calc.: $C_{26}H_{30}N_6O_4S$ (522.63) found: [MH$^+$]=523.88; [MH$^+$-Boc]=423.13

B71. tert-butyl 4-{1-[(1-methyl-1H-imidazol-2-yl)methyl]-2,4-dioxo-6-phenyl-1,4-dihydrothieno[3,2-d]pyrimidin-3(2H)-yl}piperidine-1-carboxylate To a solution of tert-butyl 4-(2,4-dioxo-6-phenyl-1,4-dihydrothieno[3,2-d]pyrimidin-3(2H)-yl)piperidine-1-carboxylate (1.16 g, compound B50) and 2-(chloromethyl)-1-methyl-1H-imidazole hydrochloride (500 mg, compound D31) in dry DMF (15 ml) is added potassium carbonate (753 mg). The mixture is stirred for 3 h at 50° C. and subsequently poured into ice-cold water. After stirring for 5 min the resulting precipitate is filtered off and dried in vacuo. The residue is taken up in EtOAc, filtered off and dried in vacuo to afford the title compound as a solid MS: calc.: $C_{27}H_{31}N_5O_4S$ (521.64) found: [MH$^+$]=522.98; [MH$^+$-Boc]=422.15

B72. tert-butyl 4-{1-[(4-methyl-1,3-oxazol-5-yl)methyl]-2,4-dioxo-6-phenyl-1,4-dihydrothieno[3,2-d]pyrimidin-3(2H)-yl}piperidine-1-carboxylate To a solution of (4-methyl-1,3-oxazol-5-yl)methanol (489 mg, compound D26) in dry DCM (0.6 ml) are added tetrabromomethane (1.87 g) and triphenylphosphane (1.48 g) and the mixture is stirred for 1 h at RT. Subsequently the reaction mixture is transferred to a microwave vial and tert-butyl 4-(2,4-dioxo-6-phenyl-1,4-dihydrothieno[3,2-d]pyrimidin-3(2H)-yl)piperidine-1-carboxylate (1.00 g, compound B50), dry DMF (150 ml) and potassium carbonate (1.23 g) are added. The mixture is stirred for 4 h at 50° C. and subsequently poured into ice-cold water. After stirring for 5 min the resulting precipitate is filtered off, taken up in EtOAc and dried in vacuo at −78° C. The residue is taken up in EtOAc and dried in vacuo three more times to afford the title compound as a solid.

MS: calc.: $C_{27}H_{30}N_4O_5S$ (522.62) found: [MH$^+$]=523.73; [MH$^+$-Boc]=423.12

B73. tert-butyl 4-{1-[(5-ethylthiophen-2-yl)methyl]-2,4-dioxo-6-phenyl-1,4-dihydrothieno[3,2-d]pyrimidin-3(2H)-yl}piperidine-1-carboxylate To a solution of tert-butyl 4-(2,4-dioxo-6-phenyl-1,4-dihydrothieno[3,2-d]pyrimidin-3(2H)-yl)piperidine-1-carboxylate (1.20 g, compound B50) and 2-(chloromethyl)-5-ethylthiophene (480 mg, compound D27) in dry DMF (15 ml) is added potassium carbonate (778 mg). The mixture is stirred for 1 h at 100° C. and subsequently poured into ice-cold water. After stirring for 5 min the resulting precipitate is filtered off and dried in vacuo. The residue is purified by flash column chromatography [silica gel, eluent: cyclohexane/EtOAc, 5/1 (v/v)] to afford the title compound as a solid.

MS: calc.: $C_{29}H_{33}N_3O_4S_2$ (551.73) found: [MH$^+$]=552.71; [MH$^+$-Boc]=452.14

B74. tert-butyl 4-{1-[(3-methylthiophen-2-yl)methyl]-2,4-dioxo-6-phenyl-1,4-dihydrothieno[3,2-d]pyrimidin-3(2H)-yl}piperidine-1-carboxylate According to the procedure described for compound B71 tert-butyl 4-(2,4-dioxo-6-phenyl-1,4-dihydrothieno[3,2-d]pyrimidin-3(2H)-yl)piperidine-1-carboxylate (1.09 g, compound B50) is reacted with 2-(chloromethyl)-3-methylthiophene (410 mg, compound D28) in the presence of potassium carbonate (778 mg) in dry DMF (14 ml) for 1 h at 100° C. to afford the title compound as a solid.

MS: calc.: $C_{28}H_{31}N_3O_4S_2$ (537.70) found: [MH$^+$]=538.70; [MH$^+$-Boc]=438.07

B75. tert-butyl 4-{1-[(5-ethyl-2H-tetrazol-2-yl)methyl]-2,4-dioxo-6-phenyl-1,4-dihydrothieno[3,2-d]pyrimidin-3(2H)-yl}piperidine-1-carboxylate To a solution of 5-ethyl-2-{[(tripropan-2-ylsilyl)oxy]methyl}-2H-tetrazole (1.53 g; compound D30) in DCM is added n-Bu$_4$NF (5.34 ml of 1M solution in THF) and stirred for 30 min at RT. After completion of the reaction (TLC monitoring, eluent system: EtOAc/c-Hexan, 1/6, (v/v)) CBr$_4$ (2.13 g) and PPh$_3$ (1.68 g) are added and the reaction mixture is stirred for 30 min at RT. The reaction mixture is added to a mixture of tert-butyl 4-(2,4-dioxo-6-phenyl-1,4-dihydrothieno[3,2-d]pyrimidin-3(2H)-yl)piperidine-1-carboxylate (913 mg; compound B50) and potassium carbonate (1.33 g) in DMF and the combined reaction mixture is stirred for 12 h at 80° C. All volatiles are evaporated under reduced pressure and the resulting residue is purified by flash chromatography (silica gel, eluent EtOAc/cyclohexane, 1/6, (v/v)) to give the title compound as a solid.

MS: calc.: $C_{26}H_{31}N_7O_4S$ (537.64) found: [MH$^+$]=538.96; [MH$^+$-Boc]=438.11

B76. tert-butyl 4-{1-[(5-tert-butyl-1,3,4-oxadiazol-2-yl)methyl]-2,4-dioxo-6-phenyl-1,4-dihydrothieno[3,2-d]pyrimidin-3(2H)-yl}piperidine-1-carboxylate To a solution of tert-butyl 4-(2,4-dioxo-6-phenyl-1,4-dihydrothieno[3,2-d]pyrimidin-3(2H)-yl)piperidine-1-carboxylate (2.565 g, compound B50) and 2-tert-butyl-5-(chloromethyl)-1,3,4-oxadiazole (1050 mg, compound D29) in dry DMF (50 ml) is added potassium carbonate (829 mg). The mixture is stirred for 3 h at 100° C. and subsequently poured into ice-cold water. After stirring for 5 min the resulting precipitate is filtered off and dried in vacuo to afford the title compound as a solid MS: calc.: $C_{23}H_{35}N_5O_5S$ (565.69) found: [MH$^+$]=565.97; [MH$^+$-Boc]=466.22

B77. 6-(1,3-benzodioxol-5-yl)-1-[(2-ethyl-2H-tetrazol-5-yl)methyl]-3-(piperidin-4-yl)thieno[3,2-d]pyrimidine-2,4(1H,3H)-dione hydrochloride To a solution of tert-butyl 4-[6-(1,3-benzodioxol-5-yl)-1-[(2-ethyl-2H-tetrazol-5-yl)methyl]-2,4-dioxo-1,4-dihydrothieno[3,2-d]pyrimidin-3(2H)-yl]piperidine-1-carboxylate (239 mg; compound B50) in 1,4 dioxane (6 ml) is added a solution of hydrogen chloride in 1,4-dioxane (1.028 ml, 4.0 M). The reaction mixture is stirred for 3 d at RT. All volatiles are evaporated and the residue is treated with DCM and after removal of the solvent under reduced pressure the title compound is obtained as a solid.

MS: calc.: $C_{22}H_{23}N_7O_4S$ (481.53) found: [MH$^+$-Boc]= 482.16

B78. 1-[(2-ethyl-2H-tetrazol-5-yl)methyl]-6-(4-fluoro-2-methoxyphenyl)-3-(piperidin-4-yl)thieno[3,2-d]pyrimidine-2,4(1H,3H)-dione hydrochloride To a solution of tert-butyl 4-{1-[(2-ethyl-2H-tetrazol-5-yl)methyl]-6-(4-fluoro-2-methoxyphenyl)-2,4-dioxo-1,4-dihydrothieno[3,2-d]pyrimidin-3(2H)-yl}piperidine-1-carboxylate (432 mg, compound B56) in 1,4 dioxane (10 ml) is added a solution of hydrogen chloride in 1,4-dioxane (1.845 ml, 4.0 M). The reaction mixture is stirred for 3 d at RT. All volatiles are evaporated, the residue is treated with DCM and after removal of the solvent under reduced pressure the title compound is obtained as a solid.
MS: calc.: $C_{22}H_{24}FN_7O_3S$ (485.54) found: [MH$^+$]=486.18

B79. 1-[(2-ethyl-2H-tetrazol-5-yl)methyl]-6-(5-fluoro-2-methoxyphenyl)-3-(piperidin-4-yl)thieno[3,2-d]pyrimidine-2,4(1H,3H)-dione hydrochloride To a solution of tert-butyl 4-{1-[(2-ethyl-2H-tetrazol-5-yl)methyl]-6-(5-fluoro-2-methoxyphenyl)-2,4-dioxo-1,4-dihydrothieno[3,2-d]pyrimidin-3(2H)-yl}piperidine-1-carboxylate (435 mg; compound B57) in 1,4 dioxane (10 ml) is added a solution of hydrogen chloride in 1,4-dioxane (1.858 ml, 4.0 M). The reaction mixture is stirred for 3 d at RT. To complete the reaction an additional amount of a solution of hydrogen chloride in 1,4-dioxane (0.9 ml, 4.0 M) is added and the mixture is stirred for 1 h at 60° C. Subsequently all volatiles are evaporated and the residue is treated with DCM and after removal of the solvent under reduced pressure the title compound is obtained as a solid.
MS: calc.: $C_{22}H_{24}FN_7O_3S$ (485.54) found: [MH$^+$]=486.16

B80. 6-(2,5-dimethoxyphenyl)-1-[(2-ethyl-2H-tetrazol-5-yl)methyl]-3-(piperidin-4-yl)thieno[3,2-d]pyrimidine-2,4(1H,3H)-dione hydrochloride Tert-butyl 4-[6-(2,5-dimethoxyphenyl)-1-[(2-ethyl-2H-tetrazol-5-yl)methyl]-2,4-dioxo-1,4-dihydrothieno[3,2-d]pyrimidin-3(2H)-yl]piperidine-1-carboxylate (331 mg, compound B58) and a solution of hydrogen chloride in 1,4-dioxane (1.4 ml+0.9 ml, 4.0 M) in 1,4 dioxane (20 ml) are reacted according to the procedure described in example B79 to afford the title compound.
MS: calc.: $C_{23}H_{27}N_7O_4S$ (497.58) found: [MH$^+$]=498.14

B81. 1-[(2-ethyl-2H-tetrazol-5-yl)methyl]-6-(2-fluorophenyl)-3-(piperidin-4-yl)thieno[3,2-d]pyrimidine-2,4(1H,3H)-dione hydrochloride Tert-butyl 4-{1-[(2-ethyl-2H-tetrazol-5-yl)methyl]-6-(2-fluorophenyl)-2,4-dioxo-1,4-dihydrothieno[3,2-d]pyrimidin-3(2H)-yl}piperidine-1-carboxylate (364 mg, compound B59) and a solution of hydrogen chloride in 1,4-dioxane (1.6 ml, 4.0 M) in 1,4 dioxane (10 ml) are reacted according to the procedure described in example B78 to afford the title compound.
MS: calc.: $C_{21}H_{22}FN_7O_2S$ (455.52) found: [MH$^+$]=456.15

B82. 1-[(2-ethyl-2H-tetrazol-5-yl)methyl]-6-(4-fluorophenyl)-3-(piperidin-4-yl)thieno[3,2-d]pyrimidine-2,4(1H,3H)-dione hydrochloride Tert-butyl 4-{1-[(2-ethyl-2H-tetrazol-5-yl)methyl]-6-(4-fluorophenyl)-2,4-dioxo-1,4-dihydrothieno[3,2-d]pyrimidin-3(2H)-yl}piperidine-1-carboxylate (292 mg, compound B60) and a solution of hydrogen chloride in 1,4-dioxane (1.3 ml, 4.0 M) in 1,4 dioxane (8 ml) are reacted according to the procedure described in example B78 to afford the title compound.
MS: calc.: $C_{21}H_{22}FN_7O_2S$ (455.52) found: [MH$^+$]=456.14

B83. 6-(2,3-difluorophenyl)-1-[(2-ethyl-2H-tetrazol-5-yl)methyl]-3-(piperidin-4-yl)thieno[3,2-d]pyrimidine-2,4(1H,3H)-dione hydrochloride Tert-butyl 4-[6-(2,3-difluorophenyl)-1-[(2-ethyl-2H-tetrazol-5-yl)methyl]-2,4-dioxo-1,4-dihydrothieno[3,2-d]pyrimidin-3(2H)-yl]piperidine-1-carboxylate (44 mg, compound B61) and a solution of hydrogen chloride in 1,4-dioxane (0.2 ml+0.9 ml, 4.0 M) in 1,4 dioxane (2 ml) are reacted according to the procedure described in example B79 to afford the title compound.
MS: calc.: $C_{21}H_{21}F_2N_7O_2S$ (473.51) found: [MH$^+$]=474.15

B84. 6-(4-fluoro-2-methoxyphenyl)-1-{[3-(methoxymethyl)-1,2,4-oxadiazol-5-yl]methyl}-3-(piperidin-4-yl)thieno[3,2-d]pyrimidine-2,4(1H,3H)-dione hydrochloride To a solution of tert-butyl 4-[6-(4-fluoro-2-methoxyphenyl)-1-{[3-(methoxymethyl)-1,2,4-oxadiazol-5-yl]methyl}-2,4-dioxo-1,4-dihydrothieno[3,2-d]pyrimidin-3(2H)-yl]piperidine-1-carboxylate (890 mg, compound B62) in 1,4 dioxane (13 ml) is added a solution of hydrogen chloride in 1,4-dioxane (7.4 ml, 4.0 M). The reaction mixture is stirred for 2.5 h at RT. All volatiles are evaporated and the residue is treated with DCM and after removal of the solvent under reduced pressure the title compound is obtained as a solid.
MS: calc.: $C_{23}H_{24}FN_5O_5S$ (501.53) found: [MH$^+$]=502.15

B85. 1-[(3-ethyl-1,2,4-oxadiazol-5-yl)methyl]-6-(4-fluoro-2-methoxyphenyl)-3-(piperidin-4-yl)thieno[3,2-d]pyrimidine-2,4(1H,3H)-dione hydrochloride Step 1
Tert-butyl 4-{6-bromo-1-[(3-ethyl-1,2,4-oxadiazol-5-yl)methyl]-2,4-dioxo-1,4-dihydrothieno[3,2-d]pyrimidin-3(2H)-yl}piperidine-1-carboxylate (1.00 g, compound B99), (4-fluoro-2-methoxyphenyl)boronic acid (409 mg), dichlorobis(tricyclohexylphosphine)palladium (137 mg) and aqueous cesium carbonate solution (1.4 ml, 2.0 M) are placed in a microwave tube and DME (15 ml) is added.

The reaction vessel is sealed and the mixture is subjected to microwave irradiation at 150° C. with stirring for 40 min. The mixture is allowed to cool to RT and then filtered over a plug of silica (eluent: DCM). After removal of all volatile materials the residue is purified by flash column chromatography [silica gel, eluation gradient: DCM/EtOAc, 1/0 to 4/1 (v/v)] to afford tert-butyl 4-{1-[(3-ethyl-1,2,4-oxadiazol-5-yl)methyl]-6-(4-fluoro-2-methoxyphenyl)-2,4-dioxo-1,4-dihydrothieno[3,2-d]pyrimidin-3(2H)-yl}piperidine-1-carboxylate as a solid which is used for step 2.

Step 2
A solution of tert-butyl 4-{1-[(3-ethyl-1,2,4-oxadiazol-5-yl)methyl]-6-(4-fluoro-2-methoxyphenyl)-2,4-dioxo-1,4-dihydrothieno[3,2-d]pyrimidin-3(2H)-yl}piperidine-1-carboxylate (719 mg) from step 1 in DCM (15 ml) is reacted with a solution of hydrogen chloride in 1,4-dioxane (4.3 ml, 4.0 M)

according to the procedure described in example B28 to afford the title compound as a solid.

MS: calc.: $C_{23}H_{24}FN_5O_4S$ (485.53) found: [MH$^+$]=486.23

B86. 6-(1,3-benzodioxol-5-yl)-1-[(3-ethyl-1,2,4-oxadiazol-5-yl)methyl]-3-(piperidin-4-yl)thieno[3,2-d]pyrimidine-2,4(1H,3H)-dione hydrochloride To a solution of tert-butyl 4-[6-(1,3-benzodioxol-5-yl)-1-[(3-ethyl-1,2,4-oxadiazol-5-yl)methyl]-2,4-dioxo-1,4-dihydrothieno[3,2-d]pyrimidin-3(2H)-yl]piperidine-1-carboxylate (3.75 g; compound B64) in 1,4 dioxane (130 ml) is added a solution of hydrogen chloride in 1,4-dioxane (31 ml, 4.0 M). The reaction mixture is stirred for 12 h at RT. To complete the reaction an additional amount of a solution of hydrogen chloride in 1,4-dioxane (5.0 ml, 4.0 M) is added and the mixture is stirred for 20 h at RT. Subsequently the suspension is filtered to give title compound as a solid.

MS: calc.: $C_{23}H_{23}N_5O_5S$ (481.53) found: [MH$^+$]=482.18

B87. 1-[(3-ethyl-1,2,4-oxadiazol-5-yl)methyl]-6-(4-fluorophenyl)-3-(piperidin-4-yl)thieno[3,2-d]pyrimidine-2,4(1H,3H)-dione hydrochloride To a solution of tert-butyl 4-{1-[(3-ethyl-1,2,4-oxadiazol-5-yl)methyl]-6-(4-fluorophenyl)-2,4-dioxo-1,4-dihydrothieno[3,2-d]pyrimidin-3(2H)-yl}piperidine-1-carboxylate (360 mg, compound B65) in 1,4 dioxane (13 ml) is added a solution of hydrogen chloride in 1,4-dioxane (3 ml, 4.0 M) and the reaction mixture is stirred for 48 h at RT. Subsequently the suspension is filtered to give title compound as a solid.

MS: calc.: $C_{22}H_{22}FN_5O_3S$ (455.51) found: [MH$^+$]=456.23

B88. 1-[(3-ethyl-1,2,4-oxadiazol-5-yl)methyl]-6-(2-fluorophenyl)-3-(piperidin-4-yl)thieno[3,2-d]pyrimidine-2,4(1H,3H)-dione hydrochloride Step 1
Tert-butyl 4-{6-bromo-1-[(3-ethyl-1,2,4-oxadiazol-5-yl)methyl]-2,4-dioxo-1,4-dihydrothieno[3,2-d]pyrimidin-3(2H)-yl}piperidine-1-carboxylate (1.00 g, B99), (2-fluorophenyl)boronic acid (337 mg), dichlorobis(tricyclohexylphosphine)palladium (137 mg) and aqueous cesium carbonate solution (1.4 ml, 2.0 M) are placed in a microwave tube and DME (15 ml) is added. The reaction vessel is sealed and the mixture is subjected to microwave irradiation at 150° C. with stirring for 40 min. The mixture is allowed to cool to RT, additional (2-fluorophenyl)boronic acid (52 mg) is added and the vessel is subjected to microwave irradiation at 150° C. for additional 40 min. The mixture is allowed to cool to RT and then filtered over a plug of silica (eluent: DCM). After removal of all volatile materials the residue is purified by flash column chromatography [silica gel, eluation gradient: cyclohexane/EtOAc, 1/0 to 2/3 (v/v)] to afford tert-butyl 4-{1-[(3-ethyl-1,2,4-oxadiazol-5-yl)methyl]-6-(2-fluorophenyl)-2,4-dioxo-1,4-dihydrothieno[3,2-d]pyrimidin-3(2H)-yl}piperidine-1-carboxylate which is crystallized from toluene and directly used for step 2.

Step 2
To a solution of tert-butyl 4-{1-[(3-ethyl-1,2,4-oxadiazol-5-yl)methyl]-6-(2-fluorophenyl)-2,4-dioxo-1,4-dihydrothieno[3,2-d]pyrimidin-3(2H)-yl}piperidine-1-carboxylate (333 mg) from step 1 in DCM (8 ml) is added a solution of hydrogen chloride in 1,4-dioxane (2.5 ml, 4.0 M). The reaction mixture is stirred for 12 h at RT. The precipitate is filtered off and dried in vacuo at 40° C. to afford the title compound which is purified by preparative HPLC to give the title compound as a solid.

MS: calc.: $C_{22}H_{22}FN_5O_3S$ (455.51) found: [MH$^+$]=456.17

B89. 6-(3,4-difluorophenyl)-1-[(3-ethyl-1,2,4-oxadiazol-5-yl)methyl]-3-(piperidin-4-yl)thieno[3,2-d]pyrimidine-2,4(1H,3H)-dione hydrochloride To a solution of tert-butyl 4-[6-(3,4-difluorophenyl)-1-[(3-ethyl-1,2,4-oxadiazol-5-yl)methyl]-2,4-dioxo-1,4-dihydrothieno[3,2-d]pyrimidin-3(2H)-yl]piperidine-1-carboxylate (400 mg, compound B67) in 1,4-dioxane (7 ml) is added a solution of hydrogen chloride in 1,4-dioxane (1.7 ml, 4.0 M). The reaction mixture is stirred for 3 h at 50° C. and subsequently for 12 h at RT. In order to complete the reaction an additional amount of a solution of hydrogen chloride in 1,4-dioxane (0.9 ml, 4.0 M) is added and the reaction mixture is stirred for 1 h at 65° C. Afterwards all volatiles are removed under reduced pressure to afford the title compound as a solid.

MS: calc.: $C_{22}H_{21}F_2N_5O_3S$ (473.50) found: [MH$^+$]=474.10

B90. 1-{[3-(3-methoxypropyl)-1,2,4-oxadiazol-5-yl]methyl}-6-phenyl-3-(piperidin-4-yl)thieno[3,2-d]pyrimidine-2,4(1H,3H)-dione hydrochloride Tert-butyl 4-[1-{[3-(3-methoxypropyl)-1,2,4-oxadiazol-5-yl]methyl}-2,4-dioxo-6-phenyl-1,4-dihydrothieno[3,2-d]pyrimidin-3(2H)-yl]piperidine-1-carboxylate (780 mg, compound B68) is dissolved in a solution of hydrogen chloride in 1,4-dioxane (20 ml, 6.8 M). The reaction mixture is stirred for 30 min at RT. Then diethyl ether is added and the resulting precipitate is filtered off, washed with diethyl ether and dried in vacuo to afford the title compound as a solid.

MS: calc.: $C_{24}H_{27}N_5O_4S$ (481.57) found: [MH$^+$]=482.11

B91. 6-phenyl-3-(piperidin-4-yl)-1-{[3-(propoxymethyl)-1,2,4-oxadiazol-5-yl]methyl}thieno[3,2-d]pyrimidine-2,4(1H,3H)-dione trifluoroacetate To a solution of tert-butyl 4-[2,4-dioxo-6-phenyl-1-{[3-(propoxymethyl)-1,2,4-oxadiazol-5-yl]methyl]-1,4-dihydrothieno[3,2-d]pyrimidin-3(2H)-yl}piperidine-1-carboxylate (500 mg, compound B69) in DCM (10 ml) is added trifluoroacetic acid (10 ml). After 1 h at RT all volatile materials are removed in vacuo. The residue is taken up in diethyl ether, the resulting precipitate is filtered off, washed with diethyl ether and dried in vacuo to afford the title compound as a solid.

MS: calc.: $C_{24}H_{27}N_5O_4S$ (481.57) found: [MH$^+$]=482.12

B92. 1-[(1-methyl-1H-1,2,4-triazol-3-yl)methyl]-6-phenyl-3-(piperidin-4-yl)thieno[3,2-d]pyrimidine-2,4(1H,3H)-dione hydrochloride To a solution of tert-butyl 4-{1-[(1-methyl-1H-1,2,4-triazol-3-yl)methyl]-2,4-dioxo-6-phenyl-1,4-dihydrothieno[3,2-d]pyrimidin-3(2H)-yl}piperidine-1-carboxylate (944 mg, compound B70) in 1,4-dioxane (25 ml) is added a solution of hydrogen chloride in 1,4-dioxane (5.0 ml, 6.8 M). The reaction mixture is stirred for 17 h at RT. The resulting precipitate is filtered off, washed with diethyl ether and dried in vacuo to afford the title compound as a solid.

MS: calc.: $C_{21}H_{22}N_6O_2S$ (422.51) found: [MH$^+$]=423.09

B93. 1-[(1-methyl-1H-imidazol-2-yl)methyl]-6-phenyl-3-(piperidin-4-yl)thieno[3,2-d]pyrimidine-2,4(1H,3H)-dione hydrochloride According to the procedure described for compound B92 tert-butyl 4-{1-[(1-methyl-1H-imidazol-2-yl)methyl]-2,4-dioxo-6-phenyl-1,4-dihydrothieno[3,2-d]pyrimidin-3(2H)-yl}piperidine-1-carboxylate (1.00 g, compound B71) and a solution of hydrogen chloride in 1,4-dioxane (5.0 ml, 6.8 M) are reacted in 1,4-dioxane (25 ml) to afford the title compound as a solid.

MS: calc.: $C_{22}H_{23}N_5O_2S$ (421.52) found: [MH$^+$]=422.09

B94. 1-[(4-methyl-1,3-oxazol-5-yl)methyl]-6-phenyl-3-(piperidin-4-yl)thieno[3,2-d]pyrimidine-2,4(1H,3H)-dione hydrochloride According to the procedure described for compound B92 tert-butyl 4-{1-[(4-methyl-1,3-oxazol-5-yl)methyl]-2,4-dioxo-6-phenyl-1,4-dihydrothieno[3,2-d]pyrimidin-3(2H)-yl}piperidine-1-carboxylate (701 mg, compound B72) and a solution of hydrogen chloride in 1,4-dioxane (5.0 ml, 6.8 M) are reacted in 1,4-dioxane (25 ml) to afford the title compound as a solid.

MS: calc.: $C_{22}H_{22}N_4O_3S$ (422.51) found: [MH$^+$]=423.15

B95. 1-[(5-ethylthiophen-2-yl)methyl]-6-phenyl-3-(piperidin-4-yl)thieno[3,2-d]pyrimidine-2,4(1H,3H)-dione hydrochloride According to the procedure described for compound B92 tert-butyl 4-{1-[(5-ethylthiophen-2-yl)methyl]-2,4-dioxo-6-phenyl-1,4-dihydrothieno[3,2-d]pyrimidin-3(2H)-yl}piperidine-1-carboxylate (1.18 g, compound B73) and a solution of hydrogen chloride in 1,4-dioxane (8.0 ml, 6.8 M) are reacted in 1,4-dioxane (35 ml) to afford the title compound as a solid.

MS: calc.: $C_{24}H_{25}N_3O_2S_2$ (451.61) found: [MH$^+$]=452.13

B96. 1-[(3-methylthiophen-2-yl)methyl]-6-phenyl-3-(piperidin-4-yl)thieno[3,2-d]pyrimidine-2,4(1H,3H)-dione hydrochloride According to the procedure described for compound B92 tert-butyl 4-{1-[(3-methylthiophen-2-yl)methyl]-2,4-dioxo-6-phenyl-1,4-dihydrothieno[3,2-d]pyrimidin-3(2H)-yl}piperidine-1-carboxylate (825 mg, compound B74) and a solution of hydrogen chloride in 1,4-dioxane (5.0 ml, 6.8 M) are reacted in 1,4-dioxane (25 ml) to afford the title compound as a solid.

MS: calc.: $C_{23}H_{23}N_3O_2S_2$ (437.59) found: [MH$^+$]=438.07

B97. 1-[(5-ethyl-2H-tetrazol-2-yl)methyl]-6-phenyl-3-(piperidin-4-yl)thieno[3,2-d]pyrimidine-2,4(1H,3H)-dione hydrochloride According to the procedure described for compound B90 tert-butyl 4-{1-[(5-ethyl-2H-tetrazol-2-yl)methyl]-2,4-dioxo-6-phenyl-1,4-dihydrothieno[3,2-d]pyrimidin-3(2H)-yl}piperidine-1-carboxylate (290 mg, compound B75) is reacted with hydrogen chloride in 1,4-dioxane (5.0 ml, 6.8 M) to afford the title compound as a solid.

MS: calc.: $C_{21}H_{23}N_7O_2S$ (437.53) found: [MH$^+$]=438.11

B98. 1-[(5-tert-butyl-1,3,4-oxadiazol-2-yl)methyl]-6-phenyl-3-(piperidin-4-yl)thieno[3,2-d]pyrimidine-2,4(1H,3H)-dione hydrochloride To a solution of tert-butyl 4-{1-[(5-tert-butyl-1,3,4-oxadiazol-2-yl)methyl]-2,4-dioxo-6-phenyl-1,4-dihydrothieno[3,2-d]pyrimidin-3(2H)-yl}piperidine-1-carboxylate (4.09 g, compound B76) in 1,4-dioxane (21 ml) is added a solution of hydrogen chloride in 1,4-dioxane (9.0 ml, 4.0 M). The reaction flask is placed in an ultrasonic bath for 15 min at RT and afterwards the reaction mixture is stirred for 3 h at RT. All volatiles are removed under reduced pressure and the resulting residue is treated twice with DCM. After evaporation of DCM under reduced pressure the title compound is obtained as a solid.

MS: calc.: $C_{24}H_{27}N_5O_3S$ (465.58) found: [MH$^+$]=466.23

B99. Tert-butyl 4-{6-bromo-1-[(3-ethyl-1,2,4-oxadiazol-5-yl)methyl]-2,4-dioxo-1,4-dihydrothieno[3,2-d]pyrimidin-3(2H)-yl}piperidine-1-carboxylate Tert-butyl 4-(6-bromo-2,4-dioxo-1,4-dihydrothieno[3,2-d]pyrimidin-3(2H)-yl)piperidine-1-carboxylate (5.00 g, compound B53) and potassium carbonate (1.60 g) are suspended in dry DMF (50 ml) and 5-(chloromethyl)-3-ethyl-1,2,4-oxadiazole (1.70 g, compound D7) is added. The reaction mixture is stirred at 100° C. for 2 h and then poured into ice-cold water (250 ml). The resulting precipitate is filtered off and dried in vacuo to afford the title compound as a solid.

MS: calc.: $C_{21}H_{26}BrN_5O_5S$ (540.44) found: [MH$^+$-Boc]= 442.7

B100. tert-butyl 4-[6-bromo-1-{[3-(methoxymethyl)-1,2,4-oxadiazol-5-yl]methyl}-2,4-dioxo-1,4-dihydrothieno[3,2-d]pyrimidin-3(2H)-yl]piperidine-1-carboxylate According to the procedure describe for compound B99 of tert-butyl 4-(6-bromo-2,4-dioxo-1,4-dihydrothieno[3,2-d]pyrimidin-3(2H)-yl)piperidine-1-carboxylate (10.00 g; compound B53) is reacted with 5-(chloromethyl)-3-(methoxymethyl)-1,2,4-oxadiazole (3.78 g, D14) in the presence of potassium carbonate (3.21 g) in DMF (93 ml) to afford the title compound as a solid.

MS: calc.: $C_{21}H_{26}BrN_5O_6S$ (556.44) found: [MH$^+$-Boc]= 456.19, [MH$^+$—$C_4H_8$]=499.87

B101. tert-butyl 4-{6-bromo-1-[(2-ethyl-2H-tetrazol-5-yl)methyl]-2,4-dioxo-1,4-dihydrothieno[3,2-d]pyrimidin-3(2H)-yl}piperidine-1-carboxylate To a solution of tert-butyl 4-(6-bromo-2,4-dioxo-1,4-dihydrothieno[3,2-d]pyrimidin-3(2H)-yl)piperidine-1-carboxylate (5.00 g, compound B53) in anhydrous THF (100 ml) is slowly added 5-(chloromethyl)-2-ethyl-2H-tetrazole (5.62 g, compound D32), sodium bis(trimethylsilyl)amide (11.6 ml, 1.0 M solution in THF) and sodium iodide (348 mg). The reaction mixture is stirred for 48 h at 45° C. Afterwards all volatiles are removed under reduced pressure and the residue is treated with DCM (100 ml) and water (50 ml). The organic layer is separated and dried over sodium sulfate. After purification by flash column chromatography [silica gel, eluation gradient: EtOAc/cyclohexane, 1/1 (v/v)] the title compound is obtained as a solid.

MS: calc.: $C_{20}H_{26}BrN_7O_4S$ (540.44) found: [MH$^+$-Boc]= 440.064

C1. Methyl 4-[(2R,4aR,10bR)-9-ethoxy-8-methoxy-
2-oxido-3,4,4a,10b-tetrahydro-1H-thiopyrano[4,3-c]
isoquinolin-6-yl]benzoate, Methyl 4-[(2S,4aR,
10bR)-9-ethoxy-8-methoxy-2-oxido-3,4,4a,10b-
tetrahydro-1H-thiopyrano[4,3-c]isoquinolin-6-yl]
benzoate and Methyl 4-[(4aR,10bR)-9-ethoxy-8-
methoxy-2,2-dioxido-3,4,4a,10b-tetrahydro-1H-
thiopyrano[4,3-c]isoquinolin-6-yl]benzoate A solution of methyl 4-[(4aR,10bR)-9-ethoxy-8-methoxy-3,4,4a,10b-tetrahydro-1H-thiopyrano[4,3-c]isoquinolin-6-yl]benzoate (16 g; compound C9) in DCM (150 ml) is stirred at −50° C. (dry ice/acetone bath). m-CPBA (17.4 g) is dissolved in DCM and dried over sodium sulfate. After filtration additional DCM is added to the solution under stirring until a final volume of 200 ml is reached. 120 ml of this solution are slowly added to the starting solution at below −50° C. (dry ice/acetone bath) under nitrogen atmosphere until all starting material has disappeared. Subsequently the reaction solution is poured into a mixture of a $Na_2S_2O_3$ solution (10% w/w, 100 ml) and a saturated solution of sodium hydrogen carbonate (100 ml). The mixture is stirred at RT for 2 h. The organic phase is extracted, washed with water, dried over sodium sulfate and filtered under nitrogen atmosphere. The solvent is evaporated in vacuo to obtain a viscous oil which is purified by flash column chromatography [silica gel, eluation gradient: EtOAc/MeOH/n-hexane, 19/1/6 to 19/1/0 (v/v/v)] to yield the three separated compounds, methyl 4-[(2R,4aR,10bR)-9-ethoxy-8-methoxy-2-oxido-3,4,4a,10b-tetrahydro-1H-thiopyrano[4,3-c]isoquinolin-6-yl]benzoate, methyl 4-[(2S,4aR,10bR)-9-ethoxy-8-methoxy-2-oxido-3,4,4a,10b-tetrahydro-1H-thiopyrano[4,3-c]isoquinolin-6-yl]benzoate and methyl 4-[(4aR,10bR)-9-ethoxy-8-methoxy-2,2-dioxido-3,4,4a,10b-tetrahydro-1H-thiopyrano[4,3-c]isoquinolin-6-yl]benzoate.

Diastereomer 1 (Rf: 0.26; $Et_2O$/MeOH, 19/1 (v/v))
MS: calc.: $C_{23}H_{25}NO_5S$ (427.52) found: [MH$^+$]=428.0
Diastereomer 2: (Rf: 0.14; $Et_2O$/MeOH, 19/1 (v/v))
MS: calc.: $C_{23}H_{25}NO_5S$ (427.52) found: [MH$^+$]=428.0
Absolute configuration at sulfur (from Diastereomer 1 and 2) is not assigned. Therefore, it cannot be said whether Diastereomer 1 is methyl 4-[(2R,4aR,10bR)-9-ethoxy-8-methoxy-2-oxido-3,4,4a,10b-tetrahydro-1H-thiopyrano[4,3-c]isoquinolin-6-yl]benzoate or methyl 4-[(2S,4aR,10bR)-9-ethoxy-8-methoxy-2-oxido-3,4,4a,10b-tetrahydro-1H-thiopyrano[4,3-c]isoquinolin-6-yl]benzoate; the same applies for Diastereomer 2.
Methyl 4-[(4aR,10bR)-9-ethoxy-8-methoxy-2,2-dioxido-3,4,4a,10b-tetrahydro-1H-thiopyrano[4,3-c]isoquinolin-6-yl]benzoate (Rf: 0.81; $Et_2O$/MeOH, 19/1 (v/v)); M.p. 178° C.
MS: calc.: $C_{23}H_{25}NO_6S$ (443.52) found: [MH$^+$]=444.0

C2. One of 4-[(2R,4aR,10bR)-9-ethoxy-8-methoxy-
2-oxido-3,4,4a,10b-tetrahydro-1H-thiopyrano[4,3-c]
isoquinolin-6-yl]benzoic acid or 4-[(2S,4aR,10bR)-
9-ethoxy-8-methoxy-2-oxido-3,4,4a,10b-tetrahydro-
1H-thiopyrano[4,3-c]isoquinolin-6-yl]benzoic acid
(Acid Diastereomer 1)

To a solution of Diastereomer 1 (9.3 g; C1) in 1,4-dioxane (150 ml; degassed by stream of nitrogen) is added an aqueous solution of sodium hydroxide (20 ml, 2.0 M) and the solution is stirred for 18 h at RT. A solution of hydrogen chloride (20 ml, 2.0 M) is added dropwise until a pH of 6 is reached. The solvent is removed in vacuo and the resulting residue is treated with DCM (250 ml) and MeOH (20 ml). The resulting suspension is filtered, the filtrate is evaporated to dryness, the residue is treated with DIP (100 ml) and the resulting suspension is stirred for 24 h at RT under a nitrogen atmosphere. The suspension is filtered, the filter cake is washed with DIP and dried in vacuo at 65° C. to give the title compound as a mixture.
MS: calc.: $C_{22}H_{23}NO_5S$ (413.49) found: [MH$^+$]=414.0

C3. One of 4-[(2R,4aR,10bR)-9-ethoxy-8-methoxy-
2-oxido-3,4,4a,10b-tetrahydro-1H-thiopyrano[4,3-c]
isoquinolin-6-yl]benzoic acid or 4-[(2S,4aR,10bR)-
9-ethoxy-8-methoxy-2-oxido-3,4,4a,10b-tetrahydro-
1H-thiopyrano[4,3-c]isoquinolin-6-yl]benzoic acid
(BYK463324) (Acid Diastereomer 2)

The title compound is prepared analogously as described for example C2 using Diastereomer 2 (5.0 g; from C1), 10 ml of a 2M aqueous solution of sodium hydroxide, 10 ml of an 2 M solution of hydrogen chloride and 200 ml of 1,4-dioxane.
MS: calc.: $C_{22}H_{23}NO_5S$ (413.49) found: [MH$^+$]=414.0

C4. Methyl 4-{[(3R,4R)-3-(3-ethoxy-4-methoxyphenyl)-1,1-dioxidotetrahydro-2H-thiopyran-4-yl]
carbamoyl}benzoate A solution of m-CPBA (40.1 g) in DCM (350 ml) is dried over sodium sulfate, filtered and the filtrate is refilled with DCM to a final volume of 500 ml. 420 ml of this solution is slowly added (7 h) to a solution of methyl 4-{[(3R,4R)-3-(3-ethoxy-4-methoxyphenyl)tetrahydro-2H-thiopyran-4-yl]carbamoyl}benzoate (23.3 g; compound C12) in DCM (200 ml) at 0° C. until all starting material has disappeared. The reaction solution is quenched by addition of a mixture of 30% aqueous $Na_2SO_3$ solution (250 ml) and saturated aqueous sodium bicarbonate solution (200 ml) and stirred for 12 h at RT. The organic phase is separated and extracted two times with saturated aqueous sodium bicarbonate solution (200 ml), dried over sodium sulfate and evaporated in vacuo to obtain a solid residue. The residue is treated with 300 ml of DIP and the suspension is cooled to 0° C. (ice bath). After filtration and drying in vacuo at 60° C. the title compound is obtained as a solid.
MS: calc.: $C_{23}H_{27}NO_7S$ (461.53) found: [MH$^+$]=462.11

C5. Methyl 4-[(4aR,10bR)-9-ethoxy-8-methoxy-2,2-
dioxido-3,4,4a,10b-tetrahydro-1H-thiopyrano[4,3-c]
isoquinolin-6-yl]benzoate To a stirred mixture of methyl 4-{[(3R,4R)-3-(3-ethoxy-4-methoxyphenyl)-1,1-dioxidotetrahydro-2H-thiopyran-4-yl]carbamoyl}benzoate (22.8 g; compound C4) and $K_2CO_3$ (6.82 g) in absolute ACN (200 ml) is added $POCl_3$ (13.6 ml) at 0° C. (ice bath). The suspension is allowed to come to RT within 1 h and is subsequently refluxed at 85° C. for 6 h. Afterwards the mixture is stirred for 12 h at RT under nitrogen atmosphere. The mixture is quenched with water (500 ml) and adjusted to pH7 by addition of 0.4 M NaOH. The ACN is destilled of and to the remaining suspension DCM (500 ml) is added. The pH value is adjusted to 8.1 by addition of aqueous sodium hydroxide solution (0.4 M) and saturated aqueous solution of sodium bicarbonate and the mixture is stirred at RT for 12 h. The organic layer is separated and the aqueous layer is extracted with DCM (300 ml). The combined organic layers are dried over sodium sulfate, filtered and evaporated in vacuo to dryness. The resulting residue is purified by flash column chromatography [silica gel, eluent system: n-hexane/EtOAc/triethylamine 11/8/1 (v/v/v)] to obtain a crude solid.

The residue is treated with DIP (400 ml) and stirred at reflux temperature for 3 h. The suspension is cooled to 0° C. with an ice bath and filtered off. The filter cake is washed with DIP and dried in vacuo at 70° C. to obtain the title compound as a solid.

MS: calc.: $C_{23}H_{25}NO_6S$ (443.52) found: $[MH^+]=444.27$

C6. 4-[(4aR,10bR)-9-ethoxy-8-methoxy-2,2-dioxido-3,4,4a,10b-tetrahydro-1H-thiopyrano[4,3-c]isoquinolin-6-yl]benzoic acid A solution of methyl 4-[(4aR,10bR)-9-ethoxy-8-methoxy-2,2-dioxido-3,4,4a,10b-tetrahydro-1H-thiopyrano[4,3-c]isoquinolin-6-yl]benzoate (380 mg; compound C5) in 1,4-dioxane (10 ml) is treated with an 2 M aqueous solution of sodium hydroxide (1 ml) and the reaction solution is stirred for about 20 h at 45° C. to 50° C. The solution is allowed to come to RT and afterwards a 2 M aqueous solution of hydrogen chloride (1 ml) is added. The mixture is stirred for 20 min at RT, filtered and the filtrate is evaporated to dryness in vacuo. Subsequently, the residue is treated with DCM (30 ml) and the resulting suspension is filtered. The solvent is removed in vacuo to yield the title compound as a solid.

MS: calc.: $C_{22}H_{23}NO_6S$ (429.49) found: $[MH^+]=430.25$

C7. Methyl 3-[(4aR,10bR)-9-ethoxy-8-methoxy-3,4,4a,10b-tetrahydro-1H-thiopyrano[4,3-c]isoquinolin-6-yl]benzoate To a solution of methyl 3-{[(3R,4R)-3-(3-ethoxy-4-methoxyphenyl)tetrahydro-2H-thiopyran-4-yl]carbamoyl}benzoate (2.58 g; compound C11) and 2-chloropyridin (0.68 ml) in toluene (60 ml) is slowly added a solution of POCl$_3$ (1.65 ml) in toluene (6 ml). The reaction mixture is stirred for 12 h at 100° C. The reaction mixture is allowed to come to RT and then quenched by slow addition of water (15 ml). Additional water (30 ml) is added and the pH is adjusted to about 9 by addition of 5 M aqueous solution of sodium hydroxide. The organic phase is separated and the aqueous phase is extracted with toluene (30 ml). The combined organic phases are dried over sodium sulfate and the solvent is removed in vacuo. The resulting residue is purified flash column chromatography [silica gel, eluation gradient: cyclohexane/EtOAc, 3/1 to 1/1 (v/v)] to yield the title compound as a solid.

MS: calc.: $C_{23}H_{25}NO_4S$ (411.52) found: $[MH^+]=411.9$

C8. 3-[(4aR,10bR)-9-ethoxy-8-methoxy-3,4,4a,10b-tetrahydro-1H-thiopyrano[4,3-c]isoquinolin-6-yl]benzoic acid To a solution of methyl 3-[(4aR,10bR)-9-ethoxy-8-methoxy-3,4,4a,10b-tetrahydro-1H-thiopyrano[4,3-c]isoquinolin-6-yl]benzoate (0.5 g; compound C7) in 1,4-dioxane (8 ml) is added an 2 M aqueous solution of sodium hydroxide (1.3 ml) and the reaction mixture is stirred at RT for 12 h. An aqueous solution of hydrogen chloride (1.3 ml, 2.0 M) is added under stirring. The reaction mixture is evaporated to dryness in vacuo and the resulting residue is used for the next step without further purification.

MS: calc.: $C_{22}H_{23}NO_4S$ (397.49) found: $[MH^+]=398.23$

C9. Methyl 4-[(4aR,10bR)-9-ethoxy-8-methoxy-3,4,4a,10b-tetrahydro-1H-thiopyrano[4,3-c]isoquinolin-6-yl]benzoate To a suspension of methyl 4-{[(3R,4R)-3-(3-ethoxy-4-methoxyphenyl)tetrahydro-2H-thiopyran-4-yl]carbamoyl}benzoate (20.5 g; compound C12) and potassium carbonate (6.6 g) in ACN (400 ml) is slowly added a solution of POCl$_3$ (13.2 ml) in CAN (50 ml) at 0° C. Subsequently the mixture is heated under reflux for 17 h. The reaction is quenched by addition of water (300 ml) at RT and the pH value is adjusted to pH 7.6 by addition of a 40% aqueous sodium hydroxide solution. The acetonitrile is removed in vacuo and diethyl ether is added to the suspension. The pH is adjusted to pH 8.6 by further addition of a 40% aqueous sodium hydroxide solution and a saturated solution of sodium hydrogen carbonate. After extraction the organic phase is separated, washed with water and dried over sodium sulfate. Filtration and evaporation of the solvent give a solid that is purified by flash chromatography (silica gel, eluation gradient: n-hexane/isopropyl acetate, 19/1 to 12/8 (v/v)) to yield the title compound as a solid.

MS: calc.: $C_{23}H_{25}NO_4S$ (411.52) found: $[MH+]=412.2$

C10. 4-[(4aR,10bR)-9-ethoxy-8-methoxy-3,4,4a,10b-tetrahydro-1H-thiopyrano[4,3-c]isoquinolin-6-yl]benzoic acid To a solution of methyl 4-[(4aR,10bR)-9-ethoxy-8-methoxy-3,4,4a,10b-tetrahydro-1H-thiopyrano[4,3-c]isoquinolin-6-yl]benzoate (5.0 g; compound C9) in dioxane (40 ml) is added a 2.0 M aqueous sodium hydroxide solution (18.3 ml) and the reaction mixture is stirred for 1.5 h at RT. Afterwards a aqueous hydrogen chloride solution (1.83 ml, 2.0 M) is added and all volatiles are removed under vacuo to give the title compound with parts of sodium chloride.

MS: calc.: $C_{22}H_{23}NO_4S$ (397.49) found: $[MH+]=398.2$

C11. Methyl 3-{[(3R,4R)-3-(3-ethoxy-4-methoxyphenyl)tetrahydro-2H-thiopyran-4-yl]carbamoyl}benzoate To a suspension of (3R,4R)-3-(3-ethoxy-4-methoxyphenyl)tetrahydro-2H-thiopyran-4-amine hydrochloride (1.82 g; compound C13), 3-(methoxycarbonyl)benzoic acid (1.08 g) and HBTU (2.50 g) in DCM (50 ml) is added DIPEA (4.2 ml) and the mixture is stirred for 1 h at RT. A saturated aqueous solution of sodium hydrogen carbonate (30 ml) is added, the organic phase is separated and dried over sodium sulfate. After filtration the solvent is removed in vacuo and the resulting residue is purified by flash column chromatography [silica gel, eluation gradient: DCM/MeOH, 100/0 to 95/5 (v/v)] to give the title compound as a solid.

MS: calc.: $C_{23}H_{27}NO_5S$ (429.35) found: $[MH+]=430.0$

C12. Methyl 4-{[(3R,4R)-3-(3-ethoxy-4-methoxyphenyl)tetrahydro-2H-thiopyran-4-yl]carbamoyl}benzoate To a suspension of 4-(methoxycarbonyl)benzoic acid (11.35 g) in DCM (300 ml) are added 5 drops of DMF and the reaction mixture is stirred for 20 min at RT under a nitrogen atmosphere. To this suspension oxalyl chloride (5.67 ml) dissolved in DCM (60 ml) is slowly added at 0° C. (ice bath The ice bath is removed and the mixture is stirred for 4 h at RT. DCM (3×200 ml) is added to the reaction mixture and the volatiles are co-evaporated under reduced pressure (three times). Finally all volatiles are removed under vacuo to obtain an oil, which is dissolved in DCM (200 ml) and added dropwise to a solution of (3R,4R)-3-(3-ethoxy-4-methoxyphenyl)tetrahydro-2H-thiopyran-4-amine hydrochloride (18.23 g; compound C13) and DIPEA (41.1 ml) in DCM (200 ml) at 0° C. under nitrogen atmosphere. After stirring for 12 h at RT the reaction is quenched by addition of a saturated aqueous solution of sodium hydrogen carbonate. The organic phase is separated, dried over sodium sulfate, filtered and evaporated to dryness in vacuo. The resulting residue is suspended in DIP (300 ml) and heated under reflux for 3.5 h. The suspension is stirred for 2 d at RT and subsequently cooled to 0° (ice bath). The suspension is filtered and the filter cake is washed with little amounts of DIP and dried in vacuo for 12 h at 60° C. to give the title compound as a solid.

MS: calc.: $C_{23}H_{27}NO_5S$ (429.35) found: [MH+]=430.0

C13. (3R,4R)-3-(3-Ethoxy-4-methoxy-phenyl)-tetrahydro-2H-thiopyran-4-amine hydrochloride A mixture of (3R,4R)-3-(3-Ethoxy-4-methoxy-phenyl)-N-[(1R)-1-(4-methoxy-phenyl)-ethyl]-tetrahydro-2H-thiopyran-4-amine hydrochloride (1.0 g; compound C14) and trifluoroacetic acid (2 ml) is stirred at reflux temperature for 30 min yielding a dark red solution. Cooled to RT the solution is evaporated, the dark viscous residue is dissolved in a mixture of diethylether (5 ml) and water (5 ml) and the pH of the solution is increased up to 10 by adding some drops of a 40% aqueous solution of sodium hydroxide. The mixture is extracted with diethylether, the organic phase is washed with a saturated aqueous solution of $NaHCO_3$ and then extracted two times with a 20% aqueous solution of citric acid. The pH of the collected aqueous acid solutions of about 2.4 is increased up to 10 by adding a 40% NaOH solution and the basic mixture is extracted with diethylether. The organic phase is washed two times with water, dried over sodium sulfate and then evaporated to give an oily residue. This is dissolved in 2-propanol (10 ml) and to the stirred solution a 5-6 M solution of hydrogen chloride in 2-propanol (1 ml) is added dropwise at RT inducing a spontaneous crystallization. The slurry is concentrated to about half of the volume and stirred for 15 h at RT. The crystals are filtered off, washed with 2-propanol (2 ml), dried in vacuo at 40° C. to give the title compound. M.p. 233° C. (decomposition).

MS: calc.: $C_{14}H_{21}NO_2S$ (267.85) found.: [MH+] 268.0
$[d]_D^{20}$=−40.8° (MeOH, c=1)

C14. (3R,4R)-3-(3-Ethoxy-4-methoxy-phenyl)-N-[(1R)-1-(4-methoxy-phenyl)-ethyl]-tetrahydro-2H-thiopyran-4-amine hydrochloride 3-(3-ethoxy-4-methoxy-phenyl)-tetrahydro-4H-thiopyran-4-one (0.67 g; compound C15) and (R)-1-(4-methoxy-phenyl)-ethanamine are dissolved at RT in 12.5 ml of DCM. Keeping the temperature at about 20° C. acetic acid (0.3 g) is added dropwise to the solution followed by addition of sodium-triacetoxyborohydride (0.84 g) and the mixture is stirred for 15 h at RT. After evaporation of about 11 ml of the solvent the residue is extracted with diethylether (8 ml) and with a 20% aqueous solution of citric acid (three times with 2.5 ml each). The collected aqueous acid solution is washed two times with diethylether (2 ml each) and the pH is increased from of about 2.4 up to 6.0 by adding a 40% aqueous solution of sodium hydroxide. Then the solution is extracted with diethylether (three times with 4 ml each), the collected organic phase is washed two times with water (2 ml each), filtered and concentrated in vacuo to dryness yielding a solid residue. This is dissolved in 2-propanol (12 ml) at about 60° C. and a concentrated aqueous solution of hydrogen chloride (0.32 ml) is added. Keeping the temperature at about 60° C. the solution is stirred for about 1 h while a slow crystallization occurs. The suspension is then heated to reflux temperature for about 1 h and then slowly cooled to RT and stirred for additional 15 h. The suspension is filtered off and the solid filter residue is washed with 2-propanol (1 ml) yielding a crystalline material.

This is suspended in 2-propanol (11 ml), the suspension is heated to reflux temperature and water (1.6 ml) is added giving a clear solution. This is slowly cooled down to about 70° C. under continuous stirring inducing a spontaneous crystallization. Following further stirring at 70° C. for about 1 h the suspension is slowly cooled down to RT and stirred for additional 15 h. The crystals are filtered off, washed with 2-propanol (1 ml) and dried in vacuo at about 50° C. for 24 h yielding the title compound. M.p. 214-214.5° C. (decomposition).

MS: calc.: $C_{23}H_{31}NO_3S$ (free base) (401.57) found.: [MH+] 401.7
$[d]_D^{20}$=+82.5° (MeOH, c=1)

C15. 3-(3-Ethoxy-4-methoxy-phenyl)-tetrahydro-2H-thiopyran-4-one

To a suspension of 3-(3-ethoxy-4-methoxy-phenyl)-1-methyl-piperidin-4-one (0.88 g) in 8.5 ml of 4-methyl-pentan-2-one, which is cooled to about 2° C., trifluoro-methansulfonic acid methylester (0.6 g) is added dropwise within about 9 min. Following 20 min stirring at RT a combined solution of sodium hydrogensulfide monohydrate (0.82 g) and sodium sulfide nonahydrate (0.98 g) in 8.5 ml of water is added and the stirred reaction mixture is then heated to reflux temperature for 4 h. Cooled to RT the stirring is stopped and the building up organic layer is separated. The water phase is washed three times with 2 ml each of EtOAc. The collected organic phase is washed two times with 3 ml each of water, filtered and concentrated in vacuo giving a solid residue. This is suspended in 2-propanol (4 ml) and the suspension is heated to reflux temperature giving a clear solution. The continuously stirred solution is slowly cooled down to RT inducing a spontaneous crystallization. Following stirring for 15 h at RT, the suspension is further stirred at about 2° C. for 2 h and then the crystals are filtered of, washed with 2-propanol (1 ml) and dried in vacuo at about 60° C. for 24 h yielding the title compound.

M.p. 108.5-109.5° C.
MS: calc.: $C_{14}H_{18}O_3S$ (266.36) found.: [MH+] 266.2

C16. 4-[(4aR,10bR)-8,9-dimethoxy-3,4,4a,10b-tetrahydro-1H-thiopyrano[4,3-c]isoquinolin-6-yl]benzoic acid 4-[(4aR,10bR)-8,9-dimethoxy-3,4,4a,10b-tetrahydro-1H-thiopyrano[4,3-c]isoquinolin-6-yl]benzoic acid can be prepared in analogy to the procedure described for 4-[(4aR,10bR)-9-ethoxy-8-methoxy-3,4,4a,10b-tetrahydro-1H-thiopyrano[4,3-c]isoquinolin-6-yl]benzoic acid (compound C10).

MS: calc.: $C_{21}H_{21}NO_4S$ (383.47) found: [MH+]=384.2

C17. Methyl 4-[(4aR,10bR)-8,9-dimethoxy-3,4,4a,10b-tetrahydro-1H-thiopyrano[4,3-c]isoquinolin-6-yl]benzoate Methyl 4-[(4aR,10bR)-8,9-dimethoxy-3,4,4a,10b-tetrahydro-1H-thiopyrano[4,3-c]isoquinolin-6-yl]benzoate can be prepared in analogy to the procedure described for methyl 4-[(4aR,10bR)-9-ethoxy-8-methoxy-3,4,4a,10b-tetrahydro- 1H-thiopyrano[4,3-c]isoquinolin-6-yl]benzoate (compound C9).

MS: calc.: $C_{22}H_{23}NO_4S$ (397.49) found: [MH$^+$]=398.2

C18. Methyl 4-{[(3R,4R)-3-(3,4-dimethoxyphenyl) tetrahydro-2H-thiopyran-4-yl]carbamoyl}benzoate Methyl 4-{[(3R,4R)-3-(3,4-dimethoxyphenyl)tetrahydro-2H-thiopyran-4-yl]carbamoyl}benzoate can be prepared in analogy to the procedure described for methyl 3-{[(3R,4R)-3-(3-ethoxy-4-methoxyphenyl)tetrahydro-2H-thiopyran-4-yl]carbamoyl}benzoate (compound C11).

MS: calc.: $C_{22}H_{25}NO_5S$ (415.51) found: [MH$^+$]=416.1

C19. (3R,4R)-3-(3,4-dimethoxyphenyl)tetrahydro-2H-thiopyran-4-amine hydrochloride (3R,4R)-3-(3,4-dimethoxyphenyl)tetrahydro-2H-thiopyran-4-amine hydrochloride can be prepared in analogy to the procedure described for (3R,4R)-3-(3-Ethoxy-4-methoxyphenyl)-tetrahydro-2H-thiopyran-4-amine hydrochloride (compound C13). M.p. 269.5° C.

MS: calc.: $C_{13}H_{19}NO_2S$ (253.36) found: [MH$^+$]=254.1
$[\alpha]_D^{20}$=−43.1 (c=1, MeOH)

C20. (3R,4R)-3-(3,4-dimethoxyphenyl)-N-[(1R)-1-(4-methoxyphenyl)ethyl]tetrahydro-2H-thiopyran-4-amine hydrochloride (3R,4R)-3-(3,4-dimethoxyphenyl)-N-[(1R)-1-(4-methoxyphenyl)ethyl]tetrahydro-2H-thiopyran-4-amine hydrochloride can be prepared in analogy to the procedure described for (3R,4R)-3-(3-Ethoxy-4-methoxy-phenyl)-N-[(1R)-1-(4-methoxy-phenyl)-ethyl]-tetrahydro-2H-thiopyran-4-amine hydrochloride (compound C14). M.p. 204.5-205.0° C.

MS calc.: $C_{22}H_{29}NO_3S$ (387.54) found: [MH$^+$]=388.0
$[\alpha]_D^{20}$=77.1 (c=1, MeOH)

C21. 3-(3,4-dimethoxyphenyl)tetrahydro-4H-thiopyran-4-one 3-(3,4-dimethoxyphenyl)tetrahydro-4H-thiopyran-4-one can be prepared in analogy to the procedure described for 3-(3-Ethoxy-4-methoxy-phenyl)-tetrahydro-4H-thiopyran-4-one (compound C15) or in analogy to the method described in US20080103168.

MS: calc.: $C_{13}H_{16}O_3S$ (252.33) found [M$^+$]=252.1

C22. 3-(3,4-dimethoxyphenyl)-1-methylpiperidin-4-one 3-(3,4-dimethoxyphenyl)-1-methylpiperidin-4-one can be prepared in analogy to the procedure described for the synthesis of 3-(3-ethoxy-4-methoxyphenyl)-1-methylpiperidin-4-one in the international patent application WO9855481 or as described in DE4217401.

D1. 2-(Chloromethyl)-5-ethyl-1,3-oxazole 2-(Chloromethyl)-5-ethyl-1,3-oxazole can be prepared in analogy to the procedure described for 2-(chloromethyl)-5-methyl-1,3-oxazole in EP1813603 (EP1813603; example 13).

D2. 3-(Chloromethyl)-5-methyl-1,2,4-oxadiazole 3-(Chloromethyl)-5-methyl-1,2,4-oxadiazole is a commercially available compound.

D3. 5-(Chloromethyl)-3-ethylisoxazole 5-(Chloromethyl)-3-ethylisoxazole is a commercially available compound.

D4. 2-(Chloromethyl)-5-ethyl-1,3,4-oxadiazole 2-(Chloromethyl)-5-ethyl-1,3,4-oxadiazole is a commercially available compound.

D5. 2-(Chloromethyl)-4-ethyl-1,3-oxazole 2-(Chloromethyl)-4-ethyl-1,3-oxazole can be prepared as described in Journal of Medicinal Chemistry 45 (2002), 3905-3927.

D6. 3-(Chloromethyl)-5-methylisoxazole

3-Chloromethyl-5-methylisoxazole is a commercially available compound.

D7. 5-(Chloromethyl)-3-ethyl-1,2,4-oxadiazole 5-(Chloromethyl)-3-ethyl-1,2,4-oxadiazole is a commercially available compound.

D8. 2-(Chloromethyl)-5-(methoxymethyl)-1,3,4-oxadiazole 2-(Chloromethyl)-5-(methoxymethyl)-1,3,4-oxadiazole can be prepared analogously to 2-(chloromethyl)-5-(ethoxymethyl)-1,3,4-oxadiazole as described by H. Mildenberger et al. in DE2047465.

D9. 5-(Chloromethyl)-2-ethyl-1,3-oxazole

5-Chloromethyl-2-ethyl-1,3-oxazole can be synthesized from 5-bromomethyl-2-ethyl-1,3-oxazole by hydrolysation to the corresponding alcohol by treatment with sodium carbonate solution and chlorination of the alcohol by treatment with thionylchlorid. 5-Bromomethyl-2-ethyl-1,3-oxazole can be prepared in analogy to procedures described in Journal of the American Chemical Society 1982, 4461-4465.

D10. 4-(Chloromethyl)-2-methyl-1,3-thiazole 4-(Chloromethyl)-2-methyl-1,3-thiazole is a commercially available compound.

D11. 5-(Chloromethyl)-3-[(methylsulfanyl)methyl]-1,2,4-oxadiazole 5-(Chloromethyl)-3-[(methylsulfanyl)methyl]-1,2,4-oxadiazole is a commercially available compound.

D12. 2-(Chloromethyl)-5-methyl-1,3-thiazole 2-(Chloromethyl)-5-methyl-1,3-thiazole is a commercially available compound.

D13. 2-(Chloromethyl)-4-methyl-1,3-thiazole 2-(Chloromethyl)-4-methyl-1,3-thiazole is a commercially available compound.

D14. 5-(Chloromethyl)-3-(methoxymethyl)-1,2,4-oxadiazole 5-(Chloromethyl)-3-(methoxymethyl)-1,2,4-oxadiazole is a commercially available compound.

D15. 4-(Chloromethyl)-2-ethyl-1,3-oxazole 4-(Chloromethyl)-2-ethyl-1,3-oxazole can be prepared in analogy to the procedure described for the synthesis of 4-(chloromethyl)-2-propyl-1,3-oxazole in EP0177353 (reference example 1).

D16. 4-(Chloromethyl)-1-ethyl-1H-pyrazole

4-Chloromethyl-1-ethyl-1H-pyrazole can be prepared from (1-ethyl-1H-pyrazol-5-yl)methanol by treatment with thionyl chloride under standard conditions. (1-ethyl-1H-pyrazol-5-yl)methanol is a commercially available compound.

D17. 3-(Chloromethyl)-1-ethyl-1H-pyrazole

3-Chloromethyl-1-ethyl-1H-pyrazole can be prepared from (1-ethyl-1H-pyrazol-3-yl)methanol by treatment with thionyl chloride under standard conditions. (1-ethyl-1H-pyrazol-3-yl)methanol is a commercially available compound.

D18. 5-(Chloromethyl)-2-methyl-1,3-thiazole 5-(Chloromethyl)-2-methyl-1,3-thiazole can be prepared from commercially available ethyl 2-methyl-1,3-thiazole-5-carboxylate by treatment with lithium aluminium hydride and subsequent treatment of the resulting alcohol with thionyl chloride under standard conditions.

D19. 4-(Chloromethyl)-2-ethyl-2H-1,2,3-triazole 4-(Chloromethyl)-2-ethyl-2H-1,2,3-triazole can be prepared in two steps from methyl 2-ethyl-2H-1,2,3-triazole-4-carboxylate in analogy to the procedure described in Bioorganic Medicinal Chemistry, 13 (2005), 363-386. The synthesis of methyl 2-ethyl-2H-1,2,3-triazole-4-carboxylate is described in WO 98/50385 A1 (example 97, step a).

D20. 5-(Chloromethyl)-3-ethyl-1,2,4-thiadiazole 5-(Chloromethyl)-3-ethyl-1,2,4-thiadiazole can be synthesized from (3-ethyl-1,2,4-thiadiazol-5-yl)methanol by conversion with thionyl chloride in DCM. (3-Ethyl-1,2,4-thiadiazol-5-yl)methanol can be prepared analogously to (3-isopropyl-1,2,4-thiadiazol-5-yl)methanol as described in EP1227084 A1 (example 13, step A and B).

D21. 4-(Chloromethyl)-1-ethyl-1H-1,2,3-triazole 4-(Chloromethyl)-1-ethyl-1H-1,2,3-triazole can be synthesized from (1-ethyl-1H-1,2,3-triazol-4-yl)methanol by conversion with thionyl chloride in DCM. (1-ethyl-1H-1,2,3-triazol-4-yl)methanol can be prepared as described in WO 98/50385 A1 (example 98, step a).

D22. [3-(propoxymethyl)-1,2,4-oxadiazol-5-yl]methanol

Step 1: (1Z)—N'-hydroxy-2-propoxyethanimidamide

A mixture of propoxyacetonitrile (3.03 g) and hydroxylamine (2.01 g, 50 wt % in water) is stirred for 2 h at 100° C. At RT DCM is added, the organic phase is separated, dried over sodium sulfate and concentrated under reduced pressure to give the title compound as an oil.

Step 2: Methyl 3-(propoxymethyl)-1,2,4-oxadiazole-5-carboxylate

To a solution of (1Z)—N'-hydroxy-2-propoxyethanimidamide (3.1 g) in absolute THF under Ar atmosphere is added $CaH_2$ (1.09 g) and molecular sieves (4 A°). The mixture is stirred for 10 min and subsequently methyl chloro(oxo)acetate (3.16 g) is added and the reaction mixture is stirred for 3 h under reflux conditions. The mixture is filtered through celite and the filtrate is evaporated to dryness under vacuo. The resulting residue is purified by flash column chromatography (silica gel, eluent: cyclohexane/EtOAc, 3/2 (v/v)) to give the title compound as an oil.

Step 3: [3-(propoxymethyl)-1,2,4-oxadiazol-5-yl]methanol

To a solution of methyl 3-(propoxymethyl)-1,2,4-oxadiazole-5-carboxylate (2.05 g) in MeOH is added sodium borohydride (386 mg) at −10° C. and the mixture is stirred for 15 min at this temperature. The reaction mixture is quenched with ice, stirred for 20 min and extracted with EtOAc three times. The combined organic phases are dried over sodium sulfate and concentrated under reduced pressure. The resulting residue is purified by flash column chromatography (silica gel) to give the title compound as a solid.

D23. [3-(3-methoxypropyl)-1,2,4-oxadiazol-5-yl]methanol

Step 1: (1Z)—N'-hydroxy-4-methoxybutanimidamide

In analogy to the procedure described for example D28 4-methoxybutanenitrile (3.1 g) and hydroxylamine (2.07 g, 50 wt % in water) yield the title compound as a solid.

Step 2: Methyl 3-(3-methoxypropyl)-1,2,4-oxadiazole-5-carboxylate

In analogy to the procedure described for example D27 (1Z)—N'-hydroxy-4-methoxybutanimidamide (1.29 g), $CaH_2$ (452 mg) and methyl chloro(oxo)acetate (1.32 g) yield the title compound as an oil.

Step 3: [3-(3-methoxypropyl)-1,2,4-oxadiazol-5-yl]methanol

In analogy to the procedure described for example D26 methyl 3-(3-methoxypropyl)-1,2,4-oxadiazole-5-carboxylate (990 mg) and sodium borohydride (386 mg) in MeOH yield the title compound as an oil.

D24. (1-methyl-1H-1,2,4-triazol-3-yl)methanol (1-methyl-1H-1,2,4-triazol-3-yl)methanol is a commercially available compound.

D25. 2-(chloromethyl)-1-methyl-1H-imidazole 2-(chloromethyl)-1-methyl-1H-imidazole is a commercially available compound.

D26. (4-methyl-1,3-oxazol-5-yl)methanol (4-methyl-1,3-oxazol-5-yl)methanol is a commercially available compound.

D27. 2-(chloromethyl)-5-ethylthiophene 2-(chloromethyl)-5-ethylthiophene can be prepared from commercially available 5-ethylthiophene-2-carbaldehyde by treatment with lithium aluminium hydride and treatment of the resulting alcohol with thionyl chloride under standard conditions.

D28. 2-(chloromethyl)-3-methylthiophene 2-(chloromethyl)-3-methylthiophene can be prepared from commercially available 3-methylthiophene-2-carboxylic acid by treatment with lithium aluminium hydride and treatment of the resulting alcohol with thionyl chloride under standard conditions.

D29. 2-tert-butyl-5-(chloromethyl)-1,3,4-oxadiazole 2-tert-butyl-5-(chloromethyl)-1,3,4-oxadiazole is a commercially available compound

D30. 5-ethyl-2-{[(tripropan-2-ylsilyl)oxy]methyl}-2H-tetrazole

To a solution of commercially available 5-ethyl-1H-tetrazole (2.11 g) and potassium carbonate (2.98 g) in anhydrous DMF is added Tri(isopropylsiloxy)-methylchlorid (5.0 ml) and the solution is stirred for 20 min at RT. The solvent is removed under reduced pressure and the resulting residue is treated with chloroform and water. After extraction the organic phase is dried over $Na_2SO_4$ and the solvent is removed under reduced pressure. The resulting residue is purified by flash chromatography (silica gel, eluent methyl-tert-butylether/cyclohexane, 1/6 (v/v)) to give the title product as an oil.

D31. 2-(chloromethyl)-1-methyl-1H-imidazole hydrochloride 2-(chloromethyl)-1-methyl-1H-imidazole hydrochloride is a commercially available compound.

D32. 5-(chloromethyl)-2-ethyl-2H-tetrazole 5-(chloromethyl)-2-ethyl-2H-tetrazole can be prepared as described in Chemische Berichte 1975, 887-896.

Commercial Utility

Medical Uses

The compounds of formula 1 and the stereoisomers of the compounds of formula 1 according to the invention are hereinafter referred to as the compounds of the invention. In particular, the compounds of the invention are pharmaceutically acceptable.

The compounds of the invention have—as type 4/type 5 phosphodiesterase (PDE4/5) inhibitors—valuable pharmaceutical properties, which make them commercially utilizable.

PDE4 inhibitors are thought to be useful in the treatment or prophylaxis of a variety of diseases and disorders. They are thought to be suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways, of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases.

In particular, PDE4 inhibitors are thought to be useful in the treatment or prophylaxis of a variety of diseases and disorders, such as for example:

acute and chronic airway diseases, such as, but not limited to, chronic bronchitis, allergic bronchitis, bronchial asthma, emphysema, COPD (chronic obstructive pulmonary disease) and interstitial lung disease such as pulmonary fibrosis; pulmonary hypertension;

diseases which are based on allergic and/or chronic, immunological false reactions in the region of the upper airways (pharynx, nose) and the adjacent regions (paranasal sinuses, eyes), such as, but not limited to, allergic rhinitis/sinusitis, chronic rhinitis/sinusitis, allergic conjunctivitis and also nasal polyps;

ocular inflammatory diseases such as, but not limited to, uveitis, scleritis, keratitis, retinal vasculitis, age-related macula degeneration, diabetic nephropathy, and chronic and allergic conjunctivitis;

dermatological diseases especially of proliferative, inflammatory and allergic type, such as, but not limited to psoriasis (vulgaris), toxic and allergic contact eczema, atopic dermatitis (eczema), seborrhoeic eczema, Lichen simplex, sunburn, pruritus in the anogenital area, alopecia greata, hypertrophic scars, discoid lupus erythematosus, follicular and widespread pyodermias, endogenous and exogenous acne, acne rosacea and other proliferative, inflammatory and allergic skin disorders;

diseases which are based on an excessive release of TNF and leukotrienes, such as, for example, diseases of the arthritis type like rheumatoid arthritis, rheumatoid spondylitis, osteoarthritis and other arthritic conditions;

fibrotic diseases, such as, but not limited to, cystic fibrosis, pulmonary fibrosis, hepatic fibrosis renal fibrosis, myelofibrosis, retroperitoneal fibrosis, endomyocardial fibrosis, mediastinal fibrosis, nephrogenic systemic fibrosis, hypertrophic scars or toxic liver damage;

viral, alcoholic or drug-induced acute and fulminant hepatitis, hepatic steatosis (alcoholic and non-alcoholic steatiohepatitis);

diseases of the immune system, such as, but not limited to, AIDS, multiple sclerosis, graft versus host reaction, allograft rejections;

cachexia, cancer cachexia, AIDS cachexia;

types of shock, such as, but not limited to, septic shock, endotoxin shock, gram-negative sepsis, toxic shock syndrome and ARDS (adult respiratory distress syndrome);

diseases in the gastrointestinal region, such as Crohn's disease and ulcerative colitis;

diseases of the heart which can be treated by PDE inhibitors, such as cardiac insufficiency;

diseases which can be treated on account of the tissue-relaxant action of the PDE inhibitors, such as, for example, erectile dysfunction, colics of the kidneys and of the ureters in connection with kidney stones or oncolytic action (to treat preterm delivery); nephritis such as glomerulonephritis, diabetic nephropathy and urinary tract infections;

diabetes insipidus, diabetes mellitus (type I and in particular type II); cancer (in particular lymphoid and myeloid leukaemia); osteoporosis;

conditions associated with cerebral metabolic inhibition, such as, but not limited to, cerebral senility, senile dementia (Alzheimer's disease), memory impairment associated with Parkinson's disease or multiinfarct dementia;

and also diseases of the central nervous system, such as, but not limited to, depressions, anxiety states, spinal cord injury, schizophrenia or arteriosclerotic dementia.

PDE5 inhibitors are thought to be able to influence the physiological and pathophysiological function of various cells, e.g., but not limited to, smooth muscle cells, fibroblasts, myofibroblasts and platelets, which are involved in a great variety of physiological and pathophysiological mechanisms. In particular, PDE5 inhibitors are thought to be able to effect relaxation of the vasculature, thus increasing blood flow, improve the spatial balance between blood perfusion and ventilation within the lung ("rematching" effect) thereby reducing the amount of so-called low V/Q-areas [areas within the lung with high perfusion (Q) but no or reduced ventilation (V)] and high V/Q-areas (areas within the lung with low perfusion but high ventilation), induce neurogenesis, inhibit platelet function, such as aggregation, adhesion and mediator release and, thus, have an anti-inflammatory effect.

In particular, PDE5 inhibitors are thought to be useful in the treatment or prophylaxis of a variety of diseases and disorders, such as for example:

male and female sexual dysfunction, such as, but not limited to, male erectile dysfunction, premature ejaculation, Peyronie's disease;

acute and chronic airway diseases, such as, but not limited to, COPD (chronic obstructive pulmonary disease), bronchitis, emphysema, pulmonary vascular remodeling, interstitial lung disease such as idiopathic pulmonary lung fibrosis (IPF), asthma, cystic fibrosis, bronchiectasis, bronchiolitis obliterans, connective tissue diseases, sarcoidosis, kyphoscoliosis, pneumoconiosis, amyotrophic lateral sclerosis, thoracoplasty, extrinsic allergic alveolitis;

pulmonary hypertension;

inflammatory diseases, such as, but not limited to, vasculature inflammation, acute respiratory distress syndrome, nephritis, mesangial glomerulonephritis, chronic inflammatory bowel disease, disseminated intravascular inflammation, allergic vasculitis, dermatoses (e.g., but not limited to, psoriasis, toxic and allergic contact eczema, atopic eczema, seborrhoeic eczema, Lichen simplex, sunburn, pruritus in the anogenital area, alopecia greata, hypertrophic scars, discoid lupus erythematosus, follicular and widespread pyodermias, endogenous and exogenous acne, acne rosacea), disorders of the arthritis type (e.g., but not limited to, rheumatoid arthritis, rheumatoid spondylitis, osteoarthritis), disorders of the immune system [e.g., but not limited to, AIDS (acquired immunodeficiency syndrome), multiple sclerosis], graft versus host reaction, allograft rejections, shock [e.g., but not limited to, septic shock, endotoxin shock, gram-negative sepsis shock, toxic shock syndrome and ARDS (adult respiratory distress syndrome)], gastrointestinal inflammations (e.g., but not limited to, Crohn's disease and ulcerative colitis); disorders which are based on allergic and/or chronic, immunological false reactions (e.g., but not limited to, allergic rhinitis, allergic sinusitis, chronic rhinitis, chronic sinusitis, allergic conjunctivitis, nasal polyps);

pain, such as, but not limited to, inflammatory pain;

right-heart failure, right heart hypertrophy (car pulmonale), hypertension, hypercholesterolemia, hypertriglyceridemia;

ischaemic diseases, such as, but not limited to, diabetes mellitus (type I and type II), stroke, coronary artery disease, angina (including, but not limited to, vasospastic angina), myocardial infarction, peripheral artery disease, cerebrovascular obstruction, sleep apnea, macular ischaemia, arterial and venous occlusion, congestive heart failure;

ocular inflammatory diseases such as, but not limited to, uveitis, scleritis, keratitis, retinal vasculitis, age-related macula degeneration, diabetic nephropathy, and chronic and allergic conjunctivitis;

diabetic gastroparesis and diseases with symptoms of gastroparesis;

diseases or conditions in which it is desirable to suppress platelet function, for example, but not limited to, after stent implantations (e.g., but not limited to, coronary stenting), after bypass operations, in pulmonary hypertension, thrombotic diseases, post-angioplasty stenosis, coronary artery disease, infarction (e.g., but not limited to, myocardial infarction), instable angina pectoris, stroke, and arterial and venous occlusion diseases (e.g., but not limited to, claudicatio intermittens);

diseases or conditions with an impairment or dysfunction of cerebral vascular reactivity and/or neurovascular coupling, such as, but not limited to, arteriosclerotic dementia, multiinfarct dementia, cerebral senility;

diseases which are based on neuronal damage or degradation, such as but not limited to, stroke, spinal cord injury, brain injury, morbus parkinson, amyotrophic lateral sclerosis, morbus alzheimer, amyloidosis, prion diseases and neuropathy;

peripheral arterial diseases, chronic renal failure, chronic heart failure, sepsis, senile dementia (Alzheimer's disease), Creutzfeld-Jacob disease, septic encephalopathy, arteriosclerotic encephalopathy, diabetes associated encephalopathy, toxic encephalopathy, vascular and neuronal dementia, Huntington's disease, Parkinson's disease, multiple sclerosis and preeclampsia;

portal hypertension, liver cirrhosis, toxic liver damage (e.g., but not limited to, alcohol-induced liver damage), hepatitis, thrombosis of the portal vein, Budd-Chiari syndrome, malformation of liver veins, compression of liver veins (e.g., but without limitation, due to tumors), arteriovenous fistula, diseases associated with an enlarged spleen, schistosomiasis (bilharziosis), sarcoidosis and other granulomatous diseases, primary biliary cirrhosis, myeloproliferative disorders (e.g., but not limited to, chronic myeloid leukemia, osteomyelofibrosis), lymphatic systemic diseases, collagenosis (e.g., but not limited to, systemic lupus erythematodes, sclerodermia), morbus Osler (congenital arteriovenous malformations, inter alia in the liver), nodular regenerative hyperplasia, tricuspid insufficiency, pericarditis constrictiva, veno-occlusive disease (VOD), non-alcoholic steatohepatitis (NASH);

fibrotic diseases, such as, but not limited to, cystic fibrosis, pulmonary fibrosis, hepatic fibrosis renal fibrosis, myelofibrosis, retroperitoneal fibrosis, endomyocardial fibrosis, mediastinal fibrosis, nephrogenic systemic fibrosis, hypertrophic scars or toxic liver damage;

benign prostatic hyperplasia;

insufficient uteroplacental blood flow in pregnancies with fetal growth restriction;

insufficient brain skills, such as but not limited to, verbal attainment, attention, concentration, deductive thinking, central auditory processing, cognition, learning, vigilance, apprehension and reagibility;

Overactive Bladder; LUTS=lower urinary tract symptoms; Raynauds syndrome/phenomenon.

In this respect, the term "pulmonary hypertension" in particular embraces pulmonary arterial hypertension including primary pulmonary hypertension (e.g. sporadic or familial) and pulmonary arterial hypertension related, for example, but without limitation, to collagen vascular disease, congenital systemic-to-pulmonary shunts, portal hypertension, human immunodeficiency virus infection, drugs or toxins (e.g., but not limited to, anorexigens), persistent pulmonary hypertension of the newborn;

pulmonary venous hypertension due to, for example, but without limitation, left-sided atrial or ventricular heart disease, left-sided valvular heart disease, extrinsic compression of central pulmonary veins (e.g. fibrosing mediastinitis, adenopathy in relation to tumors), pulmonary veno-occlusive disease;

pulmonary hypertension associated with disorders of the respiratory system or hypoxemia including, for example, but without limitation, chronic obstructive pulmonary disease (COPD), interstitial lung disease, sleep-disordered breathing, alveolar hypoventilation disorders, chronic exposure to high altitude, neonatal lung disease, alveolar-capillary dysplasia;

pulmonary hypertension caused by chronic thrombotic or embolic diseases including thromboembolic obstruction of proximal pulmonary arteries and obstruction of distal pulmonary arteries, such as pulmonary embolism (due to thrombus, tumor, ova, parasites, or foreign material), in situ thrombosis and sickle-cell disease, in particular chronic thromboembolic pulmonary hypertension (CTEPH);

pulmonary hypertension caused by disorders directly affecting the pulmonary vasculature including inflammatory disorders (e.g., but not limited to, schistosomiasis, sarcoidosis) and pulmonary capillary hemangiomatosis.

It is noteworthy that compounds of the invention, which are inhibitors of type 4 phosphodiesterase (PDE4) and of type 5 phosphodiesterase (PDE5), have the potential to be more effective in treatment of distinct disease identities than compounds inhibiting only one of those two enzymes, since inhibition of PDE4 and PDE5 might address divers and different pathophysiologies occurring within one disease as e.g. lung fibrosis.

In respect to lung fibrosis it has been described that inhibitors of type 4 phosphodiesterase inhibit TGF-e induced transition of lung fibroblasts to myofibroblasts (Dunkern et al., Eur. J. Pharmacol., 572(1): 12-22, 2007), which is a hallmark of fibrosis progression. They have further been described to inhibit matrix metalloproteinase production from lung fibroblasts (Martin-Chouly C A et al., Life Sci. 75(7): 823-40, 2004) and to prevent chemotaxis of these cells (Kohyama T et al., Am. J. Respir. Cell Mol. Biol., 26(6): 694-701, 2002), which are important pathophysiological aspects of lung fibrosis. In addition the selective type 4 phosphodiesterase inhibitor roflumilast have also been shown in-vivo in the bleomycin-induced lung fibrosis model in mice to inhibit fibrosis development (Cortijo J et al., Br. J. Pharmacol., 156(3): 534-44, 2009).

On the other hand it has been shown in respect to lung fibrosis that PDE5 inhibition by means of the selective PDE5 inhibitor sildenafil attenuates bleomycin-induced pulmonary fibrosis and pulmonary hypertension through inhibition of ROS generation and RhoA/Rho kinase activation (Hemnes A R, Zaiman A, Champion H C, Am. J. Physiol. Lung Cell. Mol. Physiol. 2008 January; 294(1):L24-33. Epub 2007 Oct. 26) and it has been shown in clinical human open-label trials that sildenafil improves lung hemodynamic (vascular resistance and ventilation/perfusion matching) and increases exercise tolerance in patients with pulmonary fibrosis (Ghofrani et al., Lancet 360, 895-900, 2002; Collard et al., Chest 131, 897-899, 2007).

Accordingly, the invention further relates to the compounds of the invention for use in the treatment or prophylaxis of diseases, especially diseases alleviated by inhibition of type 4 and type 5 phosphodiesterase, in particular the diseases exemplified above.

Preferably, the invention relates to the compounds of the invention for use in the treatment or prophylaxis of the following diseases:

acute and chronic airway diseases, such as interstitial lung disease such as pulmonary fibrosis, cystic fibrosis, bronchial asthma, chronic bronchitis, allergic bronchitis, allergic rhinitis, emphysema, chronic obstructive pulmonary disease (COPD) and COPD associated with pulmonary hypertension;

pulmonary hypertension, in particular thromboembolic pulmonary hypertension;

dermatological diseases, such as psoriasis and atopic dermatitis (eczema);

ocular diseases, such as uveitis, scleritis, keratitis, retinal vasculitis, age-related macula degeneration, diabetic nephropathy, and chronic and allergic conjunctivitis;

rheumatoid arthritis; and inflammations in the gastrointestinal region, such as Crohn's disease and ulcerative colitis.

The invention also relates to the use of a compound of the invention in the manufacture of a pharmaceutical composition inhibiting the type 4 and type 5 phosphodiesterase, in particular a pharmaceutical composition for the treatment or prophylaxis of diseases alleviated by inhibition of type 4 and type 5 phosphodiesterase, preferably, a pharmaceutical composition for the treatment or prophylaxis of the diseases exemplified above.

In particular, the invention relates to the use of a compound of the invention in the manufacture of a pharmaceutical composition for the treatment or prophylaxis of an acute or chronic airway disease, such as, but not limited to, interstitial lung disease, pulmonary fibrosis, cystic fibrosis, bronchial asthma, chronic bronchitis, emphysema, chronic obstructive pulmonary disease (COPD) or COPD associated with pulmonary hypertension.

The invention also relates to the use of a compound of the invention in the manufacture of a pharmaceutical composition for the treatment or prophylaxis of pulmonary hypertension or thromboembolic pulmonary hypertension.

The invention relates also to the use of a compound of the invention in the manufacture of a pharmaceutical composition for the treatment or prophylaxis of allergic rhinitis or allergic asthma.

Furthermore, the invention relates to the use of a compound of the invention in the manufacture of a pharmaceutical composition for the treatment or prophylaxis of dermatological diseases, such as, but not limited to, psoriasis or atopic dermatitis (eczema).

In addition, the invention relates to the use of a compound of the invention in the manufacture of a pharmaceutical composition for the treatment or prophylaxis of ocular diseases, such as, but not limited to uveitis, scleritis, keratitis, retinal vasculitis, age-related macula degeneration, diabetic nephropathy, or chronic or allergic conjunctivitis.

The invention relates as well to the use of a compound of the invention in the manufacture of a pharmaceutical composition for the treatment or prophylaxis of rheumatoid arthritis.

Additionally, the invention relates to the use of a compound of the invention in the manufacture of a pharmaceutical composition for the treatment or prophylaxis of inflammations in the gastrointestinal region, such as, but not limited to, Crohn's disease or ulcerative colitis.

In a particularly preferred embodiment of the invention, in the above-mentioned uses the compound of the invention is a compound of the examples according to the invention.

The invention further relates to a method of treating or preventing a disease comprising administering to a patient in need thereof a therapeutically effective amount of at least one of the compounds of the invention.

In particular, the invention relates to a method of treating or preventing one of the above mentioned diseases comprising administering to a patient in need thereof a therapeutically effective amount of at least one of the compounds of the invention.

Especially, the invention relates to a method of treating or preventing a disease, which is alleviated by inhibition of the type 4 and type 5 phosphodiesterase comprising administering to a patient in need thereof a therapeutically effective amount of at least one of the compounds of the invention.

Preferably, the invention relates to a method of treating or preventing an acute or chronic airway disease, for example, but not limited to interstitial lung disease, pulmonary fibrosis, cystic fibrosis, bronchial asthma, chronic bronchitis, emphysema, chronic obstructive pulmonary disease (COPD) or COPD associated with pulmonary hypertension comprising administering to a patient in need thereof a therapeutically effective amount of at least one of the compounds of the invention.

The invention relates also to a method of treating or preventing pulmonary hypertension or thromboembolic pulmonary hypertension comprising administering to a patient in need thereof a therapeutically effective amount of at least one of the compounds of the invention.

The invention relates also to a method of treating or preventing allergic rhinitis or allergic asthma comprising administering to a patient in need thereof a therapeutically effective amount of at least one of the compounds of the invention.

Furthermore, the invention preferably relates to a method of treating or preventing dermatological diseases, such as, but not limited to, psoriasis or atopic dermatitis (eczema) comprising administering to a patient in need thereof a therapeutically effective amount of at least one of the compounds of the invention.

In addition, the invention preferably relates to a method of treating or preventing diseases of the eye, such as, but not limited to, uveitis, scleritis, keratitis, retinal vasculitis, age-related macula degeneration, diabetic nephropathy or chronic or allergic conjunctivitis comprising administering to a patient in need thereof a therapeutically effective amount of at least one of the compounds of the invention.

The invention relates as well to a method of treating or preventing rheumatoid arthritis comprising administering to a patient in need thereof a therapeutically effective amount of at least one of the compounds of the invention.

Additionally, the invention preferably relates to a method of treating or preventing diseases in the gastrointestinal region, such as, but not limited to, Crohn's disease or ulcerative colitis comprising administering to a patient in need thereof a therapeutically effective amount of at least one of the compounds of the invention.

In the above methods, the patient is preferably a mammal, more preferably a human. Furthermore, in the above methods, at least one of the compounds of the invention can be used. Preferably, one or two of the compounds of the invention are used, more preferably, one of the compounds of the invention is used.

In a particularly preferred embodiment of the invention, the above methods of treating or preventing one of the above mentioned diseases comprise administering to a patient in need thereof a therapeutically effective amount of a compound of the examples according to the present invention.

Pharmaceutical Compositions

The invention furthermore relates to a pharmaceutical composition, which comprises at least one of the compounds of the invention together with at least one pharmaceutically acceptable auxiliary.

Preferably, the pharmaceutical composition comprises one or two of the compounds of the invention. More preferably, the pharmaceutical composition comprises one of the compounds of the invention.

In a particularly preferred embodiment of the invention, the pharmaceutical composition comprises a compound of the examples according to the present invention together with at least one pharmaceutically acceptable auxiliary.

The invention furthermore relates to a pharmaceutical composition according to the invention inhibiting the type 4 and type 5 phosphodiesterase, especially for (use in) the treatment or prophylaxis of diseases alleviated by inhibition of type 4 and type 5 phosphodiesterase, in particular for the treatment or prophylaxis of the diseases exemplified above.

The invention encompasses pharmaceutical compositions according to the invention, as defined above, in particular for (use in) the treatment or prophylaxis of one or more of the following diseases:

interstitial lung disease such as pulmonary fibrosis, cystic fibrosis, bronchial asthma, chronic bronchitis, allergic bronchitis, allergic rhinitis, emphysema, chronic obstructive pulmonary disease (COPD) and COPD associated with pulmonary hypertension;

pulmonary hypertension, in particular thromboembolic pulmonary hypertension;

dermatological diseases, such as psoriasis and atopic dermatitis (eczema);

ocular diseases, such as uveitis, scleritis, keratitis, retinal vasculitis, age-related macula degeneration, diabetic nephropathy, and chronic and allergic conjunctivitis rheumatoid arthritis; and
inflammations in the gastrointestinal region, such as Crohn's disease and ulcerative colitis.

Although the compounds of the invention may be administered orally, oral administration is not presently thought to be a preferred route of administration. This is because, without intending to be bound by this data, preliminary tests appear to indicate low systemic exposure after oral administration of the compounds of the invention in rats at a dose level of about 10 µmol/kg of the compound of the invention per kg bodyweight when formulated in aqueous suspension with polyethyleneglycol 400 (1.3%) and hypromellose (4%).

The compounds of the invention respectively the pharmaceutical compositions comprising the compounds of the invention therefore preferably may be administered, for example, by external topical (i.e. through the skin/transdermal or via the eye), parenteral (e.g. intravenous, subcutaneous, intraarterial, intraperitoneal, intraarticular, or intramuscular), inhaled or nasal administration. The compounds may also be administered via the rectal route, for example in form of a suppository or a foam.

Accordingly, the pharmaceutical composition can be suitable for (e.g. adapted for) external topical (i.e. through the skin/transdermal or via the eye), parenteral (e.g. intravenous, subcutaneous, intraarterial, intraperitoneal, intraarticular, or intramuscular), inhaled or nasal administration. The pharmaceutical composition is preferably suitable for inhaled administration. Inhaled administration involves topical administration to the lung e.g. by aerosol or dry powder composition.

Inhalable and Intranasal Pharmaceutical Compositions

Formulations for inhalation include powder compositions, which will preferably contain lactose, and spray compositions which may be formulated, for example, as aqueous solutions or suspensions or as aerosols delivered from pressurised packs, with the use of a suitable propellant, e.g. 1,1,1,2-tetrafluorethane, 1,1,1,2,3,3,3-heptafluoropropane, carbon dioxide or other suitable gas.

A class of propellants, which is believed to have minimal ozone-depleting effects in comparison to conventional chlorofluorocarbons comprise hydrofluorocarbons and a number of medicinal aerosol formulations using such propellant systems are disclosed in, for example, EP 0372777, WO91/04011, WO91/11173, WO91/11495, WO91/14422, WO93/11743, and EP-0553298. These applications are all concerned with the preparation of pressurised aerosols for the administration of medicaments and seek to overcome problems associated with the use of this new class of propellants, in particular the problems of stability associated with the pharmaceutical formulations prepared. The applications propose, for example, the addition of one or more of excipients such as polar cosolvents or wetting agents (e.g. alcohols such as ethanol), alkanes, dimethyl ether, surfactants (including fluorinated and non-fluorinated surfactants, carboxylic acids such as oleic acid, polyethoxylates etc.) or bulking agents such as a sugar (see for example WO02/30394) and vehicles such as cromoglicic acid and/or nedocromil which are contained at concentrations, which are not therapeutically and prophylactically active (see WO00/07567). The aerosol dosage form can also take the form of a pump-atomizer.

For suspension aerosols, the compound of the invention should be micronised so as to permit inhalation of substantially all of the compound of the invention into the lungs upon administration of the aerosol formulation, thus the compound of the invention will have a mean particle size of less than 100 µm, desirably less than 20 µm, and preferably in the range of 1 to 10 µm (D50 value, e.g. as measured using laser diffraction).

Dry powder inhalable compositions: For pharmaceutical compositions suitable (e.g. adapted for) inhaled administration, the pharmaceutical composition may for example be a dry powder inhalable composition. The dry powder composition comprises finely divided compound of the invention optionally together with a finely divided pharmaceutically acceptable carrier, which is preferably present and may be one or more materials known as carriers in dry powder inhalation compositions, for example saccharides, including monosaccharides, disaccharides, polysaccharides and sugar alcohols such as arabinose, glucose, fructose, ribose, mannose, sucrose, trehalose, lactose, maltose, starches, dextran or mannitol. An especially preferred carrier is lactose, particularly in the form of the monohydrate.

The dry powder may be in capsules of gelatine or plastic, or in blisters, for use in a dry powder inhalation device, preferably in dosage units of the compound of the invention together with the carrier in amounts to bring the total weight of powder in each capsule to from 5 mg to 50 mg. Alternatively the dry powder may be contained in a reservoir of a multi-dose dry powder inhalation device. Capsules and cartridges of for example gelatin, or blisters of for example laminated aluminium foil, for use in an inhaler or insulator may be formulated containing a powder mix of the compounds of the invention and a suitable powder base such as lactose or starch, preferably lactose. In this aspect, the compound of the invention is suitably micronised so as to permit inhalation of substantially all of the compound of the invention into the lungs upon administration of the dry powder formulation, thus the compound of the invention will have a particle size of less than 100 µm, desirably less than 20 µm, and preferably in the range 1 to 10 µm (D50 value, e.g. as measured using laser diffraction). The solid carrier, where present, generally has a maximum particle diameter of 300 µm, preferably 200 µm, and conveniently has a mean particle diameter of 40 to 100 µm, preferably 50 to 75 µm. The particle size of the compound of the invention and that of a solid carrier where present in dry powder compositions, can be reduced to the desired level by conventional methods, for example by grinding in an air-jet mill, ball mill or vibrator mill, microprecipitation, spray drying, lyophilisation or recrystallisation from supercritical media.

Where the inhalable form of the composition of the invention is the finely divided particulate form, the inhalation device may be, for example a dry powder inhalation device adapted to deliver dry powder from a capsule or blister containing a dosage unit of the dry powder or a multi-dose dry powder inhalation device. Such dry powder inhalation devices are known in the art. Examples which may be mentioned are Cyclohaler®, Diskhaler®, Rotadisk®, Turbohaler®, Novolizeré, Easyhaleré, Jethaleré, Clickhaleré or the dry powder inhalation devices disclosed in EP 0 505 321, EP 407028, EP 650410, EP 691865 or EP 725725 (Ultrahaler®).

Formulations for inhalation by nebulization may be formulated with an aqueous vehicle with the addition of agents such as acid or alkali, buffer salts, isotonicity adjusting agents or antimicrobials. They may be sterilised by filtration or heating in an autoclave. Suitable technologies for this type of administration are known in the art. As an example the Mystic® technology is to be mentioned (see for example U.S. Pat. No. 6,397,838, U.S. Pat. No. 6,454,193 and U.S. Pat. No. 6,302,331).

Preferred unit dosage formulations are those containing a pharmaceutical effective dose, as hereinbelow recited, or an appropriate fraction thereof, of the active ingredient. Thus, in the case of formulations designed for delivery by metered dose pressurised aerosols, one actuation of the aerosol may deliver half of the therapeutical effective amount such that two actuations are necessary to deliver the therapeutically effective dose.

In the dry powder inhalable composition, the compound of the invention can for example be present in about 0.1% to about 70% (e.g. about 1% to about 50%, e.g. about 5% to about 40%, e.g. about 20 to about 30%) by weight of the composition.

In case of intranasal administration, for example, sprays and solutions to be applied in drop form are preferred formulations. Intranasal sprays or nasal drops may be formulated with aqueous or non-aqueous vehicles with or without the addition of agents such as thickening agents, buffer salts or acid or alkali to adjust the pH, isotonicity adjusting agents, preservatives or anti-oxidants.

Pharmaceutical Compositions Suitable for External Topical Administration

"External topical" administration means topical administration to an external body part (i.e. excluding, for example, the lung or mouth, but including the lips or the eye). External topical administration (e.g. through the skin/transdermal) can for example be to those parts of the skin affected by or susceptible to a dermatological disease, such as for example, atopic dermatitis or psoriasis.

In case of external topical administration (i.e. through the skin/transdermal), suitable pharmaceutical formulations are, for example, ointments, creams (usually an oil-in-water or water-in-oil pharmaceutical composition, usually an emulsion), lotions, pastes, gels, powders, solutions, emulsions, suspensions, oils, sprays and patches (e.g., but not limited to, transdermal therapeutic systems).

In an external-topical pharmaceutical composition, e.g. an ointment or an oil-in-water or water-in-oil composition, the compound of the invention is suitably present in 0.05 to 10%, preferably 0.1 to 5%, more preferably 0.1 to 3%, still more preferably 0.5 to about 2.5%, by weight of the composition (w/w).

External topical administration (e.g. via the eye) can for example be to the eye affected by or susceptible to an ocular disease, such as for example, uveitis, scleritis, keratitis, retinal vasculitis, age-related macula degeneration, diabetic nephropathy, and chronic and allergic conjunctivitis.

Examples, which may be mentioned in connection with pharmaceutical formulations for the eye are eyebaths or eye lotions, eye inserts, eye ointments, eye sprays, eye drops, preparations for intraocular application [e.g. intravitreale application, intraocular injection] and eyelid ointments.

Pharmaceutical Compositions for Oral or Parenteral Administration

For parenteral modes of administration such as, for example, intravenous, subcutaneous or intramuscular administration, preferably solutions (e.g., but not limited to, sterile solutions, isotonic solutions) are used. They are preferably administered by injection or infusion techniques.

A pharmaceutical composition suitable for parenteral (e.g. intravenous, subcutaneous or intramuscular) administration can comprise a solution or suspension of the compound of the invention in a sterile parenterally acceptable carrier (e.g. sterile water) or parenterally acceptable oil. Alternatively, the solution can be lyophilised. A lyophilised pharmaceutical composition suitable for parenteral administration may, in use, optionally be reconstituted with a suitable solvent, e.g. sterile water or a sterile parenterally acceptable aqueous solution, just prior to administration.

Oral administration is not preferred, as described above. However, a pharmaceutical composition for oral administration may be liquid or solid; for example, it may be a syrup, suspension or emulsion; as well it may be, for example, a tablet, coated tablet (dragee), pill, cachet, capsule (caplet), or in form of granules.

A liquid formulation may optionally consist of a suspension or solution of the compound of the invention in a pharmaceutically acceptable liquid carrier, for example an aqueous solvent such as water, ethanol or glycerine, or a non-aqueous solvent, such as polyethylene glycol or an oil. The formulation may contain in addition, a suspending agent, a preservative, a flavouring and/or a colouring agent.

A pharmaceutical composition for oral administration being a tablet, through not preferred, may comprise one or more pharmaceutically acceptable auxiliaries (for example, carriers and/or excipients) suitable for preparing tablet formulations. The carrier may, for example, be or include lactose, cellulose or mannitol. The tablet may also or instead contain one or more pharmaceutically acceptable excipients, for example, a binding agent, a lubricant and/or a tablet disintegrant.

The pharmaceutical compositions according to the invention for oral or parenteral administration preferably contain the compound or compounds of the invention in a total amount of from 0.1 to 99.9%, more preferably 5 to 95%, in particular 20 to 80% by weight of the composition (w/w).

In general, as pharmaceutically acceptable auxiliaries, any auxiliaries known to be suitable for preparing a particular pharmaceutical composition can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The pharmaceutical compositions/formulations can be manufactured in a manner known to a person skilled in the art, e.g. by dissolving, mixing, granulating, dragee-making, levigating, emulsifying, encapsulating, entrapping or lyophilizing processes.

Dosages

Generally, the pharmaceutical compositions according to the invention can be administered such that the dose of the compound of the invention is in the range customary for type 4 phosphodiesterase inhibitors.

The pharmaceutically acceptable compounds of the invention are preferably administered in a daily dose (for an adult patient) of, for example an oral or parenteral dose of 0.01 mg to 250 mg per day, preferably 0.05 mg to 100 mg per day, more preferably 0.05 mg to 10 mg per day, or a nasal or inhaled dose of 0.001 mg to 30 mg per day, preferably 0.01 mg to 10 mg per day, more preferably 0.1 mg to 4 mg per day, of the compound of the invention, calculated as the free compound (=the unsolvated, unhydrated, non-salt form of the compound).

In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical compositions of the invention can be administered in a single dose per day or in multiple subdoses, for example, 2 to 4 doses per day. A single dose unit of the pharmaceutical composition can contain, in case of inhalative administration e.g. from 0.001 mg to 10 mg, preferably 0.01 mg to 7.5 mg, more preferably 0.1 mg to 4 mg of the compound of the invention. Administration of the pharmaceutical composition in a single dose per day is preferred.

Combinations

Depending on the particular disease to be treated or prevented, additionally therapeutic agents, which are normally administered to treat or prevent that disease, may optionally be co-administered with the compounds of the invention.

In a preferred embodiment, at least one of the compounds of the invention is co-administered with at least one therapeutic agent selected from the group consisting of corticosteroids, anticholinergics, $e_2$-adrenoreceptor agonists, H1 receptor antagonists, leukotriene receptor antagonists, 5-lipoxygenase inhibitors, endothelin receptor antagonists, prostacyclines, calcium channel blockers, beta-blockers, type 4 phosphodiesterase inhibitors, type 5 phosphodiesterase inhibitors, immunosuppressants, vitamin D analogues, HMG-CoA reductase-inhibitors, lung surfactants, antibiotics, guanylyl-cyclase activators/stimulators, tetrahydrobiopterin and tetrahydrobiopterin derivatives, anticoagulants, diuretics, pirfenidone and digitalis glycosides.

In this respect, the "therapeutic agent" includes the corticosteroids, anticholinergics, $e_2$-adrenoreceptor agonists, H1 receptor antagonists, leukotriene receptor antagonists, 5-lipoxygenase inhibitors, endothelin receptor antagonists, prostacyclines, calcium channel blockers, beta-blockers, type 4 phosphodiesterase inhibitors, type 5 phosphodiesterase inhibitors, immunosuppressants, vitamin D analogues, HMG-CoA reductase-inhibitors, lung surfactants, antibiotics, guanylyl-cyclase activators/stimulators, tetrahydrobiopterin and tetrahydrobiopterin derivatives, anticoagulants, diuretics, pirfenidone and digitalis glycosides in form of the free compounds, the pharmaceutically acceptable salts thereof, the pharmaceutically acceptable derivatives thereof (e.g., but not limited to, ester derivatives, N-oxides etc.), the solvates (hydrates) thereof and the stereoisomers of the compounds, salts, derivatives and solvates.

Co-administration of at least one of the compounds of the invention with at least one therapeutic agent selected from the group consisting of corticosteroids, anticholinergics, $e_2$-adrenoreceptor agonists, H1 receptor antagonists, leukotriene receptor antagonists, 5-lipoxygenase inhibitors, endothelin receptor antagonists, prostacyclines, calcium channel blockers, beta-blockers, type 4 phosphodiesterase inhibitors, type 5 phosphodiesterase inhibitors, immunosuppressants, vitamin D analogues, HMG-CoA reductase-inhibitors, lung surfactants, antibiotics, guanylyl-cyclase activators/stimulators, tetrahydrobiopterin and tetrahydrobiopterin derivatives, anticoagulants, diuretics, pirfenidone and digitalis glycosides can take place in form of a fixed combination, a non-fixed combination or a kit of parts.

A "fixed combination" is defined as a combination wherein the compound of the invention and the therapeutic agent intended for co-administration are present in one dosing unit or in a single entity.

One example of a fixed combination is a pharmaceutical composition wherein the compound of the invention and the therapeutic agent are present in admixture for simultaneous administration. Another example of a fixed combination is a pharmaceutical composition wherein the compound of the invention and the therapeutic compound are present in one dosing unit without being in admixture.

A "non-fixed combination" or "kit of parts" is defined as a combination wherein the compound of the invention and the therapeutic agent are present in more than one dosing unit. In a non-fixed combination or a kit of parts the compound of the invention and the therapeutic agent are provided as separate formulations. They might be packaged and presented together as separate components of a combination pack for simultaneous, sequential or separate use in combination therapy. Simultaneous or sequential administration of the compound of the invention and the therapeutic agent are preferred. In case of sequential or separate administration of the compound of the invention and the therapeutic agent, the compound of the invention can be administered before or after administration of the therapeutic agent.

Sequential administration encompasses a short time period between the administration of the compound of the invention and the therapeutic agent or vice versa (for example, the time that is needed to swallow one tablet after the other).

Separate administration encompasses longer time periods between the administration of the compound of the invention and the therapeutic agent. In a preferred embodiment of the invention, the compound of the invention is administered while the therapeutic agent (or vice versa) still has an therapeutic effect on the patient being treated.

In a particularly preferred embodiment of the invention the co-administration of at least one of the compounds of the invention with at least one therapeutic agent selected from the group consisting of corticosteroids, anticholinergics, $e_2$-adrenoreceptor agonists, H1 receptor antagonists, leukotriene receptor antagonists, 5-lipoxygenase inhibitors, endothelin receptor antagonists, prostacyclines, calcium channel blockers, beta-blockers, type 4 phosphodiesterase inhibitors, type 5 phosphodiesterase inhibitors, immunosuppressants, vitamin D analogues, HMG-CoA reductase-inhibitors, lung surfactants, antibiotics, guanylyl-cyclase activators/stimulators, tetrahydrobiopterin and tetrahydrobiopterin derivatives, anticoagulants, diuretics, pirfenidone and digitalis glycosides leads to a therapeutic effect that is greater than the sum of the therapeutic effects that will be achieved in case the compound of the invention respectively the additional therapeutic agent are given alone.

The type of formulation of the compound of the invention and the therapeutic agent of a non-fixed combination or a kit of parts can be identical, i.e. both, the compound of the invention and the therapeutic agent are formulated, for example, as powder, solution or suspension suitable for inhalative administration, or can be different, i.e. suited for different administration forms, such as e.g. the compound of the invention is formulated as powder, solution or suspension suitable for inhalative administration and the therapeutic agent is formulated as tablet or capsule for oral administration.

Accordingly, the invention additionally relates to a pharmaceutical composition presented either as a fixed combination, a non-fixed combination or kit of parts comprising at least one of the compounds of the invention, at least one therapeutic agent selected from the group consisting of corticosteroids, anticholinergics, $e_2$-adrenoreceptor agonists, H1 receptor antagonists, leukotriene receptor antagonists, 5-lipoxygenase inhibitors, endothelin receptor antagonists, prostacyclines, calcium channel blockers, beta-blockers, type 4 phosphodiesterase inhibitors, type 5 phosphodiesterase inhibitors, immunosuppressants, vitamin D analogues, HMG-CoA reductase-inhibitors, lung surfactants, antibiotics, guanylyl-cyclase activators/stimulators, tetrahydrobiopterin and tetrahydrobiopterin derivatives, anticoagulants, diuretics, pirfenidone and digitalis glycosides, and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), a e2-adrenoreceptor agonist and at least one pharmaceutically acceptable auxiliary. In a particularly preferred embodiment, the above-mentioned fixed combination, non-fixed combination or kit of parts comprise:
a compound of the invention and salbutamol,
a compound of the invention and milveterol,
a compound of the invention and indacaterol,
a compound of the invention and carmoterol,
a compound of the invention and salmeterol,
a compound of the invention and formoterol,
a compound of the invention and vilanterol, or
a compound of the invention and olodaterol,
and at least one pharmaceutically acceptable auxiliary.

In a preferred embodiment, the pharmaceutically acceptable salt of salbutamol is salbutamol sulfate. In a preferred embodiment, the pharmaceutically acceptable salt of milveterol is milveterol hydrochloride. In a preferred embodiment, the pharmaceutically acceptable salt of carmoterol is carmoterol hydrochloride. In a preferred embodiment, the pharmaceutically acceptable salt of salmeterol is salmeterol xinafoate. In another preferred embodiment, the pharmaceutically acceptable salt of formoterol is formoterol hemifumarate monohydrate. In another preferred embodiment, the stereoisomer of formoterol is R,R-formoterol. In another preferred embodiment, the pharmaceutically acceptable salt of R,R-formoterol is R,R-formoterol L-tartrate. In a preferred embodiment, the pharmaceutically acceptable salt of vilanterol is vilanterol trifenatate. In another preferred embodiment, the pharmaceutically acceptable salt of vilanterol is vilanterol d-phenyl cinnamate. In a preferred embodiment, the pharmaceutically acceptable salt of olodaterol is olodaterol hydrochloride.

Preferably the e2-adrenoreceptor agonist is a long-acting e2-adrenoreceptor agonist; particularly preferred in this respect are those e2-adrenoreceptor agonists having a therapeutic effect over a 12-24 hours period. Furthermore, the e2-adrenoreceptor agonist is preferably for inhaled administration, for once daily administration and for simultaneous inhaled administration.

Preferably, the combination comprising a compound of the invention and a e2-adrenoreceptor agonist is for the treatment or prophylaxis of bronchial asthma and COPD.

In a preferred embodiment, the above-mentioned fixed combination, non-fixed combination or kit of parts comprise a compound of the invention (in particular the compound of the invention is one of the examples of the invention), a corticosteroid and at least one pharmaceutically acceptable auxiliary. In a particularly preferred embodiment, the above-mentioned fixed combination, non-fixed combination or kit of parts comprise:
a compound of the invention and budesonide,
a compound of the invention and fluticasone,
a compound of the invention and beclometasone,
a compound of the invention and mometasone,
a compound of the invention and triamcinolone acetonide, or
a compound of the invention and ciclesonide,
and at least one pharmaceutically acceptable auxiliary.

In a preferred embodiment, the pharmaceutically acceptable derivative of fluticasone is fluticasone-17-propionate. In another preferred embodiment, the pharmaceutically acceptable derivative of fluticasone is fluticasone-17-furoate. In another preferred embodiment, the pharmaceutically acceptable derivative of beclometasone is beclometasone 17,21-dipropionate ester. In a preferred embodiment, the pharmaceutically acceptable derivative of mometasone is mometasone furoate.

The combination comprising a compound of the invention and a corticosteroid preferably is for the treatment and prophylaxis of bronchial asthma, COPD, allergic rhinitis or a dermatological disease, such as for example atopic dermatitis. Preferably the corticosteroid is used for external topical, intranasal or inhaled administration; in severe cases, the corticosteroid may also be used orally.

In a preferred embodiment, the above-mentioned fixed combination, non-fixed combination or kit of parts comprise a compound of the invention (in particular the compound of the invention is one of the examples of the invention), an anticholinergic and at least one pharmaceutically acceptable auxiliary.

In a particularly preferred embodiment, the above-mentioned fixed combination, non-fixed combination or kit of parts comprise:
a compound of the invention and glycopyrronium bromide,
a compound of the invention and aclidinium bromide,
a compound of the invention and tiotropium bromide,
a compound of the invention and ipratropium bromide, or
a compound of the invention and darotropium bromide,
and at least one pharmaceutically acceptable auxiliary.

In a preferred embodiment, the stereoisomer of glycopyrronium bromide is (R,R)-glycopyrronium bromide. In a preferred embodiment, tiotropium bromide is used in form of its monohydrate.

Preferably, the anticholinergic is for inhaled administration. The combination comprising a compound of the invention and an anticholinergic is preferably for the treatment or prophylaxis of COPD.

In a preferred embodiment, the above-mentioned fixed combination, non-fixed combination or kit of parts comprise a compound of the invention (in particular the compound of the invention is one of the examples of the invention), a H1 receptor antagonist and at least one pharmaceutically acceptable auxiliary. In a particularly preferred embodiment, the above-mentioned fixed combination, non-fixed combination or kit of parts comprise:
a compound of the invention and azelastine,
a compound of the invention and olopatadine,
a compound of the invention and loratadine,
a compound of the invention and desloratadine, or
a compound of the invention and cetirizine,
and at least one pharmaceutically acceptable auxiliary.

In a preferred embodiment, the pharmaceutically acceptable salt of azelastine is azelastine hydrochloride. In a preferred embodiment, the pharmaceutically acceptable salt of olapatadine is olapatadine hydrochloride. In a preferred embodiment, the pharmaceutically acceptable salt of cetirizine is cetirizine dihydrochloride. In a preferred embodiment, the stereoisomer of cetirizine is levocetirizine. In another preferred embodiment, the pharmaceutically acceptable salt of levocetirizine is levocetirizine dihydrochloride.

The combination comprising a compound of the invention and a H1 receptor agonist is preferably for the treatment or prophylaxis of allergic rhinitis.

In a preferred embodiment, the above-mentioned fixed combination, non-fixed combination or kit of parts comprise a compound of the invention (in particular the compound of the invention is one of the examples of the invention), a leukotriene receptor antagonist and at least one pharmaceutically acceptable auxiliary. In a particularly preferred embodiment, the above-mentioned fixed combination, non-fixed combination or kit of parts comprise:

a compound of the invention and montelukast,
a compound of the invention and pranlukast, or
a compound of the invention and zafirlukast,
and at least one pharmaceutically acceptable auxiliary.

In a preferred embodiment, the pharmaceutically acceptable salt of montelukast is montelukast sodium. In another preferred embodiment, pranlukast is used in form of its monohydrate.

The combination comprising a compound of the invention and a leukotriene receptor antagonist is preferably for the treatment or prophylaxis of bronchial asthma.

In a preferred embodiment, the above-mentioned fixed combination, non-fixed combination or kit of parts comprise a compound of the invention (in particular the compound of the invention is one of the examples of the invention), a 5-lipoxygenase inhibitor and at least one pharmaceutically acceptable auxiliary. In a particularly preferred embodiment, the above-mentioned fixed combination, non-fixed combination or kit of parts comprise:
a compound of the invention and zileuton,
and at least one pharmaceutically acceptable auxiliary.

The combination comprising a compound of the invention and a 5-lipoxygenase inhibitor is preferably for the treatment or prophylaxis of bronchial asthma.

In a preferred embodiment, the above-mentioned fixed combination, non-fixed combination or kit of parts comprise a compound of the invention (in particular the compound of the invention is one of the examples of the invention), an endothelin antagonist and at least one pharmaceutically acceptable auxiliary. In a particularly preferred embodiment, the above-mentioned fixed combination, non-fixed combination or kit of parts comprise:
a compound of the invention and bosentan,
a compound of the invention and ambrisentan,
a compound of the invention and atrasentan,
a compound of the invention and darusentan,
a compound of the invention and clazosentan, or
a compound of the invention and avosentan,
and at least one pharmaceutically acceptable auxiliary.

In another preferred embodiment, bosentan is used in form of its monohydrate. In another preferred embodiment the pharmaceutically acceptable salt of clazosentan is the disodium salt of clazosentan. In another preferred embodiment the pharmaceutically acceptable salts of atrasentan are atrasentan hydrochloride or the sodium salt of atrasentan. In another preferred embodiment the R-enantiomer of atrasentan is used. In another preferred embodiment the S-enantiomer of darusentan is used.

The combination comprising a compound of the invention and an endothelin antagonist is preferably for the treatment or prophylaxis of pulmonary hypertension and COPD.

In a preferred embodiment, the above-mentioned fixed combination, non-fixed combination or kit of parts comprise a compound of the invention (in particular the compound of the invention is one of the examples of the invention), a prostacyclin and at least one pharmaceutically acceptable auxiliary. In a particularly alternative embodiment, the above-mentioned fixed combination, non-fixed combination or kit of parts comprise:
a compound of the invention and iloprost,
a compound of the invention and epoprostenol, or
a compound of the invention and triprostinil,
and at least one pharmaceutically acceptable auxiliary.

The combination comprising a compound of the invention and a prostacyclin is preferably for the treatment or prophylaxis of pulmonary hypertension.

In a preferred embodiment, the above-mentioned fixed combination, non-fixed combination or kit of parts comprise a compound of the invention (in particular the compound of the invention is one of the examples of the invention), a calcium channel blocker and at least one pharmaceutically acceptable auxiliary. In a particularly alternative embodiment, the above-mentioned fixed combination, non-fixed combination or kit of parts comprise:
a compound of the invention and amlodipine,
a compound of the invention and nifedipine,
a compound of the invention and diltiazem,
a compound of the invention and verapamil, or
a compound of the invention and felodipine,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), a beta-blocker and at least one pharmaceutically acceptable auxiliary. In a particularly preferred embodiment, the above-mentioned fixed combination, non-fixed combination or kit of parts comprise:
a compound of the invention and bisoprolol,
a compound of the invention and nebivolol,
a compound of the invention and metoprolol,
a compound of the invention and carvedilol,
a compound of the invention and atenolol, or
a compound of the invention and nadolol,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), a type 4 phosphodiesterase inhibitor and at least one pharmaceutically acceptable auxiliary. In a particularly preferred embodiment, the above-mentioned fixed combination, non-fixed combination or kit of parts comprise:
a compound of the invention and roflumilast,
a compound of the invention and roflumilast N-oxide,
a compound of the invention and apremilast, or
a compound of the invention and oglemilast,
and at least one pharmaceutically acceptable auxiliary.

The combination comprising a compound of the invention and an additional PDE4 inhibitor is preferably for the treatment or prophylaxis of pulmonary hypertension and COPD.

In a preferred embodiment, the above-mentioned fixed combination, non-fixed combination or kit of parts comprise a compound of the invention (in particular the compound of the invention is one of the examples of the invention), a type 5 phosphodiesterase inhibitor and at least one pharmaceutically acceptable auxiliary. In a particularly preferred embodiment, the above-mentioned fixed combination, non-fixed combination or kit of parts comprise:
a compound of the invention and sildenafil,
a compound of the invention and vardenafil,
a compound of the invention and tadalafil,
a compound of the invention and udenafil, or
a compound of the invention and avanafil,
and at least one pharmaceutically acceptable auxiliary.

In another preferred embodiment, the pharmaceutically acceptable salts of sildenafil are sildenafil hemi-citrate, sildenafil citrate and sildenafil mesilate; particularly preferred is the citrate salt of sildenafil. In another preferred embodiment, the pharmaceutically acceptable salts of vardenafil are vardenafil hydrochloride or vardenafil dihyrochloride. In another preferred embodiment, the pharmaceutically acceptable salt of avanafil is avanafil besilate.

The combination comprising a compound of the invention and an additional PDE5 inhibitor is preferably for the treatment or prophylaxis of pulmonary hypertension and COPD.

In a preferred embodiment, the above-mentioned fixed combination, non-fixed combination or kit of parts comprise a compound of the invention (in particular the compound of the invention is one of the examples of the invention), a guanyl-cyclase activator/stimulator and at least one pharmaceutically acceptable auxiliary. In a particularly preferred embodiment, the above-mentioned fixed combination, non-fixed combination or kit of parts comprise:
a compound of the present subject matter and BAY63-2521 (Riociguat), or
a compound of the present subject matter and Ataciguat,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), tetrahydrobiopterin or a tetrahydrobiopterin derivative and at least one pharmaceutically acceptable auxiliary. In a particularly preferred embodiment, the above-mentioned fixed combination, non-fixed combination or kit of parts comprise:
a compound of the invention and (6R)-L-erythro-5,6,7,8-tetrahydrobiopterin,
a compound of the invention and (6R,S)-5,6,7,8-tetrahydrobiopterin,
a compound of the invention and 1',2'-diacetyl-5,6,7,8-tetrahydrobiopterin,
a compound of the invention and sepiapterin,
a compound of the invention and 6-methyl-5,6,7,8-tetrahydropterin,
a compound of the invention and 6-hydroxymethyl-5,6,7,8-tetrahydropterin, or
a compound of the invention and 6-phenyl-5,6,7,8-tetrahydropterin,
and at least one pharmaceutically acceptable auxiliary.

In a preferred embodiment, the pharmaceutically acceptable derivative of (6R)-L-erythro-5,6,7,8-tetrahydrobiopterin is (6R)-L-erythro-5,6,7,8-tetrahydrobiopterin dihydrochloride.

In a preferred embodiment, the above-mentioned fixed combination, non-fixed combination or kit of parts comprise a compound of the invention (in particular the compound of the invention is one of the examples of the invention), a HMG-CoA reductase inhibitor and at least one pharmaceutically acceptable auxiliary. In a particularly preferred embodiment, the above-mentioned fixed combination, non-fixed combination or kit of parts comprise:
a compound of the invention and lovastatin,
a compound of the invention and pravastatin,
a compound of the invention and simvastatin,
a compound of the invention and atorvastatin,
a compound of the invention and fluvastatin,
a compound of the invention and rosuvastatin,
a compound of the invention and pitavastatin,
a compound of the invention and bervastatin,
a compound of the invention and dalvastatin, or
a compound of the invention and glenvastatin,
and at least one pharmaceutically acceptable auxiliary.

In a preferred embodiment the pharmaceutically acceptable salts of pravastatin are the potassium, lithium, sodium and hemi-calcium salt of pravastatin. A particularly preferred pharmaceutically acceptable salt of pravastatin is the sodium salt of pravastatin. In a preferred embodiment the pharmaceutically acceptable salt of simvastatin is the sodium salt of simvastatin. In a preferred embodiment the pharmaceutically acceptable salts of atorvastatin are the potassium, sodium and the hemi-calcium salt of atorvastatin. A particularly preferred pharmaceutically acceptable salt of atorvastatin is the hemi-calcium salt of atorvastatin. As an example for a hydrate of atorvastatin may be mentioned the tri-hydrate and the sesquihydrate of the hemi-calcium salt of atorvastatin. In a preferred embodiment of the pharmaceutically acceptable salt of fluvastatin is the sodium salt of fluvastatin. In a preferred embodiment the pharmaceutically acceptable salts of rosuvastatin are the potassium, lithium, sodium, hemi-magnesium and the hemi-calcium salt of rosuvastatin. A particularly preferred pharmaceutically acceptable salt of rosuvastatin is the hemi-calcium salt of rosuvastatin. Another particularly preferred pharmaceutically acceptable salt of rosuvastatin is the sodium salt of rosuvastatin. In a preferred embodiment the pharmaceutically acceptable salts of pitavastatin are the potassium, sodium and the hemi-calcium salt of pitavastatin. A particularly preferred pharmaceutically acceptable salt of pitavastatin is the hemi-calcium salt of pitavastatin.

The combination comprising a compound of the invention and a HMG-CoA reductase inhibitor is preferably for the treatment or prophylaxis of COPD.

In a preferred embodiment, the above-mentioned fixed combination, non-fixed combination or kit of parts comprise a compound of the invention (in particular the compound of the invention is one of the examples of the invention), a lung surfactant and at least one pharmaceutically acceptable auxiliary. In a particularly preferred embodiment, the above-mentioned fixed combination, non-fixed combination or kit of parts comprise:
a compound of the invention and lusupultide,
a compound of the invention and poracant alfa,
a compound of the invention and sinapultide,
a compound of the invention and beracant,
a compound of the invention and bovacant,
a compound of the invention and colfosceril palmitate,
a compound of the invention and surfactant-TA, or
a compound of the invention and calfacant,
and at least one pharmaceutically acceptable auxiliary.

The combination comprising a compound of the invention and a lung surfactant is preferably for the treatment or prophylaxis of bronchial asthma or COPD.

In a preferred embodiment, the above-mentioned fixed combination, non-fixed combination or kit of parts comprise a compound of the invention (in particular the compound of the invention is one of the examples of the invention), an antibiotic and at least one pharmaceutically acceptable auxiliary. In a particularly preferred embodiment, the above-mentioned fixed combination, non-fixed combination or kit of parts comprise:
a compound of the invention and amoxicillin,
a compound of the invention and ampicillin,
a compound of the invention and levofloxacin,
a compound of the invention and clarithromycin,
a compound of the invention and ciprofloxacin,
a compound of the invention and telithromycin, or
a compound of the invention and azithromycin,
and at least one pharmaceutically acceptable auxiliary.

In a preferred embodiment, amoxicillin is used in form of its trihydrate. In another preferred embodiment, ampicillin is used in form of its trihydrate. In another preferred embodiment, the pharmaceutically acceptable salt of ampicillin is ampicillin natrium. In another preferred embodiment levofloxacin is used in form of its hemi hydrate. In another preferred embodiment, the pharmaceutically acceptable salt of ciprofloxacin is ciprofloxacin hydrochloride monohydrate. In another preferred embodiment, azithromycin is used in form of its monohydrate.

The combination comprising a compound of the invention and an antibiotic is preferably for the treatment or prophylaxis of exacerbations associated with bronchial asthma and COPD.

In a preferred embodiment, the above-mentioned fixed combination, non-fixed combination or kit of parts comprise a compound of the invention (in particular the compound of the invention is one of the examples of the invention), an anticoagulant and at least one pharmaceutically acceptable auxiliary. In a particularly preferred embodiment, the above-mentioned fixed combination, non-fixed combination or kit of parts comprise:
a compound of the invention and clopidogrel,
a compound of the invention and enoxaparin,
a compound of the invention and cilostazol,
a compound of the invention and nadroparin,
a compound of the invention and warfarin, or
a compound of the invention and abciximab,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), a diuretic and at least one pharmaceutically acceptable auxiliary. In a particularly preferred embodiment, the above-mentioned fixed combination, non-fixed combination or kit of parts comprise:
a compound of the invention and furosemide,
a compound of the invention and bumetanide, or
a compound of the invention and torsemide,
and at least one pharmaceutically acceptable auxiliary.

The combination comprising a compound of the invention and a diuretic preferably is for the treatment and prophylaxis of cystic fibrosis.

In a preferred embodiment, the above-mentioned fixed combination, non-fixed combination or kit of parts comprise a compound of the invention (in particular the compound of the invention is one of the examples of the invention), pirfenidone and at least one pharmaceutically acceptable auxiliary. In a particularly preferred embodiment, the above-mentioned fixed combination, non-fixed combination or kit of parts comprise:
a compound of the invention and pirfenidone,
and at least one pharmaceutically acceptable auxiliary.

The combination comprising a compound of the invention and pirfenidone preferably is for the treatment and prophylaxis of lung fibrosis.

In a preferred embodiment, the above-mentioned fixed combination, non-fixed combination or kit of parts comprise a compound of the invention (in particular the compound of the invention is one of the examples of the invention), a digitalis glycoside and at least one pharmaceutically acceptable auxiliary. In a particularly preferred embodiment, the above-mentioned fixed combination, non-fixed combination or kit of parts comprise:
a compound of the invention and digoxin, or
a compound of the invention and digitoxin,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), a corticosteroid, a $e_2$-adrenoreceptor agonist and at least one pharmaceutically acceptable auxiliary. In a particularly preferred embodiment, the above-mentioned fixed combination, non-fixed combination or kit of parts comprise:
a compound of the invention, budesonide and salbutamol,
a compound of the invention, budesonide and milveterol,
a compound of the invention, budesonide and indacaterol,
a compound of the invention, budesonide and carmoterol,
a compound of the invention, budesonide and salmeterol,
a compound of the invention, budesonide and formoterol,
a compound of the invention, budesonide and vilanterol,
a compound of the invention, budesonide and olodaterol,
a compound of the invention, fluticasone and salbutamol,
a compound of the invention, fluticasone and milveterol,
a compound of the invention, fluticasone and indacaterol,
a compound of the invention, fluticasone and carmoterol,
a compound of the invention, fluticasone and salmeterol,
a compound of the invention, fluticasone and formoterol,
a compound of the invention, fluticasone and vilanterol,
a compound of the invention, fluticasone and olodaterol,
a compound of the invention, beclometasone and salbutamol,
a compound of the invention, beclometasone and milveterol,
a compound of the invention, beclometasone and indacaterol,
a compound of the invention, beclometasone and carmoterol,
a compound of the invention, beclometasone and salmeterol,
a compound of the invention, beclometasone and formoterol,
a compound of the invention, beclometasone and vilanterol,
a compound of the invention, beclometasone and olodaterol,
a compound of the invention, mometasone and salbutamol,
a compound of the invention, mometasone and milveterol,
a compound of the invention, mometasone and indacaterol,
a compound of the invention, mometasone and carmoterol,
a compound of the invention, mometasone and salmeterol,
a compound of the invention, mometasone and formoterol,
a compound of the invention, mometasone and vilanterol,
a compound of the invention, mometasone and olodaterol,
a compound of the invention, triamcinolone acetonide and salbutamol,
a compound of the invention, triamcinolone acetonide and milveterol,
a compound of the invention, triamcinolone acetonide and indacaterol,
a compound of the invention, triamcinolone acetonide and carmoterol,
a compound of the invention, triamcinolone acetonide and salmeterol,
a compound of the invention, triamcinolone acetonide and formoterol,
a compound of the invention, triamcinolone and vilanterol,
a compound of the invention, triamcinolone and olodaterol,
a compound of the invention, ciclesonide and salbutamol,
a compound of the invention, ciclesonide and milveterol,
a compound of the invention, ciclesonide and indacaterol,
a compound of the invention, ciclesonide and carmoterol,
a compound of the invention, ciclesonide and salmeterol,
a compound of the invention, ciclesonide and formoterol,
a compound of the invention, ciclesonide and vilanterol, or
a compound of the invention, ciclesonide and olodaterol,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), a $e_2$-adrenoreceptor agonist, an anticholinergic and at least one pharmaceutically acceptable auxiliary. In a particularly preferred embodiment, the above-mentioned fixed combination, non-fixed combination or kit of parts comprise:
a compound of the invention, salbutamol and glycopyrronium bromide, a compound of the invention, salbutamol and aclidinium bromide,
a compound of the invention, salbutamol and tiotropium bromide,
a compound of the invention, salbutamol and ipratropium bromide,
a compound of the invention, salbutamol and darotropium bromide,
a compound of the invention, milveterol and glycopyrronium bromide,
a compound of the invention, milveterol and aclidinium bromide,
a compound of the invention, milveterol and tiotropium bromide,
a compound of the invention, milveterol and ipratropium bromide,
a compound of the invention, milveterol and darotropium bromide,
a compound of the invention, salmeterol and glycopyrronium bromide,
a compound of the invention, salmeterol and aclidinium bromide,
a compound of the invention, salmeterol and tiotropium bromide,
a compound of the invention, salmeterol and ipratropium bromide,
a compound of the invention, salmeterol and darotropium bromide,
a compound of the invention, formoterol and glycopyrronium bromide,
a compound of the invention, formoterol and aclidinium bromide,
a compound of the invention, formoterol and tiotropium bromide,
a compound of the invention, formoterol and ipratropium bromide,
a compound of the invention, formoterol and darotropium bromide,
a compound of the invention, indacaterol and glycopyrronium bromide,
a compound of the invention, indacaterol and aclidinium bromide,
a compound of the invention, indacaterol and tiotropium bromide,
a compound of the invention, indacaterol and ipratropium bromide,
a compound of the invention, indacaterol and darotropium bromide,
a compound of the invention, carmoterol and glycopyrronium bromide,
a compound of the invention, carmoterol and aclidinium bromide,
a compound of the invention, carmoterol and tiotropium bromide,
a compound of the invention, carmoterol and ipratropium bromide,
a compound of the invention, carmoterol and darotropium bromide,
a compound of the invention, vilanterol and glycopyrronium bromide,
a compound of the invention, vilanterol and aclidinium bromide,
a compound of the invention, vilanterol and tiotropium bromide,
a compound of the invention, vilanterol and ipratropium bromide,
a compound of the invention, vilanterol and darotropium bromide,
a compound of the invention, olodaterol and glycopyrronium bromide,
a compound of the invention, olodaterol and aclidinium bromide,
a compound of the invention, olodaterol and tiotropium bromide,
a compound of the invention, olodaterol and ipratropium bromide, or
a compound of the invention, olodaterol and darotropium bromide,
and at least one pharmaceutically acceptable auxiliary.

In a preferred embodiment, the above-mentioned fixed combination, non-fixed combination or kit of parts comprise a compound of the invention (in particular the compound of the invention is one of the examples of the invention), a corticosteroid, an anticholinergic and at least one pharmaceutically acceptable auxiliary. In a particularly preferred embodiment, the above-mentioned fixed combination, non-fixed combination or kit of parts comprise:
a compound of the invention, budesonide and glycopyrronium bromide,
a compound of the invention, budesonide and aclidinium bromide,
a compound of the invention, budesonide and tiotropium bromide,
a compound of the invention, budesonide and ipratropium bromide,
a compound of the invention, budesonide and darotropium bromide,
a compound of the invention, fluticasone and glycopyrronium bromide,
a compound of the invention, fluticasone and aclidinium bromide,
a compound of the invention, fluticasone and tiotropium bromide,
a compound of the invention, fluticasone and ipratropium bromide,
a compound of the invention, fluticasone and darotropium bromide,
a compound of the invention, beclometasone and glycopyrronium bromide,
a compound of the invention, beclometasone and aclidinium bromide,
a compound of the invention, beclometasone and tiotropium bromide,
a compound of the invention, beclometasone and ipratropium bromide,
a compound of the invention, beclometasone and darotropium bromide,
a compound of the invention, mometasone and glycopyrronium bromide,
a compound of the invention, mometasone and aclidinium bromide,
a compound of the invention, mometasone and tiotropium bromide,
a compound of the invention, mometasone and ipratropium bromide,
a compound of the invention, mometasone and darotropium bromide,
a compound of the invention, triamcinolone acetonide and glycopyrronium bromide,
a compound of the invention, triamcinolone acetonide and aclidinium bromide,
a compound of the invention, triamcinolone acetonide and tiotropium bromide, a compound of the invention, triamcinolone acetonide and ipratropium bromide,
a compound of the invention, triamcinolone acetonide and darotropium bromide,
a compound of the invention, ciclesonide and glycopyrronium bromide,
a compound of the invention, ciclesonide and aclidinium bromide,
a compound of the invention, ciclesonide and tiotropium bromide,
a compound of the invention, ciclesonide and ipratropium bromide, or
a compound of the invention, ciclesonide and darotropium bromide,
and at least one pharmaceutically acceptable auxiliary.

The above-mentioned triple combinations may preferably be used in the treatment or prophylaxis of bronchial asthma or COPD.

Exemplary combinations, in particular for external topical administration (for example versus atopic dermatitis or psoriasis), may include a compound of the invention and an immunosuppressant, for example a calcineurin inhibitor, such as pimecrolimus or tacrolimus.

Therefore, in another preferred embodiment, the above-mentioned fixed combination, non-fixed combination or kit of parts comprise a compound of the invention (in particular the compound of the invention is one of the examples of the invention or a pharmaceutically acceptable salt thereof), an immunosuppressant and at least one pharmaceutically acceptable auxiliary. In a particularly preferred embodiment, the above mentioned fixed combination, non-fixed combination or kit of parts comprise:
a compound of the invention and pimecrolimus,
a compound of the invention and tacrolimus,
a compound of the invention and methotrexate,
a compound of the invention and ascomycin, or
a compound of the invention and cyclosporin A,
and at least one pharmaceutically acceptable auxiliary.

The externally topically administrable immunosuppressant can be administered or administrable in a external-topical composition separately from the compound of the invention (non-fixed combination or kit of parts) or it can be contained with the compound of the invention in a combined externally-topically administrable composition (fixed combination). In a preferred embodiment the externally topically administrable composition is a cream containing pimecrolimus at ca. 1% w/w concentration. In another preferred embodiment the externally topically administrable composition is an ointment containing tacrolimus at from about 0.03% to about 0.1% w/w concentration).

Other combinations for external topical administration, in particular for the treatment or prophylaxis of atopic dermatitis and psoriasis, may include a compound of the invention and a corticosteroid. Beside the corticosteroid combinations mentioned above also the following corticosteroid combinations may be useful.

In another preferred embodiment, the above-mentioned fixed combination, non-fixed combination or kit of parts comprise a compound of the invention (in particular the compound of the invention is one of the examples of the invention or a pharmaceutically acceptable salt thereof), a corticosteroid and at least one pharmaceutically acceptable auxiliary. In a particularly preferred embodiment, the above mentioned fixed combination, non-fixed combination or kit of parts comprise:
a compound of the invention and prednisolone,
a compound of the invention and dexamethasone,
a compound of the invention and betamethasone, or
a compound of the invention and hydrocortisone,
and at least one pharmaceutically acceptable auxiliary.

In another preferred embodiment, the above-mentioned corticosteroids are used in form of an ester, such as, for example, prednisolone valerate acetate, hydrocortisone butyrate, hydrocortisone acetate, dexamethasone valerate, dexamethasone propionate, dexamethasone dipropionate, betamethasone butyrate propionate or prednisolone valerate acetate.

Further combinations for external topical combination, in particular for the treatment of psoriasis, may include a compound of the invention and a vitamin D analogue.

Therefore, in another preferred embodiment the above-mentioned fixed combination, non-fixed combination or kit of parts comprise a compound of the invention (in particular the compound of the invention is one of the examples of the invention or a pharmaceutically acceptable salt thereof), a vitamin D analogue and at least one pharmaceutically acceptable auxiliary. In a particularly preferred embodiment, the above mentioned fixed combination, non-fixed combination or kit of parts comprise:
a compound of the invention and calcitriol,
a compound of the invention and calcipotriol, or
a compound of the invention and tacalcitol,
and at least one pharmaceutically acceptable auxiliary.

In case, both (or all) combination partners—the compound of the invention as well as the therapeutic agent(s)—of the above-defined combinations are both (or all) suitable for inhalative administration, a preferred embodiment of the invention is the simultaneous inhaled administration of both (or all) combination partners by use of a combination inhalation device. Such a combination inhalation device can comprise a combined pharmaceutical composition for simultaneous inhaled administration, the composition comprising both (or all) individual compounds of the particular combination.

In an alternative, the combination inhalation device can be such that the individual compounds of the particular combination are administrable simultaneously but are stored separately (or wholly or partly separated for triple combinations), for example in separate pharmaceutical compositions.

In case of non-fixed combinations or kit of parts comprising at least one of the compounds of the invention and at least one therapeutic agent selected from the group consisting of corticosteroids, anticholinergics, $e_2$-adrenoreceptor agonists, H1 receptor antagonists, leukotriene receptor antagonists, 5-lipoxygenase inhibitors, endothelin receptor antagonists, prostacyclines, calcium channel blockers, beta-blockers, type 4 phosphodiesterase inhibitors, type 5 phosphodiesterase inhibitors, immunosuppressants, vitamin D analogues, HMG-CoA reductase-inhibitors, lung surfactants, antibiotics, guanylyl-cyclase activators/stimulators, tetrahydrobiopterin and tetrahydrobiopterin derivatives, anticoagulants, diuretics, pirfenidone and digitalis glycosides, the compound of the invention and the therapeutic agent may be administered by the same route, e.g., without limitation, by inhalation (or external topical), or by different routes, e.g., without limitation, the compound of the invention may be, for example, administered by inhalation and the therapeutic agent may be administered orally.

In case of co-administration of at least one compound of the invention with at least one therapeutic agent selected from the group consisting of corticosteroids, anticholinergics, $e_2$-adrenoreceptor agonists, H1 receptor antagonists, leukotriene receptor antagonists, 5-lipoxygenase inhibitors, endothelin receptor antagonists, prostacyclines, calcium channel blockers, beta-blockers, type 4 phosphodiesterase inhibitors, type 5 phosphodiesterase inhibitors, immunosuppressants, vitamin D analogues, HMG-CoA reductase-inhibitors, lung surfactants, antibiotics, guanylyl-cyclase activators/stimulators, tetrahydrobiopterin and tetrahydrobiopterin derivatives, anticoagulants, diuretics, pirfenidone and digitalis glycosides, in form of a fixed combination, non-fixed combination or kit of parts the dose of the compound of the invention as well as the dose of the therapeutic agent will be in a range customary for the mono-therapy, it more likely being possible, on account of the individual action, which are mutually positively influencing and reinforcing, to reduce the respective doses in case of co-administration of the compound(s) of the invention and the therapeutic agent.

In case of co-administration of at least one compound of the invention and at least one therapeutic compound selected from the group consisting of corticosteroids, anticholinergics, $e_2$-adrenoreceptor agonists, H1 receptor antagonists, leukotriene receptor antagonists, 5-lipoxygenase inhibitors, endothelin receptor antagonists, prostacyclines, calcium channel blockers, beta-blockers, type 4 phosphodiesterase inhibitors, type 5 phosphodiesterase inhibitors, immunosuppressants, vitamin D analogues, HMG-CoA reductase-inhibitors, lung surfactants, antibiotics, guanylyl-cyclase activators/stimulators, tetrahydrobiopterin and tetrahydrobiopterin derivatives, anticoagulants, diuretics, pirfenidone and digitalis glycosides, in form of a fixed combination, a non-fixed combination or a kit of parts a single dose unit of the respective pharmaceutical composition/formulation can contain, in case of oral or parenteral administration 0.01 mg to 250 mg, preferably 0.05 mg to 100 mg, more preferably 0.05 mg to 10 mg, or in case of nasal or inhalative administration 0.001 mg to 10 mg, preferably 0.01 mg to 7.5 mg, more preferably 0.1 mg to 4 mg of the compound of the invention and from 0.01 mg to 4000 mg, preferably 0.1 mg to 2000 mg, more preferably 0.5 mg to 1000 mg, most preferably 1 mg to 500 mg, of the therapeutic agent, depending on the therapeutic agent being used the disease to be treated and the administration route selected. Preferably, the at least one compound of the invention and the at least one therapeutic agent are present in the pharmaceutical compositions/formulations in a weight ratio of from 1000:1 to 1:1000, more preferably in a weight ratio of from 100:1 to 1:100, even more preferably in a weight ratio of from 25:1 to 1:25.

Biological Investigations

Method for Measuring Inhibition of PDE4 Activity

The PDE4B1 (GB no. L20966) was a gift of Prof. M. Conti (Stanford University, USA). It was amplified from the original plasmid (pCMV5) via PCR with primers Rb18 (5'-CAGACATCCTAAGAGGGGAT-3') and Rb10 (5'-AGAGGGGGATTATGTATCCAC-3') and cloned into the pCR-Bac vector (Invitrogen, Groningen, NL).

The recombinant baculovirus was prepared by means of homologous recombination in SF9 insect cells. The expression plasmids were cotransfected with Baculo-Gold DNA (Pharmingen, Hamburg) using a standard protocol (Pharmingen, Hamburg). Wt virus-free recombinant virus supernatants were selected using plaque assay methods. After that, high-titre virus supernatants were prepared by amplifying 3 times. PDE4B1 was expressed in SF21 cells by infecting $2 \times 10^6$ cells/ml with an MOI (multiplicity of infection) between 1 and 10 in the serum-free medium Insect Express Sf9-S2 (PAA, Pasching, Austria). The cells were cultured at 28° C. for 48-72 hours, after which they were pelleted for 5-10 min at 1000×g and 4° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM e-mercaptoethanol, 2 mM benzamidine, 0.4 mM Pefablock, 10 pM leupeptin, 10 pM pepstatin A, 5 pM trypsin inhibitor) and disrupted by ultrasonication. The homogenate was then centrifuged for 10 min at 1000, g and the supernatant was stored at −80° C. until subsequent use (see below). The protein content was determined by the Bradford method (BioRad, Munich) using BSA as the standard.

PDEB1 activities were measured in a 96-well platform using SPA (scintillation proximity assay) yttrium silicate beads (RPNQ1050 from GE Healthcare). In a first step the PDE activity operates hydrolysis of either [$^3$H] cAMP (substrate) into [$^3$H] 5'AMP. In a second step substrate and product are distinguished following addition of SPA yttrium silicate beads. Indeed, in the presence of zinc sulphate the linear [$^3$H] 5'AMP binds to the beads while the cyclic [$^3$H] cAMP does not. Close proximity of bound [$^3$H] 5'AMP then allows radiation from the tritium to the scintillant within the beads resulting in a measurable signal while the unbound, hence distant [$^3$H] cAMP does not generate this signal. The test volume is 100 pl and contains 20 mM Tris buffer (pH 7.4), 0.1 mg/ml of BSA, 5 mM $Mg^{2+}$, 0.5 pM cAMP (including about 50,000 cpm of [3H]cAMP), 1 pl of the respective substance dilution in DMSO and sufficient recombinant PDE (1000, g supernatant, see above) to ensure that 10-20% of the cAMP is converted under the said experimental conditions. The final concentration of DMSO in the assays (1% v/v) does not substantially affect the activity of the PDE investigated. After a preincubation of 5 min at 37° C., the reaction is started by adding the substrate (cAMP) and the assays are incubated for a further 15 min; after that, they are stopped by adding SPA beads (50 pl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE4B1 activity are determined from the concentration-effect curves by means of non-linear regression.

For the following compounds PDE4B1 inhibitory values [measured as $-\log IC_{50}$ (mol/l)] below 8, between 8 and 9 and above 9 have been determined. The numbers of the compounds correspond to the numbers of the examples.

| PDE4B1 inhibitory values measured as −logIC50 (mol/l) | | |
| --- | --- | --- |
| below 8 | between 8 and 9 | above 9 |
| Examples 14, 19, 24, 25, 26, 31, 33, 34, 36, 37, 38, 40, 41, 42, 59 | Examples 1, 2, 3, 5, 6, 7, 9, 10, 11, 12, 13, 15, 16, 17, 18, 20, 21, 22, 23, 27, 30, 32, 35, 39, 43, 44, 45, 46, 47, 48, 49, 55, 56, 57, 58 | Examples 4, 8, 28, 29, 50, 51, 52, 53, 54 |

Method for Measuring Inhibition of PDE5 Activity

As a source for human PDE5, platelets are used. For that purpose, 150 ml fresh blood from human donors anticoagulated with citrate [final concentration 0.3% (w/v)] is centrifuged at 200 g for 10 min to obtain the so-called platelet-rich-plasma (PRP) as a supernatant. 1/10 volume of ACD solution (85 mM $Na_3$-citrate, 111 mM D-glucose, 71 mM citric acid, pH 4.4) is added to 9/10 volume of PRP. After centrifugation (1,400 g, 10 min) the cell pellet is resuspended in 3 ml homogenization buffer (NaCl 140 mM, KCl 3.8 mM, EGTA (ethylene glycol tetraacetic acid) 1 mM, MgCl$_2$ 1 mM, Tris-HCl 20 mM, beta-mercaptoethanol 1 mM, pH 8.2) plus protease-inhibitor mix giving rise to the final concentrations of 0.5 mM Pefablock (Roche), 10 µM Leupeptin, 5 µM Trypsininhibitor, 2 mM Benzamidin and 10 µM Pepstatin A. The suspension is sonified and thereafter centrifuged for 15 min at 10,000 g. The resulting supernatant (platelet lysate) is used for enzymatic testings.

PDE5 activities were measured in a 96-well platform using SPA (scintillation proximity assay) yttrium silicate beads (RPNQ1050 from GE Healthcare). In a first step the PDE activity operates hydrolysis of either [$^3$H] cGMP (substrate) into [$^3$H] 5'GMP. In a second step substrate and product are distinguished following addition of SPA yttrium silicate beads. Indeed, in the presence of zinc sulphate the linear [$^3$H] 5'GMP binds to the beads while the cyclic [$^3$H] cGMP does not. Close proximity of bound [$^3$H] 5'GMP then allows radiation from the tritium to the scintillant within the beads resulting in a measurable signal while the unbound, hence distant [$^3$H] cGMP does not generate this signal. The test volume is 100 pl and contains 20 mM Tris buffer (pH 7.4), 0.1 mg of BSA (bovine serum albumin)/ml, 5 mM Mg$^{2+}$, 1 µM motapizone (PDE3 Inhibitor), 10 nM PDE2 inhibitor 2-(3,4-dimethoxybenzyl)-7-[(1R,2R)-2-hydroxy-1-(2-phenylethyl)propyl]-5-methylimidazo[5,1-f][1,2,4]triazin-4(3H)-one, 0.5 pM cGMP (cyclic guanosine monophosphate) (including about 50,000 cpm of [3H]cGMP as a tracer), 1 pl of the respective compound dilution in dimethylsulfoxide (DMSO) and sufficient PDE5-containing platelet lysat (10,000, g supernatant, see above) to ensure that 10-20 wt % of the cGMP is converted under the said experimental conditions. The final concentration of DMSO in the assay (1% v/v) does not substantially affect the activity of the PDE investigated. After a preincubation of 5 min at 37° C., the reaction is started by adding the substrate (cGMP) and the assay is incubated for a further 15 min; after that, it is stopped by adding SPA beads (50 pl). In accordance with the manufacturer's instructions, the SPA beads had previously been resuspended in water, but are then diluted 1:3 (v/v) in water; the diluted solution also contains 3 mM 8-methoxymethyl-3-isobutyl-1-methylxanthine (IBMX) to ensure a complete PDE activity stop. After the beads have been sedimented (>30 min), the MTP's are analyzed in commercially available luminescence detection devices. The corresponding IC$_{50}$ values of the compounds for the inhibition of PDE activity are determined from the concentration-effect curves by means of non-linear regression.

For the following compounds PDE5A inhibitory values [measured as –log IC$_{50}$ (mol/l)] below 7, between 7 and 8 and above 8 have been determined. The numbers of the compounds correspond to the numbers of the examples.

| PDE5A inhibitory values measured as –logIC50 (mol/l) | | |
| --- | --- | --- |
| below 7 | between 7 and 8 | above 8 |
| Examples 10, 13, 16, 17, 18, 23, 51, 52, 53, 54, 56, 58 | Examples 4, 5, 6, 8, 9, 12, 21, 22, 33, 34, 42, 43, 50, 55, 57, | Examples 1, 2, 3, 7, 11, 14, 15, 19, 20, 24, 25, 26, 27, 28, 29, 30, 31, 32, 35, 36, 37, 38, 39, 40, 41, 44, 45, 46, 47, 48, 49, 59 |

In Vivo Assay: LPS-Induced Pulmonary Inflammation Model in Rats (Method A)

Introduction

Exposure of rats to aerosolized lipopolysaccharide (LPS) causes a pulmonary mainly neutrophilic inflammation, which can be assessed by bronchoalveolar lavage (BAL). LPS-induced pulmonary inflammation models are robust and are commonly used for the evaluation of test compounds modulating the immediate immune response. Phosphodiesterase-4 inhibitors are administered by intratracheal dry powder insufflation 2 h prior nose-only LPS challenge in rats. The antiinflammatory activity of the phosphodiesterase inhibitors is assessed based on pulmonary total leukocyte and neutrophil counts in the bronchoalveolar lavage fluid 16 h after LPS exposure.

Materials and Methods

Animals

Male Sprague Dawley rats weighing 240-300 g are used. Rats are delivered 1 weak prior to the experiments and have free access to water and food.

Intratracheal Dry Powder Insufflation

Compound Blending

The test compound in crystalline and micronized state is blended with lactose for inhalation ad 10 mg/kg (Respitose® SV003, DMV International, Netherlands). Respitose® and test compound are transferred to 12 ml tubes and are blended for 10 min. Dilution series are prepared from the this stock blend.

Compound Insufflation Technique

A device consisting of an Abbocath®-T catheter (18G×51 mm), a one-way stop-cock and a 5 ml syringe is used for test compound insufflation. Weighed test compound blends are directly filled in the stop-cocks. Intubation of the rats is guided by sight and is done under a short time halothane anesthesia.

Compound Dosing

The administered dose of the blended material is 10 mg/kg. The expected material loss in the device is 25%, therefore the weighted dose used is 12.5 mg/kg. One day before the experiment the rat body weights are documented and the mean body weight is used to calculate the administered blend dose per rat. LPS challenged and unchallenged control animals received drug-free Respitose® as placebo. Test compound blends and Respitose are administered 2 h prior LPS challenge.

LPS Challenge

Conscious and restrained animals are connected to a nose-only exposure system (CR equipment SA, Tannay, Switzerland) and are exposed to the LPS aerosol for 30 min. The LPS-containing aerosol is generated using a compressed air driven medication nebulizer device (OCTURNO Medizintechnik GmbH, Germany). The LPS solution (E. coli, Serotype 055B5, Art. #L2880, Lot #114K4103, Sigma-Aldrich; 0.15 mg/ml, diluted in 0.1% hydroxylamine/PBS) is continuously delivered by a syringe pump (20 ml/h) to the nebulizer device. The aerosol is dispersed and transported to the exposure tower by admixture of compressed air. All rats except negative controls are exposed to LPS.

Bronchoalveolar Lavage

Sixteen hours after LPS challenge, animals are sacrificed with Trapanal (thiopental, 350 mg/rat, 2 ml/rat, i.p.), the final body weights are determined and BALs are performed. For the BAL the trachea is exposed and cannulated, followed by gently lavaging the lungs three times in situ with 4 ml PBS buffer.

Total and Differential Cell Counts

Determination of total leukocyte and neutrophil counts in BALF is performed with an automated leukocyte differentiation system (XT-2000iV, Sysmex, Norderstedt, Germany).

Data Analysis

Suppression of LPS-induced total cell and neutrophil influx into the lungs is calculated in % using the means of the cell counts of each treatment group in relation to the control groups:

$$\text{effect on cell influx } [\%] @ \frac{(\text{mean}_{treatment\ group} - \text{mean}_{negative\ control})}{(\text{mean}_{positive\ control} - \text{mean}_{negative\ control})} 100\text{O}100$$

Statistical analysis is performed on the primary cell count data using one-way ANOVA and Dunnett's multiple comparison post test vs. positive control. The Grubbs test is used to detect outliers.

Exemplary Results for Compounds Tested Using Method A (the Numbers of the Compounds Correspond to the Numbers of the Examples):

The compounds 14, 26 and one of 24 or 25 showed at a dosage of 1 mg/kg a reduction in the range of 25 to 50% of the total cell count, respectively a reduction in the range of 25 to 43% of neutrophils in comparison to the placebo group.

In Vivo Assay: LPS-Induced Pulmonary Inflammation Model in Rats (Method B)

Introduction

Exposure of rats to aerosolized lipopolysaccharide (LPS) causes a pulmonary mainly neutrophilic inflammation, which can be assessed by bronchoalveolar lavage (BAL). LPS-induced pulmonary inflammation models are robust and are commonly used for the evaluation of test compounds modulating the immediate immune response. Selective phosphodiesterase-4 inhibitors are administered by intratracheal instillation 1 h prior nose-only LPS challenge in rats. The anti-inflammatory activity of the selective phosphodiesterase inhibitors is assessed based on pulmonary total leukocyte and neutrophil counts in the bronchoalveolar lavage fluid 4 h after LPS exposure.

Materials and Methods

Animals

Male Sprague Dawley rats weighing 250-300 g are used. Rats are delivered 1 weak prior to the experiments and have free access to water and food.

Intratracheal Compound Instillation

Compound Preparation

The test compound in crystalline and micronized state is suspended in 0.9% NaCl (Saline) (Braun, Melsungen, Germany) supplemented with 0.02% Tween20 (Sigma-Aldrich, Schnelldorf, Germany) for intratracheal instillation. Suspensions of test compound are treated in an ultrasonic bath to shear agglomerates and to obtain homogenous suspensions. The aimed doses are prepared by dilution series from the stock suspension, which is prepared for the administration of the highest dose in each experiment.

Compound Instillation Technique

The compound suspension is administered intratracheally. The intubation is guided by sight and is done under a short time isoflurane anesthesia. The suspension is then instilled into the lungs. The compound suspension is administered by liquid instillation. Therefore, the trachea is intubated with a device consisting of a catheter which contained a blunted cannula (size 14 G, Dispomed, Gelnhausen, Germany). The length of the catheter is adjusted to avoid disruption of the tracheal bifurcation. A 1 ml syringe, filled with the compound suspension and air, is connected to the intubation device via the Luer Lock adapter and the whole content of the syringe is directly administered to the lungs.

Compound Dosing

The administered volume of the compound suspension is 0.5-1 ml/kg. LPS challenged and unchallenged control animals received drug-free NaCl/Tween20 solution as placebo. Test compounds and placebo are administered 1 h prior to LPS challenge.

LPS Challenge

Conscious and restrained animals are connected to a nose-only exposure system (CR equipment SA, Tannay, Switzerland) and are exposed to the LPS aerosol for 30 min. The LPS-containing aerosol is generated using a compressed air driven medication nebulizer device (Pari LC Sprint Star, Pari GmbH, Starnberg, Germany). The LPS solution (*E. coli*, Serotype 055B5, Art. #L2880, Lot #L048K4126, Sigma-Aldrich, 3 mg/ml diluted in PBS) is prepared 30 minutes in advance. The aerosol is dispersed and transported to the exposure tower by a sheath air flow of 600l/h. All rats except negative controls are exposed to LPS.

Bronchoalveolar Lavage 4 hours after LPS challenge, animals are anesthetized by isoflurane and sacrificed by cervical dislocation. BALs are performed. For the BAL the trachea is exposed and cannulated, followed by gently lavaging the lungs two times in situ with 5 ml PBS buffer supplemented with 0.5% Bovine Serum Albumin (Serve, Darmstadt, Germany).

Total and Differential Cell Counts

Determination of total leukocyte and neutrophil counts in BALF is performed with an automated leukocyte differentiation system (XT-2000iV, Sysmex, Norderstedt, Germany).

Data Analysis

The baseline correction is done for each sample according to the formula:

Baseline-corrected cell count value=cell count−Median (negative control group)

All further calculations are performed with the baseline-corrected values.

Effect of compound on LPS-induced total cell and neutrophil influx into the lungs is calculated in % using the medians of the cell counts of each treatment group in relation to the control groups according to the formula:

% effect=$(Y-K)/K*100$

With defining:

Y=Median of the baseline-corrected cell count value of compound-treated group

K=Median of the baseline-corrected cell count value of placebo-treated group

Statistical analysis is performed on the primary cell count data using one-way ANOVA and Dunnett's multiple comparison post test vs. positive control. The Grubbs test is used to detect statistical outliers.

Exemplary Results for Compounds Tested Using Method B (the Numbers of the Compounds Correspond to the Numbers of the Examples):

The compounds 14 and 58 showed at a dosage of 1 mg/kg a reduction in the range of 29 to 67% of the total cell count, respectively a reduction in the range of 29 to 55% of neutrophils in comparison to the placebo group.

The invention claimed is:

1. A compound of formula 1

(1)

[Chemical structure diagram showing formula 1 with substituents A, R1, R2, R3, R5 on a fused ring system connected via a phenyl-carbonyl-piperidine-pyrimidinedione-thiophene framework]

wherein

A is S, S(O) or S(O)₂, either

R1 is 1-4C-alkoxy, 3-7C-cycloalkoxy, 3-7C-cycloalkylmethoxy, or 1-4C-alkoxy predominantly or completely substituted by fluorine and R2 is 1-4C-alkoxy, 3-7C-cycloalkoxy, 3-7C-cycloalkylmethoxy, or 1-4C-alkoxy predominantly or completely substituted by fluorine, or R1 and R2 together form a 1-2C-alkylenedioxy group, R3 is a five membered heterocyclic ring, which is substituted by R4 and is selected from the group consisting of pyrazol-3-yl, pyrazol-4-yl, thiophen-2-yl, thiophen-3-yl, imidazol-2-yl, imidazol-4-yl, isoxazol-3-yl, isoxazol-4-yl, isoxazol-5-yl, 1,3-oxazol-2-yl, 1,3-oxazol-4-yl, 1,3-oxazol-5-yl, 1,3-thiazol-2-yl, 1,3-thiazol-4-yl, 1,3-thiazol-5-yl, 1,2,3-triazol-4-yl, 1,2,4-triazol-3-yl, 1,2,4-oxadiazol-3-yl, 1,2,4-oxadiazol-5-yl, 1,3,4-oxadiazol-2-yl, 1,2,4-thiadiazol-5-yl, 1,2,4-thiadiazol-3-yl, 1,3,4-thiadiazol-2-yl, tetrazol-2-yl and tetrazol-5-yl, wherein R4 is 1-4C-alkyl, methoxymethyl, methoxyethyl, methoxypropyl, ethoxymethyl, propyloxymethyl, ethoxyethyl, methyl sulfanylmethyl, methyl sulfanylethyl, methylsulfanylpropyl, ethylsulfanylmethyl, propylsulfanylmethyl or ethylsulfanylethyl, R5 is unsubstituted phenyl, phenyl substituted by R6 or phenyl substituted by R6 and R7, wherein R6 is halogen, 1-4C-alkyl or 1-4C-alkoxy, and R7 is halogen, 1-4C-alkyl or 1-4C-alkoxy, or R6 and R7 together form a 1-2C-alkylenedioxy group, or a stereoisomer thereof.

2. A compound of formula 1 according to claim 1 wherein

A is S, S(O) or S(O)₂, either

R1 is 1-4C-alkoxy, 3-7C-cycloalkoxy, 3-7C-cycloalkylmethoxy, or 1-4C-alkoxy predominantly or completely substituted by fluorine and R2 is 1-4C-alkoxy, 3-7C-cycloalkoxy, 3-7C-cycloalkylmethoxy, or 1-4C-alkoxy predominantly or completely substituted by fluorine, or R1 and R2 together form a 1-2C-alkylenedioxy group, R3 is a five membered heterocyclic ring, which is substituted by R4 and is selected from the group consisting of pyrazol-3-yl, pyrazol-4-yl, isoxazol-3-yl, isoxazol-4-yl, isoxazol-5-yl, 1,3-oxazol-2-yl, 1,3-oxazol-4-yl, 1,3-oxazol-5-yl, 1,3-thiazol-2-yl, 1,3-thiazol-4-yl, 1,3-thiazol-5-yl, 1,2,4-triazol-3-yl, 1,2,4-oxadiazol-3-yl, 1,2,4-oxadiazol-5-yl, 1,3,4-oxadiazol-2-yl, 1,2,4-thiadiazol-5-yl, 1,2,4-thiadiazol-3-yl, 1,3,4-thiadiazol-2-yl and tetrazol-5-yl, wherein R4 is 1-4C-alkyl, methylsulfanylmethyl, ethylsulfanylmethyl, methylsulfanylethyl, methoxymethyl, ethoxymethyl or methoxyethyl, and R5 is an unsubstituted phenyl, or a stereoisomer thereof.

3. A compound of formula 1 according to claim 1, wherein

A is S, S(O) or S(O)₂, either

R1 is 1-2C-alkoxy, or 1-2C-alkoxy predominantly or completely substituted by fluorine and R2 is 1-2C-alkoxy, or 1-2C-alkoxy predominantly or completely substituted by fluorine, or R1 and R2 together form a 1-2C-alkylenedioxy group, R3 is 1-methyl-1H-imidazol-2-yl, 1-ethyl-1H-imidazol-2-yl, 5-ethyl-thiophen-2-yl, 5-methyl-thiophen-2-yl, 3-methyl-thiophen-2-yl, 3-ethyl-thiophen-2-yl, 1-methyl-pyrazol-3-yl, 1-ethyl-pyrazol-3-yl, 1-methyl-pyrazol-4-yl, 2-ethyl-pyrazol-4-yl, 4-methyl-1,3-oxazol-2-yl, 4-ethyl-1,3-oxazol-2-yl, 5-methyl-1,3-oxazol-2-yl, 5-ethyl-1,3-oxazol-2-yl, 2-methyl-1,3-oxazol-4-yl, 2-methyl-1,3-oxazol-4-yl, 2-ethyl-1,3-oxazol-4-yl, 2-methyl-1,3-oxazol-5-yl, 2-ethyl-1,3-oxazol-5-yl, 4-methyl-1,3-oxazol-5-yl, 4-ethyl-1,3-oxazol-5-yl, 3-methyl-isoxazol-5-yl, 3-ethyl-isoxazol-5-yl, 5-methyl-isoxazol-3-yl, 5-ethyl-isoxazol-3-yl, 4-methyl-1,3-thiazol-2-yl, 4-ethyl-1,3-thiazol-2-yl, 5-methyl-1,3-thiazol-2-yl, 2-methyl-1,3-thiazol-4-yl, 2-ethyl-1,3-thiazol-4-yl, 2-methyl-1,3-thiazol-5-yl, 2-ethyl-1,3-thiazol-5-yl, 3-methoxymethyl-1,2,4-oxadiazol-5-yl, 3-ethoxymethyl-1,2,4-oxadiazol-5-yl, 3-methoxypropyl-1,2,4-oxadiazol-5-yl, 3-propoxymethyl-1,2,4-oxadiazol-5-yl, 3-methylsulfanylmethyl-1,2,4-oxadiazol-5-yl, 3-ethylsulfanylmethyl-1,2,4-oxadiazol-5-yl, 3-methylsulfanylpropyl-1,2,4-oxadiazol-5-yl, 3-propylsulfanylmethyl-1,2,4-oxadiazol-5-yl, 3-methyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 5-tert-butyl-1,3,4-oxadiazol-2-yl, 5-methoxymethyl-1,3,4-oxadiazol-2-yl, 5-ethoxymethyl-1,3,4-oxadiazol-2-yl, 5-methylsulfanylmethyl-1,3,4-oxadiazol-2-yl, 5-ethylsulfanylmethyl-1,3,4-oxadiazol-2-yl, 5-methyl-1,2,4-oxadiazol-3-yl, 5-ethyl-1,2,4-oxadiazol-3-yl, 3-methyl-1,2,4-thiadiazol-5-yl, 3-methyl-1,2,4-thiadiazol-5-yl, 3-ethyl-1,2,4-thiadiazol-5-yl, 2-methyl-1,2,3-triazol-4-yl, 2-ethyl-1,2,3-triazol-4-yl, 1-methyl-1,2,3-triazol-4-yl, 1-ethyl-1,2,3-triazol-4-yl, 1-methyl-1H-1,2,4-triazol-3-yl, 1-ethyl-1H-1,2,4-triazol-3-yl, 1-methyl-1H-tetrazol-5-yl, 1-ethyl-1H-tetrazol-5-yl, 2-methyl-2H-tetrazol-5-yl, 2-ethyl-2H-tetrazol-5-yl, 5-methyl-2H-tetrazol-2-yl, 1-methoxymethyl-1H-tetrazol-5-yl, 1-ethoxymethyl-1H-tetrazol-5-yl, 2-methoxymethyl- 2H-tetrazol-5-yl, 2-ethoxymethyl-2H-tetrazol-5-yl, 1-methylsulfanylmethyl-1H-tetrazol-5-yl, 1-ethylsulfanylmethyl-1H-tetrazol-5-yl, 2-methylsulfanylmethyl-2H-tetrazol-5-yl or 2-ethylsulfanylmethyl-2H-tetrazol-5-yl, R5 is unsubstituted phenyl, phenyl substituted by R6 or phenyl substituted by R6 and R7
wherein
R6 is fluorine, methyl or methoxy, and
R7 is fluorine, methyl or methoxy,
or a stereoisomer thereof.

4. A compound of formula 1 according to claim 1 wherein
A is S, S(O) or S(O)$_2$,
either
R1 is 1-2C-alkoxy, or 1-2C-alkoxy predominantly or completely substituted by fluorine and
R2 is 1-2C-alkoxy, or 1-2C-alkoxy predominantly or completely substituted by fluorine,
or
R1 and R2 together form a 1-2C-alkylenedioxy group,
R3 is 1-methyl-pyrazol-3-yl, 1-ethyl-pyrazol-3-yl, 1-methyl-pyrazol-4-yl, 2-ethyl-pyrazol-4-yl, 4-methyl-1,3-oxazol-2-yl, 4-ethyl-1,3-oxazol-2-yl, 5-methyl-1,3-oxazol-2-yl, 5-ethyl-1,3-oxazol-2-yl, 2-methyl-1,3-oxazol-4-yl, 2-methyl-1,3-oxazol-4-yl, 2-ethyl-1,3-oxazol-4-yl, 2-methyl-1,3-oxazol-5-yl, 2-ethyl-1,3-oxazol-5-yl, 3-methyl-isoxazol-5-yl, 3-ethyl-isoxazol-5-yl, 5-methyl-isoxazol-3-yl, 5-ethyl-isoxazol-3-yl, 4-methyl-1,3-thiazol-2-yl, 4-ethyl-1,3-thiazol-2-yl, 5-methyl-1,3-thiazol-2-yl, 2-methyl-1,3-thiazol-4-yl, 2-ethyl-1,3-2-methyl-1,3-thiazol-5-yl, 2-ethyl-1,3-thiazol-5-yl, 3-methoxymethyl-1,2,4-oxadiazol-5-yl, 3-ethoxymethyl-1,2,4-oxadiazol-5-yl, 3-methylsulfanylmethyl-1,2,4-oxadiazol-5-yl, 3-ethylsulfanylmethyl-1,2,4-oxadiazol-5-yl, 3-methyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 5-methoxymethyl-1,3,4-oxadiazol-2-yl, 5-ethoxymethyl-1,3,4-oxadiazol-2-yl, 5-methylsulfanylmethyl-1,3,4-oxadiazol-2-yl, 5-ethylsulfanylmethyl-1,3,4-oxadiazol-2-yl, 5-methyl-1,2,4-oxadiazol-3-yl, 5-ethyl-1,2,4-oxadiazol-3-yl, 3-methyl-1,2,4-thiadiazol-5-yl, 3-methyl-1,2,4-thiadiazol-5-yl, 3-ethyl-1,2,4-thiadiazol-5-yl, 2-methyl-1,2,3-triazol-4-yl, 2-ethyl-1,2,3-triazol-4-yl, 1-methyl-1,2,3-triazol-4-yl, 1-ethyl-1,2,3-triazol-4-yl, 1-methyl-1H-tetrazol-5-yl, 1-ethyl-1H-tetrazol-5-yl, 2-methyl-2H-tetrazol-5-yl, 2-ethyl-2H-tetrazol-5-yl, 1-methoxymethyl-1H-tetrazol-5-yl, 1-ethoxymethyl-1H-tetrazol-5-yl, 2-methoxymethyl-2H-tetrazol-5-yl, 2-ethoxymethyl-2H-tetrazol-5-yl, 1-methylsulfanylmethyl-1H-tetrazol-5-yl, 1-ethylsulfanylmethyl-1H-tetrazol-5-yl, 2-methylsulfanylmethyl-2H-tetrazol-5-yl or 2-ethylsulfanylmethyl-2H-tetrazol-5-yl, and
R5 is an unsubstituted phenyl,
or a stereoisomer thereof.

5. A compound of formula 1 according to claim 1, wherein
A is S, S(O) or S(O)$_2$,
R1 is methoxy or ethoxy,
R2 is methoxy,
R3 is 1-methyl-1H-imidazol-2-yl, 5-ethyl-thiophen-2-yl, 3-methyl-thiophen-2-yl, 1-ethyl-pyrazol-3-yl, 2-ethyl-pyrazol-4-yl, 4-ethyl-1,3-oxazol-2-yl, 5-ethyl-1,3-oxazol-2-yl, 2-ethyl-1,3-oxazol-4-yl, 2-ethyl-1,3-oxazol-5-yl, 4-methyl-1,3-oxazol-5-yl, 3-ethyl-isoxazol-5-yl, 5-methyl-isoxazol-3-yl, 4-methyl-1,3-thiazol-2-yl, 5-methyl-1,3-thiazol-2-yl, 2-methyl-1,3-thiazol-4-yl, 2-methyl-1,3-thiazol-5-yl, 3-methoxymethyl-1,2,4-oxadiazol-5-yl, 3-methoxypropyl-1,2,4-oxadiazol-5-yl, 3-propoxymethyl-1,2,4-oxadiazol-5-yl, 3-methylsulfanylmethyl-1,2,4-oxadiazol-5-yl, 3-ethyl-1,2,4-oxadiazol-5-yl, 5-ethyl-1,3,4-oxadiazol-2-yl, 5-tert-butyl-1,3,4-oxadiazol-2-yl, 5-methoxymethyl-1,3,4-oxadiazol-2-yl, 5-methyl-1,2,4-oxadiazol-3-yl, 3-ethyl-1,2,4-thiadiazol-5-yl, 2-ethyl-1,2,3-triazol-4-yl, 1-ethyl-1,2,3-triazol-4-yl, 1-methyl-1H-1,2,4-triazol-3-yl, 1-ethyl-1H-tetrazol-5-yl, 2-ethyl-2H-tetrazol-5-yl, 5-ethyl-2H-tetrazol-2-yl, 1-methoxymethyl-1H-tetrazol-5-yl or 2-methoxymethyl-2H-tetrazol-5-yl, and
R5 is phenyl, 1,3-benzodioxol-5-yl, 2-fluorophenyl, 4-fluorophenyl, 2,3-difluorophenyl, 3,4-difluorophenyl, 2-methoxy-4-fluorophenyl, 2-methoxy-5-fluorophenyl or 2,5-dimethoxyphenyl,
or a stereoisomer thereof.

6. A compound of formula 1 according to claim 1 wherein
A is S, S(O) or S(O)$_2$,
R1 is methoxy or ethoxy,
R2 is methoxy,
R3 is 1-ethyl-pyrazol-3-yl, 2-ethyl-pyrazol-4-yl, 4-ethyl-1,3-oxazol-2-yl, 5-ethyl-1,3-oxazol-2-yl, 2-ethyl-1,3-oxazol-4-yl, 2-ethyl-1,3-oxazol-5-yl, 3-ethyl-isoxazol-5-yl, 5-methyl-isoxazol-3-yl, 4-methyl-1,3-thiazol-2-yl, 5-methyl-1,3-thiazol-2-yl, 2-methyl-1,3-thiazol-4-yl, 2-methyl-1,3-thiazol-5-yl, 3-methoxymethyl-1,2,4-oxadiazol-5-yl, 3-methylsulfanylmethyl-1,2,4-oxadiazol-5-yl, 3-ethyl-1,2,4-oxadiazol-5-yl, 5-ethyl-1,3,4-oxadiazol-2-yl, 5-methoxymethyl-1,3,4-oxadiazol-2-yl, 5-methyl-1,2,4-oxadiazol-3-yl, 3-ethyl-1,2,4-thiadiazol-5-yl, 2-ethyl-1,2,3-triazol-4-yl, 1-ethyl-1,2,3-triazol-4-yl, 1-ethyl-1H-tetrazol-5-yl, 2-ethyl-2H-tetrazol-5-yl, 1-methoxymethyl-1H-tetrazol-5-yl or 2-methoxymethyl-2H-tetrazol-5-yl, and
R5 is an unsubstituted phenyl,
or a stereoisomer thereof.

7. A compound of formula 1 according to claim 1 wherein
A is S, S(O) or S(O)$_2$,
R1 is ethoxy,
R2 is methoxy,
R3 is 5-ethyl-1,3-oxazol-2-yl, 3-ethyl-isoxazol-5-yl, 5-methyl-isoxazol-3-yl, 2-methyl-1,3-thiazol-5-yl, 3-methoxymethyl-1,2,4-oxadiazol-5-yl, 3-methylsulfanylmethyl-1,2,4-oxadiazol-5-yl, 3-ethyl-1,2,4-oxadiazol-5-yl, 5-methyl-1,2,4-oxadiazol-3-yl, 1-ethyl-1H-tetrazol-5-yl, 2-ethyl-2H-tetrazol-5-yl, 1-methoxymethyl-1H-tetrazol-5-yl or 2-methoxymethyl-2H-tetrazol-5-yl, and
R5 is an unsubstituted phenyl,
or a stereoisomer thereof.

8. A compound according to claim 1 selected from the group consisting of
3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-ethyl-1,3-oxazol-2-yl)methyl]-6-phenylthieno[3,2-d]pyrimidine-2,4(1H,3H)-dione;
3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-methyl-1,2,4-oxadiazol-3-yl)methyl]-6-phenylthieno[3,2-d]pyrimidine-2,4(1H,3H)-dione;
3-[1-({4-[(4aR,10bR)-9-ethoxy-8-methoxy-3,4,4a,10b-tetrahydro-1H-thiopyrano[4,3-c]isoquinolin-6-yl]

phenyl}carbonyl)piperidin-4-yl]-1-[(3-ethylisoxazol-5-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-ethyl-1,3,4-oxadiazol-2-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(4-ethyl-1,3-oxazol-2-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-methylisoxazol-3-yl)methyl]-6-phenylthieno[3,2-d]pyrimidine-2,4(1H,3H)-dione;

3-(1-{4-[(4aR,10bR)-9-ethoxy-8-methoxy-3,4,4a,10b-tetrahydro-1H-thiopyrano[4,3-c]isoquinolin-6-yl]benzoyl piperidin-4-yl)-1-[(3-ethyl-1,2,4-oxadiazol-5-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-{[5-(methoxymethyl)-1,3,4-oxadiazol-2-yl]methyl-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-1,3-oxazol-5-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-methyl-1,3-thiazol-4-yl)methyl]-6-phenylthieno[3,2-d]pyrimidine-2,4(1H,3H)-dione;

3-[1-(4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-({3-[(methylsulfanyl)methyl]-1,2,4-oxadiazol-5-yl}methyl)-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(5-methyl-1,3-thiazol-2-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(4-methyl-1,3-thiazol-2-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione;

3-(1-{4-[(4aR,10bR)-9-ethoxy-8-methoxy-3,4,4a,10b-tetrahydro-1H-thiopyrano[4,3-c]isoquinolin-6-yl]benzoyl}piperidin-4-yl)-1-{[3-(methoxymethyl)-1,2,4-oxadiazol-5-yl]methyl}-6-phenylthieno[3,2-d]pyrimidine-2,4(1H,3H)-dione;

3-[1-({ 4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-1,3-oxazol-4-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(1-ethyl-1H-pyrazol-4-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(1-ethyl-1H-pyrazol-3-yl)methyl]-6-phenylthieno[3,2-d]pyrimidine-2,4(1H,3H)-dione;

3-[1-({4-[(4aR,10bR)-9-ethoxy-8-methoxy-2,2-dioxido-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione;

3-[1-({4-[(4aR,10bR)-9-ethoxy-8-methoxy-3,4,4a, 10b-tetrahydro-1H-thiopyrano[4,3-c]isoquinolin-6-yl]phenyl}carbonyl)piperidin-4-yl]-1-[(2-methyl-1,3-thiazol-5-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-1,2,3-triazol-4-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(3-ethyl-1,2,4-thiadiazol-5-yl)methyl]-6-phenylthieno[3,2-d]pyrimidine-2,4(1H,3H)-dione;

3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(1-ethyl-1H-1,2,3-triazol-4-yl)methyl]-6-phenylthieno[3,2-d]pyrimidine-2,4(1H,3H)-dione;

3-[1-({4-[(2R,4aR,10bR)-9-ethoxy-8-methoxy-2-oxido-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione;

3-[1-({4-[(2S,4aR,10bR)-9-ethoxy-8-methoxy-2-oxido-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione;

3-[1-({3-[(4aR,10bR)-9-ethoxy-8-methoxy-3,4,4a, 10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione;

3-[1-({3-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(3-ethyl-1,2,4-oxadiazol-5-yl)methyl]-6-phenylthieno[3,2-d]pyrimidine-2,4(1H,3H)-dione;

3-[1-({4-[(4aR,10bR)-9-ethoxy-8-methoxy-3,4,4a, 10b-tetrahydro-1H-thiopyrano[4,3-c]isoquinolin-6-yl]phenyl}carbonyl)piperidin-4-yl]-1-{[2-(methoxyethyl)-2H-tetrazol-5-yl]methyl}-6-phenylthieno[3,2-d]pyrimidine-2,4(1H,3H)-dione and 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-{[1-(methoxymethyl)-1H-tetrazol-5-yl]methyl}-6-phenylthieno[3,2-d]pyrimidine-2,4(1H,3H)-dione.

9. A pharmaceutical composition comprising at least one of the compounds of formula 1 or a stereoisomer thereof according to claim 1, together with at least one pharmaceutically acceptable auxiliary.

10. A composition comprising at least one compound of formula 1 or a stereoisomer thereof according to claim 1, at least one therapeutic agent selected from the group consisting of corticosteroids, anticholinergics, β₂-adrenoreceptor agonists, H1 receptor antagonists, leukotriene receptor antagonists, 5-lipoxygenase inhibitors, endothelin receptor antagonists, prostacyclins, calcium channel blockers, beta-blockers, type 4 phosphodiesterase inhibitors, type 5 phosphodiesterase inhibitors, immunosuppressants, vitamin D analogues, HMG-CoA reductase-inhibitors, lung surfactants, antibiotics, guanylyl-cyclase activators/stimulators, tetrahydrobiopterin tetrahydrobiopterin derivatives, anticoagulants, diuretics, pirfenidone and digitalis glycosides, and at least one pharmaceutically acceptable auxiliary.

11. A method of treating a disease, which is alleviated by inhibition of the type 4 and type 5 phosphodiesterase, comprising administering to a patient in need thereof a therapeutically effective amount of a compound of formula 1 or a stereoisomer thereof according to claim 1.

12. A method of treating an acute or chronic airway disease in a patient comprising administering to a patient in need thereof a therapeutically effective amount of a compound of formula 1 or a stereoisomer thereof according to claim 1.

13. The method according to claim 12, wherein the acute or chronic airway disease is selected from the group consisting of interstitial lung disease, pulmonary fibrosis, cystic fibrosis, bronchial asthma, chronic bronchitis, emphysema, chronic obstructive pulmonary disease (COPD) and COPD associated with pulmonary hypertension.

14. A compound of formula 1p or 1m

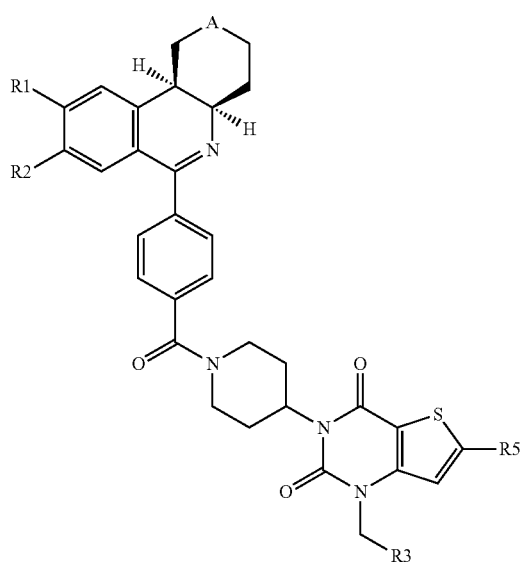

(1p)

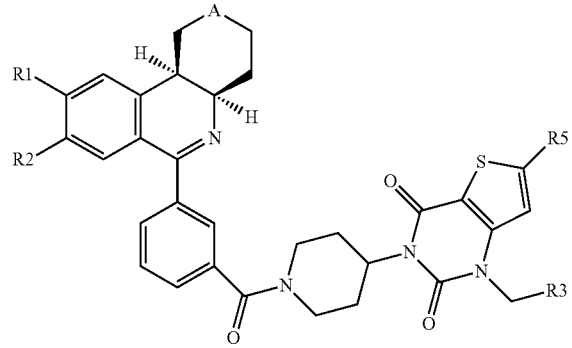

(1m)

wherein

A is S, S(O) or S(O)₂,

R1 is ethoxy,

R2 is methoxy,

R3 is 2-ethyl-2H-tetrazol-5-yl, and

R5 is an unsubstituted phenyl, or a stereoisomer thereof.

15. A compound of formula 1 according to claim 1, which is 3-[1-({4-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione.

16. A compound of formula 1 according to claim 1, which is 3-[1-({3-[(4aR,10bR)-9-ethoxy-8-methoxy-3,4,4a,10b-tetrahydro-1H-thiopyrano[4,3-c]isoquinolin-6-yl]phenyl}carbonyl)piperidin-4-yl]-1-[(2-ethyl-2H-tetrazol-5-yl)methyl]-6-phenylthieno[3,2-d]pyrimidine-2,4(1H,3H)-dione.

17. A pharmaceutical composition comprising a compound of formula 1p or 1m or a stereoisomer thereof according to claim 14, together with at least one pharmaceutically acceptable auxiliary.

18. A pharmaceutical composition comprising the compound of formula 1 according to claim 15, together with at least one pharmaceutically acceptable auxiliary.

19. A pharmaceutical composition comprising the compound of formula 1 according to claim 16, together with at least one pharmaceutically acceptable auxiliary.

* * * * *

UNITED STATES PATENT AND TRADEMARK OFFICE
CERTIFICATE OF CORRECTION

PATENT NO. : 9,018,175 B2  
APPLICATION NO. : 13/515214  
DATED : April 28, 2015  
INVENTOR(S) : Dieter Flockerzi et al.

Page 1 of 1

It is certified that error appears in the above-identified patent and that said Letters Patent is hereby corrected as shown below:

On the Title Page, Item (54), and in the Specification, Col. 1, lines 1-3, please amend the title to read: "3,4,4A,10B-TETRAHYDRO-1H-THIOPYRANO-[4,3-C] ISOQUINOLINE DERIVATIVES"

In the Claims  
Claim 2, Col. 126, Line 11: after "5-yl," and before "1,2,4-triazol-3-yl," please insert --1,2,3-triazol-4-yl,--.  
Claim 4, Col. 127, Line 31: please replace "2-ethyl-1,3,2-methyl-1,3-thiazol-5-yl" with "2-ethyl-1,3-thiazol-4-yl, 2-methyl-1,3-thiazol-5-yl".  
Claim 8, Col. 129, Line 28: after "methyl" and before "-6-phenylthieno" please insert --}--.  
Claim 8, Col. 129, Line 41: after "3-[1-(" and before "4-[(4aR,10bR)" please insert --{--.  
Claim 10, Col. 131, Line 18: after "drobiopterin" and before "tetrahydrobiopterin" please insert --,--.

Signed and Sealed this  
Twenty-first Day of July, 2015

Michelle K. Lee  
*Director of the United States Patent and Trademark Office*